(12) United States Patent
Lipson et al.

(10) Patent No.: US 9,340,830 B2
(45) Date of Patent: May 17, 2016

(54) OPTIMIZATION OF MULTIGENE ANALYSIS OF TUMOR SAMPLES

(75) Inventors: Doron Lipson, Chestnut Hill, MA (US); Geoffrey Alan Otto, Brookline, MA (US); Alexander N. Parker, Boston, MA (US); Philip James Stephens, Lexington, MA (US); Sean R. Downing, Methuen, MA (US); Mima Jarosz, Palo Alto, CA (US); Mikhail G. Shapiro, San Francisco, CA (US); Roman Yelensky, Newton, MA (US)

(73) Assignee: FOUNDATION MEDICINE, INC., Cambridge, MA (US)

( * ) Notice: Subject to any disclaimer, the term of this patent is extended or adjusted under 35 U.S.C. 154(b) by 269 days.

(21) Appl. No.: 13/339,986

(22) Filed: Dec. 29, 2011

(65) Prior Publication Data

US 2012/0208706 A1 Aug. 16, 2012

Related U.S. Application Data

(60) Provisional application No. 61/428,568, filed on Dec. 30, 2010, provisional application No. 61/428,602, filed on Dec. 30, 2010, provisional application No. 61/428,626, filed on Dec. 30, 2010, provisional (Continued)

(51) Int. Cl.
*G01N 33/48* (2006.01)
*G01N 31/00* (2006.01)
*G06G 7/48* (2006.01)

(Continued)

(52) U.S. Cl.
CPC ............ *C12Q 1/6827* (2013.01); *C12Q 1/6874* (2013.01)

(58) Field of Classification Search
CPC ...... C12Q 1/68; C12Q 1/6869; C12Q 1/6886; C40B 30/04; C12N 15/1003
See application file for complete search history.

(56) References Cited

U.S. PATENT DOCUMENTS

| 7,381,526 B2 * | 6/2008 | Polansky ..................... 435/6.14 |
| 2005/0209787 A1 | 9/2005 | Waggener et al. |
| 2006/0246497 A1 | 11/2006 | Huang et al. |

(Continued)

FOREIGN PATENT DOCUMENTS

| JP | 2008017853 A | 1/2008 |
| WO | 2009099602 A1 | 8/2009 |
| WO | 2010028098 A2 | 3/2010 |

OTHER PUBLICATIONS

Bazan, et al., "Specific Condon 13 K-ras Mutations are Predictive of Clinical Outcome in Colorectal Cancer Pateients, whereas Codon 12 K-ras Mutations are Associated with Mucinous Histotype", Annals. Oncol., 13(1438-1446, Especially p. 1440, col. 2 para. 1-2, Sep. 2002.

(Continued)

*Primary Examiner* — Larry D Riggs, II
(74) *Attorney, Agent, or Firm* — Lando & Anastasi, LLP

(57) ABSTRACT

A method of analyzing a tumor sample comprising:
(a) acquiring a library comprising a plurality of tumor members from a tumor sample;
(b) contacting the library with a bait set to provide selected members;
(c) acquiring a read for a subgenomic interval from a tumor member from said library;
(d) aligning said read; and
(e) assigning a nucleotide value (e.g., calling a mutation) from said read for the preselected nucleotide position, thereby analyzing said tumor sample.

85 Claims, 10 Drawing Sheets

Sample Receipt and QC; DNA Isolation

Related U.S. Application Data application No. 61/428,638, filed on Dec. 30, 2010, provisional application No. 61/467,748, filed on Mar. 25, 2011, provisional application No. 61/467,798, filed on Mar. 25, 2011, provisional application No. 61/486,006, filed on May 13, 2011, provisional application No. 61/486,026, filed on May 13, 2011, provisional application No. 61/486,012, filed on May 13, 2011, provisional application No. 61/486,033, filed on May 13, 2011, provisional application No. 61/552,884, filed on Oct. 28, 2011.

(51) Int. Cl.
*G06G 7/58* (2006.01)
*C12Q 1/68* (2006.01)

(56) References Cited

U.S. PATENT DOCUMENTS

| | | |
|---|---|---|
| 2006/0275779 A1 | 12/2006 | Li et al. |
| 2007/0087362 A1 | 4/2007 | Church et al. |
| 2007/0194225 A1 | 8/2007 | Zorn |
| 2010/0029498 A1* | 2/2010 | Gnirke et al. ............ 506/9 |
| 2010/0105052 A1 | 4/2010 | Drmanac et al. |

OTHER PUBLICATIONS

Rhei et al., Mutation Analysis of the Putative Tumor Supressor Gene PTEN/MMAC1 in Primary Breast Carcinomas., Cancer Res., 57(17):3657-3659, Sep. 1, 1997.
Bazan, et al., "Specific Condon 13 K-ras Mutations are Predictive of Clinical Outcome in Colorectal Cancer Patients, whereas Codon 12 K-ras Mutations are Associated with Mucinous Histotype", Annals. Oncol., 13(1438-1446, Especially p. 1440, col. 2 para. 1-2, Sep. 2002.
International Search Report for PCT/US11/67725 dated Apr. 27, 2012.
Gnirke, A., et al., "Solution Hybrid Selection with Ultra-long Oligonucleotides for Massively Parallel Targeted Sequencing," Nat. Biotechnol. 27(2):182-189 (2009).
Blumenstiel, B., et al., "Targeted Exon Sequencing by In-Solution Hybrid Selection," Curr. Protoc. Hum. Genet., Chapter 18.4, (2010).
Aslanidis and de Jong, "Ligation-Independent Cloning of PCR Products (LIC-PCR)," Nucleic Acids Res. 18:6069-6074 (1990).
Branton, D., et al., "The Potential and Challenges of Nanopore Sequencing," Nat. Biotechnol. 26(10):1146-1153 (2008).
Hanna, G.J., et al., "Comparison of Sequencing by Hybridization and Cycle Sequencing for Genotype of Human Immunodeficiency Virus Type 1 Reverse Transcriptase," J. Clin. Microbiol., 38(7):2715-21 (2000).
Edwards, J.R., et al., "Mass-Spectrometry DNA Sequencing," Mut. Res. 573(1-2):3-12 (2005).
Trapnell, C. and Salzberg, S.L., "How to Map Billions of Short Reads Onto Genomes," Nature Biotech., 27:455-457 (2009).
Warren, R., et al., "Assembling Millions of Short DNA Sequences Using SSAKE," Bioinformatics, 23:500-501 (2007).
Butler, J., et al., "Allpaths: De Novo Assemly of Whole-Genome Shotgun Microreads," Genome Res., 18:810-820 (2008).
Zerbino, D.R. and Birney, E., "Velvet: Algorithms for De Novo Short Read Assembly Using De Bruijn Graphs," Genome Res., 18:821-829 (2008).
Li, H. and Durbin, R., "Fast and Accurate Long-Read Alignment with Burrows-Wheeler Transform," Bioinformatics, 26(5):589-595 (2010).
Browning, B.L. and Yu, Z., "Simultaneous Genotype Calling and Haplotype Phasing Improves Genotype Accuracy and Reduces False-Positive Associations for Genome-Wide Association Studies," Am. J. Hum. Genet., 85(6):847-861 (2009).
Li, Y., et al., "Genotype Imputation," Annu. Rev. Genomics Hum. Genet., 10:387-406 (2009).
McKenna, A., et al., "The Genome Analysis Toolkit: A MapReduce Framework for Analyzing Next-Generation DNA Sequencing Data," Genome Res., 20(9):1297-1303 (2010).
Ye, K., et al., "Pindel: A Pattern Growth Approach to Detect Break Points of Large Deletions and Medium Sized Insertions from Paired-End Short Reads," Bioinformatics, 25(21):2865-71 (2009).
Lunter, G. and Goodson, M., "Stampy: A Statistical Algorithm for Sensitive and Fast Mapping of Illumina Sequence Reads," Genome Res. epub ahead of print (2010).
Li, H., et al., "The Sequence Alignment/Map Format and SAMtools," Bioinformatics, 25(16):2078-2079 (2009).
Albers, C.A., et al., "Dindel: Accurate Indel Calls from Short-Read Data," Genome Res. (Oct. 27, 2010) epub ahead of print.
Le, S.Q. and Durbin, R., "SNP Detection and Genotyping from Low-Coverage Sequencing Data on Multiple Diploid Samples," Genome Res., Oct. 27, 2010, epub ahead of print.
Wong, K.K., et al., "Use of Tagged Random Hexamer Amplification (TRHA) to Clone and Sequence Minute Quantities of DNA-Application to a 180 kb Plasmid Isolated from Sphingomonas F199," Nucleic Acids Res. 24 (19):3778-3783 (1996).
Berger, et al., "Integrative Analysis of the Melanoma Transcriptome," Genome Res., 20(4):413-427 (2010) (PMID 20179022).
Garber, et al., "Computational Methods for Transcriptome Annotation and Quantification Using RNA-seq," Nat. Methods. 8(6):469-477 (2011) (PMID21623353).
Levin, et al., "Targeted Next-Generation Sequencing of a Cancer Transcriptome Enhances Detection of Sequence Variants and Novel Fusion Transcripts," Genome Biol., 10(10):R115 (PMID19835606) (2009).
Summerer D., et al., "Targeted high Throughput Sequencing of a Cancer-Related Exome Subset by specific Sequence Capture with a Fully Automated Microarray Platform", Genomics, 95(4), Apr. 1, 2010, pp. 241-246.
Dahl, Fredrik et al., "Multigene Amplification and Massively Parallel Sequencing for Cancer Mutation Discovery", Proceedings of the National Academy of Sciences, 104(22), May 29, 2007, pp. 9387-9392.
Ding, L., et al., "Analysis of Next-Generation Genomic Data in Cancer: Accomplishments and Challenges", Human Molecular Genetics, 19(R2), Sep. 15, 2010, pp. R188-R196.
Craig, David W., et al., "Identification of Genetic Variants Using Bar-Coded Multiplexed Sequencing", Nature Methods, 5(10), Oct. 1, 2008, pp. 887-893.
Teer, J.K., et al., "Systematic Comparison of Three Genomic Enrichment Methods for Massively Parallel DNA Sequencing", Genome Research, 20(10), Sep. 1, 2010, pp. 1420-1431.
Supplemental European Search Report dated Apr. 24, 2014 from European Application No. 11853462.
Singapore Search Report dated Oct. 8, 2014 from Singapore Application No. 201305122.2.
Singapore Written Opinion dated Nov. 18, 2014 from Singapore Application No. 201305122.2.
Written Opinion of the International Searching Authority for PCT/US 11/67725 mailed Apr. 27, 2012.
Drilon et al. "Broad, Hybrid Capture-Based Next-Generation Sequencing Identifies Actionable Genomic Alternations in Lung Adenocarcinomas Otherwise Negative for Such Alterations by Other Genomic Testing Approaches" Clinical cancer Research (2015) vol. 21 No. 16 pp. 3631-3639.
Hutchinson et al. "BRAF Fusions Define a Distinct Molecular Subset of Melanomas with Potential Sensitivity to MEK Inhibition" Clinical Cancer Research (2013) vol. 19 No. 24 pp. 6696-6702.
Imielinski et al., "Mapping the Hallmarks of Lung Adenocarcinoma with Massively Parallel Sequencing" Cell (2012) vol. 150 pp. 1107-1120.

\* cited by examiner

SEQUENCE LISTING

```
<160> NUMBER OF SEQ ID NOS: 51

<210> SEQ ID NO 1
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (16)..(135)
```

<223> OTHER INFORMATION: a, c, t, g, unknown or other

<400> SEQUENCE: 1

```
atcgcaccag cgtgtnnnnn nnnnnnnnnn nnnnnnnnnn nnnnnnnnnn nnnnnnnnnn    60
nnnnnnnnnn nnnnnnnnnn nnnnnnnnnn nnnnnnnnnn nnnnnnnnnn nnnnnnnnnn   120
nnnnnnnnnn nnnnncactg cggctcctca                                    150
```

<210> SEQ ID NO 2
<211> LENGTH: 36
<212> TYPE: DNA
<213> ORGANISM: Homo sapiens

<400> SEQUENCE: 2

```
ccaaaactaa actgctcttt aaatatctta gacact                              36
```

<210> SEQ ID NO 3
<211> LENGTH: 36
<212> TYPE: DNA
<213> ORGANISM: Homo sapiens

<400> SEQUENCE: 3

```
ccaaaactaa actgctcttt aaatatctta gacact                              36
```

<210> SEQ ID NO 4
<211> LENGTH: 36
<212> TYPE: DNA
<213> ORGANISM: Homo sapiens

<400> SEQUENCE: 4

```
ccaacactaa actgctcttt aaatatctta gacact                              36
```

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 5

```
ccaaaactaa actgctcttt aaatatctta gacact                              36
```

<210> SEQ ID NO 6
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
ccattgtgtg tgagcaaagg caccctgtcc agtctaacct gaatctctgt aggaagaggc    60
gtgcggctct actacatcgg agggaggtc ttcgcagagt gcctcagtga cagcgctatt   120
```

<210> SEQ ID NO 7
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ctgtccagtc taacctgaat ctctgtagga agaggcgtgc ggctctacta catcggaggg    60
gaggtcttcg cagagtgcct cagtgacagc gctattttg tccagtctcc caactgtaac   120

<210> SEQ ID NO 8
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gtaggaagag gcgtgcggct ctactacatc ggagggagg tcttcgcaga gtgcctcagt    60
gacagcgcta ttttgtcca gtctcccaac tgtaaccagc gctatggctg gcacccggcc   120

<210> SEQ ID NO 9
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
tacatcggag gggaggtctt cgcagagtgc ctcagtgaca gcgctatttt tgtccagtct    60
cccaactgta accagcgcta tggctggcac cggccaccg tctgcaagat cccaccaggt   120

<210> SEQ ID NO 10
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gagtgcctca gtgacagcgc tattttgtc cagtctccca actgtaacca gcgctatggc    60
tggcacccgg ccaccgtctg caagatccca ccaggtaaac gagccgcaca ggcaccctg   120

<210> SEQ ID NO 11
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
tttgtccagt ctcccaactg taaccagcgc tatggctggc acccggccac cgtctgcaag    60
atcccaccag gtaaacgagc cgcacaggca cccctgcctt gaggtccctc tccgagtgca   120

<210> SEQ ID NO 12
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gacctggcca cttccatccc cacagccctg tttctgtgtt tttggcagga tgcaacctga    60
agatcttcaa caaccaggag ttcgctgccc tcctggccca gtcggtcaac cagggctttg   120

<210> SEQ ID NO 13
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gccctgtttc tgtgtttttg gcaggatgca acctgaagat cttcaacaac caggagttcg    60
ctgccctcct ggcccagtcg gtcaaccagg gctttgaggc tgtctaccag ttgacccgaa   120

<210> SEQ ID NO 14
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gatgcaacct gaagatcttc aacaaccagg agttcgctgc cctcctggcc cagtcggtca    60
accagggctt tgaggctgtc taccagttga cccgaatgtg caccatccgc atgagcttcg   120

<210> SEQ ID NO 15
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
accaggagtt cgctgccctc ctggcccagt cggtcaacca gggctttgag gctgtctacc    60
agttgacccg aatgtgcacc atccgcatga gcttcgtcaa aggctgggga gcggagtaca   120

<210> SEQ ID NO 16
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
cccagtcggt caaccagggc tttgaggctg tctaccagtt gacccgaatg tgcaccatcc    60
gcatgagctt cgtcaaaggc tggggagcgg agtacaggtc agttatgggt gctgcctaca   120

<210> SEQ ID NO 17
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
aggctgtcta ccagttgacc cgaatgtgca ccatccgcat gagcttcgtc aaaggctggg    60
gagcggagta caggtcagtt atgggtgctg cctacatcag gggacccaac tccaggtgac   120

<210> SEQ ID NO 18
<211> LENGTH: 120
<212> TYPE: DNA

```
<213> ORGANISM: Artificial Sequence
<220> FEATURE:
<223> OTHER INFORMATION: Description of Artificial Sequence: Synthetic
      polynucleotide

<400> SEQUENCE: 18
tgtaaccccc tggagatttt ttaagtcccc caccccaccc ctttccctat ttcttacagg    60
agacagactg tgaccagtac cccctgctgg attgagctgc acctgaatgg gcctttgcag   120

<210> SEQ ID NO 19
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
gtcccccacc ccaccccttt ccctatttct tacaggagac agactgtgac cagtaccccc    60
tgctggattg agctgcacct gaatgggcct ttgcagtggc ttgacaaggt cctcacccag   120

<210> SEQ ID NO 20
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atttcttaca ggagacagac tgtgaccagt acccctgct ggattgagct gcacctgaat     60
gggcctttgc agtggcttga caaggtcctc acccagatgg gctccccaag catccgctgt  120

<210> SEQ ID NO 21
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
accagtaccc cctgctggat tgagctgcac ctgaatgggc ctttgcagtg gcttgacaag    60
gtcctcaccc agatgggctc cccaagcatc cgctgttcca gtgtgtctta gagacatcaa  120

<210> SEQ ID NO 22
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ctgcacctga atgggccttt gcagtggctt gacaaggtcc tcacccagat gggctcccca    60
agcatccgct gttccagtgt gtcttagaga catcaagtat ggtaggggag ggcaggcttg   120

<210> SEQ ID NO 23
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 23
tggcttgaca aggtcctcac ccagatgggc tccccaagca tccgctgttc cagtgtgtct      60
tagagacatc aagtatggta ggggagggca ggcttgggga aaatggccat gcaggaggtg     120

<210> SEQ ID NO 24
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
cgtcgcgcgc caacgccggc atggcctccg agcccgggg tccccaggcc gcgccggccc       60
agccctgcga tgccgcctgg agcggcgcgc ctcgcgctgc aggtggctct cttaaggatg    120

<210> SEQ ID NO 25
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
cgtctcacgc caacgcaagc atgtcctccg agcccgggg tccccaggcc gcgccggccc       60
agccctgcga tgccgcctgg agcggcgcgc ctcgcactgc agatggctct cttaaggatg    120

<210> SEQ ID NO 26
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
taccgagcag cggcagctgg ccgccgtcgc gcgccaacgc cggcatggcc tccggagccc      60
ggggtcccca ggccgcgccg gcccagccct gcgatgccgc ctggagcggc gcgcctcgcg    120

<210> SEQ ID NO 27
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
taccgagcag cggcagctgg ccgccgtcgc gcgccaacgc cggcatggcc tccggagccc      60
ggggtcccca ggccgcgcat gcccagccct gcgatgccgc cttgagcaac gcgcctcacg    120

<210> SEQ ID NO 28
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gctgcgagcg agcgagcggg gccttaccga gcagcggcag ctggccgccg tcgcgcgcca      60
```
acgccggcat ggcctccgga gcccggggtc cccaggccgc gccggcccag ccctgcgatg    120

<210> SEQ ID NO 29
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gcttcgagag agcgagcggg gccttaccga gcagcagcag ctggccgccg tcgcgcgcca    60
acgccggcat ggcctccgga gcccggggtc cccaggccgc gccagcccag ccctgagatg    120

<210> SEQ ID NO 30
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30 gtggggctg agggaccgcg aggggctgcg agcgagcgag cggggcctta ccgagcagcg    60
gcagctggcc gccgtcgcgc gccaacgccg gcatggcctc cggagcccgg ggtccccagg    120

<210> SEQ ID NO 31
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gaggtggctg agagaccgcg aggagctgcg agcgagcgag cggggcctta ccgagcagcg    60
gcagctggcc gccgtcgcgc gccaacgcag gcatggcctc cggagcccag ggtccccagg    120

<210> SEQ ID NO 32
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
cgaggcggct gggccggagg aggcgcgcgc ccgggtccac actgcggggt gggggctgag    60
ggaccgcgag gggctgcgag cgagcgagcg gggccttacc gagcagcggc agctggccgc    120

<210> SEQ ID NO 33
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
cgaggcggct gggccggagg aggcgcgcgc ccggatccac actgcggggt gggggctgag    60
ggaccgcgag gggctgcgag cgagcgagcg gggacttacc gagcagcggc aactggacgc    120

```
<210> SEQ ID NO 34
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
gcgcgcccgg gtccacactg cggggtgggg gctgagggac cgcgaggggc tgcgagcgag      60
cgagcggggc cttaccgagc agcggcagct ggccgccgtc gcgcgccaac gccggcatgg     120

<210> SEQ ID NO 35
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
gcacgcacgg atccacactg cggggtgggg gctgagggac cgcgaggagc tgcgagcgag      60
cgagcggggc cttaccgagc agcggcagct ggcagccgtc gcgcgccaac gccggcatgg     120

<210> SEQ ID NO 36
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
tcgcaggcac agcgcggcgc cccgctgcat ctccggccgc tgcgcgtggg tccgacccga      60
gcggccgcgg ctcggggctg aaagtgtccg cgcgggcgcc ggctggcctg gggcggggcg     120

<210> SEQ ID NO 37
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
cacacacaca agcgcggcgc cccgctgcat ctccggccgc tgcgcgtggg tccgacccga      60
gcggccgcgg ctcggggctg aaagtgtccg cgcgggcgcc ggctggcctg cacacacaca     120

<210> SEQ ID NO 38
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
ggcggagcgg tctcagcgcc cgccccaggt gcgcggtacc ccctcccggg ccagccccac      60
gctcgggcgg gtggcccgtt cgccgcgctc accgtccagg agtcccaggc agagccacag     120

<210> SEQ ID NO 39
<211> LENGTH: 120
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 39
cacacacaca tctcagcgcc cgccccaggt gcgcggtacc ccctcccggg ccagccccac      60
gctcgggcgg gtggcccgtt cgccgcgctc accgtccagg agtcccaggc cacacacaca    120

<210> SEQ ID NO 40
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
ccaggtgcgc ggtacccccct cccggccag ccccacgctc gggcgggtgg cccgttcgcc      60
gcgctcaccg tccaggagtc ccaggcagag ccacagtcgc aggcacagcg cggcgccccg    120

<210> SEQ ID NO 41
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
cacacacaca ggtacccccct cccggccag ccccacgctc gggcgggtgg cccgttcgcc      60
gcgctcaccg tccaggagtc ccaggcagag ccacagtcgc aggcacagcg cacacacaca    120

<210> SEQ ID NO 42
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
ggcccgttcg ccgcgctcac cgtccaggag tcccaggcag agccacagtc gcaggcacag      60
cgcggcgccc cgctgcatct ccggccgctg cgcgtgggtc cgacccgagc ggccgcggct    120

<210> SEQ ID NO 43
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
cacacacaca ccgcgctcac cgtccaggag tcccaggcag agccacagtc gcaggcacag      60
cgcggcgccc cgctgcatct ccggccgctg cgcgtgggtc cgacccgagc cacacacaca    120

<210> SEQ ID NO 44
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 44
ggccagcccc acgctcgggc gggtggcccg ttcgccgcgc tcaccgtcca ggagtcccag    60
gcagagccac agtcgcaggc acagcgcggc gccccgctgc atctccggcc gctgcgcgtg   120

<210> SEQ ID NO 45
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
cacacacaca acgctcgggc gggtggcccg ttcgccgcgc tcaccgtcca ggagtcccag    60
gcagagccac agtcgcaggc acagcgcggc gccccgctgc atctccggcc cacacacaca   120

<210> SEQ ID NO 46
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
caggagtccc aggcagagcc acagtcgcag gcacagcgcg gcgccccgct gcatctccgg    60
ccgctgcgcg tgggtccgac ccgagcggcc gcggctcggg gctgaaagtg tccgcgcggg   120

<210> SEQ ID NO 47
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
cacacacaca aggcagagcc acagtcgcag gcacagcgcg gcgccccgct gcatctccgg    60
ccgctgcgcg tgggtccgac ccgagcggcc gcggctcggg gctgaaagtg cacacacaca   120

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aatgatacgg cgaccaccga gat                                             23

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caagcagaag acggcatacg a                                               21

<210> SEQ ID NO 50
```

```
<211> LENGTH: 10
<212> TYPE: DNA
<213> ORGANISM: Homo sapiens

<400> SEQUENCE: 50
ttaagagaag                                                         10

<210> SEQ ID NO 51
<211> LENGTH: 11
<212> TYPE: DNA
<213> ORGANISM: Homo sapiens

<400> SEQUENCE: 51
acagaaagac a                                                       11
```

OPTIMIZATION OF MULTIGENE ANALYSIS OF TUMOR SAMPLES

RELATED APPLICATIONS

This application claims the benefit of U.S. Provisional Application No. 61/428,568, filed Dec. 30, 2010; U.S. Provisional Application No. 61/428,602, filed Dec. 30, 2010; U.S. Provisional Application No. 61/428,626, filed Dec. 30, 2010; U.S. Provisional Application No. 61/428,638, filed Dec. 30, 2010; U.S. Provisional Application No. 61/467,798, filed Mar. 25, 2011; U.S. Provisional Application No. 61/467,748, filed Mar. 25, 2011; U.S. Provisional Application No. 61/486,006, filed May 13, 2011; U.S. Provisional Application No. 61/486,012, filed May 13, 2011; U.S. Provisional Application No. 61/486,026, filed May 13, 2011; U.S. Provisional Application No. 61/486,033, filed May 13, 2011; and U.S. Provisional Application No. 61/552,884, filed Oct. 28, 2011. The contents of all these prior applications are incorporated herein by reference in their entirety. This application also incorporates by reference the contents of PCT/US11/67725, entitled "Optimization of Multigene Analysis of Tumor Samples" filed Dec. 29, 2011.

SEQUENCE LISTING

The instant application contains a Sequence Listing which has been submitted in ASCII format via EFS-Web and is hereby incorporated by reference in it entirety. Said ASCII copy, created on Jan. 9, 2012, is named F2036710.txt and is 15,883 bytes in size.

BACKGROUND OF THE INVENTION

The invention relates to optimized methods for analyzing nucleic acids from tumor samples, e.g., methods having integrated optimized nucleic acid selection, read alignment, and mutation calling.

SUMMARY OF THE INVENTION

Methods disclosed herein provide integration of one or more optimized elements including bait-based selection, alignment, and mutation calling, as applied, e.g., to optimized sets of subgenomic intervals, e.g., sets of cancer related segments of the genome described herein. Methods described herein provide for next generation sequencing (NGS)-based analysis of tumors that can be optimized on a cancer-by-cancer, gene-by-gene and/or site-by-site basis.

Accordingly, in one aspect, the invention features a method of analyzing a tumor sample. The method comprises:

(a) acquiring a library comprising a plurality of target members, e.g., tumor members, from a sample, e.g., a tumor sample;

(b) optionally, contacting the library with a bait set (or plurality of bait sets) to provide selected members (sometimes referred to herein as "library catch");

(c) acquiring a read for a subgenomic interval from a tumor member from said library or library catch, e.g., by sequencing, e.g., with a next generation sequencing method;

(d) aligning said read; and (e) assigning a nucleotide value (e.g., calling a mutation, e.g., with a Bayeisan method) from said read for a preselected nucleotide position, e.g., for a preselected nucleotide position in each of a plurality of subgenomic intervals, e.g., each of a plurality genes, thereby analyzing said sample, wherein:

(i) each of X nucleotide positions is analyzed under a unique set of conditions for one or a combination of steps (b), (c), (d), or (e) (wherein unique means different from the other X−1 sets of conditions and wherein X is at least 2, 5, 10, 20, 30, 40, 50, 100, 200, 300 or 500). E.g., a first set of conditions, e.g., a set of conditions described herein, is used for a first nucleotide position, e.g., in a first subgenomic interval or gene, and a second set of conditions, e.g., a second set of conditions described herein, is used for a second nucleotide position, e.g., in a second subgenomic interval or gene;

(ii) for each of X nucleotide positions, responsive to a characteristic, e.g., a characteristic described herein, of a preselected alteration, e.g., mutation, that can occur at the nucleotide position, the nucleotide position is analyzed under a unique set of conditions (wherein unique means different from the other X−1 sets of conditions and wherein X is at least 2, 5, 10, 20, 30, 40, 50, 100, 200, 300 or 500). E.g., responsive to a characteristic, e.g., a characteristic described herein, of a preselected alteration, e.g., mutation, that can occur at a nucleotide position in a first subgenomic interval, the nucleotide position is analyzed under a first set of conditions, and responsive to a characteristic, e.g., a characteristic described herein, of a preselected alteration, e.g., mutation, that can occur at a nucleotide position in a second subgenomic interval, the nucleotide position is analyzed under second set of conditions; (iii) wherein said method is performed on a sample, e.g., a preserved tumor sample, under conditions that allow for 95, 98, or 99% sensitivity or specificity for nucleotide positions in at least 2, 5, 10, 20, 50 or 100 subgenomic intervals, e.g., genes; or (iv) wherein the method comprises one or more or all of:

a) sequencing a first subgenomic interval to provide for about 500× or higher sequencing depth, e.g., to sequence a mutation present in no more than 5% of the cells from the sample;

b) sequencing a second subgenomic interval to provide for about 200× or higher, e.g., about 200×—about 500×, sequencing depth, e.g., to sequence a mutation present in no more than 10% of the cells from the sample;

c) sequencing a third subgenomic interval to provide for about 10-100× sequencing depth, e.g., to sequence one or more subgenomic intervals (e.g., exons) that are chosen from: a) a pharmacogenomic (PGx) single nucleotide polymorphism (SNP) that may explain the ability of patient to metabolize different drugs, or b) a genomic SNPs that may be used to uniquely identify (e.g., fingerprint) a patient;

d) sequencing a fourth subgenomic interval to provide for about 5-50× sequencing depth, e.g., to detect a structural breakpoint, such as a genomic translocation or an indel. For example, detection of an intronic breakpoint requires 5-50× sequence-pair spanning depth to ensure high detection reliability. Such bait sets can be used to detect, for example, translocation/indel-prone cancer genes; or e) sequencing a fifth subgenomic interval to provide for about 0.1-300× sequencing depth, e.g., to detect copy number changes. In one embodiment, the sequencing depth ranges from about 0.1-10× sequencing depth to detect copy number changes. In other embodiments, the sequencing depth ranges from about 100-300× to detect a genomic SNPs/loci that is used to assess copy number gains/losses of genomic DNA or loss-of-heterozygosity (LOH).

Exemplary first and second sets of conditions include those wherein:

a first bait set is used for the first subgenomic interval and a second bait set is used for the second subgenomic interval;

a first alignment method is applied to a read for the first subgenomic interval and a second alignment method is applied to a read for second subgenomic interval;

a first mutation calling method is applied to a nucleotide position of the first subgenomic interval and a second mutation calling method is applied to a nucleotide position of the second subgenomic interval.

In an embodiment:

a first nucleotide position is analyzed with a first set of bait conditions, a first alignment method, and a first mutation calling method;

a second nucleotide position is analyzed with said first set of bait conditions, a second alignment method, and said first mutation calling method;

a third nucleotide position is analyzed with said first set of bait conditions, said first alignment method, and a second mutation calling method, to provide three nucleotide positions each analyzed under unique, as compared to the other two, conditions.

In an embodiment, the conditions comprise those wherein:

a first bait set is used for the first subgenomic interval and a second bait set is used for the second subgenomic interval;

a first alignment method is applied to a read for the first subgenomic interval and a second alignment method is applied to a read for second subgenomic interval; or a first mutation calling method is applied to a nucleotide position of the first subgenomic interval and a second mutation calling method is applied to a nucleotide position of the second subgenomic interval.

Exemplary characteristics include:

(i) the gene, or type of gene, in which the alteration is located, e.g., an oncogene or tumor suppressor, a gene or type of gene characterized by a preselected or variant or type of variant, e.g., a mutation, or by a mutation of a preselected frequency, or other gene or type of gene described herein;

(ii) the type of alteration, e.g., a substitution, insertion, deletion, or translocation;

(iii) the type of sample, e.g., an FFPE sample, being analyzed for the alteration;

(iv) sequence in or near said the nucleotide position of the alteration being evaluated, e.g., sequence which can affect the expected propensity for misalignment for the subgenomic interval, e.g., the presence of repeated sequences in or near the nucleodited position;

(v) a prior (e.g., literature) expectation of observing a read showing the alteration, e.g., mutation, e.g., in a tumor of preselected type;

(vi) the probability of observing a read showing the alteration due to base-calling error alone); or (vii) a preselected depth of sequencing desired for detecting the alteration.

In an embodiment, the characteristic is other than the identity of the nucleotide being sequenced, i.e., the characteristic is not whether the sequence is a or t.

In an embodiment, step (b) is present. In an embodiment, step (b) is absent.

In an embodiment, subgenomic intervals from at least X genes, e.g. at least X genes from Tables 1 and 1A, e.g., genes having the priority 1 annotation in Table 1 and 1A, are analyzed under different conditions, and X is equal to 2, 3, 4, 5, 10, 15, 20, or 30.

In an embodiment, the method comprises one or more of the following:

(i) the method, e.g., (b) of the method above, comprises the use of a bait set described herein, e.g., a bait set as described under the heading Bait, or in the BAIT Module;

(ii) the method, e.g., (c) of the method above, comprises acquiring reads for a set or group of subgenomic intervals or from a set or group of genes described herein;

(iii) the method, e.g., (d) of the method above, comprises the use of a plurality of alignment methods described herein, e.g., methods described under the heading Alignment, or in the Alignment Module;

(iv) the method, e.g., (e) of the method above, comprises the use of a plurality of methods for assigning a nucleotide value to a preselected nucleotide position, described herein, e.g., methods described under the heading Mutation Calling, or in the Mutation Calling Module or in the section entitled "A Bayesian Approach for Sensitive Detection of Somatic Genomic Alterations from Next-generation Sequencing of Clinical Cancer Specimens;" or (v) the method comprises assigning a nucleotide value to a set of subgenomic intervals described herein, e.g., in the sections entitled "Gene Selection or Gene Selection Module."

In an embodiment, the method includes: (i) and one, two, three, or all of (ii)-(v).

In an embodiment, the method includes: (ii) and one, two, three, or all of (i) and (iii)-(v).

In an embodiment, the method includes: (iii) and one, two, three, or all of (i), (ii), (iv) and (v).

In an embodiment, the method includes: (iv) and one, two, three, or all of (i)-(iii) and (v).

In an embodiment, the method includes: (v) and one, two, three, or all of (i)-(iv).

Alignment

Methods disclosed herein can integrate the use of multiple, individually tuned, alignment methods or algorithms to optimize performance in sequencing methods, particularly in methods that rely on massively parallel sequencing of a large number of diverse genetic events in a large number of diverse genes, e.g., methods of analyzing tumor samples. In embodiments, multiple alignment methods that are individually customized or tuned to each of a number of variants in different genes are used to analyze reads. In embodiments, tuning can be a function of (one or more of) the gene (or other subgenomic interval) being sequenced, the tumor type in the sample, the variant being sequenced, or a characteristic of the sample or the subject. The selection or use of alignment conditions that are individually tuned to a number of subgenomic intervals to be sequenced allows optimization of speed, sensitivity and specificity. The method is particularly effective when the alignments of reads for a relatively large number of diverse subgenomic intervals are optimized.

Accordingly, in one aspect, the invention features, a method of analyzing a sample, e.g., a tumor sample. The method comprises:

(a) acquiring a library comprising a plurality members from a sample, e.g., a plurality of tumor members from a tumor sample;

(b) optionally, enriching the library for preselected sequences, e.g., by contacting the library with a bait set (or plurality of bait sets) to provide selected members (sometimes referred to herein as library catch);

(c) acquiring a read for a subgenomic interval from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayesian method) from said read for the preselected nucleotide position, thereby analyzing said tumor sample, wherein a read from each of X unique subgenomic intervals is aligned with a unique alignment method, wherein unique subgenomic interval means different from the other X−1 subgenoimc intervals, and wherein unique alignment method means different from the other X−1 alignment methods, and X is at least 2.

In an embodiment, step (b) is present. In an embodiment step (b) is absent.

In an embodiment, X is at least 3, 4, 5, 10, 15, 20, 30, 50, 100, 500, or 1,000.

In an embodiment subgenomic intervals from at least X genes, e.g. at least X genes from Tables 1 and 1A, e.g., genes having the priority 1 annotation in Table 1 and 1A, are aligned with unique alignment methods, and X is equal to 2, 3, 4, 5, 10, 15, 20, or 30.

In an embodiment, a method (e.g., element (d) of the method recited above) comprises selecting or using an alignment method for analyzing, e.g., aligning, a read, wherein said alignment method is a function of, is selected responsive to, or is optimized for, one or more or all of:

(i) tumor type, e.g., the tumor type in said sample;
(ii) the gene, or type of gene, in which said subgenomic interval being sequenced is located, e.g., a gene or type of gene characterized by a preselected or variant or type of variant, e.g., a mutation, or by a mutation of a preselected frequency;
(iii) the site (e.g., nucleotide position) being analyzed;
(iv) the type of variant, e.g., a substitution, within the subgenomic interval being evaluated;
(v) the type of sample, e.g., an FFPE sample; and
(vi) sequence in or near said subgenomic interval being evaluated, e.g., the expected propensity for misalignment for said subgenomic interval, e.g., the presence of repeated sequences in or near said subgenomic interval.

As referred to elsewhere herein, a method is particularly effective when the alignment of reads for a relatively large number of subgenomic intervals is optimized. Thus, in an embodiment, at least X unique alignment methods are used to analyze reads for at least X unique subgenomic intervals, wherein unique means different from the other X−1, and X is equal to 2, 3, 4, 5, 10, 15, 20, 30, 50, 100, 500, or 1,000.

In an embodiment, subgenomic intervals from at least X genes from Tables 1 and 1A, e.g., having the priority 1 annotation in Table 1 and 1A, are analyzed, and X is equal to 2, 3, 4, 5, 10, 15, 20, or 30.

In an embodiment, a unique alignment method is applied to subgenomic intervals in each of at least 3, 5, 10, 20, 40, 50, 60, 70, 80, 90, or 100 different genes.

In an embodiment, a nucleotide position in at least 20, 40, 60, 80, 100, 120, 140, 160 or 180 genes, e.g., genes from Tables 1 and 1A, is assigned a nucleotide value. In an embodiment a unique alignment method is applied to subgenomic intervals in each of at least 10, 20, 30, 40, or 50% of said genes analyzed.

Methods disclosed herein allow for the rapid and efficient alignment of troublesome reads, e.g., a read having a rearrangment. Thus, in embodiment where a read for a subgenomic interval comprises a nucleotide position with a rearrangement, e.g., an indel, the method can comprise using an alignment method that is appropriately tuned and that includes:

selecting a rearrangement reference sequence for alignment with a read, wherein said rearrangement reference sequence is preselected to align with a preselected rearrangement (in embodiments the reference sequence is not identical to the genomic rearrangement);

comparing, e.g., aligning, a read with said preselected rearrangement reference sequence.

In embodiments, other methods are used to align troublesome reads. These methods are particularly effective when the alignment of reads for a relatively large number of diverse subgenomic intervals is optimized. By way of example, a method of analyzing a tumor sample can comprise:

performing a comparison, e.g., an alignment comparison, of a read under a first set of parameters (e.g., a first mapping algorithm or with a first reference sequence), and determining if said read meets a first predetermined alignment criterion (e.g., the read can be aligned with said first reference sequence, e.g., with less than a preselected number of mismatches);

if said read fails to meet the first predetermined alignment criterion, performing a second alignment comparison under a second set of parameters, (e.g., a second mapping algorithm or with a second reference sequence); and, optionally, determining if said read meets said second predetermined criterion (e.g., the read can be aligned with said second reference sequence with less than a preselected number of mismatches), wherein said second set of parameters comprises use of a set of parameters, e.g., said second reference sequence, which, compared with said first set of parameters, is more likely to result in an alignment with a read for a preselected variant, e.g., a rearrangement, e.g., an insertion, deletion, or translocation.

These and other alignment methods are discussed in more detail elsewhere herein, e.g., in the section entitled "Alignment Module." Elements of that module can be included in methods of analyzing a tumor. In embodiments, alignment methods from the "Alignment Module" are combined with mutation calling methods from the "Mutation Calling Module" and/or a bait set from the "Bait Module." The method can be applied to set of subgenomic intervals from the "Gene Selection Module."

Mutation Calling

Methods disclosed herein can integrate the use of customized or tuned mutation calling parameters to optimize performance in sequencing methods, particularly in methods that rely on massively parallel sequencing of a large number of diverse genetic events in a large number of diverse genes, e.g., from tumor samples. In embodiments of the method mutation calling for each of a number of preselected subgenomic intervals is, individually, customized or fine tuned. The customization or tuning can be based on one or more of the factors described herein, e.g., the type of cancer in a sample, the gene in which subgenomic interval to be sequenced is located, or the variant to be sequenced. This selection or use of alignment conditions finely tuned to a number of subgenomic intervals to be sequenced allows optimization of speed, sensitivity and specificity. The method is particularly effective when the alignment of reads for a relatively large number of diverse subgenomic intervals is optimized.

Accordingly, in one aspect, the invention features, a method of analyzing a sample, e.g., a tumor sample. The method comprises:

(a) acquiring a library comprising a plurality members from a sample, e.g., a plurality of tumor members from the sample, e.g., the tumor sample;

(b) optionally, enriching the library for preselected sequences, e.g., by contacting the library with a bait set (or plurality of bait sets) to provide selected members, e.g., a library catch;

(c) acquiring a read for a subgenomic interval from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayesian method or a calling method described herein) from said read for the preselected nucleotide position, thereby analyzing said tumor sample.

wherein a nucleotide value is assigned for a nucleotide position in each of X unique subgenomic intervals is assigned by a unique calling method, wherein unique subgenomic interval means different from the other X−1 subgenoimc intervals, and wherein unique calling method means different from the other X−1 calling methods, and X is at least 2. The calling methods can differ, and thereby be unique, e.g., by relying on different Bayesian prior values.

In an embodiment, step (b) is present. In an embodiment, step (b) is absent.

In an embodiment, assigning said nucleotide value is a function of a value which is or represents the prior (e.g., literature) expectation of observing a read showing a preselected variant, e.g., a mutation, at said preselected nucleotide position in a tumor of type.

In an embodiment, them method comprises assigning a nucleotide value (e.g., calling a mutation) for at least 10, 20, 40, 50, 60, 70, 80, 90, or 100 preselected nucleotide positions, wherein each assignment is a function of a unique (as opposed to the value for the other assignments) value which is or represents the prior (e.g., literature) expectation of observing a read showing a preselected variant, e.g., a mutation, at said preselected nucleotide position in a tumor of type.

In an embodiment, assigning said nucleotide value is a function of a set of values which represent the probabilities of observing a read showing said preselected variant at said preselected nucleotide position if the variant is present in the sample at a frequency (e.g., 1%, 5%, 10%, etc.) and/or if the variant is absent (e.g., observed in the reads due to base-calling error alone).

In an embodiment, a method (e.g., element (e) of the method recited above) comprises a mutation calling method. The mutation calling methods described herein can include the following:

acquiring, for a preselected nucleotide position in each of said X subgenomic intervals:
(i) a first value which is or represents the prior (e.g., literature) expectation of observing a read showing a preselected variant, e.g., a mutation, at said preselected nucleotide position in a tumor of type X; and
(ii) a second set of values which represent the probabilities of observing a read showing said preselected variant at said preselected nucleotide position if the variant is present in the sample at a frequency (e.g., 1%, 5%, 10%, etc.) and/or if the variant is absent (e.g., observed in the reads due to base-calling error alone);

responsive to said values, assigning a nucleotide value (e.g., calling a mutation) from said reads for each of said preselected nucleotide positions by weighing, e.g., by a Bayesian method described herein, the comparison among the values in the second set using the first value (e.g., computing the posterior probability of the presence of a mutation), thereby analyzing said sample.

In an embodiment, the method comprises one or more or all of:
(i) assigning a nucleotide value (e.g., calling a mutation) for at least 10, 20, 40, 50, 60, 70, 80, 90, or 100 preselected nucleotide positions, wherein each assignment is based on a unique (as opposed to the other assignments) first and/or second values;
(ii) the assignment of method of (i), wherein at least 10, 20, 30 or 40 of the assignments are made with first values which are a function of a probability of a preselected variant being present of less than 5, 10, or 20%, e.g., of the cells in a preselected tumor type;
(iii) assigning a nucleotide value (e.g., calling a mutation) for at least X preselected nucleotide positions, each of which of which being associated with a preselected variant having a unique (as opposed to the other X−1 assignments) probability of being present in a tumor of preselected type, e.g., the tumor type of said sample, wherein, optionally, each said of X assignments is based on a unique (as opposed to the other X−1 assignments) first and/or second value (wherein X=2, 3, 5, 10, 20, 40, 50, 60, 70, 80, 90, or 100);
(iv) assigning a nucleotide value (e.g., calling a mutation) at a first and a second nucleotide position, wherein the likelihood of a first preselected variant at said first nucleotide position being present in a tumor of preselected type (e.g., the tumor type of said sample) is at least 2, 5, 10, 20, 30, or 40 times greater than the likelihood of a second preselected variant at said second nucleotide position being present, wherein, optionally, each assignment is based on a unique (as opposed to the other assignments) first and/or second value;
(v) assigning a nucleotide value to a plurality of preselected nucleotide positions (e.g., calling mutations), wherein said plurality comprises an assignment for variants falling into one or more, e.g., at least 3, 4, 5, 6, 7, or all, of the following probability ranges:

less than 0.01; 0.01-0.02;
greater than 0.02 and less than or equal to 0.03;
greater than 0.03 and less than or equal to 0.04;
greater than 0.04 and less than or equal to 0.05;
greater than 0.05 and less than or equal to 0.1;
greater than 0.1 and less than or equal to 0.2;
greater than 0.2 and less than or equal to 0.5;
greater than 0.5 and less than or equal to 1.0;
greater than 1.0 and less than or equal to 2.0;
greater than 2.0 and less than or equal to 5.0;
greater than 5.0 and less than or equal to 10.0;
greater than 10.0 and less than or equal to 20.0;
greater than 20.0 and less than or equal to 50.0; and
greater than 50 and less than or equal to 100.0%;

wherein, a probability range is the range of probabilities that a preselected variant at a preselected nucleotide position will be present in a tumor of preselected type (e.g., the tumor type of said sample) or the probability that a preselected variant at a preselected nucleotide position will be present in the recited % of the cells in a tumor sample, a library from the tumor sample, or library catch from that library, for a preselected type (e.g., the tumor type of said sample), and wherein, optionally, each assignment is based on a unique first and/or second value (e.g., unique as opposed to the other assignments in a recited probability range or unique as opposed to the first and/or second values for one or more or all of the other listed probability ranges).

(vi) assigning a nucleotide value (e.g., calling a mutation) for at least 1, 2 3, 5, 10, 20, 40, 50, 60, 70, 80, 90, or 100 preselected nucleotide positions each, independently, having a preselected variant present in less than 50, 40, 25, 20, 15, 10, 5, 4, 3, 2, 1, 0.5, 0.4, 0.3, 0.2, or 0.1% of the DNA in said sample, wherein, optionally, each assignment is based on a unique (as opposed to the other assignments) first and/or second value;

(vii) assigning a nucleotide value (e.g., calling a mutation) at a first and a second nucleotide position, wherein the likelihood of a preselected variant at the first position in the DNA of said sample is at least 2, 5, 10, 20, 30, or 40 times greater than a the likelihood of a preselected variant at said second nucleotide position in the DNA of said sample, wherein, optionally, each assignment is based on a unique (as opposed to the other assignments) first and/or second value;

(viii) assigning a nucleotide value (e.g., calling a mutation) in one or more or all of the following:

(1) at least 1, 2 3, 4 or 5 preselected nucleotide positions having a preselected variant present in less than 1.0% of the cells in said sample, of the nucleic acid in a library from said sample, or the nucleic acid in a library catch from that library;

(2) at least 1, 2 3, 4 or 5 preselected nucleotide positions having a preselected variant present in 1.0-2.0% of the cells in said sample, of the nucleic acid in a library from said sample, or the nucleic acid in a library catch from that library;

(3) at least 1, 2 3, 4 or 5 preselected nucleotide positions having a preselected variant present in greater than 2.0% and less than or equal to 3% of the cells in said sample, of the nucleic acid in a library from said sample, or the nucleic acid in a library catch from that library (4) at least 1, 2 3, 4 or 5 preselected nucleotide positions having a preselected variant present in greater than 3.0% and less than or equal to 4% of the cells in said sample, of the nucleic acid in a library from said sample, or the nucleic acid in a library catch from that library;

(5) at least 1, 2 3, 4 or 5 preselected nucleotide positions having a preselected variant present in greater than 4.0% and less than or equal to 5% of the cells in said sample, of the nucleic acid in a library from said sample, or the nucleic acid in a library catch from that library;

(6) at least 1, 2 3, 4 or 5 preselected nucleotide positions having a preselected variant present in greater than 5.0% and less than or equal to 10% of the cells in said sample, of the nucleic acid in a library from said sample, or the nucleic acid in a library catch from that library;

(7) at least 1, 2 3, 4 or 5 preselected nucleotide positions having a preselected variant present in greater than 10.0% and less than or equal to 20% of the cells in said sample, of the nucleic acid in a library from said sample, or the nucleic acid in a library catch from that library;

(8) at least 1, 2 3, 4 or 5 preselected nucleotide positions having a preselected variant present in greater than 20.0% and less than or equal to 40% of the cells in said sample, of the nucleic acid in a library from said sample, or the nucleic acid in a library catch from that library;

(9) at least 1, 2 3, 4 or 5 preselected nucleotide positions having a preselected variant present at greater than 40.0% and less than or equal to 50% of the cells in said sample, of the nucleic acid in a library from said sample, or the nucleic acid in a library catch from that library; or

(10) at least 1, 2 3, 4 or 5 preselected nucleotide positions having a preselected variant present in greater than 50.0% and less than or equal to 100% of the cells in said sample, of the nucleic acid in a library from said sample, or the nucleic acid in a library catch from that library;

wherein, optionally, each assignment is based on a unique first and/or second value (e.g., unique as opposed to the other assignments in the recited range (e.g., the range in (i) of less than 1%) or unique as opposed to a first and/or second values for a determination in one or more or all of the other listed ranges); or (ix) assigning a nucleotide value (e.g., calling a mutation) at each of X nucleotide positions, each nucleotide position, independently, having a likelihood (of a preselected variant being present in the DNA of said sample) that is unique as compared with the likelihood for a preselected variant at the other X−1 nucleotide positions, wherein X is equal to or greater than 1, 2 3, 5, 10, 20, 40, 50, 60, 70, 80, 90, or 100, and wherein each assignment is based on a unique (as opposed to the other assignments) first and/or second value.

In embodiments of the method, a "threshold value" is used to evaluate reads, and select from the reads a value for a nucleotide position, e.g., calling a mutation at a specific position in a gene. In embodiments of the method, a threshold value for each of a number of preselected subgenomic intervals is customized or fine tuned. The customization or tuning can be based on one or more of the factors described herein, e.g., the type of cancer in a sample, the gene in which subgenomic interval to be sequenced is located, or the variant to be sequenced. This provides for calling that is finely tuned to each of a number of subgenomic intervals to be sequenced. The method is particularly effective when a relatively large number of diverse subgenomic intervals are analyzed.

Thus, in another embodiment the method of analyzing a tumor comprises the following mutation calling method:

acquiring, for each of said X subgenomic intervals, a threshold value, wherein each of said acquired X threshold values is unique as compared with the other X−1 threshold values, thereby providing X unique threshold values;

for each of said X subgenomic intervals, comparing an observed value which is a function of the number of reads having a preselected nucleotide value at a preselected nucleotide position with its unique threshold value, thereby applying to each of said X subgenomic intervals, its unique threshold value: and optionally, responsive to the result of said comparison, assigning a nucleotide value to a preselected nucleotide position, wherein X is equal to or greater than 2.

In an embodiment, the method includes assigning a nucleotide value at least 2, 3, 5, 10, 20, 40, 50, 60, 70, 80, 90, or 100 preselected nucleotide positions, each having, independently, a first value that is a function of a probability that is less than 0.5, 0.4, 0.25, 0.15, 0.10, 0.05, 0.04, 0.03, 0.02, or 0.01.

In an embodiment, the method includes assigning a nucleotide value at each of at least X nucleotide positions, each independently having a first value that is unique as compared with the other X−1 first values, and wherein each of said X first values is a function of a probability that is less than 0.5, 0.4, 0.25, 0.15, 0.10, 0.05, 0.04, 0.03, 0.02, or 0.01, wherein X is equal to or greater than 1, 2 3, 5, 10, 20, 40, 50, 60, 70, 80, 90, or 100.

In an embodiment, a nucleotide position in at least 20, 40, 60, 80, 100, 120, 140, 160 or 180 genes, e.g., genes from Table 1, is assigned a nucleotide value. In an embodiment unique first and/or second values are applied to subgenomic intervals in each of at least 10, 20, 30, 40, or 50% of said genes analyzed.

Embodiments of the method can be applied where threshold values for a relatively large number of subgenomic intervals are optimized, as is seen, e.g., from the following embodiments.

In an embodiment, a unique threshold value is applied to subgenomic intervals in each of at least 3, 5, 10, 20, 40, 50, 60, 70, 80, 90, or 100 different genes.

In an embodiment, a nucleotide position in at least 20, 40, 60, 80, 100, 120, 140, 160 or 180 genes, e.g., genes from Table 1, is assigned a nucleotide value. In an embodiment a unique threshold value is applied to a subgenomic interval in each of at least 10, 20, 30, 40, or 50% of said genes analyzed.

In an embodiment, a nucleotide position in at least 5, 10, 20, 30, or 40 genes from Table 1 having the priority 1 annotation is assigned a nucleotide value. In an embodiment a unique threshold value is applied to a subgenomic interval in each of at least 10, 20, 30, 40, or 50% of said genes analyzed.

These and other mutation calling methods are discussed in more detail elsewhere herein, e.g., in the section entitled "Mutation Calling Module." Elements of that module can be included in methods of analyzing a tumor. In embodiments, alignment methods from the "Mutation Calling Module" are combined with alignment methods from the "Alignment Module" and/or a bait set from the "Bait Module." The method can be applied to set of subgenomic intervals from the "Gene Selection Module."

Bait

Methods described herein provide for optimized sequencing of a large number of genes and gene products from samples, e.g., tumor samples, from one or more subjects by the appropriate selection of baits, e.g., baits for use in solution hybridization, for the selection of target nucleic acids to be sequenced. The efficiency of selection for various subgenomic intervals, or classes thereof, are matched according to bait sets having preselected efficiency of selection. As used in this section, "efficiency of selection" refers to the level or depth of sequence coverage as it is adjusted according to a target subgenomic interval(s).

Thus a method (e.g., element (b) of the method recited above) comprises contacting the library with a plurality of baits to provide selected members (e.g., a library catch).

Accordingly, in one aspect, the invention features, a method of analyzing a sample, e.g., a tumor sample. The method comprises:

(a) acquiring a library comprising a plurality of members (e.g., target members) from a sample, e.g., a plurality of tumor members from a tumor sample;

(b) contacting the library with a bait set to provide selected members (e.g., a library catch);

(c) acquiring a read for a subgenomic interval from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayesian method or a method described herein) from said read for the preselected nucleotide position, thereby analyzing said tumor sample, wherein the method comprises contacting the library with a plurality, e.g., at least two, three, four, or five, of baits or bait sets, wherein each bait or bait set of said plurality has a unique (as opposed to the other bait sets in the plurality), preselected efficiency for selection. E.g., each unique bait or bait set provides for a unique depth of sequencing. The term "bait set", as used herein, collectively refers to one bait or a plurality of bait molecules.

In an embodiment, the efficiency of selection of a first bait set in the plurality differs from the efficiency of a second bait set in the plurality by at least 2 fold. In an embodiment, the first and second bait sets provide for a depth of sequencing that differs by at least 2 fold.

In an embodiment, the method comprises contacting one, or a plurality of the following bait sets with the library:

a) a bait set that selects sufficient members comprising a subgenomic interval to provide for about 500× or higher sequencing depth, e.g., to sequence a mutation present in no more than 5% of the cells from the sample;

b) a bait set that selects sufficient members comprising a subgenomic interval to provide for about 200× or higher, e.g., about 200×—about 500×, sequencing depth, e.g., to sequence a mutation present in no more than 10% of the cells from the sample;

c) a bait set that selects sufficient members comprising a subgenomic interval to provide for about 10-100× sequencing depth, e.g., to sequence one or more subgenomic intervals (e.g., exons) that are chosen from: a) a pharmacogenomic (PGx) single nucleotide polymorphism (SNP) that may explain the ability of patient to metabolize different drugs, or b) a genomic SNPs that may be used to uniquely identify (e.g., fingerprint) a patient;

d) a bait set that selects sufficient members comprising a subgenomic interval to provide for about 5-50× sequencing depth, e.g., to detect a structural breakpoint, such as a genomic translocation or an indel. For example, detection of an intronic breakpoint requires 5-50× sequence-pair spanning depth to ensure high detection reliability. Such bait sets can be used to detect, for example, translocation/indel-prone cancer genes; or e) a bait set that selects sufficient members comprising a subgenomic interval to provide for about 0.1-300× sequencing depth, e.g., to detect copy number changes. In one embodiment, the sequencing depth ranges from about 0.1-10× sequencing depth to detect copy number changes. In other embodiments, the sequencing depth ranges from about 100-300× to detect a genomic SNPs/loci that is used to assess copy number gains/losses of genomic DNA or loss-of-heterozygosity (LOH). Such bait sets can be used to detect, for example, amplification/deletion-prone cancer genes.

The level of sequencing depth as used herein (e.g., X-fold level of sequencing depth) refers to the level of coverage of reads (e.g., unique reads), after detection and removal of duplicate reads, e.g., PCR duplicate reads.

In one embodiment, the bait set selects a subgenomic interval containing one or more rearrangements, e.g., an intron containing a genomic rearrangement. In such embodiments, the bait set is designed such that repetitive sequences are masked to increase the selection efficiency. In those embodiments where the rearrangement has a known juncture sequence, complementary bait sets can be designed to the juncture sequence to increase the selection efficiency.

In embodiments, the method comprises the use of baits designed to capture two or more different target categories, each category having a different bait design strategies. In embodiments, the hybrid capture methods and compositions disclosed herein capture a defined subset of target sequences (e.g., target members) and provide homogenous coverage of the target sequence, while minimizing coverage outside of that subset. In one embodiment, the target sequences include the entire exome out of genomic DNA, or a selected subset thereof. The methods and compositions disclosed herein provide different bait sets for achieving different depths and patterns of coverage for complex target nucleic acid sequences (e.g., nucleic acid libraries).

In an embodiment, the method comprises providing selected members of a nucleic acid library (e.g., a library catch). The method includes:

providing a library (e.g., a nucleic acid library) comprising a plurality of members, e.g., target nucleic acid members (e.g., including a plurality of tumor members, reference members, and/or PGx members);

contacting the library, e.g., in a solution-based reaction, with a plurality of baits (e.g., oligonucleotide baits) to form a hybridization mixture comprising a plurality of bait/member hybrids;

separating the plurality of bait/member hybrids from said hybridization mixture, e.g., by contacting said hybridization mixture with a binding entity that allows for separation of said plurality of bait/member hybrid, thereby providing a library-catch (e.g., a selected or enriched subgroup of nucleic acid molecules from the library), wherein the plurality of baits includes two or more of the following:

a) a first bait set that selects a high-level target (e.g., one or more tumor members that include a subgenomic interval, such a gene, an exon, or a base) for which the deepest coverage is required to enable a high level of sensitivity for an alteration (e.g., one or more mutations) that appears at a low frequency, e.g., about 5% or less (i.e., 5% of the cells from the sample harbor the alteration in their genome). In one embodiment; the first bait set selects (e.g., is complementary to) a tumor member that includes an alteration (e.g., a point mutation) that requires about 500× or higher sequencing depth;

b) a second bait set that selects a mid-level target (e.g., one or more tumor members that include a subgenomic interval, such as a gene, an exon, or a base) for which high coverage is required to enable high level of sensitivity for an alteration (e.g., one or more mutations) that appears at a higher frequency than the high-level target in a), e.g., a frequency of about 10% (i.e., 10% of the cells from the sample harbor the alteration in their genome). In one embodiment; the second bait set selects (e.g., is complementary to) a tumor member that includes an alteration (e.g., a point mutation) that requires about 200× or higher sequencing depth;

c) a third bait set that selects a low-level target (e.g., one or more PGx members that includes a subgenomic interval, such as a gene, an exon, or a base) for which low-medium coverage is required to enable high level of sensitivity, e.g., to detect heterozygous alleles. For example, detection of heterozygous alleles requires 10-100× sequencing depth to ensure high detection reliability. In one embodiment, third bait set selects one or more subgenomic intervals (e.g., exons) that are chosen from: a) a pharmacogenomic (PGx) single nucleotide polymorphism (SNP) that may explain the ability of patient to metabolize different drugs, or b) a genomic SNPs that may be used to uniquely identify (e.g., fingerprint) a patient;

d) a fourth bait set that selects a first intron target (e.g., a member that includes an intron sequence) for which low-medium coverage is required, e.g., to detect a structural breakpoint, such as a genomic translocation or an indel. For example, detection of an intronic breakpoint requires 5-50× sequence-pair spanning depth to ensure high detection reliability. Said fourth bait sets can be used to detect, for example, translocation/indel-prone cancer genes; or e) a fifth bait set that selects a second intron target (e.g., an intron member) for which sparse coverage is required to improve the ability to detect copy number changes. For example, detection of a one-copy deletion of several terminal exons requires 0.1-300× coverage to ensure high detection reliability. In one embodiment, the coverage depth ranges from about 0.1-10× to detect copy number changes. In other embodiments, the coverage depth ranges from about 100-300× to detect a genomic SNPs/loci that is used to assess copy number gains/losses of genomic DNA or loss-of-heterozygosity (LOH). Said fifth bait sets can be used to detect, for example, amplification/deletion-prone cancer genes.

Any combination of two, three, four or more of the aforesaid bait sets can be used, for example, a combination of the first and the second bait sets; first and third bait sets; first and fourth bait sets; first and fifth bait sets; second and third bait sets; second and fourth bait sets; second and fifth bait sets; third and fourth bait sets; third and fifth bait sets; fourth and fifth bait sets; first, second and third bait sets; first, second and fourth bait sets; first, second and fifth bait sets; first, second, third, fourth bait sets; first, second, third, fourth and fifth bait sets, and so on.

In one embodiment, each of the first, second, third, fourth, or fifth bait set has a preselected efficiency for selection (e.g., capture). In one embodiment, the value for efficiency of selection is the same for at least two, three, four of all five baits according to a)-e). In other embodiments, the value for efficiency of selection is different for at least two, three, four of all five baits according to a)-e).

In some embodiments, at least two, three, four, or all five bait sets have a preselected efficiency value that differ. For example, a value for efficiency of selection chosen from one of more of:

(i) the first preselected efficiency has a value for first efficiency of selection that is at least about 500× or higher sequencing depth (e.g., has a value for efficiency of selection that is greater than the second, third, fourth or fifth preselected efficiency of selection (e.g., about 2-3 fold greater than the value for the second efficiency of selection; about 5-6 fold greater than the value for the third efficiency of selection; about 10 fold greater than the value for the fourth efficiency of selection; about 50 to 5000-fold greater than the value for the fifth efficiency of selection);

(ii) the second preselected efficiency has a value for second efficiency of selection that is at least about 200× or higher sequencing depth (e.g., has a value for efficiency of selection that is greater than the third, fourth or fifth preselected efficiency of selection (e.g., about 2 fold greater than the value for the third efficiency of selection; about 4 fold greater than the value for the fourth efficiency of selection; about 20 to 2000-fold greater than the value for the fifth efficiency of selection);

(iii) the third preselected efficiency has a value for third efficiency of selection that is at least about 100× or higher sequencing depth (e.g., has a value for efficiency of selection that is greater than the fourth or fifth preselected efficiency of selection (e.g., about 2 fold greater than the value for the fourth efficiency of selection; about 10 to 1000-fold greater than the value for the fifth efficiency of selection);

(iv) the fourth preselected efficiency has a value for fourth efficiency of selection that is at least about 50× or higher sequencing depth (e.g., has a value for efficiency of selection that is greater than the fifth preselected efficiency of selection (e.g., about 50 to 500-fold greater than the value for the fifth efficiency of selection); or (v) the fifth preselected efficiency has a value for fifth efficiency of selection that is at least about 10× to 0.1× sequencing depth.

In certain embodiments, the value for efficiency of selection is modified by one or more of: differential representation of different bait sets, differential overlap of bait subsets, differential bait parameters, mixing of different bait sets, and/or using different types of bait sets. For example, a variation in efficiency of selection (e.g., relative sequence coverage of each bait set/target category) can be adjusted by altering one or more of:

(i) Differential representation of different bait sets—The bait set design to capture a given target (e.g., a target member) can be included in more/fewer number of copies to enhance/reduce relative target coverage depths;

(ii) Differential overlap of bait subsets—The bait set design to capture a given target (e.g., a target member) can include a longer or shorter overlap between neighboring baits to enhance/reduce relative target coverage depths;

(iii) Differential bait parameters—The bait set design to capture a given target (e.g., a target member) can include sequence modifications/shorter length to reduce capture efficiency and lower the relative target coverage depths;

(iv) Mixing of different bait sets—Bait sets that are designed to capture different target sets can be mixed at different molar ratios to enhance/reduce relative target coverage depths;

(v) Using different types of oligonucleotide bait sets—In certain embodiments, the bait set can include:

(a) one or more chemically (e.g., non-enzymatically) synthesized (e.g., individually synthesized) baits, (b) one or more baits synthesized in an array, (c) one or more enzymatically prepared, e.g., in vitro transcribed, baits;

(d) any combination of (a), (b) and/or (c), (e) one or more DNA oligonucleotides (e.g., a naturally or non-naturally occurring DNA oligonucleotide), (f) one or more RNA oligonucleotides (e.g., a naturally or non-naturally occurring RNA oligonucleotide), (g) a combination of (e) and (f), or (h) a combination of any of the above.

The different oligonucleotide combinations can be mixed at different ratios, e.g., a ratio chosen from 1:1, 1:2, 1:3, 1:4, 1:5, 1:10, 1:20, 1:50; 1:100, 1:1000, or the like. In one embodiment, the ratio of chemically-synthesized bait to array-generated bait is chosen from 1:5, 1:10, or 1:20. The DNA or RNA oligonucleotides can be naturally- or non-naturally-occurring. In certain embodiments, the baits include one or more non-naturally-occurring nucleotide to, e.g., increase melting temperature. Exemplary non-naturally occurring oligonucleotides include modified DNA or RNA nucleotides. Exemplary modified nucleotides (e.g., modified RNA or DNA nucleotides) include, but are not limited to, a locked nucleic acid (LNA), wherein the ribose moiety of an LNA nucleotide is modified with an extra bridge connecting the 2' oxygen and 4' carbon; peptide nucleic acid (PNA), e.g., a PNA composed of repeating N-(2-aminoethyl)-glycine units linked by peptide bonds; a DNA or RNA oligonucleotide modified to capture low GC regions; a bicyclic nucleic acid (BNA); a crosslinked oligonucleotide; a modified 5-methyl deoxycytidine; and 2,6-diaminopurine. Other modified DNA and RNA nucleotides are known in the art.

In certain embodiments, a substantially uniform or homogeneous coverage of a target sequence (e.g., a target member) is obtained. For example, within each bait set/target category, uniformity of coverage can be optimized by modifying bait parameters, for example, by one or more of:

(i) Increasing/decreasing bait representation or overlap can be used to enhance/reduce coverage of targets (e.g., target members), which are under/over-covered relative to other targets in the same category;

(ii) For low coverage, hard to capture target sequences (e.g., high GC content sequences), expand the region being targeted with the bait sets to cover, e.g., adjacent sequences (e.g., less GC-rich adjacent sequences);

(iii) Modifying a bait sequence can be made to reduce secondary structure of the bait and enhance its efficiency of selection;

(iv) Modifying a bait length can be used to equalize melting hybridization kinetics of different baits within the same category. Bait length can be modified directly (by producing baits with varying lengths) or indirectly (by producing baits of consistent length, and replacing the bait ends with arbitrary sequence);

(v) Modifying baits of different orientation for the same target region (i.e. forward and reverse strand) may have different binding efficiencies. The bait set with either orientation providing optimal coverage for each target may be selected;

(vi) Modifying the amount of a binding entity, e.g., a capture tag (e.g. biotin), present on each bait may affect its binding efficiency. Increasing/decreasing the tag level of baits targeting a specific target may be used to enhance/reduce the relative target coverage;

(vii) Modifying the type of nucleotide used for different baits can be altered to affect binding affinity to the target, and enhance/reduce the relative target coverage; or (viii) Using modified oligonucleotide baits, e.g., having more stable base pairing, can be used to equalize melting hybridization kinetics between areas of low or normal GC content relative to high GC content.

For example, different types of oligonucleotide bait sets can be used.

In one embodiment, the value for efficiency of selection is modified by using different types of bait oligonucleotides to encompass pre-selected target regions. For example, a first bait set (e.g., an array-based bait set comprising 10,000-50,000 RNA or DNA baits) can be used to cover a large target area (e.g., 1-2 MB total target area). The first bait set can be spiked with a second bait set (e.g., individually synthesized RNA or DNA bait set comprising less than 5,000 baits) to cover a pre-selected target region (e.g., selected subgenomic intervals of interest spanning, e.g., 250 kb or less, of a target area) and/or regions of higher secondary structure, e.g., higher GC content. Selected subgenomic intervals of interest may correspond to one or more of the genes or gene products described herein, or a fragment thereof. The second bait set may include about 1-5,000, 2-5,000, 3-5,000, 10-5,000, 100-5,000, 500-5,000, 100-5,000, 1000-5,000, 2,000-5,000 baits depending on the bait overlap desired. In other embodiments, the second bait set can include selected oligo baits (e.g., less than 400, 200, 100, 50, 40, 30, 20, 10, 5, 4, 3, 2 or 1 baits) spiked into the first bait set. The second bait set can be mixed at any ratio of individual oligo baits. For example, the second bait set can include individual baits present as a 1:1 equimolar ratio. Alternatively, the second bait set can include individual baits present at different ratio (e.g., 1:5, 1:10, 1:20), for example, to optimize capture of certain targets (e.g., certain targets can have a 5-10× of the second bait compared to other targets).

In other embodiments, the efficiency of selection is adjusted by leveling the efficiency of individual baits within a group (e.g., a first, second or third plurality of baits) by adjusting the relative abundance of the baits, or the density of the binding entity (e.g., the hapten or affinity tag density) in reference to differential sequence capture efficiency observed when using an equimolar mix of baits, and then introducing a differential excess of internally-leveled group 1 to the overall bait mix relative to internally-leveled group 2.

In an embodiment, the method comprises the use of a plurality of bait sets that includes a bait set that selects a tumor member, e.g., a nucleic acid molecule comprising a subgenomic interval from a tumor cell (also referred to herein as "a tumor bait set"). The tumor member can be any nucleotide sequence present in a tumor cell, e.g., a mutated, a wild-type, a PGx, a reference or an intron nucleotide sequence, as described herein, that is present in a tumor or cancer cell. In one embodiment, the tumor member includes an alteration (e.g., one or more mutations) that appears at a low frequency, e.g., about 5% or less of the cells from the tumor sample harbor the alteration in their genome. In other embodiments, the tumor member includes an alteration (e.g., one or more mutations) that appears at a frequency of about 10% of the cells from the tumor sample. In other embodiments, the tumor member includes a subgenomic interval from a PGx gene or gene product, an intron sequence, e.g., an intron sequence as described herein, a reference sequence that is present in a tumor cell.

In another aspect, the invention features, a bait set described herein, combinations of individual bait sets described herein, e.g., combinations described herein. The bait set(s) can be part of a kit which can optionally comprise instructions, standards, buffers or enzymes or other reagenats.

Gene Selection

Preselected subgenomic intervals for analysis, e.g., a group or set of subgenomic intervals for sets or groups of genes and other regions, are described herein.

Thus, in embodiments a method comprises sequencing, e.g., by a next generation sequencing method, a subgenomic interval from at least five, six, seven, eight, nine, ten, fifteen, twenty, twenty-five, thirty or more genes or gene products from the acquired nucleic acid sample, wherein the genes or gene products are chosen from: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53, thereby analyzing the tumor sample.

Accordingly, in one aspect, the invention features, a method of analyzing a sample, e.g., a tumor sample. The method comprises:

(a) acquiring a library comprising a plurality members from a sample, e.g., a plurality of tumor members from a tumor sample;

(b) optionally, enriching the library for preselected sequences, e.g., by contacting the library with a bait set (or plurality of bait sets) to provide selected members (e.g., a library catch);

(c) acquiring a read for a subgenomic interval from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayesian method or a method described herein) from said read for the preselected nucleotide position, thereby analyzing said tumor sample, wherein the method comprises sequencing, e.g., by a next generation sequencing method, a subgenomic interval from at least five, six, seven, eight, nine, ten, fifteen, twenty, twenty-five, thirty or more genes or gene products from the sample, wherein the genes or gene products are chosen from: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53.

In an embodiment, step (b) is present. In an embodiment, step (b) is absent.

In another embodiment, subgenomic intervals of one of the following sets or groups are analyzed. E.g., subgenomic intervals associated with a tumor or cancer gene or gene product, a reference (e.g., a wild type) gene or gene product, and a PGx gene or gene product, can provide a group or set of subgenomic intervals from the tumor sample.

In an embodiment, the method acquires a read, e.g., sequences, a set of subgenomic intervals from the tumor sample, wherein the subgenomic intervals are chosen from at least 1, 2, 3, 4, 5, 6, 7, 8, 9, 10, 11, 12, 13 or all of the following:

A) at least five, six, seven, eight, nine, ten, fifteen, twenty, twenty-five, thirty or more subgenomic intervals from a mutated or wild-type gene or gene product chosen from at least five or more of: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53;

B) at least five, six, seven, eight, nine, ten, fifteen, twenty, twenty-five, thirty, thirty-five, forty, forty-five, fifty, fifty-five, sixty, sixty-five, seventy, seventy-five, eighty, eighty-five, ninety, ninety-five, one hundred, one hundred and five, one hundred and ten, one hundred and fifteen, one hundred and twenty or more of subgenomic intervals from a mutated or wild type gene or gene product chosen from at least five or more of: ABL2, ARAF, ARFRP1, ARID1A, ATM, ATR, AURKA, AURKB, BAP1, BCL2, BCL2A1, BCL2L1, BCL2L2, BCL6, BRCA1, BRCA2, CBL, CARD11, CBL, CCND2, CCND3, CCNE1, CD79A, CD79B, CDH1, CDH2, CDH20, CDH5, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, INHBA, IRS2, JAK1, JAK3, JUN, KDM6A, KDR, LRP1B, LRP6, LTK, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK2, PAK3, PAX5, PDGFRB, PKHD1, PLCG1, PRKDC, PTPN11, PTPRD, RAF1, RARA, RICTOR, RPTOR, RUNX1, SMAD2, SMAD3, SMAD4, SMARCA4, SMARCB1, SOX10, SOX2, SRC, TBX22, TET2, TGFBR2, TMPRSS2, TNFAIP3, TNK, TNKS2, TOP1, TSC1, TSC2, USP9X, VHL, or WT1;

C) at least five, six, seven, eight, nine, ten, fifteen, twenty, or more subgenomic intervals from a gene or gene product according to Table 1, 1A, 2, 3 or 4;

D) at least five, six, seven, eight, nine, ten, fifteen, twenty, or more subgenomic intervals from a gene or gene product that is associated with a tumor or cancer (e.g., is a positive or negative treatment response predictor, is a positive or negative prognostic factor for, or enables differential diagnosis of a tumor or cancer, e.g., a gene or gene product chosen from one or more of: ABL1, AKT1, ALK, AR, BRAF, BRCA1, BRCA2, CEBPA, EGFR, ERBB2, FLT3, JAK2, KIT, KRAS, MET, NPM1, PDGFRA, PIK3CA, RARA, AKT2, AKT3, MAP2K4, NOTCH1, and TP53;

E) at least five, six, seven, eight, nine, ten, or more subgenomic intervals including a mutated or a wild type codon chosen from one or more of: codon 315 of the ABL1 gene; codon 1114, 1338, 1450 or 1556 of APC; codon 600 of BRAF; codon 32, 33, 34, 37, 41 or 45 of CTNNB1; codon 719, 746-750, 768, 790, 858 or 861 of EGFR; codon 835 of FLT3; codon 12, 13, or 61 of HRAS; codon 617 of JAK2; codon 816 of KIT; codon 12, 13, or 61 of KRAS; codon 88, 542, 545, 546, 1047, or 1049 of PIK3CA; codon 130, 173, 233, or 267 of PTEN; codon 918 of RET; codon 175, 245, 248, 273, or 306 of TP53 (e.g., at least five, ten, fifteen, twenty or more subgenomic intervals that include one or more of the codons shown in Table 1).

F) at least five, six, seven, eight, nine, ten, fifteen, twenty, twenty-five, thirty, or more of subgenomic intervals from a mutated or wild type gene or gene product (e.g., single nucleotide polymorphism (SNP)) of a subgenomic interval that is present in a gene or gene product associated with one or more of drug metabolism, drug responsiveness, or toxicity (also referred to therein as "PGx" genes) chosen from: ABCB1, BCC2, ABCC4, ABCG2, C1orf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, or UMPS;

G) at least five, six, seven, eight, nine, ten, fifteen, twenty, twenty-five, thirty, or more of subgenomic intervals from a mutated or wild type PGx gene or gene product (e.g., single nucleotide polymorphism (SNP)) of a subgenomic interval that is present in a gene or gene product associated with one or more of: (i) better survival of a cancer patient treated with a drug (e.g., better survival of a breast cancer patient treated with paclitaxel (e.g., an ABCB1 gene)); (ii) paclitaxel metabolism (e.g., CYP2C8 genes at different loci and mutations shown in Table 2; CYP3A4 gene); (iii) toxicity to a drug (e.g., 6-MP toxicity as seen with ABCC4 gene (Table 2); 5-FU toxicity as seen with DPYD gene, TYMS gene, or UMPS gene (Table 2); purine toxicity as seen with a TMPT gene (Table 2); daunorubicin toxicity as seen with NRP2 gene; C1orf144 gene, CYP1B1 gene (Table 2); or (iv) a side effect to a drug (e.g., ABCG2, TYMS, UGT1A1, ESR1 and ESR2 genes (Table 2));

H) a translocation alteration of at least 5, 10, 15, 20, 25, 30, 35, 40, 45, 50, 75, 110 or more genes or gene products according to Table 3;

J) a translocation alteration of at least 5, 10, 15, 20, 25, 30, 35, 40, 45, 50, 75, 110 or more genes or gene products according to Table 3 in a solid tumor sample from the cancer types specified therein;

K) a translocation alteration of at least 5, 10, 15, 20, 25, 30, 35, 40, 45, 50, 75, 100, 150, 200 or more genes or gene products according to Table 4;

L) a translocation alteration of at least 5, 10, 15, 20, 25, 30, 35, 40, 45, 50, 75, 100, 150, 200 or more genes or gene products according to Table 4 in a heme tumor sample from the cancer types specified therein;

M) at least five genes or gene products selected from Table 1-4, wherein an allelic variation, e.g., at the preselected position, is associated with a preselected type of tumor and wherein said allelic variation is present in less than 5% of the cells in said tumor type;

N) at least five genes or gene products selected from Table 1, 1A-4, which are embedded in a GC-rich region; or O) at least five genes or gene products indicative of a genetic (e.g., a germline risk) factor for developing cancer (e.g., the gene or gene product is chosen from one or more of BRCA1, BRCA2, EGFR, HRAS, KIT, MPL, ALK, PTEN, RET, APC, CDKN2A, MLH1, MSH2, MSH6, NF1, NF2, RB1, TP53, VHL or WT1).

In yet another embodiment, the method acquires a read, e.g., sequences, a set of subgenomic intervals from the tumor sample, wherein the subgenomic intervals are chosen from one, two, three, four, five, ten, fifteen or all of the alterations described in Table 1B. In one embodiment, the subgenomic interval includes an alteration classified in one or more of Category A, B, C, D or E. In other embodiment, the subgenomic interval includes an alteration in KRAS G13D in a tumor sample, e.g., a colon, lung or breast tumor sample. In other embodiment, the subgenomic interval includes an alteration in NRAS Q61K in a tumor sample, e.g., a melanoma or colon tumor sample. In yet other embodiments, the subgenomic interval includes an alteration in BRAF V600E in a tumor sample, e.g., a melanoma, colon, or lung tumor sample. In other embodiment, the subgenomic interval includes an alteration in BRAF D594G in a tumor sample, e.g., a lung tumor sample. In other embodiment, the subgenomic interval includes an alteration in PIK3CA H1047R in a tumor sample, e.g., a breast or colon tumor sample. In yet other embodiment, the subgenomic interval includes an alteration in EGFR L858R or T790M in a tumor sample, e.g., a lung tumor sample. In other embodiment, the subgenomic interval includes an alteration in ERBB2 in a tumor sample, e.g., an ERBB2 amplification in a breast tumor sample. In other embodiment, the subgenomic interval includes an alteration in BRCA1 in a tumor sample, e.g., a BRCA1 biallelic inactivation in a breast tumor sample. In other embodiment, the subgenomic interval includes an alteration in BRCA2 in a tumor sample, e.g., a BRCA2 biallelic inactivation in a pancreatic tumor sample. In other embodiment, the subgenomic interval includes an alteration in ATM in a tumor sample, e.g., an ATM biallelic inactivation in a breast tumor sample. In other embodiment, the subgenomic interval includes an alteration in TSC in a tumor sample, e.g., a TSC biallelic inactivation in a colon tumor sample. In other embodiment, the subgenomic interval includes an alteration in PTEN in a tumor sample, e.g., a PTEN biallelic inactivation in a breast or colon tumor sample. In yet other embodiment, the subgenomic interval includes an alteration in VHL in a tumor sample, e.g., a VHL biallelic inactivation in a kidney tumor sample. In other embodiment, the subgenomic interval includes an alteration in ATR in a tumor sample, e.g., an ATR biallelic inactivation in a breast tumor sample. In other embodiment, the subgenomic interval includes an alteration in MYC in a tumor sample, e.g., a MYC biallelic inactivation in a breast tumor sample.

These and other sets and groups of subgenomic intervals are discussed in more detail elsewhere herein, e.g., in the section entitled "Gene Selection Module."

Any of the methods described herein can be combined with one or more of the embodiments below.

In other embodiments, the sample is a tumor sample, e.g., includes one or more premalignant or malignant cells. In certain, embodiments, the sample, e.g., the tumor sample, is acquired from a solid tumor, a soft tissue tumor or a metastatic lesion. In other embodiments, the sample, e.g., the tumor sample, includes tissue or cells from a surgical margin. The sample can be histologically normal tissue. In another embodiment, the sample, e.g., tumor sample, includes one or more circulating tumor cells (CTC) (e.g., a CTC acquired from a blood sample).

In one embodiment, the method further includes acquiring a sample, e.g., a tumor sample as described herein. The sample can be acquired directly or indirectly.

In other embodiments, the method includes evaluating a sample, e.g., a histologically normal sample, e.g., from a surgical margin, using the methods described herein. Applicants have discovered that samples obtained from histologically normal tissues (e.g., otherwise histologically normal tissue margins) may still have an alteration as described herein. The methods may thus further include re-classifying a tissue sample based on the presence of the detected alteration.

In another embodiment, at least 10, 20, 30, 40, 50, 60, 70, 80, or 90% of the reads acquired or analyzed are for subgenomic intervals from genes described herein, e.g., genes from Table 1-1A, or priority 1 genes from Table 1.

In an embodiment, at least 10, 20, 30, 40, 50, 60, 70, 80, or 90% of the mutation calls made in the method are for subgenomic intervals from genes described herein, e.g., genes from Table 1-1A, or priority 1 genes from Table 1.

In an embodiment, at least 10, 20, 30, 40, 50, 60, 70, 80, or 90% of the unique threshold values used the method are for subgenomic intervals from genes described herein, e.g., genes from Table 1-1A, or priority 1 genes from Table 1.

In an embodiment, at least 10, 20, 30, 40, 50, 60, 70, 80, or 90% of the mutation calls annotated, or reported to a third party, are for subgenomic intervals from genes described herein, e.g., genes from Table 1-1A, or priority 1 genes from Table 1.

In an embodiment, the method comprises acquiring a nucleotide sequence read obtained from a tumor and/or control nucleic acid sample (e.g., an FFPE-derived nucleic acid sample).

In an embodiment, the reads are provided by a NGS sequencing method.

In an embodiment, the method includes providing a library of nucleic acid members and sequencing preselected subgenomic intervals from a plurality of members of said library. In embodiments the method can include a step of selecting a subset of said library for sequencing, e.g., a solution-based selection or a solid support- (e.g., array-) based selection.

In an embodiment, the method includes the step of contacting a library with a plurality of baits to provide a selected subgroup of nucleic acids, e.g., a library catch. In one embodiment, the contacting step is effected in solution hybridization. In another embodiment, the contacting step is effected in a solid support, e.g., an array. In certain embodiments, the method includes repeating the hybridization step by one or more additional rounds of hybridization. In some embodiments, the methods further include subjecting the library catch to one or more additional rounds of hybridization with the same or different collection of baits.

In yet other embodiments, the methods further include analyzing the library catch. In one embodiment, the library catch is analyzed by a sequencing method, e.g., a next-generation sequencing method as described herein. The methods include isolating a library catch by, e.g., solution hybridization, and subjecting the library catch by nucleic acid sequencing. In certain embodiments, the library catch can be re-sequenced. Next generation sequencing methods are known in the art, and are described, e.g., in Metzker, M. (2010) *Nature Biotechnology Reviews* 11:31-46.

In an embodiment, the assigned value for a nucleotide position is transmitted to a third party, optionally, with explanatory annotation.

In an embodiment, the assigned value for a nucleotide position is not transmitted to a third party.

In an embodiment, the assigned value for a plurality of nucleotide position is transmitted to a third party, optionally, with explanatory annotations, and the assigned value for a second plurality of nucleotide position is not transmitted to a third party.

In an embodiment, at least 0.01, 0.02, 0.03, 0.05, 0.1, 0.2, 0.3, 0.4, 0.5, 0.6, 0.7, 0.8, 0.9, 1.0, 15, or 30 megabases bases, e.g., genomic bases, are sequenced.

In an embodiment, the method comprises evaluating a plurality of reads that include at least one SNP.

In an embodiment, the method comprises determining an SNP allele ratio in the sample and/or control read.

In an embodiment, the method comprises assigning one or more reads to a subject, e.g., by barcode deconvolution.

In an embodiment, the method comprises assigning one or more reads as a tumor read or a control read, e.g., by barcode deconvolution.

In an embodiment, the method comprises mapping, e.g., by alignment with a reference sequence, each of said one or more reads.

In an embodiment, the method comprises memorializing a called mutation.

In an embodiment, the method comprises annotating a called mutation, e.g., annotating a called mutation with an indication of mutation structure, e.g., a mis-sense mutation, or function, e.g., a disease phenotype.

In an embodiment, the method comprises acquiring nucleotide sequence reads for tumor and control nucleic acid.

In an embodiment, the method comprises calling a nucleotide value, e.g., a variant, e.g., a mutation, for each of X subgenomic intervals, e.g., with a Bayesian calling method or a non-Bayesian calling method.

In an embodiment, multiple samples, e.g., from different subjects, are processed simultaneously.

The methods disclosed herein can be used to detect alterations present in the genome or transcriptome of a subject, and can be applied to DNA and RNA sequencing, e.g., targeted RNA and/or DNA sequencing. Thus, another aspect featured in the invention includes methods for targeted RNA sequencing, e.g., sequencing of a cDNA derived from an RNA acquired from a sample, e.g., an FFPE-sample, to detect an alteration described herein. The alteration can be rearrangement, e.g., a rearrangement encoding a gene fusion. In other embodiments, the method includes detection of a change (e.g., an increase or decrease) in the level of a gene or gene product, e.g., a change in expression of a gene or gene product described herein. The methods can, optionally, include a step of enriching a sample for a target RNA. In other embodiments, the methods include the step of depleting the sample of certain high abundance RNAs, e.g., ribosomal or globin RNAs. The RNA sequencing methods can be used, alone or in combination with the DNA sequencing methods described herein. In one embodiment, the method includes performing a DNA sequencing step and an RNA sequencing step. The methods can be performed in any order. For example, the method can include confirming by RNA sequencing the expression of an alteration described herein, e.g., confirming expression of mutation or a fusion detected by the DNA sequencing methods of the invention. In other embodiments, the method includes performing an RNA sequencing step, followed by a DNA sequencing step.

In another aspect, the invention features a method comprising building a database of sequencing/alignment artifacts for the targeted subgenomic regions. In embodiment the database can be used to filter out spurious mutation calls and improve specificity. In an embodiment the database is built by sequencing unrelated non-tumor (e.g., FFPE) samples or cell-lines and recording non-reference allele events that appear more frequently than expected due to random sequencing error alone in 1 or more of these normal samples. This approach may classify germ-line variation as artifact, but that is acceptable in method concerned with somatic mutations. This mis-classification of germ-line variation as artifact may be ameliorated if desired by filtering this database for known germ-line variation (removing common variants) and for artifacts that appear in only 1 individual (removing rarer variation).

Methods disclosed herein allow integration of a number of optimized elements including optimized bait-based selection, optimized alignment, and optimized mutation calling, as applied, e.g., to cancer related segments of the genome. Methods described herein provide for NGS-based analysis of tumors that can be optimized on a cancer-by-cancer, gene-by-gene and site-by-site basis. This can be applied e.g., to the genes/sites and tumor types described herein. The methods optimize levels of sensitivity and specificity for mutation detection with a given sequencing technology. Cancer by cancer, gene by gene, and site by site optimization provides very high levels sensitivity/specificity (e.g., >99% for both) that are essential for a clinical product.

Methods described herein provide for clinical and regulatory grade comprehensive analysis and interpretation of genomic aberrations for a comprehensive set of plausibly actionable genes (which may typically range from 50 to 500 genes) using next generation sequencing technologies from routine, real-world samples in order to inform optimal treatment and disease management decisions.

Methods described herein provide one-stop-shopping for oncologists/pathologists to send a tumor sample and receive a comprehensive analysis and description of the genomic and other molecular changes for that tumor, in order to inform optimal treatment and disease management decisions.

Methods described herein provide a robust, real-world clinical oncology diagnostic tool that takes standard available tumor samples and in one test provides a comprehensive genomic and other molecular aberration analysis to provide the oncologist with a comprehensive description of what aberrations may be driving the tumor and could be useful for informing the oncologists treatment decisions.

Methods described herein provide for a comprehensive analysis of a patient's cancer genome, with clinical grade quality. Methods include the most relevant genes and potential alterations and include one or more of the analysis of mutations, copy number, rearrangments, e.g., translocations, expression, and epigenetic markers. The out put of the genetic analysis can be contextualized with descriptive reporting of actionable results. Methods connect the use with an up to date set of relevant scientific and medical knowledge.

Methods described herein provide for increasing both the quality and efficiency of care. This includes applications where a tumor is of a rare or poorly studied type such that there is no standard of care or the patient is refractory to established lines of therapy and a rational basis for selection of further therapy or for clinical trial participation could be useful. E.g., methods allow, at any point of therapy, selection where the oncologist would benefit by having the full "molecular image" and/or "molecular sub-diagnosis" available to inform decision making.

Methods described herein can comprise providing a report, e.g., in electronic, web-based, or paper form, to the patient or to another person or entity, e.g., a caregiver, e.g., a physician, e.g., an oncologist, a hospital, clinic, third-party payor, insurance company or government office. The report can comprise output from the method, e.g., the identification of nucleotide values, the indication of presence or absence of an alteration, mutation, or wildtype sequence, e.g., for sugenomic intervals associated with a tumor of the type of the sample. The report can also comprise information on the role of a sequence, e.g., an alteration, mutation, or wildtype sequence, in disease. Such information can include information on prognosis, resistance, or potential or suggested therapeutic options. The report can comprise information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report. E.g., the report can include information, or a recommendation on, the administration of a drug, e.g., the administration at a preselected dosage or in a preselected treatment regimen, e.g., in combination with other drugs, to the patient. In an embodiment, not all mutations identified in the method are identified in the report. E.g., the report can be limited to mutations in genes having a preselected level of correlation with the occurrence, prognosis, stage, or susceptibility of the cancer to treatment, e.g., with a preselected therapeutic option. Methods featured herein allow for delivery of the report, e.g., to an entity described herein, within 7, 14, or 21 days from receipt of the sample by the entity practicing the method.

Thus, methods featured in the invention allow a quick turn around time, e.g., within 7, 14 or 21 days of receipt of sample.

Methods described herein can also be used to evaluate a histologically normal sample, e.g., samples from surgical margins. If one or more alterations as described herein is detected, the tissue can be re-classified, e.g., as malignant or pre-maligant, and/or the course of treatment can be modified.

In certain aspects, the sequencing methods described herein are useful in non-cancer applications, e.g., in forensic applications (e.g., identification as alternative to, or in addition to, use of dental records), paternity testing, and disease diagnosis and prognosis, e.g., for cystic fibrosis, Huntington's Disease, Alzheimer's Disease, among others. For example, identification of genetic alterations by the methods described herein can indicate the presence or risk of an individual for developing a particular disorder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DESCRIPTION OF THE FIGURES

The drawings are first described.

DETAILED DESCRIPTION

Figure 1A:
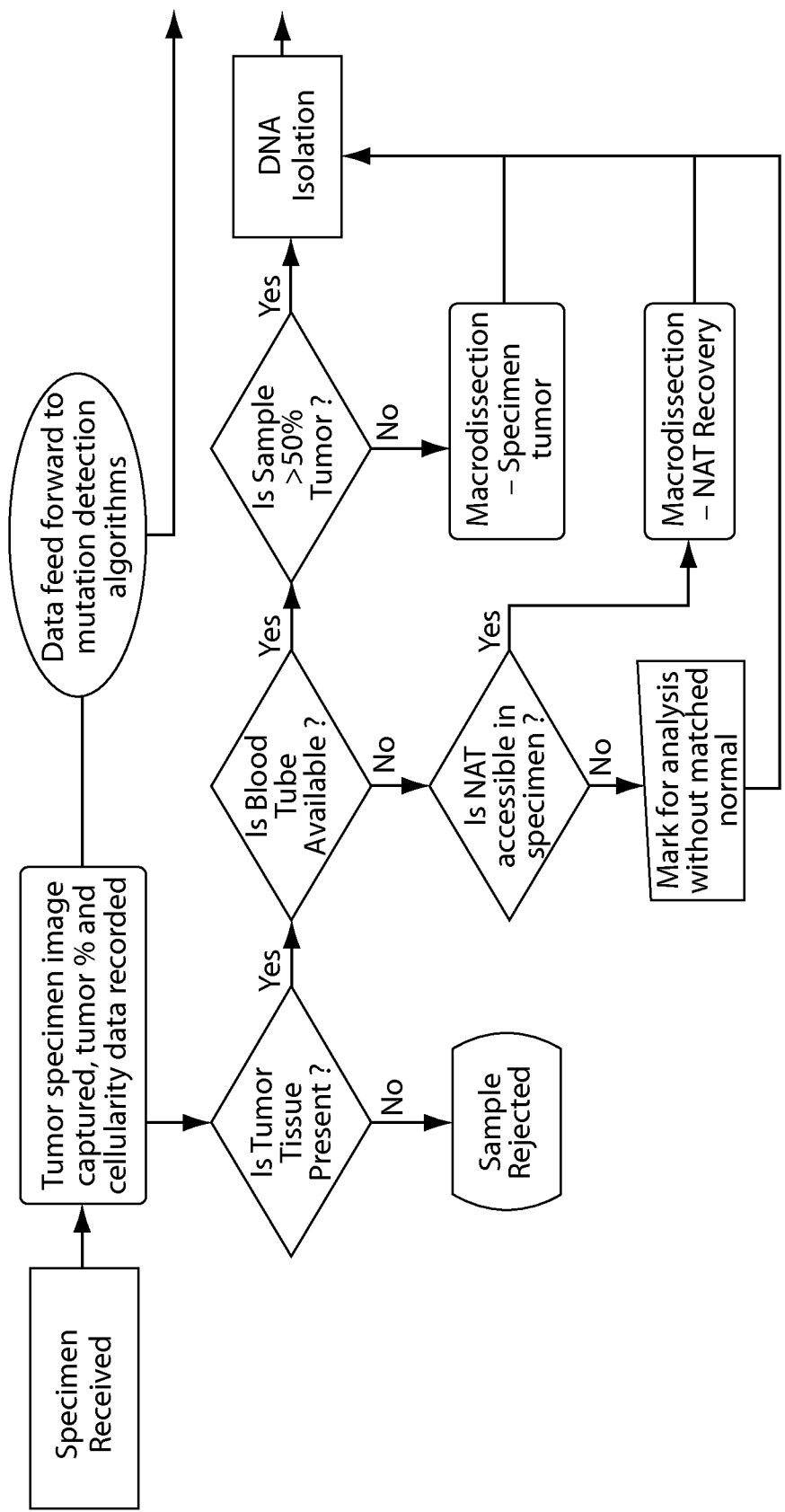
FIG. 1A-F is a flowchart depiction of an embodiment of a method for multigene analysis of a tumor sample.
Figure 1B:
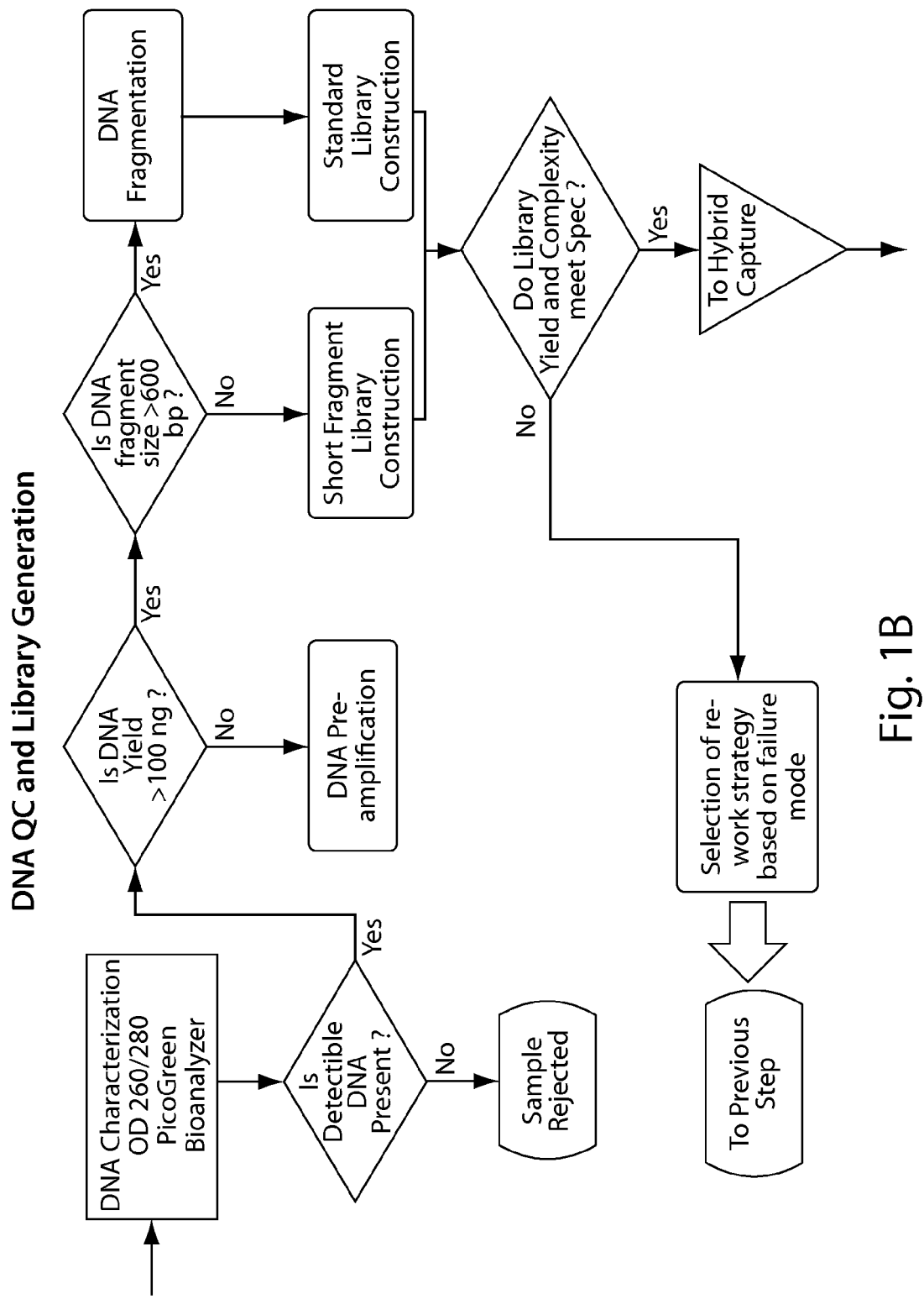
Figure 1C:
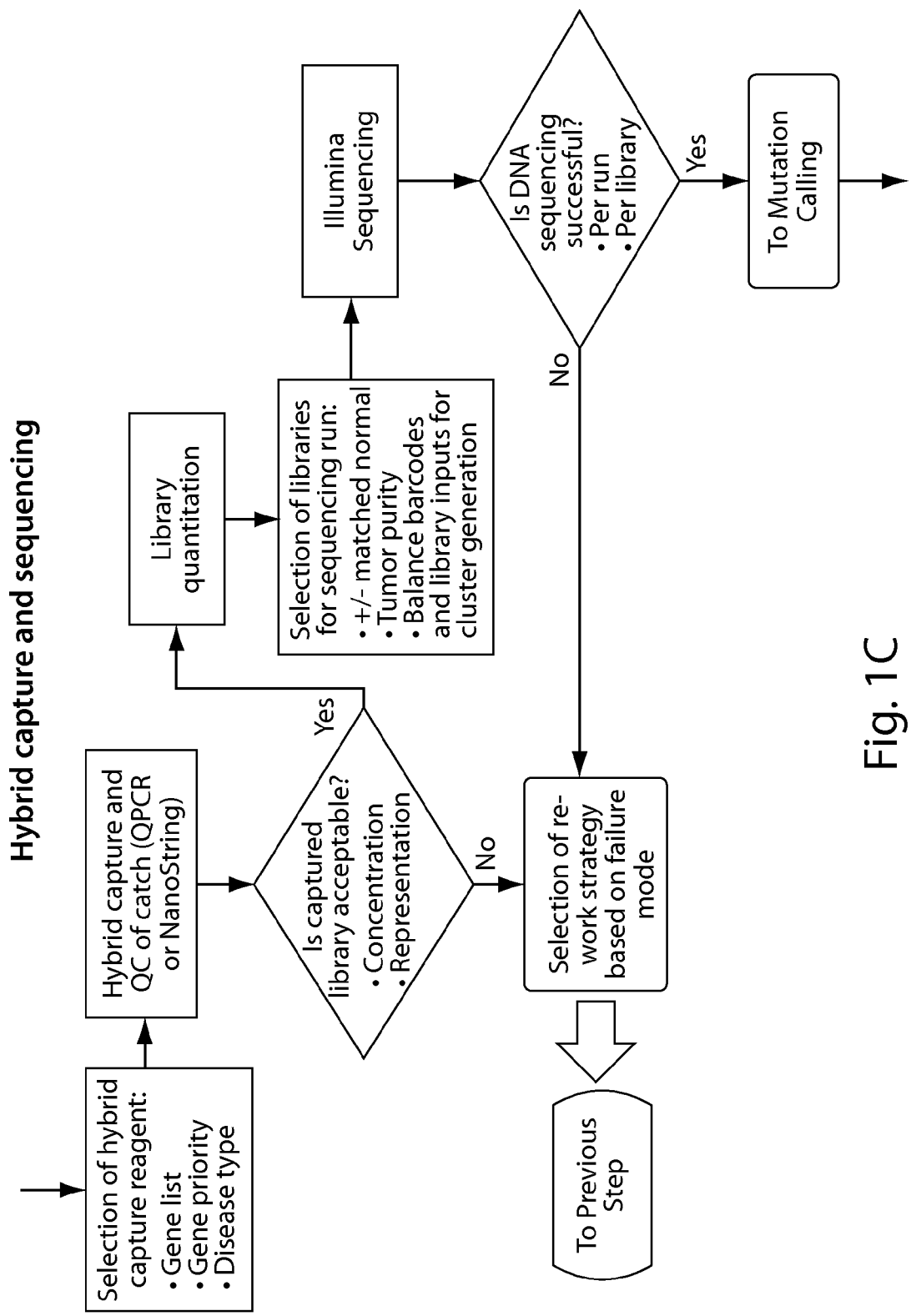
Figure 1D:
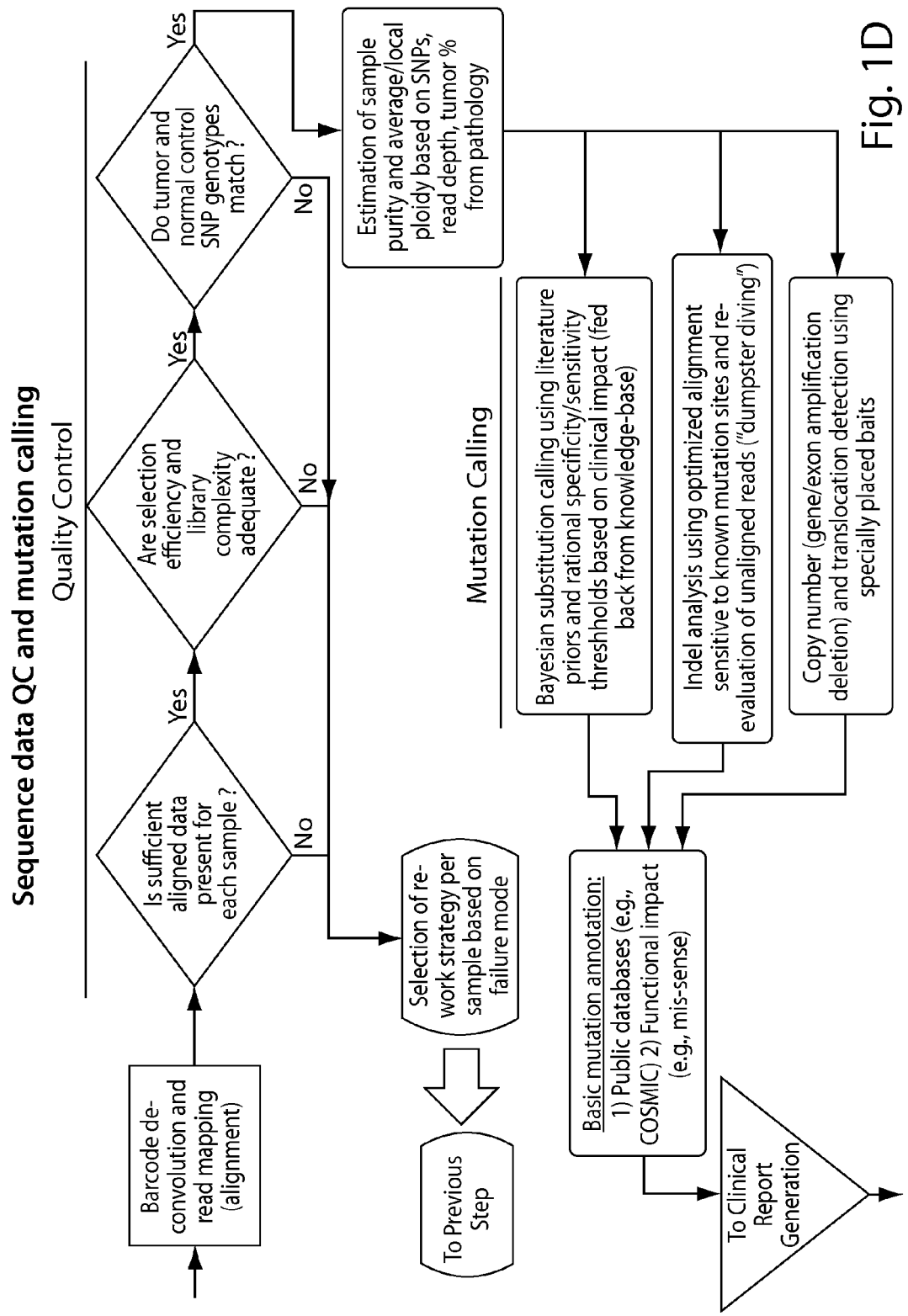
Figure 1E:
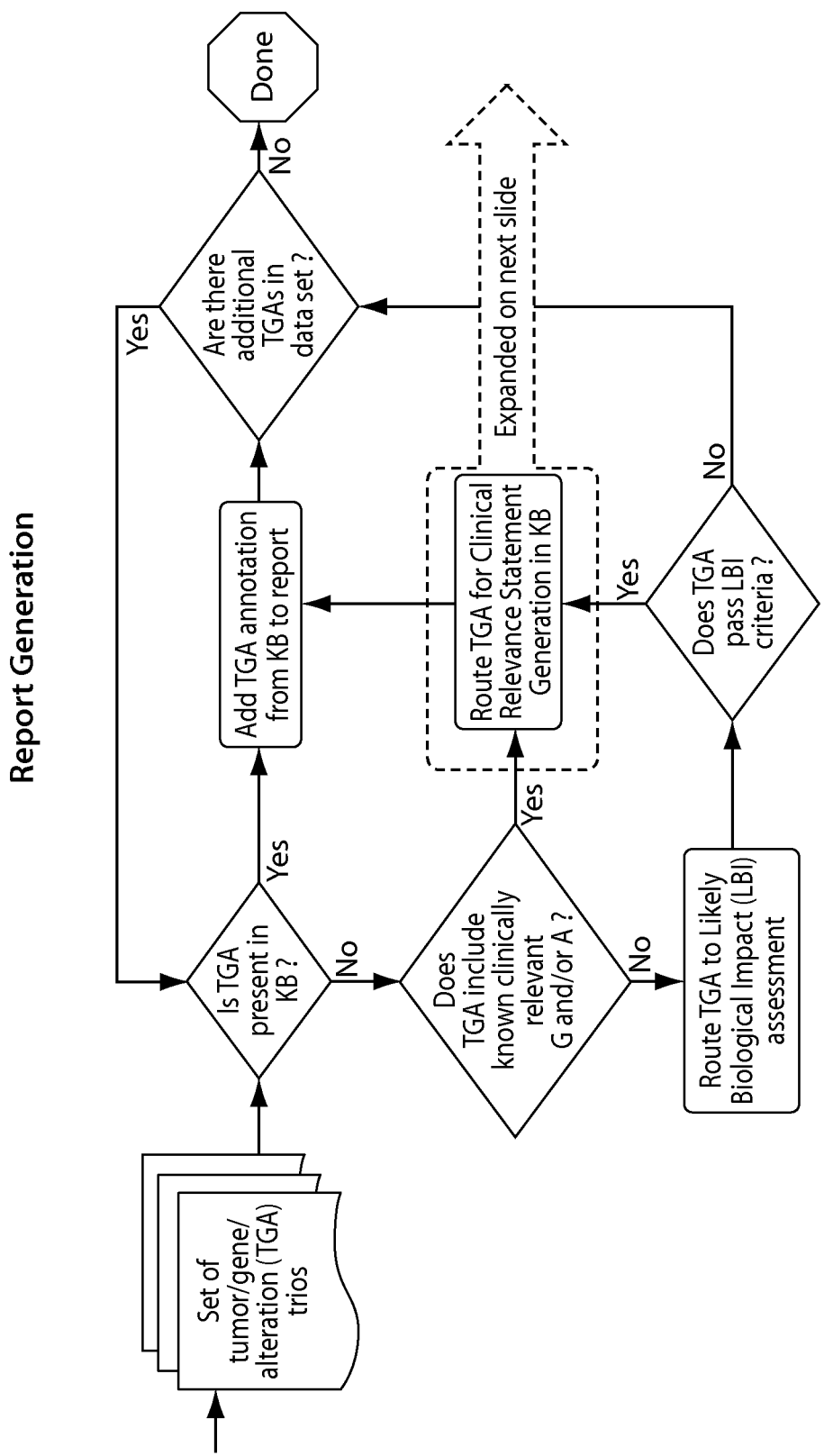
Figure 1F:
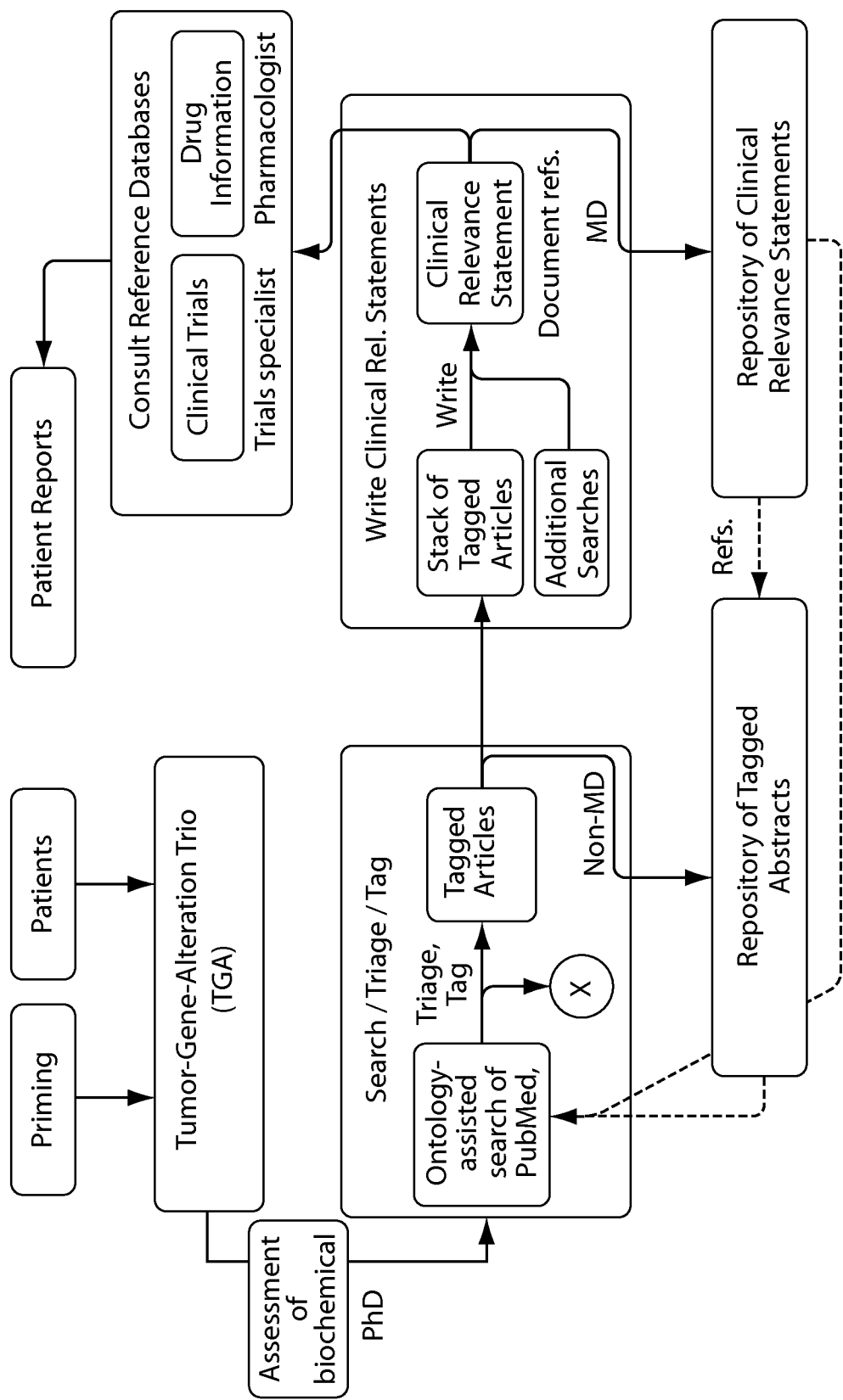

Optimized methods and assays for sequencing large numbers of genes and gene products from samples, e.g., tumor samples, from one or more subjects by evaluating a selected group of genes and gene products are disclosed. In one embodiment, the methods and assays featured in the invention are used in a multiplex assay format, e.g., assays incorporated multiple signals from a large number of diverse genetic events in a large number of genes. Disclosed herein are methods and assays that are based, at least in part, on a selected group of genes or gene products that are associated (e.g., positively or negatively) with a cancerous phenotype (e.g., one or more of cancer risk, cancer progression, cancer treatment or resistance to treatment). Such pre-selected genes or gene products enable the application of sequencing methods, particularly methods that rely on massively parallel sequencing of a large number of diverse genes, e.g., from tumor or control samples.

Certain terms are first defined. Additional terms are defined throughout the specification.

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or ore starting materials, shearing or fragmenting a substance, separating or purifying a substance, combining two or more separate entities into a mixture, performing a chemical reaction that includes breaking or forming a covalent or non covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non covalent bond, between a first and a second atom of the analyte; or by changing the structure of a reagent, or a fragment or other derivative thereof, e.g., by breaking or forming a covalent or non covalent bond, between a first and a second atom of the reagent.

"Acquiring a sequence" or "acquiring a read" as the term is used herein, refers to obtaining possession of a nucleotide sequence or amino acid sequence, by "directly acquiring" or "indirectly acquiring" the sequence or read. "Directly acquiring" a sequence or read means performing a process (e.g., performing a synthetic or analytical method) to obtain the sequence, such as performing a sequencing method (e.g., a Next Generation Sequencing (NGS) method). "Indirectly acquiring" a sequence or read refers to receiving information or knowledge of, or receiving, the sequence from another party or source (e.g., a third party laboratory that directly acquired the sequence). The sequence or read acquired need not be a full sequence, e.g., sequencing of at least one nucleotide, or obtaining information or knowledge, that identifies one or more of the alterations disclosed herein as being present in a subject constitutes acquiring a sequence.

Directly acquiring a sequence or read includes performing a process that includes a physical change in a physical substance, e.g., a starting material, such as a tissue or cellular sample, e.g., a biopsy, or an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

"Alignment selector," as used herein, refers to a parameter that allows or directs the selection of an alignment method, e.g., an alignment algorithm or parameter, that can optimize the sequencing of a preselected subgenomic interval. An alignment selector can be specific to, or selected as a function, e.g., of one or more of the following:

1. The sequence context, e.g., sequence context, of a subgenomic interval (e.g., the preselected nucleotide position to be evaluated) that is associated with a propensity for misalignment of reads for said subgenomic interval. E.g., the existence of a sequence element in or near the subgenomic interval to be evaluated that is repeated elsewhere in the genome can cause misalignment and thereby reduce performance. Performance can be enhanced by selecting an algorithm or an algorithm parameter that minimizes misalignment. In this case the value for the alignment selector can be a function of the sequence context, e.g., the presence or absence of a sequence of preselected length that is repeated at least a preselected number of times in the genome (or in the portion of the genome being analyzed).
2. The tumor type being analyzed. E.g., a specific tumor type can be characterized by increased rate of deletions. Thus, performance can be enhanced by selecting an algorithm or algorithm parameter that is more sensitive to indels. In this case the value for the alignment selector can be a function of the tumor type, e.g., an identifier for the tumor type. In an embodiment the value is the identity of the tumor type, e.g., breast cancer.
3. The gene, or type of gene, being analyzed, e.g., a gene, or type of gene, can be analyzed. Oncogenes, by way of example, are often characterized by substitutions or in-frame indels. Thus, performance can be enhanced by selecting an algorithm or algorithm parameter that is particularly sensitive to these variants and specific against others. Tumor suppressors are often characterized by frame-shift indels. Thus, performance can be enhanced by selecting an algorithm or algorithm parameter that is particularly sensitive to these variants. Thus, performance can be enhanced by selecting an algorithm or algorithm parameter matched with the subgenomic interval. In this case the value for the alignment selector can be a function of the gene or gene type, e.g., an identifier for gene or gene type. In an embodiment the value is the identity of the gene.
4. The site (e.g., nucleotide position) being analyzed. In this case the value for the alignment selector can be a function of the site or the type of site, e.g., an identifier for the site or site type. In an embodiment the value is the identity of the site. (E.g., if the gene containing the site is highly homologous with another gene, normal/fast short read alignment algorithms (e.g., BWA) may have difficulty distinguishing between the two genes, potentially necessitating more intensive alignment methods (Smith-Waterman) or even assembly (ARACHNE). Similarly, if the gene sequence contains low-complexity regions (e.g., AAAAAA), more intensive alignment methods may be necessary.
5. The variant, or type of variant, associated with the subgenomic interval being evaluated. E.g., a substitution, insertion, deletion, translocation or other rearrangement. Thus, performance can be enhanced by selecting an algorithm or algorithm parameter that is more sensitive to the specific variant type. In this case the value for the alignment selector can be a function of the type of variant, e.g., an identifier for the type of variant. In an embodiment the value is the identity of the type of variant, e.g., a substitution.
6. The type of sample, a FFPE or other fixed sample. Sample type/quality can affect error (spurious observation of non-reference sequence) rate. Thus, performance can be enhanced by selecting an algorithm or algorithm parameter that accurately model the true error rate in the sample. In this case the value for the alignment selector can be a function of the type of sample, e.g., an identifier for the sample type. In an embodiment, the value is the identity of the sample type, e.g., a fixed sample.

"Alteration" or "altered structure" as used herein, of a gene or gene product (e.g., a marker gene or gene product) refers to the presence of a mutation or mutations within the gene or gene product, e.g., a mutation, which affects amount or activity of the gene or gene product, as compared to the normal or wild-type gene. The alteration can be in amount, structure, and/or activity in a cancer tissue or cancer cell, as compared to its amount, structure, and/or activity, in a normal or healthy tissue or cell (e.g., a control), and is associated with a disease state, such as cancer. For example, an alteration which is associated with cancer, or predictive of responsiveness to anti-cancer therapeutics, can have an altered nucleotide sequence (e.g., a mutation), amino acid sequence, chromosomal translocation, intra-chromosomal inversion, copy number, expression level, protein level, protein activity, or methylation status, in a cancer tissue or cancer cell, as compared to a normal, healthy tissue or cell. Exemplary mutations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alteration(s) is detected as a rearrangement, e.g., a genomic rearrangement comprising one or more introns or fragments thereof (e.g., one or more rearrangements in the 5'—and/or 3'-UTR). In certain embodiments, the alterations are associated (or not associated) with a phenotype, e.g., a cancerous phenotype (e.g., one or more of cancer risk, cancer progression, cancer treatment or resistance to cancer treatment). In one embodiment, the alteration is associated with one or more of: a genetic risk factor for cancer, a positive treatment response predictor, a negative treatment response predictor, a positive prognostic factor, a negative prognostic factor, or a diagnostic factor.

"Bait", as used herein, is type of hybrid capture reagent. A bait can be a nucleic acid molecule, e.g., a DNA or RNA molecule, which can hybridize to (e.g., be complementary to), and thereby allow capture of a target nucleic acid. In one embodiment, a bait is an RNA molecule (e.g., a naturally-occurring or modified RNA molecule); a DNA molecule (e.g., a naturally-occurring or modified DNA molecule), or a combination thereof. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

"Bait set," as used herein, refers to one or a plurality of bait molecules.

"Binding entity" means any molecule to which molecular tags can be directly or indirectly attached that is capable of specifically binding to an analyte. The binding entity can be an affinity tag on each bait sequence. In certain embodiments, the binding entity allows for separation of the bait/member hybrids from the hybridization mixture by binding to a partner, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers.

"Likely to" or "increased likelihood," as used herein, refers to an increased probability that an item, object, thing or person will occur. Thus, in one example, a subject that is likely to respond to treatment has an increased probability of responding to treatment relative to a reference subject or group of subjects.

"Unlikely to" refers to a decreased probability that an event, item, object, thing or person will occur with respect to a reference. Thus, a subject that is unlikely to respond to treatment has a decreased probability of responding to treatment relative to a reference subject or group of subjects.

"Control member" refers to a member having sequence from a non-tumor cell.

"Indel alignment sequence selector," as used herein, refers to a parameter that allows or directs the selection of a sequence to which a read is to be aligned with in the case of a preselcted indel. Use of such a sequence can optimize the sequencing of a preselected subgenomic interval comprising an indel. The value for an indel alignment sequence selector is a function of a preselected indel, e.g., an identifier for the indel. In an embodiment the value is the identity of the indel.

As used herein, the term "library" refers to a collection of members. In one embodiment, the library includes a collection of nucleic acid members, e.g., a collection of whole genomic, subgenomic fragments, cDNA, cDNA fragments, RNA, RNA fragments, or a combination thereof. In one embodiment, a portion or all of the library members comprises an adapter sequence. The adapter sequence can be located at one or both ends. The adapter sequence can be useful, e.g., for a sequencing method (e.g., an NGS method), for amplification, for reverse transcription, or for cloning into a vector.

The library can comprise a collection of members, e.g., a target member (e.g., a tumor member, a reference member, a PGx member, or a combination thereof). The members of the library can be from a single individual. In embodiments, a library can comprise members from more than one subject (e.g., 2, 3, 4, 5, 6, 7, 8, 9, 10, 20, 30 or more subjects), e.g., two or more libraries from different subjects can be combined to from a library having members from more than one subject. In one embodiment, the subject is human having, or at risk of having, a cancer or tumor.

"Library-catch" refers to a subset of a library, e.g., a subset enriched for preselected subgenomic intervals, e.g., product captured by hybridization with preselected baits.

"Member" or "library member" or other similar term, as used herein, refers to a nucleic acid molecule, e.g., a DNA, RNA, or a combination thereof, that is the member of a library. Typically, a member is a DNA molecule, e.g., genomic DNA or cDNA. A member can be fragmented, e.g., sheared or enzymatically prepared, genomic DNA. Members comprise sequence from a subject and can also comprise sequence not derived from the subject, e.g., adapters sequence, a primer sequence, or other sequences that allow for identification, e.g., "barcode" sequences.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a high through-putfashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample.

"Nucleotide value" as referred herein, represents the identity of the nucleotide(s) occupying or assigned to a preselected nucleotide position. Typical nucleotide values include: missing (e.g., deleted); additional (e.g., an insertion of one or more nucleotides, the identity of which may or may not be included); or present (occupied); A; T; C; or G. Other values can be, e.g., not Y, wherein Y is A, T, G, or C; A or X, wherein X is one or two of T, G, or C; T or X, wherein X is one or two of A, G, or C; G or X, wherein X is one or two of T, A, or C; C or X, wherein X is one or two of T, G, or A; a pyrimidine nucleotide; or a purine nucleotide. A nucleotide value can be a frequency for 1 or more, e.g., 2, 3, or 4, bases (or other value described herein, e.g., missing or additional) at a nucleotide position. E.g., a nucleotide value can comprise a frequency for A, and a frequency for G, at a nucleotide position.

"Or" is used herein to mean, and is used interchangeably with, the term "and/or", unless context clearly indicates otherwise. The use of the term "and/or" in some places herein does not mean that uses of the term "or" are not interchangeable with the term "and/or" unless the context clearly indicates otherwise.

"Primary control" refers to a non tumor tissue other than NAT tissue in a tumor sample. Blood is a typical primary control.

"Rearrangement alignment sequence selector," as used herein, refers to a parameter that allows or directs the selection of a sequence to which a read is to be aligned with in the case of a preselected rearrangement. Use of such a sequence can optimize the sequencing of a preselected subgenomic interval comprising a rearrangement. The value for a rearrangement alignment sequence selector is a function of a preselected rearrangement, e.g., an identifier for the rearrangement. In an embodiment the value is the identity of the rearrangement. An "indel alignment sequence selector" (also defined elsewhere herein) is an example of a rearrangement alignment sequence selector.

"Sample," "tissue sample," "patient sample," "patient cell or tissue sample" or "specimen" each refers to a collection of similar cells obtained from a tissue, or circulating cells, of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

In one embodiment, the sample is a tumor sample, e.g., includes one or more premalignant or malignant cells. In certain, embodiments, the sample, e.g., the tumor sample, is acquired from a solid tumor, a soft tissue tumor or a metastatic lesion. In other embodiments, the sample, e.g., the tumor sample, includes tissue or cells from a surgical margin. In another embodiment, the sample, e.g., tumor sample, includes one or more circulating tumor cells (CTC) (e.g., a CTC acquired from a blood sample).

"Sensitivity," as used herein, is a measure of the ability of a method to detect a preselected sequence variant in a heterogeneous population of sequences. A method has a sensitivity of S % for variants of F % if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%). Exemplary sensitivities include those of S=90%, 95%, 99% for sequence variants at F=1%, 5%, 10%, 20%, 50%, 100% at confidence levels of C=90%, 95%, 99%, and 99.9%.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include 90, 95, 98, and 99%.

A "tumor nucleic acid sample" as used herein, refers to nucleic acid molecules from a tumor or cancer sample. Typically, it is DNA, e.g., genomic DNA, or cDNA derived from RNA, from a tumor or cancer sample. In certain embodiments, the tumor nucleic acid sample is purified or isolated (e.g., it is removed from its natural state).

A "control" or "reference" "nucleic acid sample" as used herein, refers to nucleic acid molecules from a control or reference sample. Typically, it is DNA, e.g., genomic DNA, or cDNA derived from RNA, not containing the alteration or variation in the gene or gene product. In certain embodiments, the reference or control nucleic acid sample is a wild type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

"Sequencing" a nucleic acid molecule requires determining the identity of at least 1 nucleotide in the molecule. In embodiments the identity of less than all of the nucleotides in a molecule are determined. In other embodiments, the identity of a majority or all of the nucleotides in the molecule is determined.

"Subgenomic interval" as referred to herein, refers to a portion of genomic sequence. In an embodiment a subgenomic interval can be a single nucleotide position, e.g., a nucleotide position variants of which are associated (positively or negatively) with a tumor phenotype. In an embodiment a subgenomic interval comprises more than one nucleotide position. Such embodiments include sequences of at least 2, 5, 10, 50, 100, 150, or 250 nucleotide positions in length. Subgenomic intervals can comprise an entire gene, or a preselected portion thereof, e.g., the coding region (or portions there of), a preselected intron (or portion thereof) or exon (or portion thereof). A subgenomic interval can comprise all or a part of a fragment of a naturally occurring, e.g., genomic, nucleic acid. E.g., a subgenomic interval can correspond to a fragment of genomic DNA which is subjected to a sequencing reaction. In embodiments a subgenomic interval is continuous sequence from a genomic source. In embodiments a subgenomic interval includes sequences that are not contiguous in the genome, e.g., it can include junctions formed found at exon-exon junctions in cDNA.

In an embodiment, a subgenomic interval comprises or consists of: a single nucleotide position; an intragenic region or an intergenic region; an exon or an intron, or a fragment thereof, typically an exon sequence or a fragment thereof; a coding region or a non-coding region, e.g., a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; an alteration, e.g., a point or a single mutation; a deletion mutation (e.g., an in-frame deletion, an intragenic deletion, a full gene deletion); an insertion mutation (e.g., intragenic insertion); an inversion mutation (e.g., an intra-chromosomal inversion); a linking mutation; a linked insertion mutation; an inverted duplication mutation; a tandem duplication (e.g., an intrachromosomal tandem duplication); a translocation (e.g., a chromosomal translocation, a non-reciprocal translocation); a rearrangement (e.g., a genomic rearrangement (e.g., a rearrangement of one or more introns, or a fragment thereof; a rearranged intron can include a 5'—and/or 3'-UTR); a change in gene copy number; a change in gene expression; a change in RNA levels, or a combination thereof. The "copy number of a gene" refers to the number of DNA sequences in a cell encoding a particular gene product. Generally, for a given gene, a mammal has two copies of each gene. The copy number can be increased, e.g., by gene amplification or duplication, or reduced by deletion.

"Threshold value," as used herein, is a value that is a function of the number of reads required to be present to assign a nucleotide value to a subgenomic interval. E.g., it is a function of the number of reads having a specific nucleotide value, e.g., A, at a nucleotide position, required to assign that nucleotide value to that nucleotide position in the subgenomic interval. The threshold value can, e.g., be expressed as (or as a function of) a number of reads, e.g., an integer, or as a proportion of reads having the preselected value. By way of example, if the threshold value is X, and X+1 reads having the nucleotide value of "A" are present, then the value of "A" is assigned to the preselected position in the subgenomic interval. The threshold value can also be expressed as a function of a mutation or variant expectation, mutation frequency, or of Bayesian prior. In an embodiment, a preselected mutation frequency would require a preselected number or proportion of reads having a nucleotide value, e.g., A or G, at a preselected position, to call that that nucleotide value. In embodiments the threshold value can be a function of mutation expectation, e.g., mutation frequency, and tumor type. E.g., a preselected variant at a preselected nucleotide position could have a first threshold value if the patient has a first tumor type and a second threshold value if the patient has a second tumor type.

As used herein, "target member" refers to a nucleic acid molecule that one desires to isolate from the nucleic acid library. In one embodiment, the target members can be a tumor member, a reference member, a control member, or a PGx member as described herein.

"Tumor member," or other similar term (e.g., a "tumor or cancer-associated member"), as used herein refers to a member having sequence from a tumor cell. In one embodiment, the tumor member includes a subgenomic interval having a sequence (e.g., a nucleotide sequence) that has an alteration (e.g., a mutation) associated with a cancerous phenotype. In other embodiments, the tumor member includes a subgenomic interval having a wild type sequence (e.g., a wild type nucleotide sequence). For example, a subgenomic interval from a heterozygous or homozygous wild type allele present in a cancer cell. A tumor member can include a reference member or a PGx member.

"Reference member," or other similar term (e.g., a "control member"), as used herein, refers to a member that comprises a subgenomic interval having a sequence (e.g., a nucleotide sequence) that is not associated with the cancerous phenotype. In one embodiment, the reference member includes a wild-type or a non-mutated nucleotide sequence of a gene or gene product that when mutated is associated with the cancerous phenotype. The reference member can be present in a cancer cell or non-cancer cell.

"PGx member" or other similar term, as used herein, refers to a member that comprises a subgenomic interval that is associated with the pharmacogenetic or pharmacogenomic profile of a gene. In one embodiment, the PGx member includes an SNP (e.g., an SNP as described herein). In other embodiments, the PGx member includes a subgenomic interval according to Table 1 or Table 2.

"Variant," as used herein, refers to a structure that can be present at a subgenomic interval that can have more than one structure, e.g., an allele at a polymorphic locus.

Headings, e.g., (a), (b), (i) etc, are presented merely for ease of reading the specification and claims. The use of headings in the specification or claims does not require the steps or elements be performed in alphabetical or numerical order or the order in which they are presented.

Selection of Gene or Gene Products

The selected genes or gene products (also referred to herein as the "target genes or gene products") can include subgenomic intervals comprising intragenic regions or intergenic regions. For example, the subgenomic interval can include an exon or an intron, or a fragment thereof, typically an exon sequence or a fragment thereof. The subgenomic interval can include a coding region or a non-coding region, e.g., a promoter, an enhancer, a 5' untranslated region (5' UTR), or a 3' untranslated region (3' UTR), or a fragment thereof. In other embodiments, the subgenomic interval includes a cDNA or a fragment thereof. In other embodiments, the subgenomic interval includes an SNP, e.g., as described herein.

In other embodiments, the subgenomic intervals include substantially all exons in a genome, e.g., one or more of the subgenomic intervals as described herein (e.g., exons from selected genes or gene products of interest (e.g., genes or gene products associated with a cancerous phenotype as described herein)). In one embodiment, the subgenomic interval includes a somatic mutation, a germ line mutation or both. In one embodiment, the subgenomic interval includes an alteration, e.g., a point or a single mutation, a deletion mutation (e.g., an in-frame deletion, an intragenic deletion, a full gene deletion), an insertion mutation (e.g., intragenic insertion), an inversion mutation (e.g., an intra-chromosomal inversion), a linking mutation, a linked insertion mutation, an inverted duplication mutation, a tandem duplication (e.g., an intrachromosomal tandem duplication), a translocation (e.g., a chromosomal translocation, a non-reciprocal translocation), a rearrangement, a change in gene copy number, or a combination thereof. In certain embodiments, the subgenomic interval constitutes less than 5, 1, 0.5, 0.1%, 0.01%, 0.001% of the coding region of the genome of the tumor cells in a sample. In other embodiments, the subgenomic intervals are not involved in a disease, e.g., are not associated with a cancerous phenotype as described herein.

In one embodiment, the target gene or gene product is a biomarker. As used herein, a "biomarker" or "marker" is a gene, mRNA, or protein which can be altered, wherein said alteration is associated with cancer. The alteration can be in amount, structure, and/or activity in a cancer tissue or cancer cell, as compared to its amount, structure, and/or activity, in a normal or healthy tissue or cell (e.g., a control), and is associated with a disease state, such as cancer. For example, a marker associated with cancer, or predictive of responsiveness to anti-cancer therapeutics, can have an altered nucleotide sequence, amino acid sequence, chromosomal translocation, intra-chromosomal inversion, copy number, expression level, protein level, protein activity, or methylation status, in a cancer tissue or cancer cell as compared to a normal, healthy tissue or cell. Furthermore, a "marker" includes a molecule whose structure is altered, e.g., mutated (contains a mutation), e.g., differs from the wild type sequence at the nucleotide or amino acid level, e.g., by substitution, deletion, or insertion, when present in a tissue or cell associated with a disease state, such as cancer.

In one embodiment, the target gene or gene product includes a single-nucleotide polymorphism (SNP). In another embodiment, the gene or gene product has a small deletion, e.g., a small intragenic deletion (e.g., an in-frame or frame-shift deletion). In yet another embodiment, the target sequence results from the deletion of an entire gene. In still another embodiment, the target sequence has a small insertion, e.g., a small intragenic insertion. In one embodiment, the target sequence results from an inversion, e.g., an intrachromosal inversion. In another embodiment, the target sequence results from an interchromosal translocation. In yet another embodiment, the target sequence has a tandem duplication. In one embodiment, the target sequence has an undesirable feature (e.g., high GC content or repeat element). In another embodiment, the target sequence has a portion of nucleotide sequence that cannot itself be successfully targeted, e.g., because of its repetitive nature. In one embodiment, the target sequence results from alternative splicing. In another embodiment, the target sequence is chosen from a gene or gene product, or a fragment thereof according to Table 1, 1A, 2, 3, or 4.

Cancers include, but are not limited to, B cell cancer, e.g., multiple myeloma, melanomas, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia Vera, Hodgkin lymphoma, non-Hodgkin lymphoma (NHL), soft-tissue sarcoma, fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and the like.

In one embodiment, the target gene or gene product is chosen a full length, or a fragment thereof, selected from the group consisting of ABCB1, ABCC2, ABCC4, ABCG2, ABL1, ABL2, AKT1, AKT2, AKT3, ALK, APC, AR, ARAF, ARFRP1, ARID1A, ATM, ATR, AURKA, AURKB, BCL2, BCL2A1, BCL2L1, BCL2L2, BCL6, BRAF, BRCA1, BRCA2, C1orf144, CARD11, CBL, CCND1, CCND2, CCND3, CCNE1, CDH1, CDH2, CDH20, CDH5, CDK4, CDK6, CDK8, CDKN2A, CDKN2B, CDKN2C, CEBPA, CHEK1, CHEK2, CRKL, CRLF2, CTNNB1, CYP1B1, CYP2C19, CYP2C8, CYP2D6, CYP3A4, CYP3A5, DNMT3A, DOT1L, DPYD, EGFR, EPHA3, EPHA5, EPHA6, EPHA7, EPHB1, EPHB4, EPHB6, ERBB2, ERBB3, ERBB4, ERCC2, ERG, ESR1, ESR2, ETV1, ETV4, ETV5, ETV6, EWSR1, EZH2, FANCA, FBXW7, FCGR3A, FGFR1, FGFR2, FGFR3, FGFR4, FLT1, FLT3, FLT4, FOXP4, GATA1, GNA11, GNAQ, GNAS, GPR124, GSTP1, GUCY1A2, HOXA3, HRAS, HSP90AA1, IDH1, IDH2, IGF1R, IGF2R, IKBKE, IKZF1, INHBA, IRS2, ITPA, JAK1, JAK2, JAK3, JUN, KDR, KIT, KRAS, LRP1B, LRP2, LTK, MAN1B1, MAP2K1, MAP2K2, MAP2K4, MCL1, MDM2, MDM4, MEN1, MET, MITF, MLH1, MLL, MPL, MRE11A, MSH2, MSH6, MTHFR, MTOR, MUTYH, MYC, MYCL1, MYCN, NF1, NF2, NKX2-1, NOTCH1, NPM1, NQO1, NRAS, NRP2, NTRK1, NTRK3, PAK3, PAX5, PDGFRA, PDGFRB, PIK3CA, PIK3R1, PKHD1, PLCG1, PRKDC, PTCH1, PTEN, PTPN11, PTPRD, RAF1, RARA, RB1, RET, RICTOR, RPTOR, RUNX1, SLC19A1, SLC22A2, SLCO1B3, SMAD2, SMAD3, SMAD4, SMARCA4, SMARCB1, SMO, SOD2, SOX10, SOX2, SRC, STK11, SULT1A1, TBX22, TET2, TGFBR2, TMPRSS2, TOP1, TP53, TPMT, TSC1, TSC2, TYMS, UGT1A1, UMPS, USP9X, VHL, and WT1.

In one embodiment, the target gene or gene product, or a fragment thereof, has one or more SNPs that are relevant to pharmacogenetics and pharmacogenomics (PGx), e.g., drug metabolism and toxicity. Exemplary genes or gene products include, but not limited to, ABCB1, ABCC2, ABCC4, ABCG2, C1orf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, and UMPS.

In another embodiment, the target gene or gene product, or a fragment thereof, has one or more codons that are associated with cancer. Exemplary genes or gene products include, but not limited to, ABL1 (e.g., codon 315), AKT1, ALK, APC (e.g., codon 1114, 1338, 1450, and 1556), AR, BRAF (e.g., codon 600), CDKN2A, CEBPA, CTNNB1 (e.g., codon 32, 33, 34, 37, 41, and 45), EGFR (e.g., 719, 746-750, 768, 790, 858, and 861), ERBB2, ESR1, FGFR1, FGFR2, FGFR3, FLT3 (e.g., codon 835), HRAS (e.g., codon 12, 13, and 61), JAK2 (e.g., codon 617), KIT (e.g., codon 816), KRAS (e.g., codon 12, 13, and 61), MET, MLL, MYC, NF1, NOTCH1, NPM1, NRAS, PDGFRA, PIK3CA (e.g., codon 88, 542, 545, 546, 1047, and 1049), PTEN (e.g., codon 130, 173, 233, and 267), RB1, RET (e.g., codon 918), TP53 (e.g., 175, 245, 248, 273, and 306).

In yet another embodiment, the target gene or gene product, or a fragment thereof, are associated with cancer. Exemplary genes or gene products include, but not limited to, ABL2, AKT2, AKT3, ARAF, ARFRP1, ARID1A, ATM, ATR, AURKA, AURKB, BCL2, BCL2A1, BCL2L1, BCL2L2, BCL6, BRCA1, BRCA2, CARD11, CBL, CCND1, CCND2, CCND3, CCNE1, CDH1, CDH2, CDH20, CDH5, CDK4, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, INHBA, IRS2, JAK1, JAK3, JUN, KDR, LRP1B, LTK, MAP2K1, MAP2K2, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK3, PAK3, PAX5, PDGFRB, PIK3R1, PKHD1, PLCG1, PRKDC, PTCH1, PTPN11, PTPRD, RAF1, RARA, RICTOR, RPTOR, RUNX1, SMAD2, SMAD3, SMAD4, SMARCA4, SMARCB1, SMO, SOX10, SOX2, SRC, STK11, TBX22, TET2, TGFBR2, TMPRSS2, TOP1, TSC1, TSC2, USP9X, VHL, and WT1.

Applications of the foregoing methods include using a library of oligonucleotides containing all known sequence variants (or a subset thereof) of a particular gene or genes for sequencing in medical specimens.

Gene Selection Module

This module discloses sets of subgenomic intervals for use in methods featured in the invention, e.g., subgenomic intervals for sets or groups of genes and other regions described herein.

Optimized methods and assays for sequencing large numbers of genes and gene products from samples, e.g., tumor samples, from one or more subjects are disclosed. In one embodiment, the methods and assays featured in the invention are used in a multiplex, multi-gene assay format, e.g., assays that incorporate multiple signals from a large number of diverse genetic events in a large number of genes. Disclosed herein are methods and assays that are based, at least in part, on a pre-selected set of genes or gene products that are associated (e.g., positively or negatively) with a cancerous phenotype (e.g., one or more of cancer risk, cancer progression, cancer treatment response or resistance to cancer treatment). Such pre-selected genes or gene products enable the application of sequencing methods, particularly methods that rely on massively parallel sequencing of a large number of diverse genes, e.g., from tumor or control samples.

Accordingly, the invention features a method of analyzing a sample, e.g., a tumor sample.

The method comprises:

(a) acquiring a library comprising a plurality members from a sample, e.g., a plurality of tumor members from a tumor sample;

(b) optionally, enriching the library for preselected sequences, e.g., by contacting the library with a bait set (or plurality of bait sets) to provide selected members (sometimes referred to herein as library catch);

(c) acquiring a read for a subgenomic interval from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayesian method or a method described herein) from said read for the preselected nucleotide position, thereby analyzing said tumor sample, wherein the method comprises sequencing, e.g., by a next generation sequencing method, a subgenomic interval from at least five, six, seven, eight, nine, ten, fifteen, twenty, twenty-five, thirty or more genes or gene products from the sample, wherein the genes or gene products are chosen from: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53.

In an embodiment, step (b) is present. In an embodiment, step (b) is absent.

Thus, in embodiments a method comprises sequencing, e.g., by a next generation sequencing method, a subgenomic interval from at least five, six, seven, eight, nine, ten, fifteen, twenty, twenty-five, thirty or more genes or gene products from the acquired nucleic acid sample, wherein the genes or gene products are chosen from: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53, thereby analyzing the tumor sample.

In certain embodiments, the method, or the assay, further includes sequencing a subgenomic interval from a gene or gene product chosen from one, two, three, four, five, ten, fifteen, twenty, twenty-five, thirty, thirty-five, forty, forty-five, fifty, fifty-five, sixty, sixty-five, seventy, seventy-five, eighty, eighty-five, ninety, ninety-five, one hundred, one hundred and five, one hundred and ten, one hundred and fifteen, one hundred and twenty or more of: ABL2, ARAF, ARFRP1, ARID1A, ATM, ATR, AURKA, AURKB, BAP1, BCL2, BCL2A1, BCL2L1, BCL2L2, BCL6, BRCA1, BRCA2, CBL, CARD11, CBL, CCND2, CCND3, CCNE1, CD79A, CD79B, CDH1, CDH2, CDH20, CDH5, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, INHBA, IRS2, JAK1, JAK3, JUN, KDM6A, KDR, LRP1B, LRP6, LTK, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK2, PAK3, PAX5, PDGFRB, PKHD1, PLCG1, PRKDC, PTPN11, PTPRD, RAF1, RARA, RICTOR, RPTOR, RUNX1, SMAD2, SMAD3, SMAD4, SMARCA4, SMARCB1, SOX10, SOX2, SRC, TBX22, TET2, TGFBR2, TMPRSS2, TNFAIP3, TNK, TNKS2, TOP1, TSC1, TSC2, USP9X, VHL, or WT1.

In other embodiments, the method, or the assay, further includes sequencing a subgenomic interval that is present in a gene or gene product associated with one or more of drug metabolism, drug responsiveness, or toxicity (also referred to therein as "PGx" genes). In certain embodiments, the subgenomic interval sequenced includes an alteration (e.g., single nucleotide polymorphism (SNP)). In one embodiment, the subgenomic interval sequenced is from a gene or gene product chosen from one, two, three, four, five, ten, fifteen, twenty, twenty-five, thirty or more of: ABCB1, BCC2, ABCC4, ABCG2, C1orf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, or UMPS.

In other embodiments, the method, or the assay, further includes sequencing a subgenomic interval that is present in a gene or gene product chosen from one, two, three, four, five, ten, fifteen, twenty or more of ARFRP1, BCL2A1, CARD11, CDH20, CDH5, DDR2, EPHA3, EPHA5, EPHA7, EPHB1, FOXP4, GPR124, GUCY1A2, INSR, LRP1B, LTK, PAK3, PHLPP2, PLCG1, PTPRD, STAT3, TBX22 or USP9X.

In certain embodiments, the sequenced subgenomic interval of the nucleic acid sample includes a nucleotide sequence from at least 50, 75, 100, 150, 200 or more genes or gene products from Table 1 or 1A. In other embodiments, the sequenced subgenomic interval of the nucleic acid sample includes a nucleotide sequence from at least 50, 75, 100, 150, 200 or more genes or gene products from Table 1 or 1A acquired from a tumor sample from the cancer types specified therein. In yet other embodiments, the sequenced subgenomic interval includes a combination of the Priority 1 genes and the PGx genes according to Table 1 or 1A (e.g., at least 5, 10, 20 or 30 Priority 1 genes; and at least 5, 10, 20 or 30 PGX genes according to Table 1 or 1A). In other embodiments, the sequenced subgenomic interval includes a combination of the Priority 1 genes, Cancer genes and PGx genes according to Table 1 or 1A (e.g., at least 5, 10, 20 or 30 Priority 1 genes; at least 5, 10, 20 or 30 Cancer genes; and at least 5, 10, 20 or 30 PGX genes according to Table 1 or 1A).

In certain embodiments, the sequenced subgenomic interval of the nucleic acid sample includes a codon chosen from one or more of: codon 315 of the ABL1 gene; codon 1114, 1338, 1450 or 1556 of APC; codon 600 of BRAF; codon 32, 33, 34, 37, 41 or 45 of CTNNB1; codon 719, 746-750, 768, 790, 858 or 861 of EGFR; codon 835 of FLT3; codon 12, 13, or 61 of HRAS; codon 617 of JAK2; codon 816 of KIT; codon 12, 13, or 61 of KRAS; codon 88, 542, 545, 546, 1047, or 1049 of PIK3CA; codon 130, 173, 233, or 267 of PTEN; codon 918 of RET; codon 175, 245, 248, 273, or 306 of TP53. In certain embodiments, two, three, four, five, ten, fifteen, twenty or more of the aforesaid codons are sequenced. In other embodiments, the sequenced subgenomic interval includes one or more of the codons shown in Table 1 or 1A.

In other embodiments, the sequenced subgenomic interval of the nucleic acid sample includes a nucleotide sequence from at least one, five, ten fifteen, twenty, twenty-five or more PGx genes or gene products from Table 1. In other embodiments, the sequenced subgenomic interval of the nucleic acid sample includes a nucleotide sequence from at least 1, 5, 10, 15, 20, 25, 30, 35, 40, 45, 50, 75, or more PGx genes or gene products from Table 2. In yet other embodiments, the sequenced subgenomic interval includes a nucleotide sequence from at least one PGx gene (and/or at least one PGx gene mutation) according to Table 2 that is associated with one or more of: drug metabolism, drug responsiveness, drug toxicity or side effects. For example, the sequenced subgenomic interval can include a nucleotide sequence from at least one PGx gene associated with better survival of a cancer patient treated with a drug (e.g., better survival of a breast cancer patient treated with paclitaxel (e.g., an ABCB1 gene)). In other embodiments, the sequenced subgenomic interval is associated with paclitaxel metabolism (e.g., CYP2C8 genes at different loci and mutations shown in Table 2; a CYP3A4 gene). In yet other embodiments, the sequenced subgenomic interval is associated with toxicity to a drug (e.g., 6-MP toxicity as seen with ABCC4 gene (Table 2); 5-FU toxicity as seen with DPYD gene, TYMS gene, and UMPS gene (Table 2); purine toxicity as seen with TMPT gene (Table 2); daunorubicin toxicity as seen with NRP2 gene; C1orf144 gene, CYP1B1 gene (Table 2)). In other embodiments, the sequenced subgenomic interval is associated with a side effect to a drug (e.g., ABCG2, TYMS, UGT1A1, ESR1 and ESR2 genes (Table 2)).

In another embodiment subgenomic intervals from one of the following sets or groups are analyzed. E.g., subgenomic intervals associated with a tumor or cancer gene or gene product, a reference (e.g., a wild type) gene or gene product, or a PGx gene or gene product, thereby obtaining a selected subset of subgenomic intervals from the tumor sample.

In an embodiment, the method sequences a subset of subgenomic intervals from the tumor sample, wherein the subgenomic intervals are chosen from at least 1, 2, 3, 4, 5, 6, 7, 8, 9, 10, 11, 12, 13 or all of the following:

A) at least five, six, seven, eight, nine, ten, fifteen, twenty, twenty-five, thirty or more subgenomic intervals from a mutated or wild-type gene or gene product chosen from at least five or more of: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53;

B) at least five, six, seven, eight, nine, ten, fifteen, twenty, twenty-five, thirty, thirty-five, forty, forty-five, fifty, fifty-five, sixty, sixty-five, seventy, seventy-five, eighty, eighty-five, ninety, ninety-five, one hundred, one hundred and five, one hundred and ten, one hundred and fifteen, one hundred and twenty or more of subgenomic intervals from a mutated or wild type gene or gene product chosen from at least five or more of: ABL2, ARAF, ARFRP1, ARID1A, ATM, ATR, AURKA, AURKB, BAP1, BCL2, BCL2A1, BCL2L1, BCL2L2, BCL6, BRCA1, BRCA2, CBL, CARD11, CBL, CCND2, CCND3, CCNE1, CD79A, CD79B, CDH1, CDH2, CDH20, CDH5, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, INHBA, IRS2, JAK1, JAK3, JUN, KDM6A, KDR, LRP1B, LRP6, LTK, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK2, PAK3, PAX5, PDGFRB, PKHD1, PLCG1, PRKDC, PTPN11, PTPRD, RAF1, RARA, RICTOR, RPTOR, RUNX1, SMAD2, SMAD3, SMAD4, SMARCA4, SMARCB1, SOX10, SOX2, SRC, TBX22, TET2, TGFBR2, TMPRSS2, TNFAIP3, TNK, TNKS2, TOP1, TSC1, TSC2, USP9X, VHL, or WT1;

C) at least five, six, seven, eight, nine, ten, fifteen, twenty, or more subgenomic intervals from a gene or gene product according to Table 1, 1A, 2, 3 or 4;

D) at least five, six, seven, eight, nine, ten, fifteen, twenty, or more subgenomic intervals from a gene or gene product that is associated with a tumor or cancer (e.g., is a positive or negative treatment response predictor, is a positive or negative prognostic factor for, or enables differential diagnosis of a tumor or cancer, e.g., a gene or gene product chosen from one or more of: ABL1, AKT1, ALK, AR, BRAF, BRCA1, BRCA2, CEBPA, EGFR, ERBB2, FLT3, JAK2, KIT, KRAS, MET, NPM1, PDGFRA, PIK3CA, RARA, AKT2, AKT3, MAP2K4, NOTCH1, and TP53;

E) at least five, six, seven, eight, nine, ten, or more subgenomic intervals including a mutated or a wild type codon chosen from one or more of: codon 315 of the ABL1 gene; codon 1114, 1338, 1450 or 1556 of APC; codon 600 of BRAF; codon 32, 33, 34, 37, 41 or 45 of CTNNB1; codon 719, 746-750, 768, 790, 858 or 861 of EGFR; codon 835 of FLT3; codon 12, 13, or 61 of HRAS; codon 617 of JAK2; codon 816 of KIT; codon 12, 13, or 61 of KRAS; codon 88, 542, 545, 546, 1047, or 1049 of PIK3CA; codon 130, 173, 233, or 267 of PTEN; codon 918 of RET; codon 175, 245, 248, 273, or 306 of TP53 (e.g., at least five, ten, fifteen twenty or more subgenomic intervals that include one or more of the codons shown in Table 1 or 1A).

F) at least five, six, seven, eight, nine, ten, fifteen, twenty, twenty-five, thirty, or more of subgenomic intervals from a mutated or wild type gene or gene product (e.g., single nucleotide polymorphism (SNP)) of a subgenomic interval that is present in a gene or gene product associated with one or more of drug metabolism, drug responsiveness, or toxicity (also referred to therein as "PGx" genes) chosen from: ABCB1, BCC2, ABCC4, ABCG2, C1orf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, or UMPS;

G) at least five, six, seven, eight, nine, ten, fifteen, twenty, twenty-five, thirty, or more of subgenomic intervals from a mutated or wild type PGx gene or gene product (e.g., single nucleotide polymorphism (SNP)) of a subgenomic interval that is present in a gene or gene product associated with one or more of: (i) better survival of a cancer patient treated with a drug (e.g., better survival of a breast cancer patient treated with paclitaxel (e.g., an ABCB1 gene)); (ii) paclitaxel metabolism (e.g., CYP2C8 genes at different loci and mutations shown in Table 2; CYP3A4 gene); (iii) toxicity to a drug (e.g., 6-MP toxicity as seen with ABCC4 gene (Table 2); 5-FU toxicity as seen with DPYD gene, TYMS gene, or UMPS gene (Table 2); purine toxicity as seen with a TMPT gene (Table 2); daunorubicin toxicity as seen with NRP2 gene; C1orf144 gene, CYP1B1 gene (Table 2); or (iv) a side effect to a drug (e.g., ABCG2, TYMS, UGT1A1, ESR1 and ESR2 genes (Table 2));

H) a translocation alteration of at least 5, 10, 15, 20, 25, 30, 35, 40, 45, 50, 75, 110 or more genes or gene products according to Table 3;

J) a translocation alteration of at least 5, 10, 15, 20, 25, 30, 35, 40, 45, 50, 75, 110 or more genes or gene products according to Table 3 in a solid tumor sample from the cancer types specified therein;

K) a translocation alteration of at least 5, 10, 15, 20, 25, 30, 35, 40, 45, 50, 75, 100, 150, 200 or more genes or gene products according to Table 4;

L) a translocation alteration of at least 5, 10, 15, 20, 25, 30, 35, 40, 45, 50, 75, 100, 150, 200 or more genes or gene products according to Table 4 in a heme tumor sample from the cancer types specified therein;

M) at least five genes or gene products selected from Table 1, 1A-4, wherein an allelic variation, e.g., at the preselected position, is associated with a preselected type of tumor and wherein said allelic variation is present in less than 5% of the cells in said tumor type;

N) at least five genes or gene products selected from Table 1, 1A-4, which are embedded in a GC-rich region; or O) at least five genes or gene products indicative of a genetic (e.g., a germline risk) factor for developing cancer (e.g., the gene or gene product is chosen from one or more of BRCA1, BRCA2, EGFR, HRAS, KIT, MPL, ALK, PTEN, RET, APC, CDKN2A, MLH1, MSH2, MSH6, NF1, NF2, RB1, TP53, VHL or WT1).

In certain embodiments, the acquiring step of the method or assay includes acquiring a library that includes a plurality of tumor or cancer-associated members, reference members and/or PGx members as described herein from said tumor sample. In certain embodiments, the selecting step includes solution based hybridization (e.g., to select or enrich for the tumor or cancer-associated member, the reference member (e.g., the wild type member), or the PGx member, each comprising a subgenomic interval from a gene or gene product as described herein.

Additional embodiments or features of the present invention are as follows:

In one embodiment, the subgenomic interval of the nucleic acid sample includes an intragenic region or an intergenic region. In one embodiment, the subgenomic interval includes a gene or fragment thereof, an exon or a fragment thereof, or a preselected nucleotide position.

In another embodiment, the subgenomic interval includes an exon or an intron, or a fragment thereof, typically an exon or a fragment thereof. In one embodiment, the subgenomic interval includes a coding region or a non-coding region, e.g., a promoter, an enhancer, a 5' untranslated region (5' UTR), or a 3' untranslated region (3' UTR), or a fragment thereof.

In other embodiments, the subgenomic interval of the nucleic acid sample includes an alteration (e.g., one or more mutations) associated, e.g., positively or negatively, with a cancerous phenotype (e.g., one or more of cancer risk, cancer progression, cancer treatment or resistance to treatment). In yet another embodiment, the subgenomic interval includes an alteration, e.g., a point or a single mutation, a deletion mutation (e.g., an in-frame deletion, an intragenic deletion, a full gene deletion), an insertion mutation (e.g., intragenic insertion), an inversion mutation (e.g., an intra-chromosomal inversion), a linking mutation, a linked insertion mutation, an inverted duplication mutation, a tandem duplication (e.g., an intrachromosomal tandem duplication), a translocation (e.g., a chromosomal translocation, a non-reciprocal translocation), a rearrangement, a change in gene copy number, or a combination thereof.

In other embodiments, the subgenomic interval of the nucleic acid sample includes a nucleic acid molecule (in the same or a different subgenomic interval) not associated with the cancerous phenotype for the tumor of the type from the sample. In one embodiment, the sequenced subgenomic interval includes a wild-type or a non-mutated nucleotide sequence of a gene or gene product (e.g., an exon sequence or a fragment thereof) that when mutated is associated with a cancerous phenotype (e.g., a wild type or a non-mutated sequence of a gene or gene product as described herein). For example, the sequenced subgenomic interval is from a normal (e.g., non-cancerous) reference sample (e.g., form the same subject from whom the tumor sample was obtained); a normal adjacent tissue (NAT) or a blood sample from the same subject having or at risk of having the tumor. In other embodiments, the sequenced subgenomic interval is from a different subject as the tumor or cancer-associated member (e.g., is from one or more of the same or a different tumor sample from a different subject; a normal (e.g., non-cancerous) reference sample; a normal adjacent tissue (NAT); or a blood sample), from one or more different subjects (e.g., healthy subjects or other subjects having or at risk of having the tumor).

In other embodiments, the subgenomic interval of the nucleic acid sample includes one or more translocation alterations as shown in Table 3, Table 4, or a combination thereof. In certain embodiments, the sequenced subgenomic interval includes a translocation alteration of at least 5, 10, 15, 20, 25, 30, 35, 40, 45, 50, 75, 110 or more genes or gene products according to Table 3.

In other embodiments, the sequenced subgenomic interval includes a translocation alteration of at least 5, 10, 15, 20, 25, 30, 35, 40, 45, 50, 75, 110 or more genes or gene products according to Table 3 in a tumor sample from the cancer types specified therein. In other embodiments, the sequenced subgenomic interval includes a translocation alteration of at least 5, 10, 15, 20, 25, 30, 35, 40, 45, 50, 75, 100, 150, 200 or more genes or gene products according to Table 4. In other embodiments, the sequenced subgenomic interval includes a translocation alteration of at least 5, 10, 15, 20, 25, 30, 35, 40, 45, 50, 75, 100, 150, 200 or more genes or gene products from Table 4 in a tumor sample from the cancer types specified therein.

In one embodiment, the subgenomic interval of the nucleic acid sample includes an exon sequence that includes a single nucleotide alteration associated with a cancerous phenotype. For example, the subgenomic interval includes nucleotides 25,398,215-25,398,334 of chromosome 12. In other embodiments, the subgenomic interval includes a C-T substitution at position 25,398,286, which represents a G12S mutation in the KRAS gene.

In another embodiment, the subgenomic interval of the nucleic acid sample includes an in-frame deletion of 1, 2, 3, 4, 5, 6, 7, 8, 9, 10, 11, 12, 13, 14, 15, 16, 17, 18, 19, 20 or more codons from a reference nucleotide (e.g., chromosome) sequence. In one embodiment, the subgenomic interval includes an in-frame deletion of codons 746-750 of the EGFR gene (e.g., the subgenomic interval includes nucleotides 55,242,400 to 55,242,535 of chromosome 7, but lacks nucleotides 55,242,464 to 55,242,479).

In yet another embodiment, the subgenomic interval of the nucleic acid sample includes a deletion of the dinucleotide sequence "CA" from codon 64 of the PTEN gene (e.g., the subgenomic interval includes nucleotides 9,675,214 to 89,675,274 of chromosome 10, followed by bases 89,675,277 to 89,675,337 of chromosome 10.

In yet another embodiment, the subgenomic interval of the nucleic acid sample includes an insertion of amino acid residues "Gly-Met" following codon 136 of the PTEN (e.g., the subgenomic interval includes nucleotides 89,692,864 to 89,692,924 of chromosome 10, followed by a nucleotide sequence "GGNATG", followed by nucleotides 89,692,925 to 89,692,980 of chromosome 10).

In yet another embodiment, the subgenomic interval of the nucleic acid sample includes a deletion of the CDKN2A gene (e.g., the subgenomic interval includes nucleotides 21,961,007 to 21,961,067 of chromosome 9 adjacent to bases 22,001,175 to 22,001,235 of chromosome 9).

In another embodiment, the sequenced subgenomic interval of the nucleic acid sample includes an inversion producing an EML4:ALK fusion (e.g., the subgenomic interval includes nucleotides 42,522,893 to 42,522,953 of chromosome 2, juxtaposed with nucleotides 29,449,993 to 29,449,933 of chromosome 2).

In another embodiment, the subgenomic interval of the nucleic acid sample includes an interchromosal translocation resulting in a BCR-ABL fusion (e.g., the subgenomic interval includes nucleotides 23,632,552 to 23,632,612 of chromosome 22, juxtaposed with nucleotides 133,681,793 to 133,681,853 of chromosome 9).

In another embodiment, the subgenomic interval of the nucleic acid sample includes an internal tandem duplication (ITD) mutation in the FLT3 gene (e.g., the subgenomic interval includes nucleotides 28,608,259 to 28,608,285 of chromosome 13 repeated twice in the same orientation.

In another embodiment, the subgenomic interval of the nucleic acid sample includes a microsatellite marker sequence (e.g., the subgenomic interval includes a microsatellite marker sequence of D2S123, e.g., nucleotides 51,288,380 to 51,288,500 and nucleotides 51,288,560 to 51,288,680 of chromosome 2.

In another embodiment, the subgenomic interval of the nucleic acid sample includes a nucleotide sequence corresponding to a fusion sequence (e.g., a fusion transcript or a cancer associated alternative spliced form of a non-fusion transcript).

In other embodiments, the subgenomic interval of the nucleic acid sample includes a nucleotide sequence, wherein the presence or absence of a preselected allelic variant is indicative of a cancer-related phenotype (e.g., one or more of cancer risk, cancer progression, cancer treatment response or resistance to treatment, tumor staging, metastatic likelihood, etc.). In certain embodiments, the sequenced subgenomic interval of the nucleic acid sample includes a nucleotide sequence, wherein the presence or absence of a preselected allelic variant is predictive of a positive clinical outcome, and/or responsiveness to therapy. In other embodiments, the sequenced subgenomic interval of the nucleic acid sample includes a nucleotide sequence, wherein the presence or absence of a preselected allelic variant is predictive of a negative clinical outcome, and/or responsiveness to therapy. In certain embodiments, the sequenced subgenomic interval of the nucleic acid sample includes a nucleotide sequence, wherein the presence or absence of a preselected allelic variant is indicative of a genetic (e.g., a germline risk) factor for developing cancer (e.g., the gene or gene product is chosen from one or more of BRCA1, BRCA2, EGFR, HRAS, KIT, MPL, ALK, PTEN, RET, APC, CDKN2A, MLH1, MSH2, MSH6, NF1, NF2, RB1, TP53, VHL or WT1).

In other embodiments, the subgenomic interval of the nucleic acid sample is from one or more genes or gene products shown in Table 1, 1A, 3 or 4, that is associated with a cancerous phenotype, e.g., a cancer chosen from one or more of the cancer types described in Tables 1, 1A, 3 or 4.

In one embodiment, the subgenomic interval of the nucleic acid sample is from an ABL-1 gene or gene product, that is associated with a cancerous phenotype, e.g., a soft-tissue malignancy chosen from one or more of CML, ALL or T-ALL. In other embodiments, the sequenced subgenomic interval of the nucleic acid sample is from an AKT1 gene or gene product that is associated with a cancerous phenotype, e.g., a cancer chosen from one or more of breast, colorectal, ovarian, or non-small cell lung carcinoma (NSCLC).

In other embodiments, the subgenomic interval of the nucleic acid sample is from an ALK gene or gene product that is associated with a cancerous phenotype, e.g., a cancer chosen from one or more of ALCL, NSCLC or neuroblastoma.

In other embodiments, the subgenomic interval of the nucleic acid sample is from an APC gene or gene product that is associated with a cancerous phenotype, e.g., a cancer chosen from one or more of colorectal, pancreatic, desmoid, hepatoblastoma, glioma, or other CNS cancers or tumors.

In other embodiments, the subgenomic interval of the nucleic acid sample is from a BRAF gene or gene product that is associated with a cancerous phenotype, e.g., a cancer chosen from one or more of melanoma, colorectal cancer, lung cancer, other epithelial malignancies, or hamatological malignancies including AML or ALL.

In other embodiments, the subgenomic interval of the nucleic acid sample is from a CDKN2A gene or gene product, that is associated with a cancerous phenotype, e.g., a cancer chosen from one or more of melanoma, pancreatic, or other tumor types.

In other embodiments, the sequenced subgenomic interval of the nucleic acid sample is from a CEBPA gene or gene product, that is associated with a cancerous phenotype, e.g., a cancer chosen from one or more of AML or MDS.

In other embodiments, the subgenomic interval of the nucleic acid sample is from a CTNNB1 gene or gene product, that is associated with a cancerous phenotype, e.g., a cancer chosen from one or more of colorectal, ovarian, hepatoblastoma, or pleomorphic salivary adenoma.

In other embodiments, the subgenomic interval of the nucleic acid sample is from an EGFR gene or gene product, that is associated with a cancerous phenotype, e.g., a cancer chosen from one or more of glioma, lung cancer, or NSCLC.

In other embodiments, the subgenomic interval of the nucleic acid sample is from an ERBB2 gene or gene product, that is associated, e.g., positively or negatively, with a cancerous phenotype, e.g., a cancer chosen from one or more of breast, ovarian, NSCLC, gastric or other solid tumors.

In other embodiments, the subgenomic interval of the nucleic acid sample is from an ESR1 gene or gene product that is associated with a cancerous phenotype, e.g., a cancer chosen from one or more of breast, ovarian or endometrial tumors.

In other embodiments, the subgenomic interval of the nucleic acid sample is from an FGFR1 gene or gene product that is associated with a cancerous phenotype, e.g., a cancer chosen from one or more of MPD or NHL.

In other embodiments, the subgenomic interval of the nucleic acid sample is from an FGFR2 gene or gene product, that is associated with a cancerous phenotype, e.g., a cancer chosen from one or more of gastric, NSCLC or endometrial tumors. In one embodiment, the library, e.g., the nucleic acid library, is obtained from a sample from a subject having, or at risk of having, one or more of gastric, NSCLC or endometrial tumors.

In other embodiments, the subgenomic interval of the nucleic acid sample is from an FGFR3 gene or gene product, or a subgenomic interval thereof, that is associated with a cancerous phenotype, e.g., a cancer chosen from one or more of bladder cancer, multiple myeloma or T-cell lymphoma.

In other embodiments, the subgenomic interval of the nucleic acid sample is from an FLT3 gene or gene product, or a subgenomic interval thereof, that is associated with a cancerous phenotype, e.g., a cancer chosen from one or more of AML, melanoma, colorectal, papillary thyroid, ovarian, non small-cell lung cancer (NSCLC), cholangiocarcinoma, or pilocytic astrocytoma.

In other embodiments, the subgenomic interval of the nucleic acid sample is from an HRAS gene or gene product that is associated with a cancerous phenotype, e.g., a cancer chosen from one or more of rhabdomyosarcoma, ganglioneuroblastoma, bladder, sarcomas, or other cancer types.

In other embodiments, the subgenomic interval of the nucleic acid sample is from a JAK2 gene or gene product that is associated with a cancerous phenotype, e.g., a cancer chosen from one or more of ALL, AML, MPD or CML.

In other embodiments, the subgenomic interval of the nucleic acid sample is from a KIT gene or gene product, that is associated with a cancerous phenotype, e.g., a cancer chosen from one or more of gastrointestinal stromal tumors (GIST), AML, TGCT, mastocytosis, mucosal melanoma, or epithelioma.

In other embodiments, the subgenomic interval of the nucleic acid sample is from a KRAS gene or gene product that is associated with a cancerous phenotype, e.g., a cancer chosen from one or more of pancreatic, colon, colorectal, lung, thyroid, or AML.

In other embodiments, the subgenomic interval of the nucleic acid sample is from a MET gene or gene product that is associated with a cancerous phenotype, e.g., a cancer chosen from one or more of renal or head-neck squamous cell carcinoma.

In other embodiments, the sequenced subgenomic interval of the nucleic acid sample is from an MLL gene or gene product, that is associated with a cancerous phenotype, e.g., a cancer chosen from one or more of AML or ALL.

In other embodiments, the subgenomic interval of the nucleic acid sample is from an NF1 gene or gene product that is associated with a cancerous phenotype, e.g., a cancer chosen from one or more of neurofibroma or glioma.

In other embodiments, the subgenomic interval of the nucleic acid sample is from a NOTCH1 gene or gene product that is associated with a cancerous phenotype, e.g., a T-ALL cancer.

In other embodiments, the subgenomic interval of the nucleic acid sample is from an NPM1 gene or gene product that is associated with a cancerous phenotype, e.g., a cancer chosen from one or more of NHL, APL or AML.

In other embodiments, the subgenomic interval of the nucleic acid sample is from an NRAS gene or gene product that is associated with a cancerous phenotype, e.g., a cancer chosen from one or more of melanoma, colorectal cancer, multiple myeloma, AML, or thyroid cancer.

In other embodiments, the subgenomic interval of the nucleic acid sample is from a PDGFRA gene or gene product that is associated with a cancerous phenotype, e.g., a cancer chosen from one or more of GIST or idiopathic hypereosinophilic syndrome.

In other embodiments, the subgenomic interval of the nucleic acid sample is from a PIK3CA gene or gene product that is associated with a cancerous phenotype, e.g., a cancer chosen from one or more of colorectal, gastric, gliobastoma, or breast cancer.

In other embodiments, the subgenomic interval of the nucleic acid sample is from a PTEN gene or gene product that is associated with a cancerous phenotype, e.g., a cancer chosen from one or more of colorectal, glioma, prostate, or endometrial cancer.

In other embodiments, the subgenomic interval of the nucleic acid sample is from an RB1 gene or gene product that is associated with a cancerous phenotype, e.g., a cancer chosen from one or more of retinoblastoma, sarcoma, breast, or small cell lung carcinoma.

In other embodiments, the subgenomic interval of the nucleic acid sample is from a RET gene or gene product, that is associated with a cancerous phenotype, e.g., a cancer chosen from one or more of medullary thyroid, papillary thyroid, or pheochromocytoma.

In other embodiments, the subgenomic interval of the nucleic acid sample is from a TP53 gene or gene product that is associated with a cancerous phenotype, e.g., a cancer chosen from one or more of breast, colorectal, lung, sarcoma, adrenocortical, glioma, or other tumor types.

In one embodiment, the subgenomic interval of the nucleic acid sample is a positive predictor of therapeutic response. Examples of a positive predictor of a therapeutic response include, but are not limited to, an activating mutation in the EGFR gene that predicts responsiveness to small molecule EGFR TKIs (e.g., Iressa/gefitinib) in NSCLC patients; presence of an EML4/ALK fusion gene predicts responsiveness to ALK inhibitors (e.g. PF-02341066) in NSCLC patients; presence of a BRAF V600E mutation predicts responsiveness to BRAF inhibition (e.g. PLX-4032) in melanoma patients.

In other embodiments, the subgenomic interval of the nucleic acid sample is a negative predictor of therapeutic response. Examples of a negative predictor of a therapeutic response include, but are not limited to, an activating mutation in the KRAS gene that predict lack of response to anti-EGFR monoclonal antibodies (cetuximab, panitumumab) in CRC patients; and the presence of an M351T mutation in the BCR/Abl fusion gene predicts resistance to Gleevec/imatinib in CML patients.

In other embodiments, the subgenomic interval of the nucleic acid sample is a prognostic factor. Examples of prognostic factors include, but are not limited to, the presence of an insertion mutation in the FLT3 gene, which is a negative prognostic for relapse in AML patients; the presence of specific RET gene mutations, e.g. M918T, which are negative prognostic factors for survival in medullary thyroid carcinoma patients.

In other embodiments, the subgenomic interval of the nucleic acid sample is a diagnostic factor. Examples of prognostic factors include, but are not limited to, the presence of a BCR/Abl fusion gene, which is diagnostic for CML; and the presence of a SMARCB1 mutation, which is diagnostic of Rhabdoid tumor of the kidney.

In other embodiments, the nucleic acid sample includes a subgenomic interval from a gene or gene product that is present in a minority (e.g., less than 5%) of the cells in the tumor sample. In one embodiment, the nucleic acid sample includes a subgenomic interval from a gene or gene product that is associated, e.g., positively or negatively, with a cancer-related phenotype, but which is present in a minority (e.g., less than 5%) of the cells in the tumor sample. In other embodiments, the nucleic acid sample includes a subgenomic interval from a gene or gene product that is present in less than 50, 40, 30, 10, 5, or 1% of the cells in a tumor sample. In yet other embodiments, the nucleic acid sample includes a subgenomic interval from a gene or gene product that is present in more than 50, 60, 70, 80%, or more of the cells in a tumor sample.

In yet other embodiments, the nucleic acid sample includes a subgenomic interval from a gene or gene product that is present in less than 5, 1, 0.5, 0.1%, 0.01%, 0.001% of the coding region of the genome of the tumor cells in the tumor sample.

In one embodiment, the nucleic acid sample includes a subgenomic interval from a gene or gene product that is associated with a tumor or cancer (e.g., is a positive or negative treatment response predictor, is a positive or negative prognostic factor for, or enables differential diagnosis of a tumor or cancer, e.g., a gene or gene product chosen from one or more of: ABL1, AKT1, ALK, AR, BRAF, BRCA1, BRCA2, CEBPA, EGFR, ERBB2, FLT3, JAK2, KIT, KRAS, MET, NPM1, PDGFRA, PIK3CA, RARA, AKT2, AKT3, MAP2K4, NOTCH1, and TP53.

In one embodiment, the cancerous phenotype associated with the gene or gene product is the same tumor type as the tumor sample. In other embodiments, the cancerous phenotype associated with the gene or gene product is from a different tumor type as the tumor sample.

In certain embodiments, the method or assay includes sequencing nucleic acid samples from tumor samples from at least X subjects, (wherein X=1, 2, 3, 4, 5, 6, 7, 8, 9, 10, 20, 30, 40, or more subjects). In one embodiment, the subject is human having, or at risk of having, a cancer or tumor. The method includes sequencing at least 5, 10, 15, 20, 30, 40, 50, 75 or more genes or gene products described herein (e.g., genes or gene products from Table 1, 1A, 2, 3, or 4) from at least X subjects. In certain embodiments, the gene or gene product includes an alteration that is associated with a cancerous phenotype, e.g., one or more of cancer risk, cancer progression, cancer treatment response or resistance to treatment.

In other embodiments or in addition to the aforesaid embodiments, the method or assay includes sequencing a control or reference subgenomic interval from a gene or gene product from the same subject as the tumor sample, e.g., a wild-type or a non-mutated nucleotide sequence of a gene or gene product described herein (e.g., genes or gene products from Table 1, 1A, 2, 3, or 4). In one embodiment, the control gene or gene product is from the same subject or a different subject as the tumor sample (e.g., is from one or more of the same or a different tumor sample; a normal (e.g., non-cancerous) sample; a normal adjacent tissue (NAT); or a blood sample), from the same subject having or at risk of having the tumor, or from a different subject.

In other embodiments or in addition to the aforesaid embodiments, the method or assay includes sequencing a subgenomic interval that is present in a gene associated with drug metabolism, drug responsiveness, or toxicity (the PGx genes as described herein). In certain embodiments, the subgenomic interval sequenced includes an alteration (e.g., single nucleotide polymorphism (SNP)).

In certain embodiments, the method, or assay, includes sequencing (and/or reporting the results of sequencing) a first set of genes or gene products from Table 1, 1A, 2, 3, or 4 from a first subject. In other embodiments, the method, or assay, includes sequencing (and/or reporting the results of sequencing) a second set, a third set or more (e.g., an overlapping but different) set of genes or gene products from Table 1, 1A, 2, 3, or 4 from a first or a second subject. In certain embodiments, the tumor sample from a first subject includes a tumor of a first type and the tumor sample from a second subject includes a tumor of a second type. In other embodiments, the tumor sample from the first subject and the second subject are from the same tumor type.

In certain embodiments, the method or assay further includes one or more of:
(i) fingerprinting the nucleic acid sample;
(ii) quantifying the abundance of a gene or gene product (e.g., a gene or gene product as described herein) in the nucleic acid sample;
(iii) quantifying the relative abundance of a transcript in the sample;
(iv) identifying the nucleic acid sample as belonging to a particular subject (e.g., a normal control or a cancer patient);
(v) identifying a genetic trait in the nucleic acid sample (e.g., one or more subject's genetic make-up (e.g., ethnicity, race, familial traits));
(vi) determining the ploidy in the nucleic acid sample; determining a loss of heterozygosity in the nucleic acid sample;
(vii) determining the presence or absence of a gene duplication event in the nucleic acid sample;
(viii) determining the presence or absence of a gene amplification event in the nucleic acid sample; or
(ix) determining the level of tumor/normal cellular admixture in the nucleic acid sample.

In other embodiments, the nucleic acid sample includes a library, or a selected library output, that includes a plurality of tumor nucleic acid members, reference or control (e.g., wild type) nucleic acid members, and/or PGx associated nucleic acid members (e.g., a nucleic acid that includes a subgenomic interval as described herein) from the tumor sample. In one embodiment, the library (e.g., the nucleic acid library) includes a plurality of members, e.g., target nucleic acid members from 1, 2, 3, 4, 5, 6, 7, 8, 9, 10, 20, 30 or more subjects. In one embodiment, the subject is human having, or at risk of having, a cancer or tumor. In certain embodiments, the library further comprises tumor or cancer-associated nucleic acid members and control nucleic acid fragments from 1, 2, 3, 4, 5, 6, 7, 8, 9, 10, 20, 30 or more subjects.

In certain embodiments, the selected subset of subgenomic intervals are separated or enriched from the nucleic acid sample by solution- or solid support-based hybridization. In one embodiment, the method, or assay, provides selected members of a nucleic acid library (e.g., a library catch). The method includes:

providing a library (e.g., a nucleic acid library) comprising a plurality of members, e.g., target members (e.g., including a plurality of tumor or cancer-associated members, reference members, and/or PGx members);

contacting the library, e.g., in a solution- or solid support-based reaction, with a plurality of baits (e.g., oligonucleotide baits) to form a hybridization mixture comprising a plurality of bait/member hybrids;

separating the plurality of bait/member hybrids from said hybridization mixture, e.g., by contacting said hybridization mixture with a binding entity that allows for separation of said plurality of bait/member hybrid, thereby providing a library-catch (e.g., a selected or enriched subgroup of nucleic acid molecules from the library), wherein the plurality of baits includes at least one, or two of the following:

a) a first bait set that selects a tumor or cancer-associated or a reference (e.g., wild type) member comprising a subgenomic interval from a tumor or a reference gene or gene product as described herein, e.g., a tumor or a reference gene or gene product as described in Table 1, 1A, 3 or 4;

b) a second bait set that selects a PGx member comprising a subgenomic interval (in the same or a different subgenomic interval as in a) from a gene or gene product as described in Table 1 or 2.

In certain embodiments, the method, or assay, further includes the step of sequencing said members. In certain embodiments, tumor members from at least 1, 2, 3, 4, 5, 6, 7, 8, 9, 10, 20, or more subjects are sequenced (e.g., at least 50, 75, 100 or 150 subgenomic intervals from the genes or gene products from Table 1 or 1A are sequenced from each subject).

In certain embodiments, the method, or assay, further includes the step of detecting, in the nucleic acid sample, a preselected alteration (e.g., an allelic variation) in at least 10 (e.g., 20, 30, 40) Priority, Cancer, or PGx genes or gene products from Table 1. In certain embodiments, the alteration (e.g., the allelic variation) includes a cytogenetic abnormality, a non-reciprocal translocation, a rearrangement, an intra-chromosomal inversion, a mutation, a point mutations, a deletion, a change in gene copy number, an SNP, among others.

In certain embodiments, the method, or assay, further includes the step of comparing the detected presence or absence of the alteration (e.g., the allelic variation) to a reference value (e.g., a literature report or the sequence of a control sample, e.g., blood matched controls or NAT (normal adjacent tumor), from the same subject as the tumor sample, or a different subject).

In certain embodiments, the method, or assay, further includes the step of memorializing the presence or absence of the alteration (e.g., the preselected allelic variation), and, e.g., providing a report comprising the memorialization.

In certain embodiments, the method, or assay, further includes the step of annotating the alteration, and, e.g., annotating a preselected allelic variation with an indication of a mutation structure, e.g., a mis-sense mutation, or function, e.g., an association with a disease phenotype.

In certain embodiments, the method, or assay, further includes the step of providing a data set, wherein each element of the dataset comprises the association of a tumor type, a gene and a preselected alteration (e.g., allelic variation) (a "TGA").

In certain embodiments, the method, or assay, further includes the step of memorializing the presence or absence of a TGA, and optionally an associated annotation, of a subject to form a report.

In certain embodiments, the method, or assay, further includes the step of transmitting the report to a recipient party.

Assays, e.g., multiplex assays, that include the aforesaid selection methods and reagents are also provided.

Nucleic Acid Samples

A variety of tissue samples can be the source of the nucleic acid samples used in the present methods. Genomic or subgenomic nucleic acid (e.g., DNA or RNA) can be isolated from a subject's sample (e.g., a tumor sample, a normal adjacent tissue (NAT), a blood sample, a sample containing circulating tumor cells (CTC) or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. The isolating step can include flow-sorting of individual chromosomes; and/or micro-dissecting a subject's sample (e.g., a tumor sample, a NAT, a blood sample).

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

In certain embodiments, the nucleic acid is isolated from an aged sample, e.g., an aged FFPE sample. The aged sample, can be, for example, years old, e.g., 1 year, 2 years, 3 years, 4 years, 5 years, 10 years, 15 years, 20 years, 25 years, 50 years, 75 years, or 100 years old or older.

A nucleic acid sample can be obtained from tissue samples (e.g., a biopsy or FFPE sample) of various sizes. For example, the nucleic acid can be isolated from a tissue sample from 5 to 200 µm, or larger. For example, the tissue sample can measure 5 µm, 10 µm, 20 µm, 30 µm, 40 µm, 50 µm, 70 µm, 100 µm, 110 µm, 120 µm, 150 µm or 200 µm or larger.

Protocols for DNA isolation from a tissue sample are provided in Example 1. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), Maxwell® 16 FFPE Plus LEV DNA Purification Kit Technical Manual (Promega Literature #TM349, February 2011), E.Z.N.A.® FFPE DNA Kit Handbook (OMEGA bio-tek, Norcross, Ga., product numbers D3399-00, D3399-01, and D3399-02; June 2009), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. Maxwell® 16 FFPE Plus LEV DNA Purification Kit is used with the Maxwell® 16 Instrument for purification of genomic DNA from 1 to 10 µm sections of FFPE tissue. DNA is purified using silica-clad paramagnetic particles (PMPs), and eluted in low elution volume. The E.Z.N.A.® FFPE DNA Kit uses a spin column and buffer system for isolation of genomic DNA. QIAamp® DNA FFPE Tissue Kit uses QIAamp® DNA Micro technology for purification of genomic and mitochondrial DNA. Protocols for DNA isolation from blood are disclosed, e.g., in the Maxwell® 16 LEV Blood DNA Kit and Maxwell 16 Buccal Swab LEV DNA Purification Kit Technical Manual (Promega Literature #TM333, Jan. 1, 2011).

Protocols for RNA isolation are disclosed, e.g., in the Maxwell® 16 Total RNA Purification Kit Technical Bulletin (Promega Literature #TB351, August 2009).

The isolated nucleic acid samples (e.g., genomic DNA samples) can be fragmented or sheared by practicing routine techniques. For example, genomic DNA can be fragmented by physical shearing methods, enzymatic cleavage methods, chemical cleavage methods, and other methods well known to those skilled in the art. The nucleic acid library can contain all or substantially all of the complexity of the genome. The term "substantially all" in this context refers to the possibility that there can in practice be some unwanted loss of genome complexity during the initial steps of the procedure. The methods described herein also are useful in cases where the nucleic acid library is a portion of the genome, i.e., where the complexity of the genome is reduced by design. In some embodiments, any selected portion of the genome can be used with the methods described herein. In certain embodiments, the entire exome or a subset thereof is isolated.

Methods featured in the invention can further include isolating a nucleic acid sample to provide a library (e.g., a nucleic acid library as described herein). In certain embodiments, the nucleic acid sample includes whole genomic, subgenomic fragments, or both. The isolated nucleic acid samples can be used to prepare nucleic acid libraries. Thus, in one embodiment, the methods featured in the invention further include isolating a nucleic acid sample to provide a library (e.g., a nucleic acid library as described herein). Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a tumor sample, a normal adjacent tissue (NAT), a blood sample or any normal control)). In one embodiment, the sample (e.g., the tumor or NAT sample) is a preserved specimen. For example, the sample is embedded in a matrix, e.g., an FFPE block or a frozen sample. In certain embodiments, the isolating step includes flow-sorting of individual chromosomes; and/or microdissecting a subject's sample (e.g., a tumor sample, a NAT, a blood sample). In certain embodiments, the nucleic acid sample used to generate the nucleic acid library is less than 5 microgram, less than 1 microgram, or less than 500 ng, less than 200 ng, less than 100 ng, less than 50 ng, less than 10 ng, less than 5 ng, or less than 1 ng.

In still other embodiments, the nucleic acid sample used to generate the library includes RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample by specific or non-specific nucleic acid amplification methods that are well known to those skilled in the art. In some embodiments, certain embodiments, the nucleic acid sample is amplified, e.g., by whole-genome amplification methods such as random-primed strand-displacement amplification.

In other embodiments, the nucleic acid sample is fragmented or sheared by physical or enzymatic methods and ligated to synthetic adapters, size-selected (e.g., by preparative gel electrophoresis) and amplified (e.g., by PCR). In other embodiments, the fragmented and adapter-ligated group of nucleic acids is used without explicit size selection or amplification prior to hybrid selection.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA. Protocols for isolating and preparing libraries from whole genomic or subgenomic fragments are known in the art (e.g., Illumina's genomic DNA sample preparation kit), and are described herein as Examples 2A, 2B and 3. Alternative methods for DNA shearing are described herein as Example 2B. For example, alternative DNA shearing methods can be more automatable and/or more efficient (e.g., with degraded FFPE samples). Alternatives to DNA shearing methods can also be used to avoid a ligation step during library preparation.

The methods described herein can be performed using a small amount of nucleic acids, e.g., when the amount of source DNA is limiting (e.g., even after whole-genome amplification). In one embodiment, the nucleic acid comprises less than about 5 µg, 4 µg, 3 µg, 2 µg, 1 µg, 0.8 µg, 0.7 µg, 0.6 µg, 0.5 µg, or 400 ng, 300 ng, 200 ng, 100 ng, 50 ng, 10 ng, 5 ng, 1 ng, or less of nucleic acid sample. For example, one can typically begin with 50-100 ng of genomic DNA. One can start with less, however, if one amplifies the genomic DNA (e.g., using PCR) before the hybridization step, e.g., solution hybridization. Thus it is possible, but not essential, to amplify the genomic DNA before hybridization, e.g., solution hybridization.

The nucleic acid sample used to generate the library can also include RNA or cDNA derived from RNA. In some embodiments, the RNA includes total cellular RNA. In other embodiments, certain abundant RNA sequences (e.g., ribosomal RNAs) have been depleted. In other embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample by specific or non-specific nucleic acid amplification methods that are known to those skilled in the art. The nucleic acid sample can be amplified, e.g., by whole-genome amplification methods such as random-primed strand-displacement amplification.

The nucleic acid sample can be fragmented or sheared by physical or enzymatic methods as described herein, and ligated to synthetic adapters, size-selected (e.g., by preparative gel electrophoresis) and amplified (e.g., by PCR). The fragmented and adapter-ligated group of nucleic acids is used without explicit size selection or amplification prior to hybrid selection.

Library Members

"Member" or "library member" or other similar term, as used herein, refers to a nucleic acid molecule, e.g., DNA or RNA, that is the member of a library (or "library-catch"). The library member can be one or more of a tumor member, a reference member, or a PGx member as described herein. Typically, a member is a DNA molecule, e.g., a genomic DNA or cDNA, molecule. A member can be fragmented, e.g., enzymatically or by shearing, genomic DNA. Members can comprise a nucleotide sequence from a subject and can also comprise a nucleotide sequence not derived from the subject, e.g., primers or adapters (e.g., for PCR amplification or for sequencing), or sequences that allow for identification of a sample, e.g., "barcode" sequences.

As used herein, "target member" refers to a nucleic acid molecule that one desires to isolate from the nucleic acid library. In one embodiment, the target members can be a tumor member, a reference member, or a PGx member as described herein. The members that are actually selected from the nucleic acid library is referred to herein as the "library catch." In one embodiment, the library-catch includes a selection or enrichment of members of the library, e.g., the enriched or selected output of a library after one or more rounds of hybrid capture as described herein.

The target members may be a subgroup of the library, i.e., that not all of the library members are selected by any particular use of the processes described herein. In other embodiments, the target members are within a desired target region. For example, the target members may in some embodiments be a percentage of the library members that is as low as 10% or as high as 95%-98% or higher. In one embodiment, the library catch includes at least about 20%, 30%, 40%, 50%, 60%, 70%, 75%, 80%, 85%, 90%, 95%, 98%, 99%, 99.9% or more of the target members. In another embodiment, the library contains 100% of the target members. In one embodiment, the purity of the library catch (percentage of reads that align to the targets) is at least about 20%, 30%, 40%, 50%, 60%, 70%, 75%, 80%, 85%, 90%, 95%, 98%, 99%, 99.9% or more.

The target members (or the library catch) obtained from genomic DNA can include a small fraction of the total genomic DNA, such that it includes less than about 0.0001%, at least about 0.0001%, at least about 0.001%, at least about 0.01%, or at least about 0.1% of genomic DNA, or a more significant fraction of the total genomic DNA, such that it includes at least about 1%, 2%, 3%, 4%, 5%, 6%, 7%, 8%, 9%, or 10% of genomic DNA, or more than 10% of genomic DNA.

In one embodiment, the target members (or the library catch) are selected from a complex mixture of genome. For example, the selection of the DNA from one cell type (e.g., cancer cells) from a sample containing the DNA from other cell types (e.g., normal cells). In such applications, the target member can include less than 0.0001%, at least 0.0001%, at least about 0.001%, at least about 0.01%, or at least about 0.1% of the total complexity of the nucleic acid sequences present in the complex sample, or a more significant fraction such that it includes at least about 1%, 2%, 5%, 10% or more than 10% of the total complexity of nucleic acid sequences present in the complex sample.

In one embodiment, the target member (or the library catch) selected by the methods described herein (e.g., solution hybridization selection methods) include all or a portion of exons in a genome, such as greater than about 0.1%, 1%, 2%, 5%, 10%, 20%, 30%, 40%, 50%, 60%, 70%, 80%, 90%, or 95% of the genomic exons. In another embodiment, the target member (or the library catch) can be a specific group of exons, e.g., at least about 100, 200, 300, 400, 500, 600, 700, 800, 900, or 1000 particular exons, e.g., exons associated with particular diseases such as cancer. In yet another embodiment, the target member (or the library catch) contains exons or other parts of selected genes of interest. The use of specific bait sequences allows the practitioner to select target sequences (ideal set of sequences selected) and subgroups of nucleic acids (actual set of sequences selected) containing as many or as few exons (or other sequences) from a group of nucleic acids for a particular selection.

In one embodiment, the target member (or the library catch) includes a set of cDNAs. Capturing cDNAs can be used, for example, to find splice variants, and to identify fusion transcripts (e.g., from genomic DNA translocations). In another embodiment, the target member (and the library catch) is used to find single base changes and other sequence changes expressed in the RNA fraction of a cell, tissue, or organ, e.g., in a tumor.

The target member (or the library catch) (e.g., exons, cDNAs and other sequences) can be related or unrelated as desired. For example, selected target member (and the library catch) can be obtained from a group of nucleic acids that are genes involved in a disease, such as a group of genes implicated in one or more diseases such as cancers, a group of nucleic acids containing specific SNPs.

Design and Construction of Baits

A bait can be a nucleic acid molecule, e.g., a DNA or RNA molecule, which can hybridize to (e.g., be complementary to), and thereby allow capture of a target nucleic acid. In one embodiment, a bait is an RNA molecule. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

Typically, RNA molecules are used as bait sequences. A RNA-DNA duplex is more stable than a DNA-DNA duplex, and therefore provides for potentially better capture of nucleic acids.

RNA baits can be made as described elsewhere herein, using methods known in the art including, but not limited to, de novo chemical synthesis and transcription of DNA molecules using a DNA-dependent RNA polymerase. In one embodiment, the bait sequence is produced using known nucleic acid amplification methods, such as PCR, e.g., using human DNA or pooled human DNA samples as the template. The oligonucleotides can then be converted to RNA baits. In one embodiment, in vitro transcription is used, for example, based on adding an RNA polymerase promoter sequence to one end of the oligonucleotide. In one embodiment, the RNA polymerase promoter sequence is added at the end of the bait by amplifying or reamplifying the bait sequence, e.g., using PCR or other nucleic acid amplification methods, e.g., by tailing one primer of each target-specific primer pairs with an RNA promoter sequence. In one embodiment, the RNA polymerase is a T7 polymerase, a SP6 polymerase, or a T3 polymerase. In one embodiment, RNA bait is labeled with a tag, e.g., an affinity tag. In one embodiment, RNA bait is made by in vitro transcription, e.g., using biotinylated UTP. In another embodiment, RNA bait is produced without biotin and then biotin is crosslinked to the RNA molecule using methods well known in the art, such as psoralen crosslinking. In one embodiment, the RNA bait is an RNase-resistant RNA molecule, which can be made, e.g., by using modified nucleotides during transcription to produce RNA molecule that resists RNase degradation. In one embodiment, the RNA bait corresponds to only one strand of the double-stranded DNA target. Typically, such RNA baits are not self-complementary and are more effective as hybridization drivers.

The bait sets can be designed from reference sequences, such that the baits are optimal for selecting targets of the reference sequences. In some embodiments, bait sequences are designed using a mixed base (e.g., degeneracy). For example, the mixed base(s) can be included in the bait sequence at the position(s) of a common SNP or mutation, to optimize the bait sequences to catch both alleles (e.g., SNP and non-SNP; mutant and non-mutant). In some embodiments, all known sequence variations (or a subset thereof) can be targeted with multiple oligonucleotide baits, rather than by using mixed degenerate oligonucleotides.

In certain embodiments, the bait set includes an oligonucleotide (or a plurality of oligonucleotides) between about 100 nucleotides and 300 nucleotides in length. Typically, the bait set includes an oligonucleotide (or a plurality of oligonucleotides) between about 130 nucleotides and 230 nucleotides, or about 150 and 200 nucleotides, in length. In other embodiments, the bait set includes an oligonucleotide (or a plurality of oligonucleotides) between about 300 nucleotides and 1000 nucleotides in length.

In some embodiments, the target member-specific sequences in the oligonucleotide is between about 40 and 1000 nucleotides, about 70 and 300 nucleotides, about 100 and 200 nucleotides in length, typically between about 120 and 170 nucleotides in length.

In some embodiments, the bait set includes a binding entity. The binding entity can be an affinity tag on each bait sequence. In some embodiments, the affinity tag is a biotin molecule or a hapten. In certain embodiments, the binding entity allows for separation of the bait/member hybrids from the hybridization mixture by binding to a partner, such as an avidin molecule, or an antibody that binds to the hapten or an antigen-binding fragment thereof.

In other embodiments, the oligonucleotides in the bait set contains forward and reverse complemented sequences for the same target member sequence whereby the oligonucleotides with reverse-complemented member-specific sequences also carry reverse complemented universal tails. This can lead to RNA transcripts that are the same strand, i.e., not complementary to each other.

In other embodiments, the bait set includes oligonucleotides that contain degenerate or mixed bases at one or more positions. In still other embodiments, the bait set includes multiple or substantially all known sequence variants present in a population of a single species or community of organisms. In one embodiment, the bait set includes multiple or substantially all known sequence variants present in a human population.

In other embodiments, the bait set includes cDNA sequences or is derived from cDNAs sequences. In other embodiments, the bait set includes amplification products (e.g., PCR products) that are amplified from genomic DNA, cDNA or cloned DNA.

In other embodiments, the bait set includes RNA molecules. In some embodiments, the set includes chemically, enzymatically modified, or in vitro transcribed RNA molecules, including but not limited to, those that are more stable and resistant to RNase.

In yet other embodiments, the baits are produced by methods described in US 2010/0029498 and Gnirke, A. et al. (2009) *Nat. Biotechnol.* 27(2):182-189, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Accordingly, a method of making the aforesaid bait set is provided. The method includes selecting one or more target specific bait oligonucleotide sequences (e.g., one or more mutation capturing, reference or control oligonucleotide sequences as described herein); obtaining a pool of target specific bait oligonucleotide sequences (e.g., synthesizing the pool of target specific bait oligonucleotide sequences, e.g., by microarray synthesis); and optionally, amplifying the oligonucleotides to produce the bait set.

In other embodiments, the methods further include amplifying (e.g., by PCR) the oligonucleotides using one or more biotinylated primers. In some embodiments, the oligonucleotides include a universal sequence at the end of each oligonucleotide attached to the microarray. The methods can further include removing the universal sequences from the oligonucleotides. Such methods can also include removing the complementary strand of the oligonucleotides, annealing the oligonucleotides, and extending the oligonucleotides. In some of these embodiments, the methods for amplifying (e.g., by PCR) the oligonucleotides use one or more biotinylated primers. In some embodiments, the method further includes size selecting the amplified oligonucleotides.

In one embodiment, an RNA bait set is made. The methods include producing a set of bait sequences according to the methods described herein, adding a RNA polymerase promoter sequence at one end of the bait sequences, and synthesizing RNA sequences using RNA polymerase. The RNA polymerase can be chosen from a T7 RNA polymerase, an SP6 RNA polymerase or a T3 RNA polymerase. In other embodiments, the RNA polymerase promoter sequence is added at the ends of the bait sequences by amplifying (e.g., by PCR) the bait sequences. In embodiments where the bait sequences are amplified by PCR with specific primer pairs out of genomic or cDNA, adding an RNA promoter sequence to the 5' end of one of the two specific primers in each pair will lead to a PCR product that can be transcribed into a RNA bait using standard methods.

In other embodiments, bait sets can be produced using human DNA or pooled human DNA samples as the template. In such embodiments, the oligonucleotides are amplified by polymerase chain reaction (PCR). In other embodiments, the amplified oligonucleotides are reamplified by rolling circle amplification or hyperbranched rolling circle amplification. The same methods also can be used to produce bait sequences using human DNA or pooled human DNA samples as the template. The same methods can also be used to produce bait sequences using subfractions of a genome obtained by other methods, including but not limited to restriction digestion, pulsed-field gel electrophoresis, flow-sorting, CsCl density gradient centrifugation, selective kinetic reassociation, microdissection of chromosome preparations and other fractionation methods known to those skilled in the art.

In certain embodiments, the number of baits in the bait set is less than 1,000. In other embodiments, the number of baits in the bait set is greater than 1,000, greater than 5,000, greater than 10,000, greater than 20,000, greater than 50,000, greater than 100,000, or greater than 500,000.

In one embodiment, the bait sequence selects a base complementary to a SNP, e.g., to increase its binding capacity (e.g., affinity and/or specificity) in a target gene or gene product, or a fragment thereof, which encodes the SNP. Exemplary genes or gene products include, but not limited to, ABCB1, ABCC2, ABCC4, ABCG2, C1orf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, and UMPS.

In another embodiment, the bait set selects a codon in a target gene or gene product, or a fragment thereof, which is associated with cancer. Exemplary genes or gene products include, but not limited to, ABL1 (e.g., codon 315), AKT1, ALK, APC (e.g., codon 1114, 1338, 1450, and 1556), AR, BRAF (e.g., codon 600), CDKN2A, CEBPA, CTNNB1 (e.g., codon 32, 33, 34, 37, 41, and 45), EGFR (e.g., 719, 746-750, 768, 790, 858, and 861), ERBB2, ESR1, FGFR1, FGFR2, FGFR3, FLT3 (e.g., codon 835), HRAS (e.g., codon 12, 13, and 61), JAK2 (e.g., codon 617), KIT (e.g., codon 816), KRAS (e.g., codon 12, 13, and 61), MET, MLL, MYC, NF1, NOTCH1, NPM1, NRAS, PDGFRA, PIK3CA (e.g., codon 88, 542, 545, 546, 1047, and 1049), PTEN (e.g., codon 130, 173, 233, and 267), RB1, RET (e.g., codon 918), TP53 (e.g., 175, 245, 248, 273, and 306)

In yet another embodiment, the bait set selects a target gene or gene product, or a fragment thereof, which is associated with cancer. Exemplary genes or gene products include, but not limited to, ABL2, AKT2, AKT3, ARAF, ARFRP1, ARID1A, ATM, ATR, AURKA, AURKB, BCL2, BCL2A1, BCL2L1, BCL2L2, BCL6, BRCA1, BRCA2, CARD11, CBL, CCND1, CCND2, CCND3, CCNE1, CDH1, CDH2, CDH20, CDH5, CDK4, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, INHBA, IRS2, JAK1, JAK3, JUN, KDR, LRP1B, LTK, MAP2K1, MAP2K2, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK3, PAK3, PAX5, PDGFRB, PIK3R1, PKHD1, PLCG1, PRKDC, PTCH1, PTPN11, PTPRD, RAF1, RARA, RICTOR, RPTOR, RUNX1, SMAD2, SMAD3, SMAD4, SMARCA4, SMARCB1, SMO, SOX10, SOX2, SRC, STK11, TBX22, TET2, TGFBR2, TMPRSS2, TOP1, TSC1, TSC2, USP9X, VHL, and WT1.

The length of the bait sequence can be between about 70 nucleotides and 1000 nucleotides. In one embodiment, the bait length is between about 100 and 300 nucleotides, 110 and 200 nucleotides, or 120 and 170 nucleotides, in length. In addition to those mentioned above, intermediate oligonucleotide lengths of about 70, 80, 90, 100, 110, 120, 130, 140, 150, 160, 170, 180, 190, 200, 210, 220, 230, 240, 250, 300, 400, 500, 600, 700, 800, and 900 nucleotides in length can be used in the methods described herein. In some embodiments, oligonucleotides of about 70, 80, 90, 100, 110, 120, 130, 140, 150, 160, 170, 180, 190, 200, 210, 220, or 230 bases can be used.

Each bait sequence can include a target-specific (e.g., a member-specific) bait sequence and universal tails on one or both ends. As used herein, the term "bait sequence" can refer to the target-specific bait sequence or the entire oligonucleotide including the target-specific "bait sequence" and other nucleotides of the oligonucleotide. The target-specific sequences in the baits are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length, typically 120 nucleotides in length. Intermediate lengths in addition to those mentioned above also can be used in the methods described herein, such as target-specific sequences of about 40, 50, 60, 70, 80, 90, 100, 110, 120, 130, 140, 150, 160, 170, 180, 190, 200, 210, 220, 230, 240, 250, 300, 400, 500, 600, 700, 800, and 900 nucleotides in length, as well as target-specific sequences of lengths between the above-mentioned lengths.

In one embodiment, the bait is an oligomer (e.g., comprised of RNA oligomers, DNA oligomers, or a combination thereof) about 50 to 200 nucleotides in length (e.g., about 50, 60, 80, 90, 100, 110, 120, 130, 140, 150, 160, 170, 190, or 200 nucleotides in length). In one embodiment, each bait oligomer includes about 120 to 170, or typically, about 120 nucleotides, which are a target specific bait sequence. The bait can comprise additional non-target specific nucleotide sequences at one or both ends. The additional nucleotide sequences can be used, e.g., for PCT amplification or as a bait identifier. In certain embodiments, the bait additionally comprises a binding entity as described herein (e.g., a capture tag such as a biotin molecule). The binding entity, e.g., biotin molecule, can be attached to the bait, e.g., at the 5'-, 3'-end, or internally (e.g., by incorporating a biotinylated nucleotide), of the bait. In one embodiment, the biotin molecule is attached at the 5'-end of the bait.

In one exemplary embodiment, the bait is an oligonucleotide about 150 nucleotides in length, of which 120 nucleotides are target-specific "bait sequence". The other 30 nucleotides (e.g., 15 nucleotides on each end) are universal arbitrary tails used for PCR amplification. The tails can be any sequence selected by the user. For example, the pool of synthetic oligonucleotides can include oligonucleotides of the sequence of 5'-ATCGCACCAGCGTGTN$_{120}$CACTGCGGCTCCTCA-3' (SEQ ID NO:1) with N$_{120}$ indicating the target-specific bait sequences.

The bait sequences described herein can be used for selection of exons and short target sequences. In one embodiment, the bait is between about 100 nucleotides and 300 nucleotides in length. In another embodiment, the bait is between about 130 nucleotides and 230 nucleotides in length. In yet another embodiment, the bait is between about 150 nucleotides and 200 nucleotides in length. The target-specific sequences in the baits, e.g., for selection of exons and short target sequences, are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length.

In some embodiments, long oligonucleotides can minimize the number of oligonucleotides necessary to capture the target sequences. For example, one oligonucleotide can be used per exon. It is known in the art that the mean and median lengths of the protein-coding exons in the human genome are about 164 and 120 base pairs, respective. Longer baits can be more specific and capture better than shorter ones. As a result, the success rate per oligonucleotide bait sequence is higher than with short oligonucleotides. In one embodiment, the minimum bait-covered sequence is the size of one bait (e.g., 120-170 bases), e.g., for capturing exon-sized targets. In determining the length of the bait sequences, one also can take into consideration that unnecessarily long baits catch more unwanted DNA directly adjacent to the target. Longer oligonucleotide baits can also be more tolerant to polymorphisms in the targeted region in the DNA samples than shorter ones. Typically, the bait sequences are derived from a reference genome sequence. If the target sequence in the actual DNA sample deviates from the reference sequence, for example if it contains a single-nucleotide polymorphism (SNP), it can hybridize less efficiently to the bait and may therefore be under-represented or completely absent in the sequences hybridized to the bait sequences. Allelic drop-outs due to SNPs can be less likely with the longer synthetic baits molecules for the reason that a single mispair in, e.g., 120 to 170 bases can have less of an effect on hybrid stability than a single mismatch in, 20 or 70 bases, which are the typical bait or primer lengths in multiplex amplification and microarray capture, respectively.

For selection of targets that are long compared to the length of the capture baits, such as genomic regions, bait sequence lengths are typically in the same size range as the baits for short targets mentioned above, except that there is no need to limit the maximum size of bait sequences for the sole purpose of minimizing targeting of adjacent sequences. Alternatively, oligonucleotides can be titled across a much wider window (typically 600 bases). This method can be used to capture DNA fragments that are much larger (e.g., about 500 bases) than a typical exon. As a result, much more unwanted flanking non-target sequences are selected.

Bait Synthesis

The baits can be any type of oligonucleotide, e.g., DNA or RNA. The DNA or RNA baits ("oligo baits") can be synthesized individually, or can be synthesized in an array, as a DNA or RNA bait set ("array baits"). An oligo bait, whether provided in an array format, or as an isolated oligo, is typically single stranded. The bait can additionally comprise a binding entity as described herein (e.g., a capture tag such as a biotin molecule). The binding entity, e.g., biotin molecule, can be attached to the bait, e.g., at the 5' or 3'-end of the bait, typically, at the 5'-end of the bait.

In some embodiments, individual oligo baits can be added to an array bait set. In these cases, the oligo baits can be designed to target the same areas as those targeted by the array baits, and additional oligo baits can be designed and added to the standard array baits to achieve enhanced, or more thorough, coverage in certain areas of the genome. For example, additional oligo baits can be designed to target areas of poor sequencing coverage following an initial sequencing round with a standard array bait set. In some embodiments, the oligo baits are designed to have a tiled effect over the area of coverage for the array bait set, or a tiled effect over the area of coverage for other oligo baits.

In one embodiment, the individual oligo baits are DNA oligos that are used to supplement an RNA or DNA oligo array bait set, or a combination thereof (e.g., a commercially available array bait set). In other embodiments, individual oligo baits are DNA oligos that are used to supplement an RNA or DNA oligo bait set, or a combination thereof, that is a collection of individually designed and synthesized oligos. In one embodiment, the individual oligo baits are RNA oligos that are used to supplement an RNA or DNA oligo array bait set, or a combination thereof (e.g., a commercially available array bait set). In other embodiments individual oligo baits are RNA oligos that are used to supplement an RNA or DNA oligo bait set, or a combination thereof, that is a collection of individually designed and synthesized oligos.

In yet another embodiment, the individual oligo baits are DNA oligos that are used to supplement a DNA oligo array bait set (e.g., a commercially available array bait set), and in other embodiments individual oligo baits are DNA oligos that are used to supplement a DNA oligo bait set that is a collection of individually designed and synthesized oligos.

In yet another embodiment, the individual oligo baits are DNA oligos that are used to supplement a RNA oligo array bait set (e.g., a commercially available array bait set), and in other embodiments individual oligo baits are DNA oligos that are used to supplement a RNA oligo bait set that is a collection of individually designed and synthesized oligos.

In yet another embodiment, the individual oligo baits are RNA oligos that are used to supplement a RNA oligo array bait set (e.g., a commercially available array bait set), and in other embodiments individual oligo baits are RNA oligos that are used to supplement a RNA oligo bait set that is a collection of individually designed and synthesized oligos.

In yet another embodiment, the individual oligo baits are RNA oligos that are used to supplement a DNA oligo array bait set (e.g., a commercially available array bait set), and in other embodiments individual oligo baits are RNA oligos that are used to supplement a DNA oligo bait set that is a collection of individually designed and synthesized oligos.

In one embodiment, oligo baits are designed to target sequences in genes of particular interest, such as to achieve increased sequencing coverage of expanded gene sets.

In another embodiment, oligo baits are designed to target sequences representing a subset of the genome, and are mixed and used as a pool instead of, or in addition to, array baits.

In one embodiment, a first set of oligo baits is designed to target areas of poor sequencing coverage, and a second set of oligo baits is designed to target genes of particular interest. Then both sets of oligo baits are combined and, optionally, mixed with a standard array bait set to be used for sequencing.

In one embodiment, an oligo bait mix is used, e.g., to simultaneously sequence targeted gene panels and to screen a panel of single nucleotide polymorphisms (SNPs) created, such as for the purpose of looking for genomic rearrangements and copy number alterations (equivalent of arrayed CGH (Comprehensive Genomic Hybridization)). For example, a panel of SNPs can first be created by the array method as array baits, and then additional DNA oligonucleotide baits can be designed to target areas of poor sequencing coverage to a targeted set of genes. Sequencing of the collection of SNPs can then be repeated with the original array bait set plus the additional oligo baits to achieve total intended sequencing coverage.

In some embodiments, oligo baits are added to a standard array bait set to achieve more thorough sequencing coverage. In one embodiment, oligo baits are designed to target areas of poor sequencing coverage following an initial sequencing round with a standard array bait set.

In another embodiment, oligo baits are designed to target sequences in genes of particular interest. These oligo baits can be added to a standard array bait set or to existing oligo/array hybrid bait sets to achieve, e.g., increased sequencing coverage of expanded gene sets without going through an entire array bait pool re-design cycle.

Oligo baits can be obtained from a commercial source, such as NimbleGen (Roche) or Integrated DNA Technologies (IDT) for DNA oligos. Oligos can also be obtained from Agilent Technologies. Protocols for enrichment are publicly available, e.g., *SureSelect Target Enrichment System*.

Baits can be produced by methods described in US 2010/0029498 and Gnirke, A. et al. (2009) *Nat. Biotechnol.* 27(2): 182-189, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

For example, a large collection of baits can be generated from a custom pool of synthetic oligonucleotides originally synthesized on an oligonucleotide array, e.g., an Agilent programmable DNA microarray. Accordingly, at least about 2,500, 5,000, 10,000, 20,000, 3,000, 40,000, 50,000, or 60,000 unique oligonucleotides can be synthesized simultaneously.

In one embodiment, a minimal set of unique olignonucleotides are chosen and additional copies (e.g., alternating between reverse complements and the original forward strands) are added until the maximum capacity of the synthetic oligonucleotide array has been reached, e.g., for baits designed to capture a pre-selected set of targets (e.g., pre-selected set of exons). In another embodiment, the target is represented at least twice, e.g., by synthesizing both forward and reverse-complemented oligonucleotides. Synthesizing forward and reverse-complemented oligonucleotides for a given target can provide better redundancy at the synthesis step than synthesizing the very same sequence twice. In yet another embodiment, the PCR product or bait is the same for forward and reverse-complemented oligonucleotides.

The oligonucleotides from the chips are synthesized once, and then can be amplified to create a set of oligonucleotides that can be used many times. This approach generates a universal reagent that can be used as bait for a large number of selection experiments, thereby amortizing the chip cost to be a small fraction of the sequencing cost. Alternatively, bait sequences can be produced using known nucleic acid amplification methods, such as PCR, using human DNA or pooled human DNA samples as the template.

Following synthesis, the oligonucleotides can be liberated (e.g., stripped) from the array by chemical cleavage followed by removal of the protection groups and PCR amplified into double-stranded DNA using universal primers. A second round of PCR can be used to incorporate a promoter (e.g., T7, SP6, or T3 promoter) site into the amplicon, which is used to transcribe the DNA into single-stranded RNA.

In one embodiment, the baits are tiled along the sequences (e.g., exons) without gaps or overlaps. For example, the baits can start at the "left"-most coding base in the strand of the reference genome sequence shown in the UCSC genome browser (e.g., 5' to 3' or 3' to 5' along the coding sequence, depending on the orientation of the gene) and additional baits are added until all coding bases are covered. In another embodiment, at least two, three, four, or five baits for each target are designed, overlapping by at least about 15, 30, 45, or 60 bases. After oligonucleotide synthesis and PCR amplification using universal primers, one of the tails of the double-stranded DNA can be enzymatically followed by the degradation of one of the strands. The single-stranded products can be hybridized, made fully double stranded by filling in, and amplified by PCR. In this manner, it is possible to produce baits that contain at least about 300, 400, 500, or 600 contiguous target-specific bases which is more than can be chemically synthesized. Such long baits can be useful for applications that require high specificity and sensitivity, or for applications that do not necessarily benefit from limiting the length of the baits (e.g., capture of long contiguous genomic regions).

In one embodiment, the coverage of each target can be assessed and targets that yield similar coverage can be grouped. Distinct sets of bait sequences can be created for each group of targets, further improving the representation. In another embodiment, oligonucleotides from microarray chips are tested for efficacy of hybridization, and a production round of microarray chips ordered on which oligonucleotides are grouped by their capture efficacy, thus compensating for variation in bait efficacy. In yet another embodiment, oligonucleotide pools can be aggregated to form a relatively small number of composite pools, such that there is little variation in capture efficacy among them.

The baits described herein can be labeled with a tag, e.g., an affinity tag. Exemplary affinity tags include, but not limited to, biotin molecules, magnetic particles, haptens, or other tag molecules that permit isolation of baits tagged with the tag molecule. Such molecules and methods of attaching them to nucleic acids (e.g., the baits used in the methods disclosed herein) are well known in the art. Exemplary methods for making biotinylated baits are described, e.g., in Gnirke A. et al., *Nat. Biotechnol.* 2009; 27(2):182-9, which is incorporated herein by reference in entirety.

Also known in the art are molecules, particles or devices that bind to or are capable of separating the set of tagged baits from the hybridization mixture. In one embodiment, the molecule, particle, or device binds to the tag (e.g., the affinity tag). In one embodiment, the molecule, particle, or device is an avidin molecule, a magnet, or an antibody or antigen-binding fragment thereof. In one embodiment, the tagged baits are separated using a magnetic bead coated with streptavidin molecules.

Exemplary methods to prepare oligonucleotide libraries are described, e.g., in Gnirke A. et al., *Nat. Biotechnol.* 2009; 27(2):182-9, and Blumenstiel B. et al., *Curr. Protoc. Hum. Genet.* 2010; Chapter 18: Unit 18.4, which are incorporated herein by reference in entirety.

Hybridization Conditions

The methods featured in the invention include the step of contacting the library (e.g., the nucleic acid library) with a plurality of baits to provide a selected library catch. The contacting step can be effected in solution hybridization. In certain embodiments, the method includes repeating the hybridization step by one or more additional rounds of solution hybridization. In some embodiments, the methods further include subjecting the library catch to one or more additional rounds of solution hybridization with the same or different collection of baits.

In other embodiments, the methods featured in the invention further include amplifying the library catch (e.g., by PCR). In other embodiments, the library catch is not amplified.

In yet other embodiments, the methods further include the step of subjecting the library catch to genotyping, thereby identifying the genotype of the selected nucleic acids.

More specifically, a mixture of several thousand bait sequences can effectively hybridize to complementary nucleic acids in a group of nucleic acids and that such hybridized nucleic acids (the subgroup of nucleic acids) can be effectively separated and recovered. In one embodiment, the methods described herein use a set of bait sequences containing more than about 1,000 bait sequences, more than about 2,000 bait sequences, more than about 3,000 bait sequences, more than about 4,000 bait sequences, more than about 5,000 bait sequences, more than about 6,000 bait sequences, more than about 7,000 bait sequences, more than about 8,000 bait sequences, more than about 9,000 bait sequences, more than about 10,000 bait sequences, more than about 15,000 bait sequences, more than about 20,000 bait sequences, more than about 30,000 bait sequences, more than about 40,000 bait sequences, or more than about 50,000 bait sequences.

In some embodiments, the selection process is repeated on the selected subgroup of nucleic acids, e.g., in order to increase the enrichment of selected nucleic acids. For example, after one round of hybridization, a several thousand fold enrichment of nucleic acids can be observed. After a second round, the enrichment can rise, e.g., to about 15,000-fold average enrichment, which can provide hundreds-fold coverage of the target in a single sequencer run. Thus, for experiments that require enrichment factors not achievable in a single round of hybrid selection, the methods typically include subjecting the isolated subgroup of nucleic acids (i.e., a portion or all of the target sequences) to one or more additional rounds of solution hybridization with the set of bait sequences.

Sequential hybrid selection with two different bait sequences (bait 1, bait 2) can be used to isolate and sequence the "intersection", i.e., the subgroup of DNA sequences that binds to bait 1 and to bait 2, e.g., used for applications that include but are not limited to enriching for interchromosomal. For example, selection of DNA from a tumor sample with a bait specific for sequences on chromosome 1 followed by selection from the product of the first selection of sequences that hybridize to a bait specific for chromosome 2 may enrich for sequences at chromosomal translocation junctions that contain sequences from both chromosomes.

The molarity of the selected subgroup of nucleic acids can be controlled such that the molarity of any particular nucleic acid is within a small variation of the average molarity of all selected nucleic acids in the subgroup of nucleic acids. Methods for controlling and optimizing the evenness of target representation include, but are not limited to, rational design of bait sequences based on physicochemical as well as empirical rules of probe design well known in the art, and pools of baits where sequences known or suspected to underperform are overrepresented to compensate for their intrinsic weaknesses. In some embodiments, at least about 50%, 60%, 65%, 70%, 75%, 80%, 85%, 90%, or 95% of the isolated subgroup of nucleic acids is within about 20-fold, 15-fold, 10-fold, 5-fold, 3-fold, or 2-fold of the mean molarity. In one embodiment, at least about 50% of the isolated subgroup of nucleic acids is within about 3-fold of the mean molarity. In another embodiment, at least about 90% of the isolated subgroup of nucleic acids is within about 10-fold of the mean molarity.

Variations in efficiency of selection can be further adjusted by altering the concentration of the baits. In one embodiment, the efficiency of selection is adjusted by leveling the efficiency of individual baits within a group (e.g., a first, second or third plurality of baits) by adjusting the relative abundance of the baits, or the density of the binding entity (e.g., the hapten or affinity tag density) in reference to differential sequence capture efficiency observed when using an equimolar mix of baits, and then introducing a differential excess as much of internally-leveled group 1 to the overall bait mix relative to internally-leveled group 2.

In certain embodiments, the methods described herein can achieve an even coverage of the target sequences. In one embodiment, the percent of target bases having at least about 50% of the expected coverage is at least about 60%, 70%, 80%, or 90%, e.g., for short targets such as protein-coding exons. In another embodiment, the percent of target bases having at least about 50% of the expected coverage is at least about 80%, 90%, or 95%, e.g., for targets that are long compared to the length of the capture baits, such as genomic regions.

Prior to hybridization, baits can be denatured according to methods well known in the art. In general, hybridization steps comprise adding an excess of blocking DNA to the labeled bait composition, contacting the blocked bait composition under hybridizing conditions with the target sequences to be detected, washing away unhybridized baits, and detecting the binding of the bait composition to the target.

Baits are hybridized or annealed to the target sequences under hybridizing conditions. "Hybridizing conditions" are conditions that facilitate annealing between a bait and target nucleic acid. Since annealing of different baits will vary depending on probe length, base concentration and the like, annealing is facilitated by varying bait concentration, hybridization temperature, salt concentration and other factors well known in the art.

Hybridization conditions are facilitated by varying the concentrations, base compositions, complexities, and lengths of the baits, as well as salt concentrations, temperatures, and length of incubation. For example, hybridizations can be performed in hybridization buffer containing 5× SSPE, 5×Denhardt's, 5 mM EDTA and 0.1% SDS and blocking DNA to suppress non-specific hybridization. RNase inhibitors can be used if the bait is RNA. In general, hybridization conditions, as described above, include temperatures of about 25° C. to about 65° C., typically about 65° C., and incubation lengths of about 0.5 hours to about 96 hours, typically about 66 hours. Additional exemplary hybridization conditions are in Example 12A-12C and Table 14 herein.

The methods described herein are adaptable to standard liquid handling methods and devices. In some embodiments, the method is carried out using automated liquid handling technology as is known in the art, such as devices that handle multiwell plates (see e.g., Gnirke, A. et al. (2009) *Nat. Biotechnol.* 27(2):182-189). This can include, but not limited to, automated library construction, and steps of solution hybridization including set-up and post-solution hybridization washes. For example, an apparatus can be used for carrying out such automated methods for the bead-capture and washing steps after the solution hybridization reaction. Exemplary apparatus can include, but not limited to, the following positions: a position for a multi-well plate containing streptavidin-coated magnetic beads, a position for the multiwell plate containing the solution hybrid-selection reactions, I/O controlled heat blocks to preheat reagents and to carry out washing steps at a user-defined temperature, a position for a rack of pipet tips, a position with magnets laid out in certain configurations that facilitate separation of supernatants from magnet-immobilized beads, a washing station that washes pipet tips and disposed of waste, and positions for other solutions and reagents such as low and high-stringency washing buffers or the solution for alkaline elution of the final catch. In one embodiment, the apparatus is designed to process up to 96 hybrid selections from the bead-capture step through the catch neutralization step in parallel. In another embodiment, one or more positions have a dual function. In yet another embodiment, the user is prompted by the protocol to exchange one plate for another.

The directly selected nucleic acids can be concatenated and sheared, which is done to overcome the limitations of short sequencing reads. In one embodiment, each exon-sized sequencing target is captured with a single bait molecule that is about the same size as the target and has endpoints near the endpoints of the target. Only hybrids that form double strand molecules having approximately 100 or more contiguous base pairs survive stringent post-hybridization washes. As a result, the selected subgroup of nucleic acids (i.e., the "catch") is enriched for randomly sheared genomic DNA fragments whose ends are near the ends of the bait molecules. Mere end-sequencing of the "catch" with very short sequencing reads can give higher coverage near the end (or even outside) of the target and lower coverage near the middle.

Concatenating "catch" molecules by ligation and followed by random shearing and shotgun sequencing is one method to get sequence coverage along the entire length of the target sequence. This method produces higher percentage of sequenced bases that are on target (as opposed to near target) than end sequencing with very short reads. Methods for concatenating molecules by co-ligation are well known in the art. Concatenation can be performed by simple blunt end ligation. "Sticky" ends for efficient ligation can be produced by a variety of methods including PCR amplification of the "catch" with PCR primers that have restriction sites near their 5' ends followed by digestion with the corresponding restriction enzyme (e.g., NotI) or by strategies similar to those commonly used for ligation-independent cloning of PCR products such as partial "chew-back" by T4 DNA polymerase (Aslanidis and de Jong, Nucleic Acids Res. 18:6069-6074, 1990) or treatment of uracil-containing PCR products with UDG glycosylase and lyase endo VIII (e.g., New England Biolabs cat. E5500S).

In another embodiment, a staggered set of bait molecules is used to target a region, obtaining frequent bait ends throughout the target region. In some embodiments, merely end-sequenced "catch" (i.e., without concatenation and shearing) provides fairly uniform sequence coverage along the entire region that is covered by bait including the actual sequencing target (e.g., an exon). As staggering the bait molecules widens the segment covered by bait, the sequenced bases are distributed over a wider area. As a result, the ratio of sequence on target to near target is lower than for selections with non-overlapping baits that often require only a single bait per target.

In another embodiment, end sequencing with slightly longer reads (e.g., 76 bases) is the typical method for sequencing short selected targets (e.g., exons). Unlike end sequencing with very short reads, this method leads to a unimodal coverage profile without a dip in coverage in the middle. This method is easier to perform than the concatenate and shear method described above, results in relatively even coverage along the targets, and generates a high percentage of sequenced bases fall on bait and on target proper.

In one embodiment, the selected subgroup of nucleic acids are amplified (e.g., by PCR) prior to being analyzed by sequencing or genotyping. In another embodiment, the subgroup is analyzed without an amplification step, e.g., when the selected subgroup is analyzed by sensitive analytical methods that can read single molecules.

Bait Module

Methods described herein provide for optimized sequencing of a large number of genes and gene products from samples, e.g., tumor samples, from one or more subjects by the appropriate selection of baits, e.g., baits for use in solution hybridization, for the selection of target nucleic acids to be sequenced. The efficiency of selection for various subgenomic intervals, or classes thereof, are matched according to bait sets having preselected efficiency of selection.

Thus a method (e.g., element (b) of the method recited above) comprises contacting the library with a plurality of baits to provide selected members (sometimes referred to herein as library catch).

Accordingly, a method of analyzing a sample, e.g., a tumor sample is provided. The method comprises:

(a) acquiring a library comprising a plurality members from a sample, e.g., a plurality of tumor members from a tumor sample;

(b) contacting the library with a bait set to provide selected members (e.g., a library catch);

(c) acquiring a read for a subgenomic interval from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayesian method or a method described herein) from said read for the preselected nucleotide position, thereby analyzing said tumor sample, wherein the method comprises contacting the library with at plurality, e.g., at least two, three, four, or five, of bait sets, wherein each bait set of said plurality has a unique (as opposed to the other bait sets in the plurality), preselected efficiency for selection. E.g., each unique bait set provides for a unique depth of sequencing.

In an embodiment, the efficiency of selection of a first bait set in the plurality differs from the efficiency of a second bait set in the plurality by at least 2 fold. In an embodiment, the first and second bait sets provide for a depth of sequencing that differs by at least 2 fold.

In an embodiment, the method comprises contacting one, or a plurality of the following bait sets with the library:

a) a bait set that selects sufficient members comprising a subgenomic interval to provide for about 500× or higher sequencing depth, e.g., to sequence a mutation present in no more than 5% of the cells from the sample;

b) a bait set that selects sufficient members comprising a subgenomic interval to provide for about 200× or higher, e.g., about 200×—about 500×, sequencing depth, e.g., to sequence a mutation present in no more than 10% of the cells from the sample;

c) a bait set that selects sufficient members comprising a subgenomic interval to provide for about 10-100× sequencing depth, e.g., to sequence one or more subgenomic intervals (e.g., exons) that are chosen from: a) a pharmacogenomic (PGx) single nucleotide polymorphism (SNP) that may explain the ability of patient to metabolize different drugs, b) a genomic SNPs that may be used to uniquely identify (e.g., fingerprint) a patient, c) a genomic SNPs/loci that may be used to assess copy number gains/losses of genomic DNA and loss-of-heterozygosity (LOH);

d) a bait set that selects sufficient members comprising a subgenomic interval to provide for about 5-50× sequencing depth, e.g., to detect a structural breakpoint, such as a genomic translocation or an indel. For example, detection of an intronic breakpoint requires 5-50× sequence-pair spanning depth to ensure high detection reliability. Such bait sets can be used to detect, for example, translocation/indel-prone cancer genes; or e) a bait set that selects sufficient members comprising a subgenomic interval to provide for about 0.1-300× sequencing depth, e.g., to detect copy number changes. In one embodiment, the sequencing depth ranges from about 0.1-10× sequencing depth to detect copy number changes. In other embodiments, the sequencing depth ranges from about 100-300× to detect a genomic SNPs/loci that is used to assess copy number gains/losses of genomic DNA or loss-of-heterozygosity (LOH). Such bait sets can be used to detect, for example, amplification/deletion-prone cancer genes.

In embodiments, the method comprises the use of baits designed to capture two or more different target categories, each category having a different bait design strategies. In embodiments, the hybrid capture methods and compositions disclosed herein capture a defined subset of target sequences (e.g., target members) and provide homogenous coverage of the target sequence, while minimizing coverage outside of that subset. In one embodiment, the target sequences include the entire exome out of genomic DNA, or a selected subset thereof. The methods and compositions disclosed herein provide different bait sets for achieving different depths and patterns of coverage for complex target nucleic acid sequences (e.g., nucleic acid libraries).

In an embodiment the method comprises providing selected members of a nucleic acid library (e.g., a library catch). The method includes:

providing a library (e.g., a nucleic acid library) comprising a plurality of members, e.g., target nucleic acid members (e.g., including a plurality of tumor members, reference members, and/or PGx members);

contacting the library, e.g., in a solution- or array-based reaction, with a plurality of baits (e.g., oligonucleotide baits) to form a hybridization mixture comprising a plurality of bait/member hybrids;

separating the plurality of bait/member hybrids from said hybridization mixture, e.g., by contacting said hybridization mixture with a binding entity that allows for separation of said plurality of bait/member hybrid, thereby providing a library-catch (e.g., a selected or enriched subgroup of nucleic acid molecules from the library), wherein the plurality of baits includes two or more of the following:

a) a first bait set that selects a high-level target (e.g., one or more tumor members that include a subgenomic interval, such a gene, an exon, or a base) for which the deepest coverage is required to enable a high level of sensitivity for an alteration (e.g., one or more mutations) that appears at a low frequency, e.g., about 5% or less (i.e., 5% of the cells from the sample harbor the alteration in their genome). In one embodiment; the first bait set selects (e.g., is complementary to) a tumor member that includes an alteration (e.g., a point mutation) that requires about 500× or higher sequencing depth;

b) a second bait set that selects a mid-level target (e.g., one or more tumor members that include a subgenomic interval, such as a gene, an exon, or a base) for which high coverage is required to enable high level of sensitivity for an alteration (e.g., one or more mutations) that appears at a higher frequency than the high-level target in a), e.g., a frequency of about 10% (i.e., 10% of the cells from the sample harbor the alteration in their genome). In one embodiment; the second bait set selects (e.g., is complementary to) a tumor member that includes an alteration (e.g., a point mutation) that requires about 200× or higher sequencing depth;

c) a third bait set that selects a low-level target (e.g., one or more PGx members that includes a subgenomic interval, such as a gene, an exon, or a base) for which low-medium coverage is required to enable high level of sensitivity, e.g., to detect heterozygous alleles. For example, detection of heterozygous alleles requires 10-100× sequencing depth to ensure high detection reliability. In one embodiment, third bait set selects one or more subgenomic intervals (e.g., exons) that are chosen from: a) a pharmacogenomic (PGx) single nucleotide polymorphism (SNP) that may explain the ability of patient to metabolize different drugs, b) a genomic SNPs that may be used to uniquely identify (e.g., fingerprint) a patient, c) a genomic SNPs/loci that may be used to assess copy number gains/losses of genomic DNA and loss-of-heterozygosity (LOH);

d) a fourth bait set that selects a first intron target (e.g., a member that includes an intron sequence) for which low-medium coverage is required, e.g., to detect a structural breakpoint, such as a genomic translocation or an indel. For example, detection of an intronic breakpoint requires 5-50× sequence-pair spanning depth to ensure high detection reliability. Said fourth bait sets can be used to detect, for example, translocation/indel-prone cancer genes; or e) a fifth bait set that selects a second intron target (e.g., an intron member) for which sparse coverage is required to improve the ability to detect copy number changes. For example, detection of a one-copy deletion of several terminal exons requires 0.1-10× coverage to ensure high detection reliability. Said fifth bait sets can be used to detect, for example, amplification/deletion-prone cancer genes.

Any combination of two, three, four or more of the aforesaid bait sets can be used in methods and compositions featured herein, such as, for example, a combination of the first and the second bait sets; first and third bait sets; first and fourth bait sets; first and fifth bait sets; second and third bait sets; second and fourth bait sets; second and fifth bait sets; third and fourth bait sets; third and fifth bait sets; fourth and fifth bait sets; first, second and third bait sets; first, second and fourth bait sets; first, second and fifth bait sets; first, second, third, fourth bait sets; first, second, third, fourth and fifth bait sets, and so on.

In one embodiment, each of the first, second, third, fourth, or fifth bait set has a preselected efficiency for selection (e.g., capture). In one embodiment, the value for efficiency of selection is the same for at least two, three, four of all five baits according to a)-e). In other embodiments, the value for efficiency of selection is different for at least two, three, four of all five baits according to a)-e).

In some embodiments, at least two, three, four, or all five bait sets have a preselected efficiency value that differ. For example, a value for efficiency of selection chosen from one of more of:

(i) the first preselected efficiency has a value for first efficiency of selection that is at least about 500× or higher sequencing depth (e.g., has a value for efficiency of selection that is greater than the second, third, fourth or fifth preselected efficiency of selection (e.g., about 2-3 fold greater than the value for the second efficiency of selection; about 5-6 fold greater than the value for the third efficiency of selection; about 10 fold greater than the value for the fourth efficiency of selection; about 50 to 5000-fold greater than the value for the fifth efficiency of selection);

(ii) the second preselected efficiency has a value for second efficiency of selection that is at least about 200× or higher sequencing depth (e.g., has a value for efficiency of selection that is greater than the third, fourth or fifth preselected efficiency of selection (e.g., about 2 fold greater than the value for the third efficiency of selection; about 4 fold greater than the value for the fourth efficiency of selection; about 20 to 2000-fold greater than the value for the fifth efficiency of selection);

(iii) the third preselected efficiency has a value for third efficiency of selection that is at least about 100× or higher sequencing depth (e.g., has a value for efficiency of selection that is greater than the fourth or fifth preselected efficiency of selection (e.g., about 2 fold greater than the value for the fourth efficiency of selection; about 10 to 1000-fold greater than the value for the fifth efficiency of selection);

(iv) the fourth preselected efficiency has a value for fourth efficiency of selection that is at least about 50× or higher sequencing depth (e.g., has a value for efficiency of selection that is greater than the fifth preselected efficiency of selection (e.g., about 50 to 500-fold greater than the value for the fifth efficiency of selection); or (v) the fifth preselected efficiency has a value for fifth efficiency of selection that is at least about 10× to 0.1× sequencing depth.

In certain embodiments, the value for efficiency of selection is modified by one or more of: differential representation of different bait sets, differential overlap of bait subsets, differential bait parameters, or mixing of different bait sets. For example, a variation in efficiency of selection (e.g., relative sequence coverage of each bait set/target category) can be adjusted by altering one or more of:

(i) Differential representation of different bait sets—The bait set design to capture a given target (e.g., a target member) can be included in more/fewer number of copies to enhance/reduce relative target coverage depths;

(ii) Differential overlap of bait subsets—The bait set design to capture a given target (e.g., a target member) can include a longer or shorter overlap between neighboring baits to enhance/reduce relative target coverage depths;

(iii) Differential bait parameters—The bait set design to capture a given target (e.g., a target member) can include sequence modifications/shorter length to reduce capture efficiency and lower the relative target coverage depths;

(iv) Mixing of different bait sets—Bait sets that are designed to capture different target sets can be mixed at different molar ratios to enhance/reduce relative target coverage depths;

(v) Using different types of oligonucleotide bait sets—In certain embodiments, the bait set can include:

(a) one or more chemically (e.g., non-enzymatically) synthesized (e.g., individually synthesized) baits, (b) one or more baits synthesized in an array, (c) one or more enzymatically prepared, e.g., in vitro transcribed, baits;

(d) any combination of (a), (b) and/or (c), (e) one or more DNA oligonucleotides (e.g., a naturally or non-naturally occurring DNA oligonucleotide), (f) one or more RNA oligonucleotides (e.g., a naturally or non-naturally occurring RNA oligonucleotide), (g) a combination of (e) and (f), or (h) a combination of any of the above.

The different oligonucleotide combinations can be mixed at different ratios, e.g., a ratio chosen from 1:1, 1:2, 1:3, 1:4, 1:5, 1:10, 1:20, 1:50; 1:100, 1:1000, or the like. In one embodiment, the ratio of chemically-synthesized bait to array-generated bait is chosen from 1:5, 1:10, or 1:20. The DNA or RNA oligonucleotides can be naturally- or non-naturally-occurring. In certain embodiments, the baits include one or more non-naturally-occurring nucleotide to, e.g., increase melting temperature. Exemplary non-naturally occurring oligonucleotides include modified DNA or RNA nucleotides. Exemplary modified nucleotides (e.g., modified RNA or DNA nucleotides) include, but are not limited to, a locked nucleic acid (LNA), wherein the ribose moiety of an LNA nucleotide is modified with an extra bridge connecting the 2' oxygen and 4' carbon; peptide nucleic acid (PNA), e.g., a PNA composed of repeating N-(2-aminoethyl)-glycine units linked by peptide bonds; a DNA or RNA oligonucleotide modified to capture low GC regions; a bicyclic nucleic acid (BNA) or a crosslinked oligonucleotide; a modified 5-methyl deoxycytidine; and 2,6-diaminopurine. Other modified DNA and RNA nucleotides are known in the art.

In certain embodiments, a substantially uniform or homogeneous coverage of a target sequence (e.g., a target member) is obtained. For example, within each bait set/target category, uniformity of coverage can be optimized by modifying bait parameters, for example, by one or more of:

(i) Increasing/decreasing bait representation or overlap can be used to enhance/reduce coverage of targets (e.g., target members), which are under/over-covered relative to other targets in the same category;

(ii) For low coverage, hard to capture target sequences (e.g., high GC content sequences), expand the region being targeted with the bait sets to cover, e.g., adjacent sequences (e.g., less GC-rich adjacent sequences);

(iii) Modifying a bait sequence can be made to reduce secondary structure of the bait and enhance its efficiency of selection;

(iv) Modifying a bait length can be used to equalize melting hybridization kinetics of different baits within the same category. Bait length can be modified directly (by producing baits with varying lengths) or indirectly (by producing baits of consistent length, and replacing the bait ends with arbitrary sequence);

(v) Modifying baits of different orientation for the same target region (i.e. forward and reverse strand) may have different binding efficiencies. The bait set with either orientation providing optimal coverage for each target may be selected;

(vi) Modifying the amount of a binding entity, e.g., a capture tag (e.g. biotin), present on each bait may affect its binding efficiency. Increasing/decreasing the tag level of baits targeting a specific target may be used to enhance/reduce the relative target coverage;

(vii) Modifying the type of nucleotide used for different baits can be altered to affect binding affinity to the target, and enhance/reduce the relative target coverage; or (viii) Using modified oligonucleotide baits, e.g., having more stable base pairing, can be used to equalize melting hybridization kinetics between areas of low or normal GC content relative to high GC content.

In other embodiments, the efficiency of selection is adjusted by leveling the efficiency of individual baits within a group (e.g., a first, second or third plurality of baits) by adjusting the relative abundance of the baits, or the density of the binding entity (e.g., the hapten or affinity tag density) in reference to differential sequence capture efficiency observed when using an equimolar mix of baits, and then introducing a differential excess of internally-leveled group 1 to the overall bait mix relative to internally-leveled group 2.

In an embodiment, a library catch is provided by use of a plurality of bait sets including a bait set that selects a tumor member, e.g., a nucleic acid molecule comprising a subgenomic interval from a tumor cell (also referred to herein as "a tumor bait set"). The tumor member can be any nucleotide sequence present in a tumor cell, e.g., a mutated, a wild-type, a PGx, a reference or an intron nucleotide sequence (e.g., a member), as described herein, that is present in a tumor or cancer cell. In one embodiment, the tumor member includes an alteration (e.g., one or more mutations) that appears at a low frequency, e.g., about 5% or less of the cells from the tumor sample harbor the alteration in their genome. In other embodiments, the tumor member includes an alteration (e.g., one or more mutations) that appears at a frequency of about 10% of the cells from the tumor sample. In other embodiments, the tumor member includes a subgenomic interval from a PGx gene or gene product, an intron sequence, e.g., an intron sequence as described herein, a reference sequence, that is present in a tumor cell.

In other embodiments, the method further includes detecting a non-tumor member, e.g., a nucleic acid molecule (such as a subgenomic interval) that is present in a non-tumor cell. In one embodiment, the plurality of bait sets includes a bait set that selects the non-tumor member (also referred to herein as "a non-tumor bait set"). For example, the non-tumor member can be from a normal (e.g., non-cancerous) reference sample (e.g., form the same subject from whom the tumor sample was obtained); a normal adjacent tissue (NAT) or a blood sample from the same subject having or at risk of having the tumor. In other embodiments, the non-tumor member is from a different subject as the tumor member (e.g., is from a normal (e.g., non-cancerous) reference sample; a normal adjacent tissue (NAT); or a blood sample), from one or more different subjects (e.g., healthy subjects or other subjects having or at risk of having the tumor). In one embodiment, the non-tumor member includes a subgenomic interval from a PGx gene or gene product, an intron sequence, a reference sequence, that is present in a non-tumor cell.

In one embodiment, the tumor bait set is chosen from one, two, three, four, five, six, seven, eight, nine, ten, eleven, twelve, or all A-M of the following:

A. A bait set that selects an exon sequence that includes a single nucleotide alteration associated with a cancerous phenotype;

B. A bait set that selects an in-frame deletion of 1, 2, 3, 4, 5, 6, 7, 8, 9, 10, 11, 12, 13, 14, 15, 16, 17, 18, 19, 20 or more codons from a reference nucleotide (e.g., chromosome) sequence;

C. A bait set that selects an intragenic deletion;

D. A bait set that selects an intragenic insertion;

E. A bait set that selects a deletion of a full gene;

F. A bait set that selects an inversion, e.g., an intrachromosomal inversion;

G. A bait set that selects an interchromosal translocation;

H. A bait set that selects a tandem duplication, e.g., an intrachromosomal tandem duplication;

I. A bait set that selects a nucleotide sequence of interest flanked by adjacent non-repetitive sequences;

J. A bait set that selects one or more subgenomic intervals corresponding to a fusion sequence, e.g., a preselected pair of subgenomic intervals (e.g., a preselected pair of exons) corresponding to a fusion sequence (e.g., a fusion transcript or a cancer associated alternative spliced form of non-fusion transcript);

K. A bait set that selects a subgenomic interval adjacent to a nucleotide sequence that includes an undesirable feature, e.g., a nucleotide sequence of high GC content, a nucleotide sequence including one or more repeated elements and/or inverted repeats;

L. A bait set that selects a rearrangement, e.g., a genomic rearrangement (e.g., a rearrangement that includes an intron sequence, e.g., a 5' or 3'-UTR); or M. A bait set that selects a subgenomic interval that includes an exon adjacent to a cancer associated gene fusion.

Additional embodiments of the bait sets and methods of using them are as follows:

In one embodiment, the bait set selects a member by hybridization (e.g., a bait or plurality of baits in the bait set is complementary to one or more members, e.g., target members, such as first-fifth members, tumor or non-tumor members, as described herein).

In one embodiment, the library (e.g., the nucleic acid library) includes a plurality of members, e.g., target nucleic acid members from 1, 2, 3, 4, 5, 6, 7, 8, 9, 10, 20, 30 or more subjects. In one embodiment, the subject is human having, or at risk of having, a cancer or tumor.

In certain embodiments, the method includes sequencing tumor members from tumor samples from at least X subjects, (wherein X=1, 2, 3, 4, 5, 6, 7, 8, 9, 10, 20, 30, 40, or more subjects). In one embodiment, the subject is human having, or at risk of having, a cancer or tumor. The method includes sequencing at least 5, 10, 15, 20, 30, 40, 50, 75 or more genes or gene products described herein (e.g., genes or gene products from Table 1, 1A, 2, 3, or 4) from at least X subjects.

In other embodiments or in addition to the aforesaid embodiments, the method or includes sequencing a reference subgenomic interval from a gene or gene product from the same subject as the tumor sample, e.g., a wild-type or a non-mutated nucleotide sequence of a gene or gene product described herein (e.g., genes or gene products from Table 1, 1A, 2, 3, or 4). In one embodiment, the reference gene or gene product is from the same subject or a different subject as the tumor sample (e.g., is from one or more of the same or a different tumor sample; a normal (e.g., non-cancerous) sample; a normal adjacent tissue (NAT); or a blood sample), from the same subject having or at risk of having the tumor, or from a different subject.

In one embodiment, the member (e.g., any of the members described herein) comprises a subgenomic interval. In one embodiment, the subgenomic interval includes an intragenic region or an intergenic region. In one embodiment, the subgenomic interval includes a gene or fragment thereof, an exon or a fragment thereof, or a preselected nucleotide position (e.g., a base). In another embodiment, the subgenomic interval includes an exon or an intron, or a fragment thereof, typically an exon or a fragment thereof. In one embodiment, the subgenomic interval includes a coding region or a non-coding region, e.g., a promoter, an enhancer, a 5' untranslated region (5' UTR), or a 3' untranslated region (3' UTR), or a fragment thereof.

In another embodiment, the subgenomic interval of the member (e.g., any of the members described herein) includes an alteration (e.g., one or more mutations) associated, e.g., positively or negatively, with a cancerous phenotype (e.g., one or more of cancer risk, cancer progression, cancer treatment or resistance to cancer treatment). In yet another embodiment, the subgenomic interval includes an alteration, e.g., a point or a single mutation, a deletion mutation (e.g., an in-frame deletion, an intragenic deletion, a full gene deletion), an insertion mutation (e.g., intragenic insertion), an inversion mutation (e.g., an intra-chromosomal inversion), a linking mutation, a linked insertion mutation, an inverted duplication mutation, a tandem duplication (e.g., an intrachromosomal tandem duplication), a translocation (e.g., a chromosomal translocation, a non-reciprocal translocation), a rearrangement (e.g., a genomic rearrangement (e.g., a rearrangement of one or more introns, or a fragment thereof; a rearranged intron can include a 5'- and/or 3'-UTR); a change in gene copy number; a change in gene expression; a change in RNA levels, or a combination thereof. In one embodiment, the subgenomic interval of the first or the second member includes an alteration of a gene or gene product according to Table 1, 1A, 3, or 4.

In one embodiment, the tumor member includes one or more alterations (e.g., one or more altered or mutated subgenomic intervals from gene or gene products from a tumor sample). In some embodiments, the bait set (e.g., any of the bait sets described herein) selects (e.g., is complementary to) a tumor member, e.g., a nucleic acid molecule (e.g., a subgenomic interval, such as a gene, an exon, or a fragment thereof), that includes an alteration (e.g., one or more mutations) associated, e.g., positively or negatively, with a cancerous phenotype.

In an embodiment, the member is associated with a cancerous phenotype, e.g., one or more of cancer risk, cancer progression, cancer treatment, or resistance to cancer treatment. The association with the cancerous phenotype can include one or more of: a genetic risk factor for cancer, a positive treatment response predictor, a negative treatment response predictor, a positive prognostic factor, a negative prognostic factor, or a diagnostic factor. In one embodiment, the cancerous phenotype associated with the tumor member is the same tumor type as detected by histological analysis of the sample. In other embodiments, the cancerous phenotype associated with the tumor member is from a different tumor type as detected by histological analysis of the sample.

In certain embodiments, the subgenomic interval includes a nucleotide sequence, wherein the presence or absence of a preselected allelic variant is predictive of a positive clinical outcome, and/or responsiveness to therapy. In other embodiments, the subgenomic interval includes a nucleotide sequence, wherein the presence or absence of a preselected allelic variant is predictive of a negative clinical outcome, and/or responsiveness to therapy. In certain embodiments, the subgenomic interval of the nucleic acid sample includes a nucleotide sequence, wherein the presence or absence of a preselected allelic variant is indicative of a genetic (e.g., a germline risk) factor for developing cancer (e.g., the gene or gene product is chosen from one or more of BRCA1, BRCA2, EGFR, HRAS, KIT, MPL, ALK, PTEN, RET, APC, CDKN2A, MLH1, MSH2, MSH6, NF1, NF2, RB1, TP53, VHL or WT1).

In other embodiments, the member is not associated with the cancerous phenotype. In certain embodiments, the subgenomic interval of the member (e.g., any of the members described herein) includes a nucleic acid molecule (in the same or a different subgenomic interval) not associated with the cancerous phenotype for the tumor of the type from the sample.

In one embodiment, the subgenomic interval of the member (e.g., any of the members described herein) includes a wild-type or a non-mutated nucleotide sequence of a gene or gene product (e.g., an exon sequence or a fragment thereof). In one embodiment, the subgenomic interval of the first or the second member includes a wild-type or a non-mutated nucleotide sequence of a gene or gene product that when mutated is associated with a cancerous phenotype (e.g., a wild type or a non-mutated sequence of a gene or gene product as described herein, e.g., a gene or gene product described herein in Table 1, 1A, 3 or 4). Members containing the wild-type or non-mutated gene or gene product sequence are also referred to herein as "reference members." For example, the subgenomic interval is from one or more of: a wild type allele of a heterozygous mutation; a normal (e.g., non-cancerous) reference sample (e.g., from the same subject from whom the tumor sample was obtained); a normal adjacent tissue (NAT) or a blood sample from the same subject having or at risk of having the tumor. In other embodiments, the subgenomic interval is from a different subject as the tumor member (e.g., is from one or more of the same or a different tumor sample from a different subject; a normal (e.g., non-cancerous) reference sample; a normal adjacent tissue (NAT); or a blood sample), from one or more different subjects (e.g., healthy subjects or other subjects having or at risk of having the tumor).

In one embodiment, the first bait set, or the tumor bait set, selects (e.g., is complementary to) a subgenomic interval that includes a point mutation that appear at a frequency of about 5% or less (i.e. 5% of the cells from which the sample was prepared harbor this mutation in their genome), e.g., requires about 500× or higher sequencing depth to ensure high detection reliability.

In other embodiments, the first bait set, or the tumor bait set, selects (e.g., is complementary to) a tumor or reference member chosen from one, two, three, four, five, six, seven, eight, nine, ten, fifteen, twenty, twenty-five, thirty or more of: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53 gene or gene product. In one embodiment, the first bait set, or the tumor bait set, selects (e.g., is complementary to) one, two, three, four, five, six, seven, eight, nine, ten, fifteen, twenty, twenty-five, thirty, thirty-five codons chosen from one or more of: codon 315 of the ABL1 gene; codon 1114, 1338, 1450 or 1556 of APC; codon 600 of BRAF; codon 32, 33, 34, 37, 41 or 45 of CTNNB1; codon 719, 746-750, 768, 790, 858 or 861 of EGFR; codon 835 of FLT3; codon 12, 13, or 61 of HRAS; codon 617 of JAK2; codon 816 of KIT; codon 12, 13, or 61 of KRAS; codon 88, 542, 545, 546, 1047, or 1049 of PIK3CA; codon 130, 173, 233, or 267 of PTEN; codon 918 of RET; codon 175, 245, 248, 273, or 306 of TP53.

In one embodiment, the first bait set, or the tumor bait set, selects one or more subgenomic intervals that are frequently mutated in certain types of cancer, e.g., at least 5, 10, 20, 30 or more subgenomic intervals from a Priority 1 Cancer gene or gene product according to Table 1 or 1A.

In other embodiments, the second bait set selects (e.g., is complementary to) a tumor member that includes an alteration (e.g., a point mutation) that appears at a frequency of 10%, e.g., requires about 200× or higher sequencing depth to ensure high detection reliability.

In other embodiments, the second bait set selects (e.g., is complementary to) a tumor member chosen one, two, three, four, five, ten, fifteen, twenty, twenty-five, thirty, thirty-five, forty, forty-five, fifty, fifty-five, sixty, sixty-five, seventy, seventy-five, eighty, eighty-five, ninety, ninety-five, one hundred, one hundred and five, one hundred and ten, one hundred and fifteen, one hundred and twenty or more of: ABL2, ARAF, ARFRP1, ARID1A, ATM, ATR, AURKA, AURKB, BAP1, BCL2, BCL2A1, BCL2L1, BCL2L2, BCL6, BRCA1, BRCA2, CBL, CARD11, CBL, CCND2, CCND3, CCNE1, CD79A, CD79B, CDH1, CDH2, CDH20, CDH5, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, INHBA, IRS2, JAK1, JAK3, JUN, KDM6A, KDR, LRP1B, LRP6, LTK, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK2, PAK3, PAX5, PDGFRB, PKHD1, PLCG1, PRKDC, PTPN11, PTPRD, RAF1, RARA, RICTOR, RPTOR, RUNX1, SMAD2, SMAD3, SMAD4, SMARCA4, SMARCB1, SOX10, SOX2, SRC, TBX22, TET2, TGFBR2, TMPRSS2, TNFAIP3, TNK, TNKS2, TOP1, TSC1, TSC2, USP9X, VHL, or WT1 gene or gene product.

In one embodiment, the second bait set, or the tumor bait set, selects one or more subgenomic intervals (e.g., exons) that are chosen from at least 5, 10, 20, 30, 40, 50, 60, 70, 80, 90, 100 or more of the Cancer genes or gene products according to Table 1 or 1A.

In certain embodiments, the first or the second bait set, or the tumor bait set, selects a wild-type and/or a non-mutated nucleotide sequence, e.g., a reference member that has a wild-type or a non-mutated nucleotide sequence, e.g., a wild-type and/or a non-mutated nucleotide sequence of a subgenomic interval of a gene or gene product as described herein, e.g., as described in Table 1, 1A, 3 or 4.

In one embodiment, the first or the second bait set, or the tumor set, selects a member, e.g., a reference member, that has a wild-type or a non-mutated nucleotide sequence of a gene or gene product (e.g., an exon sequence or a fragment thereof) that when mutated is associated, e.g., positively or negatively, with a cancerous phenotype.

In one embodiment, the reference member is from the same subject as the tumor member (e.g., is from one or more of the same or a different tumor sample; a wild-type heterozygous allele of the mutated member; a normal (e.g., non-cancerous) reference sample; a normal adjacent tissue (NAT); or a blood sample), from the same subject having or at risk of having the tumor. In other embodiments, the reference member is from a different subject as the tumor member (e.g., is from one or more of the same or a different tumor sample from a different subject; a normal (e.g., non-cancerous) reference sample; a normal adjacent tissue (NAT); or a blood sample), from one or more different subjects having or at risk of having the tumor.

In one embodiment, the first or second bait set, or the tumor bait set, selects an exon sequence that includes a single nucleotide alteration associated with a cancerous phenotype. For example, the first bait set, or the tumor bait set, can include a nucleotide sequence complementary to nucleotides 25,398,215-25,398,334 of chromosome 12, and contains a base complementary to a C-T substitution at position 25,398,286, which represents a G12S mutation in the KRAS gene.

In another embodiment, the first or the second bait set, or the tumor bait set, selects a tumor member characterized by an in-frame deletion of 1, 2, 3, 4, 5, 6, 7, 8, 9, 10, 11, 12, 13, 14, 15, 16, 17, 18, 19, 20 or more codons from a reference nucleotide (e.g., chromosome) sequence.

In one embodiment, the first bait set, or the tumor bait set, includes (or consists of) two discontinuous nucleotide sequences of a reference chromosome sequence, in their reference 5' to 3' orientation, separated on the reference chromosome sequence by a gap of any of 3, 6, 9, 12, 15, 18, 21, 24, 27, 30, 33, 36, 39, 42, 45, 48, 51, 54, 57, 60 or more nucleotides. For example the first bait set, or the tumor bait set, can include a nucleotide sequence that is complementary to nucleotides 55,242,400 to 55,242,535 of chromosome 7, but lacks nucleotides 55,242,464 to 55,242,479, which represents an in-frame deletion of codons 746-750 of the EGFR gene.

In yet another embodiment, the first or the second bait set, or the tumor bait set, selects a tumor member characterized by an intragenic deletion. In one embodiment, the first bait set, or the tumor bait set, includes (or consists of) two discontinuous segments of a reference nucleotide (e.g., chromosome) sequence, in their reference 5' to 3' orientation, separated by 1, 5, 10, 15, 20, 25, 30, 35, 40, 45, 50, 55, 60 nucleotides from the reference chromosome sequence. For example, the first bait set, or the tumor bait set, can include a nucleotide sequence that is complementary to nucleotides 9,675,214 to 89,675,274 of chromosome 10, followed by bases 89,675,277 to 89,675,337 of chromosome 10, which represents a deletion of the dinucleotide sequence "CA" from codon 64 of the PTEN gene.

In yet another embodiment, the first or the second bait set, or the tumor bait set, selects a tumor member characterized by an intragenic insertion. In one embodiment, the first bait set, or the tumor bait set, includes (or consists of) two continuous segments of a reference nucleotide (e.g., chromosome) sequence, separated by a non-reference sequence of 1, 5, 10, 15, 20, 25, 30, 35, 40, 45, 50, 55, 60 nucleotides. For example, the first bait set, or the tumor bait set, can include a nucleotide sequence that is complementary to nucleotides 89,692,864 to 89,692,924 of chromosome 10, followed by a nucleotide sequence "GGNATG", followed by nucleotides 89,692,925 to 89,692,980 of chromosome 10, which represents the insertion of amino acid residues "Gly-Met" following codon 136 of the PTEN gene.

In another embodiment, the first or the second bait set, or the tumor bait set, selects a tumor member characterized by a deletion of a full gene. In one embodiment, the first bait set, or the tumor bait set, includes (or consists of) two discontinuous segments of a reference nucleotide (e.g., chromosome) sequence, in their reference 5' to 3' orientation, separated by 500, 1000, 1500, 2000, 2500, 3000, 4000, 5000 or more nucleotides from the reference chromosome sequence. For example, the first bait set, or the tumor bait set, can include a nucleotide sequence complementary to bases 21,961,007 to 21,961,067 of chromosome 9 adjacent to bases 22,001,175 to 22,001,235 of chromosome 9, which represents the deletion of the CDKN2A gene.

In another embodiment, the first or the second bait set, or the tumor bait set, selects a tumor member characterized by an inversion, e.g., an intrachromosomal inversion. In one embodiment, the first bait set, or the tumor bait set, includes a nucleotide sequence complementary to two discontinuous segments of a reference nucleotide (e.g., chromosome) sequence, one of which is inverted from its reference orientation, e.g., to capturing a member that results from an inversion. For example, the first bait set, or the tumor bait set, can include nucleotides 42,522,893 to 42,522,953 of chromosome 2, juxtaposed with nucleotides 29,449,993 to 29,449,933 of chromosome 2, which represents an inversion producing an EML4:ALK fusion.

In another embodiment, the first or the second bait set, or the tumor bait set, selects a tumor member characterized by an interchromosal translocation. In one embodiment, the first bait set, or the tumor bait set, includes a nucleotide sequence complementary to two discontinuous segments of a reference nucleotide (e.g., genomic) sequence, originating from different reference chromosome sequences, e.g., to capture a member that results from an interchromosomal translocation. For example, the first bait set, or the tumor bait set, can include nucleotides 23,632,552 to 23,632,612 of chromosome 22, juxtaposed with nucleotides 133,681,793 to 133,681,853 of chromosome 9, which represents the presence of a chromosomal translocation resulting in a BCR-ABL fusion.

In yet another embodiment, the first or the second bait set, or the tumor bait set, selects a tumor member characterized by a tandem duplication, e.g., an intrachromosomal tandem duplication. In one embodiment, the first bait set, or the tumor bait set, includes a nucleotide sequence complementary to one segment of a reference nucleotide (e.g., chromosome) sequence, of at least 3, 6, 9, 12, 15, 18, 21, 24, 27, or 30 nucleotides in length, repeated at least once, e.g., twice, three times, four times, or five times, in its reference orientation, e.g., to capture a member has a tandem duplication. For example, a bait can include bases 28,608,259 to 28,608,285 of chromosome 13 repeated twice in the same orientation, which represents an internal tandem duplication (ITD) mutation in the FLT3 gene.

In yet another embodiment, the first or the second bait set, or the tumor bait set, selects a tumor member characterized by a nucleotide sequence of interest flanked by adjacent non-repetitive sequences. In one embodiment, the first bait set, or the tumor bait set, includes at least two non-contiguous nucleotide sequences. A first nucleotide sequence complementary to the 5' flanking region of the sequence of interest, and a second nucleotide sequence complementary to the 3' flanking region of the sequence of interest. For example, a first and second pair of baits can include a first nucleotide sequence complementary to nucleotides 51,288,380 to 51,288,500 (bait 1) and a second nucleotide sequence complementary to nucleotides 51,288,560 to 51,288,680 (bait 2) of chromosome 2, which can capture members containing the microsatellite marker sequence D2S123.

In another embodiment, the first or the second bait set, or the tumor bait set, selects (e.g., is complementary to) a preselected pair of subgenomic intervals (e.g., a preselected pair of exons) corresponding to a fusion sequence (e.g., a fusion transcript or a cancer associated alternative spliced form of non-fusion transcript).

In other embodiments, the first or the second bait set, or the tumor bait set, selects a subgenomic interval adjacent to a nucleotide sequence that includes an undesirable feature, e.g., a nucleotide sequence of high GC content, a nucleotide sequence including one or more repeated elements and/or inverted repeats. In one embodiment, the first bait set, or the tumor bait set, selects a subgenomic interval that includes a repeated element, but does not hybridize to the repeated element (e.g., does not hybridize to the repeated elements in a BRCA2 gene).

In other embodiments, the first, the second, or the tumor, bait set selects a subgenomic interval that includes an exon adjacent to a cancer associated gene fusion, to thereby facilitate the capture of nucleic acid sequences (e.g., cDNA fragments) adjacent to the gene fusion.

In other embodiments, the first, the second, or the tumor, bait set selects a subgenomic interval that is from one or more genes or gene products shown in Table 1, 1A, 3 or 4, that is associated with a cancerous phenotype, e.g., a cancer chosen from one or more of the cancer types described in Tables 1, 1A, 3 or 4.

In other embodiments, the first bait set, or the tumor bait set, selects an ABL-1 gene or gene product, or a subgenomic interval thereof, that is associated with a cancerous phenotype, e.g., a soft-tissue malignancy chosen from one or more of CML, ALL or T-ALL. In one embodiment, the library, e.g., the nucleic acid library, is obtained from a sample from a subject having, or at risk of having, one or more of CML, ALL or T-ALL.

In other embodiments, the first bait set, or the tumor bait set, selects an AKT1 gene or gene product, or a subgenomic interval thereof, that is associated with a cancerous phenotype, e.g., a cancer chosen from one or more of breast, colorectal, ovarian, or non-small cell lung carcinoma (NSCLC). In one embodiment, the library, e.g., the nucleic acid library, is obtained from a sample from a subject having, or at risk of having, one or more of breast, colorectal, ovarian, or non-small cell lung carcinoma (NSCLC).

In other embodiments, the first bait set, or the tumor bait set, selects an ALK gene or gene product, or a subgenomic interval thereof, that is associated with a cancerous phenotype, e.g., a cancer chosen from one or more of ALCL, NSCLC or neuroblastoma. In one embodiment, the library, e.g., the nucleic acid library, is obtained from a sample from a subject having, or at risk of having, one or more of ALCL, NSCLC or neuroblastoma.

In other embodiments, the first bait set, or the tumor bait set, selects an APC gene or gene product, or a subgenomic interval thereof, that is associated with a cancerous phenotype, e.g., a cancer chosen from one or more of colorectal, pancreatic, desmoid, hepatoblastoma, glioma, or other CNS cancers or tumors. In one embodiment, the library, e.g., the nucleic acid library, is obtained from a sample from a subject having, or at risk of having, one or more of colorectal, pancreatic, desmoid, hepatoblastoma, glioma, or other CNS cancers or tumors.

In other embodiments, the first bait set, or the tumor bait set, selects a BRAF gene or gene product, or a subgenomic interval thereof, that is associated with a cancerous phenotype, e.g., a cancer chosen from one or more of melanoma, colorectal cancer, lung cancer, other epithelial malignancies, or hematological malignancies including AML or ALL. In one embodiment, the library, e.g., the nucleic acid library, is obtained from a sample from a subject having, or at risk of having, one or more of melanoma, colorectal cancer, lung cancer, other epithelial malignancies, or hematological malignancies including AML or ALL.

In other embodiments, the first bait set, or the tumor bait set, selects a CDKN2A gene or gene product, or a subgenomic interval thereof, that is associated with a cancerous phenotype, e.g., a cancer chosen from one or more of melanoma, pancreatic, or other tumor types. In one embodiment, the library, e.g., the nucleic acid library, is obtained from a sample from a subject having, or at risk of having, one or more of melanoma, pancreatic, or other tumor types.

In other embodiments, the first bait set, or the tumor bait set, selects a CEBPA gene or gene product, or a subgenomic interval thereof, that is associated with a cancerous phenotype, e.g., a cancer chosen from one or more of AML or MDS. In one embodiment, the library, e.g., the nucleic acid library, is obtained from a sample from a subject having, or at risk of having, one or more of AML or MDS.

In other embodiments, the first bait set, or the tumor bait set, selects a CTNNB1 gene or gene product, or a subgenomic interval thereof, that is associated with a cancerous phenotype, e.g., a cancer chosen from one or more of colorectal, ovarian, hepatoblastoma, or pleomorphic salivary adenoma. In one embodiment, the library, e.g., the nucleic acid library, is obtained from a sample from a subject having, or at risk of having, one or more of colorectal, ovarian, hepatoblastoma, or pleomorphic salivary adenoma.

In other embodiments, the first bait set, or the tumor bait set, selects an EGFR gene or gene product, or a subgenomic interval thereof, that is associated with a cancerous phenotype, e.g., a cancer chosen from one or more of glioma, lung cancer, or NSCLC. In one embodiment, the library, e.g., the nucleic acid library, is obtained from a sample from a subject having, or at risk of having, one or more of glioma, lung cancer, or NSCLC.

In other embodiments, the first bait set, or the tumor bait set, selects an ERBB2 gene or gene product, or a subgenomic interval thereof, that is associated, e.g., positively or negatively, with a cancerous phenotype, e.g., a cancer chosen from one or more of breast, ovarian, NSCLC, gastric or other solid tumors. In one embodiment, the library, e.g., the nucleic acid library, is obtained from a sample from a subject having, or at risk of having, one or more of breast, ovarian, NSCLC, gastric or other solid tumor types.

In other embodiments, the first bait set, or the tumor bait set, selects an ESR1 gene or gene product, or a subgenomic interval thereof, that is associated with a cancerous phenotype, e.g., a cancer chosen from one or more of breast, ovarian or endometrial tumors. In one embodiment, the library, e.g., the nucleic acid library, is obtained from a sample from a subject having, or at risk of having, one or more of breast, ovarian or endometrial tumors.

In other embodiments, the first bait set, or the tumor bait set, selects an FGFR1 gene or gene product, or a subgenomic interval thereof, that is associated with a cancerous phenotype, e.g., a cancer chosen from one or more of MPD or NHL. In one embodiment, the library, e.g., the nucleic acid library, is obtained from a sample from a subject having, or at risk of having, one or more of MPD or NHL.

In other embodiments, the first bait set, or the tumor bait set, selects an FGFR2 gene or gene product, or a subgenomic interval thereof, that is associated with a cancerous phenotype, e.g., a cancer chosen from one or more of gastric, NSCLC or endometrial tumors. In one embodiment, the library, e.g., the nucleic acid library, is obtained from a sample from a subject having, or at risk of having, one or more of gastric, NSCLC or endometrial tumors.

In other embodiments, the first bait set, or the tumor bait set, selects an FGFR3 gene or gene product, or a subgenomic interval thereof, that is associated with a cancerous phenotype, e.g., a cancer chosen from one or more of bladder cancer, multiple myeloma or T-cell lymphoma. In one embodiment, the library, e.g., the nucleic acid library, is obtained from a sample from a subject having, or at risk of having, one or more of bladder cancer, multiple myeloma or T-cell lymphoma.

In other embodiments, the first bait set, or the tumor bait set, selects an FLT3 gene or gene product, or a subgenomic interval thereof, that is associated with a cancerous phenotype, e.g., a cancer chosen from one or more of melanoma, colorectal, papillary thyroid, ovarian, non small-cell lung cancer (NSCLC), cholangiocarcinoma, or pilocytic astrocytoma. In one embodiment, the library, e.g., the nucleic acid library, is obtained from a sample from a subject having, or at risk of having, one or more of melanoma, colorectal, papillary thyroid, ovarian, non small-cell lung cancer (NSCLC), cholangiocarcinoma, or pilocytic astrocytoma.

In other embodiments, the first bait set, or the tumor bait set, selects an HRAS gene or gene product, or a subgenomic interval thereof, that is associated with a cancerous phenotype, e.g., a cancer chosen from one or more of rhadomyosarcoma, ganglioneuroblastoma, bladder, sarcomas, or other cancer types. In one embodiment, the library, e.g., the nucleic acid library, is obtained from a sample from a subject having, or at risk of having, one or more of rhadomyosarcoma, ganglioneuroblastoma, bladder, sarcomas, or other cancer types.

In other embodiments, the first bait set, or the tumor bait set, selects a JAK2 gene or gene product, or a subgenomic interval thereof, that is associated with a cancerous phenotype, e.g., a cancer chosen from one or more of ALL, AML, MPD or CML. In one embodiment, the library, e.g., the nucleic acid library, is obtained from a sample from a subject having, or at risk of having, one or more of ALL, AML, MPD or CML.

In other embodiments, the first bait set, or the tumor bait set, selects a KIT gene or gene product, or a subgenomic interval thereof, that is associated with a cancerous phenotype, e.g., a cancer chosen from one or more of gastrointestinal stromal tumors (GIST), AML, TGCT, mastocytosis, mucosal melanoma, or epithelioma. In one embodiment, the library, e.g., the nucleic acid library, is obtained from a sample from a subject having, or at risk of having, one or more of gastrointestinal stromal tumors (GIST), AML, TGCT, mastocytosis, mucosal melanoma, or epithelioma.

In other embodiments, the first bait set, or the tumor bait set, selects a KRAS gene or gene product, or a subgenomic interval thereof, that is associated with a cancerous phenotype, e.g., a cancer chosen from one or more of pancreatic, colon, colorectal, lung, thyroid, or AML. In one embodiment, the library, e.g., the nucleic acid library, is obtained from a sample from a subject having, or at risk of having, one or more of pancreatic, colon, colorectal, lung, thyroid, or AML.

In other embodiments, the first bait set, or the tumor bait set, selects a MET gene or gene product, or a subgenomic interval thereof, that is associated with a cancerous phenotype, e.g., a cancer chosen from one or more of renal or head-neck squamous cell carcinoma. In one embodiment, the library, e.g., the nucleic acid library, is obtained from a sample from a subject having, or at risk of having, one or more of renal or head-neck squamous cell carcinoma.

In other embodiments, the first bait set, or the tumor bait set, selects an MLL gene or gene product, or a subgenomic interval thereof, that is associated with a cancerous phenotype, e.g., a cancer chosen from one or more of AML or ALL. In one embodiment, the library, e.g., the nucleic acid library, is obtained from a sample from a subject having, or at risk of having, one or more of AML or ALL.

In other embodiments, the first bait set selects (e.g., is complementary to) an NF1 gene or gene product, or a subgenomic interval thereof, that is associated with a cancerous phenotype, e.g., a cancer chosen from one or more of neurofibroma or glioma. In one embodiment, the library, e.g., the nucleic acid library, is obtained from a sample from a subject having, or at risk of having, one or more of neurofibroma or glioma.

In other embodiments, the first bait set, or the tumor bait set, selects a NOTCH1 gene or gene product, or a subgenomic interval thereof, that is associated with a cancerous phenotype, e.g., a T-ALL cancer. In one embodiment, the library, e.g., the nucleic acid library, is obtained from a sample from a subject having, or at risk of having, a T-ALL cancer.

In other embodiments, the first bait set, or the tumor bait set, selects an NPM1 gene or gene product, or a subgenomic interval thereof, that is associated with a cancerous phenotype, e.g., a cancer chosen from one or more of NHL, APL or AML. In one embodiment, the library, e.g., the nucleic acid library, is obtained from a sample from a subject having, or at risk of having, one or more of NHL, APL or AML.

In other embodiments, the first bait set, or the tumor bait set, selects an NRAS gene or gene product, or a subgenomic interval thereof, that is associated with a cancerous phenotype, e.g., a cancer chosen from one or more of melanoma, colorectal cancer, multiple myeloma, AML, or thyroid cancer. In one embodiment, the library, e.g., the nucleic acid library, is obtained from a sample from a subject having, or at risk of having, one or more of melanoma, colorectal cancer, multiple myeloma, AML, or thyroid cancer.

In other embodiments, the first bait set, or the tumor bait set, selects a PDGFRA gene or gene product, or a subgenomic interval thereof, that is associated with a cancerous phenotype, e.g., a cancer chosen from one or more of GIST or idiopathic hypereosinophilic syndrome. In one embodiment, the library, e.g., the nucleic acid library, is obtained from a sample from a subject having, or at risk of having, one or more of GIST or idiopathic hypereosinophilic syndrome.

In other embodiments, the first bait set, or the tumor bait set, selects a PIK3CA gene or gene product, or a subgenomic interval thereof, that is associated with a cancerous phenotype, e.g., a cancer chosen from one or more of colorectal, gastric, gliobastoma, or breast cancer. In one embodiment, the library, e.g., the nucleic acid library, is obtained from a sample from a subject having, or at risk of having, one or more of colorectal, gastric, gliobastoma, or breast cancer.

In other embodiments, the first bait set, or the tumor bait set, selects a PTEN gene or gene product, or a subgenomic interval thereof, that is associated with a cancerous phenotype, e.g., a cancer chosen from one or more of colorectal, glioma, prostate, or endometrial cancer. In one embodiment, the library, e.g., the nucleic acid library, is obtained from a sample from a subject having, or at risk of having, one or more of colorectal, glioma, prostate, or endometrial cancer.

In other embodiments, the first bait set, or the tumor bait set, selects an RB1 gene or gene product, or a subgenomic interval thereof, that is associated with a cancerous phenotype, e.g., a cancer chosen from one or more of retinoblastoma, sarcoma, breast, or small cell lung carcinoma. In one embodiment, the library, e.g., the nucleic acid library, is obtained from a sample from a subject having, or at risk of having, one or more of retinoblastoma, sarcoma, breast, or small cell lung carcinoma.

In other embodiments, the first bait set, or the tumor bait set, selects a RET gene or gene product, or a subgenomic interval thereof, that is associated with a cancerous phenotype, e.g., a cancer chosen from one or more of medullary thyroid, papillary thyroid, or pheochromocytoma. In one embodiment, the library, e.g., the nucleic acid library, is obtained from a sample from a subject having, or at risk of having, one or more of medullary thyroid, papillary thyroid, or pheochromocytoma.

In other embodiments, the first bait set, or the tumor bait set, selects a TP53 gene or gene product, or a subgenomic interval thereof, that is associated with a cancerous phenotype, e.g., a cancer chosen from one or more of breast, colorectal, lung, sarcoma, adrenocortical, glioma, or other tumor types. In one embodiment, the library, e.g., the nucleic acid library, is obtained from a sample from a subject having, or at risk of having, one or more of breast, colorectal, lung, sarcoma, adrenocortical, glioma, or other tumor types.

In one embodiment, the first bait set, or the tumor bait set, selects a gene or gene product, or a subgenomic interval thereof, that is a positive predictor of therapeutic response. Examples of a positive predictor of a therapeutic response include, but are not limited to, an activating mutation in the EGFR gene that predicts responsiveness to small molecule EGFR TKIs (e.g., Iressa/gefitinib) in NSCLC patients; presence of an EML4/ALK fusion gene predicts responsiveness to ALK inhibitors (e.g. PF-02341066) in NSCLC patients; presence of a BRAF V600E mutation predicts responsiveness to BRAF inhibition (e.g. PLX-4032) in melanoma patients.

In other embodiments, the first bait set, or the tumor bait set, selects a gene or gene product, or a subgenomic interval thereof, that is a negative predictor of therapeutic response. Examples of a negative predictor of a therapeutic response include, but are not limited to, an activating mutation in the KRAS gene that predict lack of response to anti-EGFR monoclonal antibodies (cetuximab, panitumumab) in CRC patients; and the presence of an M351T mutation in the BCR/Abl fusion gene predicts resistance to Gleevec/imatinib in CML patients.

In other embodiments, the first bait set, or the tumor bait set, selects a gene or gene product, or a subgenomic interval thereof, that is a prognostic factor. Examples of prognostic factors include, but are not limited to, the presence of an insertion mutation in the FLT3 gene, which is a negative prognostic for relapse in AML patients; the presence of specific RET gene mutations, e.g. M918T, which are negative prognostic factors for survival in medullary thyroid carcinoma patients.

In other embodiments, the first bait set, or the tumor bait set, selects a gene or gene product, or a subgenomic interval thereof, that is a diagnostic factor. Examples of prognostic factors include, but are not limited to, the presence of a BCR/Abl fusion gene, which is diagnostic for CML; and the presence of a SMARCB1 mutation, which is diagnostic of Rhabdoid tumor of the kidney.

In yet other embodiments, the first or second bait set, or the tumor bait set, selects a nucleic acid molecule (e.g., a subgenomic interval) that includes an alteration that is associated with tumor progression and/or resistance, and has a late onset in cancer progression (e.g. a metastasis-associated mutation, a drug resistance associated mutation).

In yet other embodiments, the tumor member includes a subgenomic interval from a gene or gene product that is present in less than 5, 1, 0.5, 0.1%, 0.01%, 0.001% of the coding region of the genome of the tumor cells in the tumor sample.

In one embodiment, the tumor member includes a subgenomic interval from a gene or gene product that is associated with a tumor or cancer (e.g., is a positive or negative treatment response predictor, is a positive or negative prognostic factor for, or enables differential diagnosis of a tumor or cancer, e.g., a gene or gene product chosen from one or more of: ABL1, AKT1, ALK, AR, BRAF, BRCA1, BRCA2, CEBPA, EGFR, ERBB2, FLT3, JAK2, KIT, KRAS, MET, NPM1, PDGFRA, PIK3CA, RARA, AKT2, AKT3, MAP2K4, NOTCH1, and TP53.

In one embodiment, the tumor member includes a subgenomic interval selected from a wild type or mutated gene or gene product according to Tables 1, 1A-4.

In one embodiment, the tumor member includes a subgenomic interval selected from a wild type or mutated gene or gene product according to Tables 1, 1A-4, which are embedded in a GC-rich region.

In another embodiment, the tumor member includes a translocation alteration of at least 5, 10, 15, 20, 25, 30, 35, 40, 45, 50, 75, 110 or more genes or gene products according to Table 3. In other embodiments, the tumor member includes a translocation alteration of at least 5, 10, 15, 20, 25, 30, 35, 40, 45, 50, 75, 110 or more genes or gene products according to Table 3 in a solid tumor sample from the cancer types specified therein.

In one embodiment, the tumor member includes a translocation alteration of at least 5, 10, 15, 20, 25, 30, 35, 40, 45, 50, 75, 100, 150, 200 or more genes or gene products according to Table 4. In another embodiment, the tumor member includes a translocation alteration of at least 5, 10, 15, 20, 25, 30, 35, 40, 45, 50, 75, 100, 150, 200 or more genes or gene products according to Table 4 in a heme tumor sample from the cancer types specified therein.

In other embodiments, the plurality of baits further include a bait set that selects (e.g., is complementary to) a control member, e.g., a nucleic acid used for one or more of: fingerprinting the target nucleic acid member in the library; quantifying the abundance of a target nucleic acid member in the library; identifying a patient's target nucleic acid member in the library, determining the ploidy in a sample from which the library is derived; determining the loss of heterozygosity in a sample from which the library is derived; determining gene duplication in a sample from which the library is derived; determining gene amplification in a sample from which the library is derived; or determining tumor/normal cellular admixture in a sample from which the library is derived. Such baits are referred to herein as "control baits." In one embodiment, the control bait set is a third bait set or a PGx bait set. In other embodiments, the control bait set selects (e.g., is complementary to) PGx member as described herein. In other embodiments, the control bait selects a nucleic acid molecule that includes an SNP (e.g., an SNP as described herein).

In certain embodiments, the third bait set, the tumor or the non-tumor bait set, or the PGx bait set (referred to collectively herein as "the control bait set") selects a nucleic acid molecule (in the same of a different subgenomic interval as the tumor or reference member) that is a low-level target, for example, detection of heterozygous alleles requires 10-100× sequencing depth to ensure high detection reliability. In one embodiment, the third bait set, or the tumor or the PGx bait set, selects a subgenomic interval that is used for one or more of: fingerprinting the target nucleic acid member in the library; quantifying the abundance of a target nucleic acid member in the library; identifying a patient's target nucleic acid member in the library, determining the ploidy in a sample from which the library is derived; determining the loss of heterozygosity in a sample from which the library is derived; determining gene duplication in a sample from which the library is derived; determining gene amplification in a sample from which the library is derived; or determining tumor/normal cellular admixture in a sample from which the library is derived.

In one embodiment, the control bait set (e.g., the third bait set, the tumor or the non-tumor bait set, or the PGx bait set) selects one or more subgenomic intervals (e.g., exons) that are chosen from: a) pharmacogenomic SNPs that may explain the ability of patient to metabolize different drugs, b) a genomic SNPs that may be used to uniquely identify (fingerprint) a patient, c) a genomic SNPs/loci that may be used to assess copy number gains/losses of genomic DNA and loss-of-heterozygosity (LOH).

In one embodiment, the control bait set (e.g., the third bait set, the tumor or the non-tumor bait set, or the PGx bait set) selects a nucleic acid molecule comprising a variant associated with drug metabolism or toxicity. In one embodiment, the control bait set (e.g., the third bait set, the tumor or the non-tumor bait set, or the PGx bait set) selects (e.g., is complementary to) a nucleic acid molecule associated with a subject's genetic make-up (e.g., ethnicity, race, familial traits).

In other embodiments, the control bait set (e.g., the third bait set, the tumor or the non-tumor bait set, or the PGx bait set) selects a single nucleotide polymorphism (SNP). In one embodiment, the third bait set, the tumor or the non-tumor (e.g., a PGx) bait set, selects (e.g., is complementary to) an SNP chosen from one, two, three, four, five, ten, fifteen, twenty, twenty-five, or thirty of: ABCB1, ABCG2, ABCC4, ABCG2, C1orf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, and UMPS. In one embodiment, the control bait set selects a gene or gene product according to Table 2.

In other embodiments, the control bait set (e.g., the third bait set, the tumor or the non-tumor bait set, or the PGx bait set) selects a subgenomic interval from a mutated or wild type PGx gene or gene product (e.g., single nucleotide polymorphism (SNP)) of a subgenomic interval that is present in a gene or gene product associated with one or more of: (i) better survival of a cancer patient treated with a drug (e.g., better survival of a breast cancer patient treated with paclitaxel (e.g., an ABCB1 gene)); (ii) paclitaxel metabolism (e.g., CYP2C8 genes at different loci and mutations shown in Table 2; CYP3A4 gene); (iii) toxicity to a drug (e.g., 6-MP toxicity as seen with ABCC4 gene (Table 2); 5-FU toxicity as seen with DPYD gene, TYMS gene, or UMPS gene (Table 2); purine toxicity as seen with a TMPT gene (Table 2); daunorubicin toxicity as seen with NRP2 gene; C1orf144 gene, CYP1B1 gene (Table 2); or (iv) a side effect to a drug (e.g., ABCG2, TYMS, UGT1A1, ESR1 and ESR2 genes (Table 2)).

In other embodiments, the control bait set (e.g., the third bait set, the tumor or the non-tumor bait set, or the PGx bait set) selects a subgenomic interval (e.g., exon or UTR sequences) preselected to provide quantitation of the abundance of a target nucleic acid member in the library. In one embodiment, the third bait set, the tumor or the non-tumor (e.g., a PGx) provides quantitation of the relative abundance of a transcript in the library, e.g., a cDNA library.

In other embodiments, the fourth bait set selects a first intron target (e.g., a member that includes an intron sequence) for which low-medium coverage is required, e.g., to detect a structural breakpoint, such as a genomic translocation or an indel. For example, detection of an intronic breakpoint requires 5-50× sequence-pair spanning depth to ensure high detection reliability. Said fourth bait sets can be used to detect, for example, translocation/indel-prone cancer genes.

In yet other embodiments, the fifth bait set selects a second intron target (e.g., an intron member) for which sparse coverage is required to improve the ability to detect copy number changes. For example, detection of a one-copy deletion of several terminal exons requires 0.1-10× coverage to ensure high detection reliability. Said fifth bait sets can be used to detect, for example, amplification/deletion-prone cancer genes.

In yet another embodiment, any of the bait sets described herein (e.g., the first, second, third bait, fourth bait, fifth bait set, control, tumor, non-tumor bait set, or PGx bait set) is modified to reduce the formation of secondary structure (e.g., by replacement of a nucleotide with a different nucleotide that results in reduced formation of a secondary structure. In one embodiment, the modified bait set is used to capture regions of high GC content. In one embodiment, the modified bait (or the plurality of baits) includes a replacement of one or more nucleotides with a different natural nucleotide (e.g., A, C, G, U, or T). In another embodiment, the modified bait (or the plurality of baits) includes a replacement of one or more nucleotides with a non-natural nucleotide analog (e.g., inosine or deoxyinosine). In one embodiment, the bait set is modified as shown by an exemplary sequence in Table 8.

In other embodiments, two or more of the first, second or third bait set are in the same subgenomic interval (e.g., the same gene or gene product). In one embodiment, the first and second bait set are in the same subgenomic interval. In another embodiment, the first and third bait set are in the same subgenomic interval. In another embodiment, the second and third bait set are in the same subgenomic interval. In other embodiments, the first, second and third bait set are in different subgenomic intervals (e.g., different genes or gene products).

Any combination of aforesaid bait sets can be used in the methods described herein. In one embodiment, a subset or all of the aforesaid of first, second and/or third baits, or plurality of baits are used in combination.

In one embodiment, the combination includes a first bait set and a second bait set as described herein. For example, the first bait set selects a tumor member, e.g., a subgenomic interval that includes an alteration (e.g., one or more mutations) as described herein as Priority 1 in Table 1 or 1A); and the second bait set selects a member described herein as a Cancer gene in Table 1 or 1A.

In other embodiments, the combination includes a first bait and a third bait set as described herein. For example, the first bait set selects a tumor member, e.g., a subgenomic interval that includes an alteration (e.g., one or more mutations) as described herein as Priority 1 in Table 1 or 1A); and the third bait set selects a PGx member, e.g., a nucleic acid molecule (in the same of a different subgenomic interval) used for one or more of fingerprinting the sample, identifying a patient's sample, determination of ploidy, determination of loss of heterozygosity, determination of gene duplication, determination of gene amplification, or determination of tumor/normal cellular admixture (e.g., an SNP as described herein).

In other embodiments, the combination includes a second bait set and third bait set as described herein. For example, the second bait set selects a member described herein as a Cancer gene in Table 1 or 1A; and the third bait set selects a PGx member, e.g., a nucleic acid molecule (in the same of a different subgenomic interval) used for one or more of fingerprinting the sample, identifying a patient's sample, determination of ploidy, determination of loss of heterozygosity, determination of gene duplication, determination of gene amplification, or determination of tumor/normal cellular admixture (e.g., an SNP as described herein).

In yet other embodiments, the combination includes a first bait set, a second bait set, and a third bait set as described herein.

In yet other embodiments, the combination includes a first bait set that selects a mutated tumor member, e.g., a subgenomic interval that includes an alteration (e.g., one or more mutations as described herein) of a gene or gene product according to Table 1 or 1A. In one embodiment, the first bait set selects one, two, three, four, five, six, seven, eight, nine, ten, fifteen, twenty, twenty-five, thirty, thirty-five codons chosen from one or more of: codon 315 of the ABL1 gene; codon 1114, 1338, 1450 or 1556 of APC; codon 600 of BRAF; codon 32, 33, 34, 37, 41 or 45 of CTNNB1; codon 719, 746-750, 768, 790, 858 or 861 of EGFR; codon 835 of FLT3; codon 12, 13, or 61 of HRAS; codon 617 of JAK2; codon 816 of KIT; codon 12, 13, or 61 of KRAS; codon 88, 542, 545, 546, 1047, or 1049 of PIK3CA; codon 130, 173, 233, or 267 of PTEN; codon 918 of RET; codon 175, 245, 248, 273, or 306 of TP53; and a first bait set that selects a wild type sequence (e.g., a reference member) corresponding to one or more of the aforesaid genes or gene products.

In yet other embodiments, the combination includes a first bait set that selects a tumor member, e.g., a subgenomic interval that includes an alteration (e.g., one or more mutations as described herein), wherein the tumor or cancer-associated member is chosen from one, two, three, four, five, six, seven, eight, nine, ten, fifteen, twenty, twenty-five, thirty or more of: ABL1, AKT1, ALK, APC, AR, BRAF, CDKN2A, CEBPA, CTNNB1, EGFR, ERBB2, ESR1, FGFR1, FGFR2, FGFR3, FLT3, HRAS, JAK2, KIT, KRAS, MET, MLL, MYC, NF1, NOTCH1, NPM1, NRAS, PDGFRA, PIK3CA, PTEN, RB1, RET, or TP53 gene or gene product. In one embodiment, the first bait set selects one, two, three, four, five, six, seven, eight, nine, ten, fifteen, twenty, twenty-five, thirty, thirty-five codons chosen from one or more of: codon 315 of the ABL1 gene; codon 1114, 1338, 1450 or 1556 of APC; codon 600 of BRAF; codon 32, 33, 34, 37, 41 or 45 of CTNNB1; codon 719, 746-750, 768, 790, 858 or 861 of EGFR; codon 835 of FLT3; codon 12, 13, or 61 of HRAS; codon 617 of JAK2; codon 816 of KIT; codon 12, 13, or 61 of KRAS; codon 88, 542, 545, 546, 1047, or 1049 of PIK3CA; codon 130, 173, 233, or 267 of PTEN; codon 918 of RET; codon 175, 245, 248, 273, or 306 of TP53; and the third bait set selects a nucleic acid molecule (in the same of a different subgenomic interval) used for one or more of fingerprinting the sample, identifying a patient's sample, determination of ploidy, determination of loss of heterozygosity, determination of gene duplication, determination of gene amplification, or determination of tumor/normal cellular admixture (e.g., an SNP as described herein).

In yet other embodiments, the first bait set selects a nucleic acid molecule (e.g., a subgenomic interval) that includes an alteration that is associated with tumor progression and/or resistance, and has a late onset in cancer progression (e.g. a metastasis-associated mutation, a drug resistance associated mutation); and the second bait set selects (e.g., is complementary to) a nucleic acid molecule (e.g., a subgenomic interval) that includes an alteration that is associated with tumor progression and/or resistance, and has an early onset in cancer progression (e.g. an APC or a TP53 mutation in colon cancer).

In another embodiment the bait set comprises at least two, or all, of the following:

a first bait set having a first pattern of coverage for a first subgenomic interval;

a second bait set having a second pattern of coverage for a second subgenomic interval; and (optionally) a third, fourth or fifth bait set having a third pattern of coverage for a third subgenomic interval.

In one embodiment, the first subgenomic interval is chosen from one or more of a nucleotide sequence in a first gene, exon, intron, intergenic region, or region having a preselected SNP as described herein.

In one embodiment, the second subgenomic interval is chosen from one or more of a nucleotide sequence in a first gene, exon, intron, intergenic region, or region having a preselected SNP as described herein.

In one embodiment, the third subgenomic interval is chosen from one or more of a nucleotide sequence in a first gene, exon, intron, intergenic region, or region having a preselected SNP as described herein.

In one embodiment, the fourth subgenomic interval is chosen from one or more of a nucleotide sequence in a first gene, exon, intron, intergenic region, or region having a preselected SNP as described herein.

In one embodiment, the fifth subgenomic interval is chosen from one or more of a nucleotide sequence in a first gene, exon, intron, intergenic region, or region having a preselected SNP as described herein.

In one embodiment, the first, second and third subgenomic intervals are present in different genes or gene products.

In one embodiment, at least two of the first, second and third subgenomic intervals are present in the same gene or gene product.

In one embodiment, the first, second and third subgenomic intervals are present in the same gene or gene product.

In certain embodiments, the first, second and third patters of coverage are the same.

In other embodiments, at least one or more of said patterns of coverage are different.

In other embodiments, at least two or more of said patterns of coverage are different.

In yet other embodiments, the first, second and third patters of coverage are different.

In another embodiment the plurality of baits comprises at least two, or all of the following:

a first plurality of baits having a first level of overhang (positive or negative) with respect to a first subgenomic interval;

a second plurality of baits having a second level of overhang (positive or negative) with respect to a second subgenomic interval;

a third plurality of baits having a second level of overhang (positive or negative) with respect to a third subgenomic interval; and (optionally) a fourth or fifth plurality of baits having a second level of overhang (positive or negative) with respect to a third subgenomic interval, wherein at least a plurality of said levels are different.

In one embodiment, the first, second, third, fourth or fifth, subgenomic interval is chosen from one or more of a nucleotide sequence in a first gene, exon, intron, intergenic region, or region having a preselected SNP as described herein.

In another aspect, the invention features a method of providing a modified bait set. The method includes modifying a bait sequence and/or length to reduce a secondary structure.

In one embodiment, the secondary structure is formed at the 5' end of the bait sequence. In another embodiment, the secondary structure is formed in the middle of the bait sequence. In yet another embodiment, the secondary structure is formed at the 3' end of the bait sequence.

In one embodiment, the method includes the step of replacing a nucleotide with a different nucleotide that results in reduced formation of a secondary structure. In one embodiment, the modified bait (or the plurality of baits) is used to capture regions of high GC content. In one embodiment, the modified bait (or the plurality of baits) includes a replacement of one or more nucleotides with a different natural nucleotide (e.g., A, C, G, U, or T). In another embodiment, the modified bait (or the plurality of baits) includes a replacement of one or more nucleotides with a non-natural nucleotide analog (e.g., inosine or deoxyinosine. In one embodiment, the bait set is modified as shown by an exemplary sequence in Table 8.

In another embodiment the method comprises one or more of: adjusting the ratio (e.g., the molarity) of any of the baits or plurality of baits described herein (e.g., a first, second or third bait, or plurality of baits); providing an optimized hybridization buffer.

In another aspect, the invention features a bait set (e.g., a bait set as described herein).

In one embodiment, the bait or collection of baits is/includes one, a subset of, or all of, the first, second, third, fourth, fifth, tumor or control baits sets as described herein. In other embodiments, the bait set is/includes one, a subset of, or all of, the mutation capturing, reference or control bait set as described herein.

In some embodiments, the bait set selects a gene or gene product, or a subgenomic interval thereof, as described herein, and is associated, e.g., positively or negatively, with a cancerous phenotype as described herein.

In certain embodiments, the bait set selects a wild type or non-mutated nucleotide sequence.

In other embodiments, the bait set as described herein selects a nucleic acid used for one or more of: fingerprinting the target nucleic acid member in the library; quantifying the abundance of a target nucleic acid member in the library; identifying a patient's target nucleic acid member in the library, determining the ploidy in a sample from which the library is derived; determining the loss of heterozygosity in a sample from which the library is derived; determining gene duplication in a sample from which the library is derived; determining gene amplification in a sample from which the library is derived; or determining tumor/normal cellular admixture in a sample from which the library is derived. Such baits are referred to herein as "control baits." In one embodiment, the control bait (or the control plurality of baits) is complementary to a nucleic acid molecule that includes an SNP (e.g., an SNP as described herein).

In yet another embodiment, any of the bait sets described herein is modified to reduce formation of a secondary structure (e.g., by replacement of a nucleotide with a different nucleotide that results in reduced formation of a secondary structure). In one embodiment, the modified bait (or the plurality of baits) is used to capture regions of high GC content. In one embodiment, the modified bait (or the plurality of baits) includes a replacement of one or more nucleotides with a different natural nucleotide (e.g., A, C, G, U, or T). In another embodiment, the modified bait (or the plurality of baits) includes a replacement of one or more nucleotides with a non-natural nucleotide analog (e.g., inosine or deoxyinosine). In one embodiment, the bait set is modified as shown by an exemplary sequence in Table 8.

Additional embodiments or features of the present invention are as follows:

In another aspect, the invention features a method of making the aforesaid bait sets. The method includes selecting one or more target specific bait oligonucleotide sequences (e.g., any of the bait sequences corresponding to the subgenomic intervals of the gene or gene products as described herein); obtaining a pool of target specific bait oligonucleotide sequences (e.g., synthesizing the pool of target specific bait oligonucleotide sequences, e.g., by microarray synthesis); and optionally, amplifying the oligonucleotides to produce the bait sets.

In yet another aspect, the invention features a method for determining the presence or absence of an alteration associated, e.g., positively or negatively, with a cancerous phenotype (e.g, at least 10, 20, 30, 50 or more of the alterations in the genes or gene products described herein) in a nucleic acid sample. The method includes contacting the nucleic acids in the sample to solution-based selection according to any of the methods and baits described herein to obtain a nucleic acid catch; and sequencing (e.g., by next generation sequencing)

all or a subset of the nucleic acid catch, thereby determining the presence or absence of the alteration in the genes or gene products described herein).

In certain embodiments, the bait set includes an oligonucleotide (or a plurality of oligonucleotides) between about 100 nucleotides and 300 nucleotides in length. Typically, the bait set include an oligonucleotide (or a plurality of oligonucleotides) between about 130 nucleotides and 230 nucleotides, or about 150 and 200 nucleotides, in length. In other embodiments, the bait set includes an oligonucleotide (or a plurality of oligonucleotides) between about 300 nucleotides and 1000 nucleotides in length.

In some embodiments, the target member-specific sequences in the oligonucleotide is between about 40 and 1000 nucleotides, about 70 and 300 nucleotides, about 100 and 200 nucleotides in length, typically between about 120 and 170 nucleotides in length.

In some embodiments, the bait set include a binding entity. The binding entity can be an affinity tag on each bait sequence. In some embodiments, the affinity tag is a biotin molecule or a hapten. In certain embodiments, the binding entity allows for separation of the bait/member hybrids from the hybridization mixture by binding to a partner, such as an avidin molecule, or an antibody that binds to the hapten or an antigen-binding fragment thereof.

In other embodiments, the oligonucleotides in the bait set contains forward and reverse complemented sequences for the same target member sequence whereby the oligonucleotides with reverse-complemented member-specific sequences also carry reverse complemented universal tails. This can lead to RNA transcripts that are the same strand, i.e., not complementary to each other.

In other embodiments, the bait set includes oligonucleotides that contain degenerate or mixed bases at one or more positions. In still other embodiments, the bait set includes multiple or substantially all known sequence variants present in a population of a single species or community of organisms. In one embodiment, the bait set includes multiple or substantially all known sequence variants present in a human population.

In other embodiments, the bait set includes cDNA sequences or are derived from cDNAs sequences. In one embodiment, the cDNA is prepared from an RNA sequence, e.g., a tumor- or cancer cell-derived RNA, e.g., an RNA obtained from a tumor-FFPE sample. In other embodiments, the bait set includes amplification products (e.g., PCR products) that are amplified from genomic DNA, cDNA or cloned DNA.

In other embodiments, the bait set includes RNA molecules. In some embodiments, the set includes are chemically, enzymatically modified, or in vitro transcribed RNA molecules, including but not limited to, those that are more stable and resistant to RNase.

In yet other embodiments, the baits are produced by methods described in US 2010/0029498 and Gnirke, A. et al. (2009) Nat. Biotechnol. 27(2):182-189, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Accordingly, a method of making the aforesaid bait set is provided. The method includes selecting one or more target specific bait oligonucleotide sequences (e.g., one or more mutation capturing, reference or control oligonucleotide sequences as described herein); obtaining a pool of target specific bait oligonucleotide sequences (e.g., synthesizing the pool of target specific bait oligonucleotide sequences, e.g., by microarray synthesis); and optionally, amplifying the oligonucleotides to produce the bait set.

In other embodiments, the methods further include amplifying (e.g., by PCR) the oligonucleotides using one or more biotinylated primers. In some embodiments, the oligonucleotides include a universal sequence at the end of each oligonucleotide attached to the microarray. The methods can further include removing the universal sequences from the oligonucleotides. Such methods can also include removing the complementary strand of the oligonucleotides, annealing the oligonucleotides, and extending the oligonucleotides. In some of these embodiments, the methods for amplifying (e.g., by PCR) the oligonucleotides use one or more biotinylated primers. In some embodiments, the method further includes size selecting the amplified oligonucleotides.

In one embodiment, an RNA bait set is made. The methods include producing a set of bait sequences according to the methods described herein, adding a RNA polymerase promoter sequence at one end of the bait sequences, and synthesizing RNA sequences using RNA polymerase. The RNA polymerase can be chosen from a T7 RNA polymerase, an SP6 RNA polymerase or a T3 RNA polymerase. In other embodiments, the RNA polymerase promoter sequence is added at the ends of the bait sequences by amplifying (e.g., by PCR) the bait sequences. In embodiments where the bait sequences are amplified by PCR with specific primer pairs out of genomic or cDNA, adding an RNA promoter sequence to the 5' end of one of the two specific primers in each pair will lead to a PCR product that can be transcribed into a RNA bait using standard methods.

In other embodiments, bait sets can be produced using human DNA or pooled human DNA samples as the template. In such embodiments, the oligonucleotides are amplified by polymerase chain reaction (PCR). In other embodiments, the amplified oligonucleotides are reamplified by rolling circle amplification or hyperbranched rolling circle amplification. The same methods also can be used to produce bait sequences using human DNA or pooled human DNA samples as the template. The same methods can also be used to produce bait sequences using subfractions of a genome obtained by other methods, including but not limited to restriction digestion, pulsed-field gel electrophoresis, flow-sorting, CsCl density gradient centrifugation, selective kinetic reassociation, microdissection of chromosome preparations and other fractionation methods known to those skilled in the art.

In certain embodiments, the number of baits in the bait set is less than 1,000, e.g., 2, 3, 4, 5, 10, 50, 100, 500 baits. In other embodiments, the number of baits in the bait set is greater than 1,000, greater than 5,000, greater than 10,000, greater than 20,000, greater than 50,000, greater than 100,000, or greater than 500,000.

In certain embodiments, a library (e.g., a nucleic acid library) includes a collection of members. As described herein, the library members can include a target member (e.g., a tumor member, a reference member and/or a control member; also referred to herein as a first, second and/or third member, respectively). The members of the library can be from a single individual. In embodiments a library can comprise members from more than one subject (e.g., 2, 3, 4, 5, 6, 7, 8, 9, 10, 20, 30 or more subjects), e.g., two or more libraries from different subjects can be combined to from a library having members from more than one subject. In one embodiment, the subject is human having, or at risk of having, a cancer or tumor.

"Member" or "library member" or other similar term, as used herein, refers to a nucleic acid molecule, e.g., DNA or RNA, that is a member of a library. Typically, a member is a DNA molecule, e.g., genomic DNA or cDNA. A member can be sheared genomic DNA. In other embodiments, the member can be a cDNA. In other embodiments, the member can be an RNA. Members comprise sequence from a subject and can also comprise a sequence not derived from the subject, e.g., primers or sequences that allow for identification, e.g., "barcode" sequences.

In yet another embodiment, the methods featured in the invention further include isolating a nucleic acid sample to provide a library (e.g., a nucleic acid library as described herein). In certain embodiments, the nucleic acid sample includes whole genomic, subgenomic fragments, or both. Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a tumor sample, a normal adjacent tissue (NAT), a blood sample or any normal control)). In one embodiment, the sample (e.g., the tumor or NAT sample) is a preserved. For example, the sample is embedded in a matrix, e.g., an FFPE block or a frozen sample. In certain embodiments, the isolating step includes flow-sorting of individual chromosomes; and/or microdissecting a subject's sample (e.g., a tumor sample, a NAT, a blood sample). In certain embodiments, the nucleic acid sample used to generate the nucleic acid library is less than 5, less than 1 microgram, or less than 500 ng (e.g., 200 ng or less).

In still other embodiments, the nucleic acid sample used to generate the library includes RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample by specific or non-specific nucleic acid amplification methods that are well known to those skilled in the art.

In some embodiments, certain embodiments, the nucleic acid sample is amplified, e.g., by whole-genome amplification methods such as random-primed strand-displacement amplification.

In other embodiments, the nucleic acid sample is fragmented or sheared by physical or enzymatic methods and ligated to synthetic adapters, size-selected (e.g., by preparative gel electrophoresis) and amplified (e.g., by PCR). In other embodiments, the fragmented and adapter-ligated group of nucleic acids is used without explicit size selection or amplification prior to hybrid selection.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In certain embodiments, the members of the library include a subgenomic interval that includes an intragenic region or an intergenic region. In another embodiment, the subgenomic interval includes an exon or an intron, or a fragment thereof, typically an exon sequence or a fragment thereof. In one embodiment, the subgenomic interval includes a coding region or a non-coding region, e.g., a promoter, an enhancer, a 5' untranslated region (5' UTR), or a 3' untranslated region (3' UTR), or a fragment thereof. In other embodiments, the subgenomic interval includes a cDNA or a fragment thereof (e.g., cDNA obtained from a tumor RNA (e.g., RNA extracted from a tumor sample, e.g., FFPE-tumor sample). In other embodiments, the subgenomic interval includes an SNP, e.g., as described herein. In other embodiments, the target members include substantially all exons in a genome. In other embodiments, the target members include a subgenomic interval as described herein, e.g., subgenomic intervals, e.g., exons from selected genes or gene products of interest (e.g., genes or gene products associated with a cancerous phenotype as described herein).

In one embodiment, the subgenomic interval includes a somatic mutation, a germ line mutation or both. In one embodiment, the subgenomic interval includes an alteration, e.g., a point or a single mutation, a deletion mutation (e.g., an in-frame deletion, an intragenic deletion, a full gene deletion), an insertion mutation (e.g., intragenic insertion), an inversion mutation (e.g., an intra-chromosomal inversion), a linking mutation, a linked insertion mutation, an inverted duplication mutation, a tandem duplication (e.g., an intrachromosomal tandem duplication), a translocation (e.g., a chromosomal translocation, a non-reciprocal translocation), a rearrangement (e.g., a genomic rearrangement), a change in gene copy number, or a combination thereof. In certain embodiments, the subgenomic interval constitutes less than 5, 1, 0.5, 0.1%, 0.01%, 0.001% of the coding region of the genome of the tumor cells in a sample. In other embodiments, the subgenomic intervals are not involved in a disease, e.g., are not associated with a cancerous phenotype as described herein.

The methods featured in the invention include the step of contacting the library (e.g., the nucleic acid library) with a plurality of baits to provide a selected subgroup of nucleic acids, e.g., a library catch. In one embodiment, the contacting step is effected in a solid support, e.g., an array. Suitable solid supports for hybridization are described in, e.g., Albert, T. J. et al. (2007) *Nat. Methods* 4(11):903-5; Hodges, E. et al. (2007) *Nat. Genet.* 39(12):1522-7; Okou, D. T. et al. (2007) *Nat. Methods* 4(11):907-9, the contents of which are hereby incorporated by reference. In other embodiments, the contacting step is effected in solution hybridization. In certain embodiments, the method includes repeating the hybridization step by one or more additional rounds of hybridization. In some embodiments, the methods further include subjecting the library catch to one or more additional rounds of hybridization with the same or different collection of baits.

In other embodiments, the methods featured in the invention further include amplifying the library catch (e.g., by PCR). In other embodiments, the library catch is not amplified.

In yet other embodiments, the methods further include analyzing the library catch. In one embodiment, the library catch is analyzed by a sequencing method, e.g., a next-generation sequencing method as described herein. The methods include isolating a library catch by solution hybridization, and subjecting the library catch by nucleic acid sequencing.

In certain embodiments, the library catch can be re-sequenced. Next generation sequencing methods are known in the art, and are described, e.g., in Metzker, M. (2010) *Nature Biotechnology Reviews* 11:31-46.

In yet other embodiments, the methods further include the step of subjecting the library catch to genotyping, thereby identifying the genotype of the selected nucleic acids.

In certain embodiments, the method further includes one or more of:

i) fingerprinting the nucleic acid sample;
ii) quantifying the abundance of a gene or gene product (e.g., a gene or gene product as described herein) in the nucleic acid sample (e.g., quantifying the relative abundance of a transcript in the sample);
iii) identifying the nucleic acid sample as belonging to a particular subject (e.g., a normal control or a cancer patient);
iv) identifying a genetic trait in the nucleic acid sample (e.g., one or more subject's genetic make-up (e.g., ethnicity, race, familial traits));
v) determining the ploidy in the nucleic acid sample; determining a loss of heterozygosity in the nucleic acid sample;
vi) determining the presence or absence of a gene duplication event in the nucleic acid sample;
vii) determining the presence or absence of a gene amplification event in the nucleic acid sample; or
viii) determining the level of tumor/normal cellular admixture in the nucleic acid sample.

Any of the methods described herein can be combined with one or more of the embodiments below.

In an embodiment, the method comprises acquiring a nucleotide sequence read obtained from a tumor and/or control nucleic acid sample (e.g., an FFPE-derived nucleic acid sample).

In an embodiment, the reads are provided by a next-generation sequencing method.

In an embodiment, the method includes providing a library of nucleic acid members and sequencing a preselected subgenomic interval from a plurality of members of said library. In embodiments, the method can include a step of selecting a subset of said library for sequencing, e.g., a solution-based selection.

In certain embodiments, a method comprises hybrid capture methods which are designed to capture two or more different target categories, each with a different bait design strategies. The hybrid capture methods and compositions are intended to capture a defined subset of target sequences (e.g., target members) and provide homogenous coverage of the target sequence, while minimizing coverage outside of that subset. In one embodiment, the target sequences include the entire exome out of genomic DNA, or a selected subset thereof. The methods and compositions disclosed herein provide different bait sets for achieving different depths and patterns of coverage for complex target nucleic acid sequences (e.g., libraries).

In certain embodiment, the different categories of bait sets and targets are as follows.

A. A first bait set that selects a high-level target (e.g., one or more tumor members and/or reference members, such as genes, exons, or bases) for which the deepest coverage is required to enable a high level of sensitivity for mutations that appear at low frequencies. For example, detection of point mutations that appear at a frequency of about 5% or less (i.e. 5% of the cells from which the sample was prepared harbor this mutation in their genome). The first bait set typically requires about 500× or higher sequencing depth to ensure high detection reliability. In one embodiment, the first bait set selects one or more subgenomic intervals (e.g., exons) that are frequently mutated in certain types of cancer, e.g., a Priority 1 Cancer gene or gene product according to Table 1 or 1A.

B. A second bait set that selects a mid-level target (e.g., one or more tumor members and/or reference members, such as genes, exons, or bases) for which high coverage is required to enable high level of sensitivity for mutations that appear at a higher frequency than the high level target, e.g., a frequency of about 10%. For example, detection of an alteration (e.g., a point mutation) that appears at a frequency of 10% requires about 200× or higher sequencing depth to ensure high detection reliability. In one embodiment, the second bait set selects one or more subgenomic intervals (e.g., exons) that are chosen from the Cancer genes or gene products according to Table 1 or 1A.

C. A third bait set that selects a low-level target (e.g., one or more PGx members, such as genes, exons, or bases) for which low-medium coverage is required to enable high level of sensitivity, e.g., to detect heterozygous alleles. For example, detection of heterozygous alleles requires 10-100× sequencing depth to ensure high detection reliability. In one embodiment, the third bait set selects one or more subgenomic intervals (e.g., exons) that are chosen from: a) pharmacogenomic SNPs that may explain the ability of patient to metabolize different drugs, b) a genomic SNPs that may be used to uniquely identify (fingerprint) a patient, c) a genomic SNPs/loci that may be used to assess copy number gains/losses of genomic DNA and loss-of-heterozygosity (LOH).

D. A fourth bait set that selects an intron target (e.g., an intron member) for which low-medium coverage is required to detect structural breakpoints such as genomic translocations or indels. For example, detection of an intronic breakpoint requires 5-50× sequence-pair spanning depth to ensure high detection reliability. Said fourth bait sets can be used to detect, for example, translocation/indel-prone cancer genes.

E. A fifth bait set that selects an intron target (e.g., an intron member) for which sparse coverage is required to improve the ability to detect copy number changes. For example, detection of a 1 copy deletion of several terminal exon requires 0.1-10× coverage to ensure high detection reliability. Said fifth bait sets can be used to detect, for example, amplification/deletion-prone cancer genes.

The methods and compositions featured in the invention involve tuning the relative sequence coverage of each bait set/target category. Methods for implementing differences in relative sequence coverage in bait design include one or more of:

(i) Differential representation of different bait sets—The bait set design to capture a given target (e.g., a target member) can be included in more/fewer number of copies to enhance/reduce relative target coverage depths;

(ii) Differential overlap of bait subsets—The bait set design to capture a given target (e.g., a target member) can include a longer or shorter overlap between neighboring baits to enhance/reduce relative target coverage depths;

(iii) Differential bait parameters—The bait set design to capture a given target (e.g., a target member) can include sequence modifications/shorter length to reduce capture efficiency and lower the relative target coverage depths;

(iv) Mixing of different bait sets—Bait sets that are designed to capture different target sets can be mixed at different molar ratios to enhance/reduce relative target coverage depths;

(v) Using different types of oligonucleotide bait sets—In certain embodiments, the bait set can include:

(a) one or more chemically (e.g., non-enzymatically) synthesized (e.g., individually synthesized) baits, (b) one or more baits synthesized in an array, (c) one or more enzymatically prepared, e.g., in vitro transcribed, baits;

(d) any combination of (a), (b) and/or (c), (e) one or more DNA oligonucleotides (e.g., a naturally or non-naturally occurring DNA oligonucleotide), (f) one or more RNA oligonucleotides (e.g., a naturally or non-naturally occurring RNA oligonucleotide), (g) a combination of (e) and (f), or (h) a combination of any of the above.

The different oligonucleotide combinations can be mixed at different ratios, e.g., a ratio chosen from 1:1, 1:2, 1:3, 1:4, 1:5, 1:10, 1:20, 1:50; 1:100, 1:1000, or the like. In one embodiment, the ratio of chemically-synthesized bait to array-generated bait is chosen from 1:5, 1:10, or 1:20. The DNA or RNA oligonucleotides can be naturally- or normaturally-occurring. In certain embodiments, the baits include one or more non-naturally-occurring nucleotide to, e.g., increase melting temperature. Exemplary non-naturally occurring oligonucleotides include modified DNA or RNA nucleotides. An exemplary modified RNA nucleotide is a locked nucleic acid (LNA), wherein the ribose moiety of an LNA nucleotide is modified with an extra bridge connecting the 2' oxygen and 4' carbon (Kaur, H; Arora, A; Wengel, J; Maiti, S; Arora, A.; Wengel, J.; Maiti, S. (2006). "Thermodynamic, Counterion, and Hydration Effects for the Incorporation of Locked Nucleic Acid Nucleotides into DNA Duplexes". *Biochemistry* 45 (23): 7347-55). Other modified exemplary DNA and RNA nucleotides include, but are not limited to, peptide nucleic acid (PNA) composed of repeating N-(2-aminoethyl)-glycine units linked by peptide bonds (Egholm, M. et al. (1993) *Nature* 365 (6446): 566-8); a DNA or RNA oligonucleotide modified to capture low GC regions; a bicyclic nucleic acid (BNA) or a crosslinked oligonucleotide; a modified 5-methyl deoxycytidine; and 2,6-diaminopurine. Other modified DNA and RNA nucleotides are known in the art.

In certain embodiments, a substantially uniform or homogeneous coverage of a target sequence (e.g., a target member) is obtained. For example, within each bait set/target category, uniformity of coverage can be optimized by modifying bait parameters, for example, by one or more of:

(i) Increasing/decreasing bait representation or overlap can be used to enhance/reduce coverage of targets (e.g., target members), which are under/over-covered relative to other targets in the same category;

(ii) For low coverage, hard to capture target sequences (e.g., high GC content sequences), expand the region being targeted with the bait sets to cover, e.g., adjacent sequences (e.g., less GC-rich adjacent sequences);

(iii) Modifying a bait sequence can be made to reduce secondary structure of the bait and enhance its efficiency of selection;

(iv) Modifying a bait length can be used to equalize melting hybridization kinetics of different baits within the same category. Bait length can be modified directly (by producing baits with varying lengths) or indirectly (by producing baits of consistent length, and replacing the bait ends with arbitrary sequence);

(v) Modifying baits of different orientation for the same target region (i.e. forward and reverse strand) may have different binding efficiencies. The bait set with either orientation providing optimal coverage for each target may be selected;

(vi) Modifying the amount of a binding entity, e.g., a capture tag (e.g. biotin), present on each bait may affect its binding efficiency. Increasing/decreasing the tag level of baits targeting a specific target may be used to enhance/reduce the relative target coverage;

(vii) Modifying the type of nucleotide used for different baits can be altered to affect binding affinity to the target, and enhance/reduce the relative target coverage; or (viii) Using modified oligonucleotide baits, e.g., having more stable base pairing, can be used to equalize melting hybridization kinetics between areas of low or normal GC content relative to high GC content.

For example, different types of oligonucleotide bait sets can be used.

In one embodiment, the value for efficiency of selection is modified by using different types of bait oligonucleotides to encompass pre-selected target regions. For example, a first bait set (e.g., an array-based bait set comprising 10,000-50,000 RNA or DNA baits) can be used to cover a large target area (e.g., 1-2 MB total target area). The first bait set can be spiked with a second bait set (e.g., individually synthesized RNA or DNA bait set comprising less than 5,000 baits) to cover a pre-selected target region (e.g., selected subgenomic intervals of interest spanning, e.g., 250 kb or less, of a target area) and/or regions of higher secondary structure, e.g., higher GC content. Selected subgenomic intervals of interest may correspond to one or more of the genes or gene products described herein, or a fragment thereof. The second bait set may include about 2,000-5,000 baits depending on the bait overlap desired. In yet other embodiments, the second bait set can include selected oligo baits (e.g., less than 400, 200, 100, 50, 40, 30, 20, 10 baits) spiked into the first bait set. The second bait set can be mixed at any ratio of individual oligo baits. For example, the second bait set can include individual baits present as a 1:1 equimolar ratio. Alternatively, the second bait set can include individual baits present at different ratio (e.g., 1:5, 1:10, 1:20), for example, to optimize capture of certain targets (e.g., certain targets can have a 5-10× of the second bait compared to other targets).

Sequencing

The invention also includes methods of sequencing nucleic acids. In these methods, nucleic acid library members are isolated by using the methods described herein, e.g., using solution hybridization, thereby providing a library catch. The library catch or a subgroup thereof can be sequenced. Accordingly, the methods featured in the invention further include analyzing the library catch. In one embodiment, the library catch is analyzed by a sequencing method, e.g., a next-generation sequencing method as described herein. The methods include isolating a library catch by solution hybridization, and subjecting the library catch by nucleic acid sequencing. In certain embodiments, the library catch can be re-sequenced.

Any method of sequencing known in the art can be used. Sequencing of nucleic acids isolated by selection methods are typically carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference.

In one embodiment, the next-generation sequencing allows for the determination of the nucleotide sequence of an individual nucleic acid molecule (e.g., Helicos BioSciences' HeliScope Gene Sequencing system, and Pacific Biosciences' PacBio RS system). In other embodiments, the sequencing method determines the nucleotide sequence of clonally expanded proxies for individual nucleic acid molecules (e.g., the Solexa sequencer, Illumina Inc., San Diego, Calif.; 454 Life Sciences (Branford, Conn.), and Ion Torrent). e.g., massively parallel short-read sequencing (e.g., the Solexa sequencer, Illumina Inc., San Diego, Calif.), which generates more bases of sequence per sequencing unit than other sequencing methods that generate fewer but longer reads. Other methods or machines for next-generation sequencing include, but not limited to, the sequencers provided by 454 Life Sciences (Branford, Conn.), Applied Biosystems (Foster City, Calif.; SOLiD sequencer), Helicos BioSciences Corporation (Cambridge, Mass.), and emulsion and microfluidic sequencing technology nanodroplets (e.g., GnuBio droplets).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system.

NGS technologies can include one or more of steps, e.g., template preparation, sequencing and imaging, and data analysis.

Template preparation. Methods for template preparation can include steps such as randomly breaking nucleic acids (e.g., genomic DNA or cDNA) into smaller sizes and generating sequencing templates (e.g., fragment templates or mate-pair templates). The spatially separated templates can be attached or immobilized to a solid surface or support, allowing massive amount of sequencing reactions to be performed simultaneously. Types of templates that can be used for NGS reactions include, e.g., clonally amplified templates originating from single DNA molecules, and single DNA molecule templates.

Methods for preparing clonally amplified templates include, e.g., emulsion PCR (emPCR) and solid-phase amplification.

EmPCR can be used to prepare templates for NGS. Typically, a library of nucleic acid fragments is generated, and adaptors containing universal priming sites are ligated to the ends of the fragment. The fragments are then denatured into single strands and captured by beads. Each bead captures a single nucleic acid molecule. After amplification and enrichment of emPCR beads, a large amount of templates can be attached or immobilized in a polyacrylamide gel on a standard microscope slide (e.g., Polonator), chemically crosslinked to an amino-coated glass surface (e.g., Life/APG; Polonator), or deposited into individual PicoTiterPlate (PTP) wells (e.g., Roche/454), in which the NGS reaction can be performed.

Solid-phase amplification can also be used to produce templates for NGS. Typically, forward and reverse primers are covalently attached to a solid support. The surface density of the amplified fragments is defined by the ratio of the primers to the templates on the support. Solid-phase amplification can produce hundreds of millions spatially separated template clusters (e.g., Illumina/Solexa). The ends of the template clusters can be hybridized to universal sequencing primers for NGS reactions.

Other methods for preparing clonally amplified templates also include, e.g., Multiple Displacement Amplification (MDA) (Lasken R. S. *Curr Opin Microbiol.* 2007; 10(5):510-6). MDA is a non-PCR based DNA amplification technique. The reaction involves annealing random hexamer primers to the template and DNA synthesis by high fidelity enzyme, typically Φ29 at a constant temperature. MDA can generate large sized products with lower error frequency.

Template amplification methods such as PCR can be coupled with NGS platforms to target or enrich specific regions of the genome (e.g., exons). Exemplary template enrichment methods include, e.g., microdroplet PCR technology (Tewhey R. et al., *Nature Biotech.* 2009, 27:1025-1031), custom-designed oligonucleotide microarrays (e.g., Roche/NimbleGen oligonucleotide microarrays), and solution-based hybridization methods (e.g., molecular inversion probes (MIPs) (Porreca G. J. et al., *Nature Methods,* 2007, 4:931-936; Krishnakumar S. et al., *Proc. Natl. Acad. Sci. USA,* 2008, 105:9296-9310; Turner E. H. et al., *Nature Methods,* 2009, 6:315-316), and biotinylated RNA capture sequences (Gnirke A. et al., *Nat. Biotechnol.* 2009; 27(2): 182-9)

Single-molecule templates are another type of templates that can be used for NGS reaction. Spatially separated single molecule templates can be immobilized on solid supports by various methods. In one approach, individual primer molecules are covalently attached to the solid support. Adaptors are added to the templates and templates are then hybridized to the immobilized primers. In another approach, single-molecule templates are covalently attached to the solid support by priming and extending single-stranded, single-molecule templates from immobilized primers. Universal primers are then hybridized to the templates. In yet another approach, single polymerase molecules are attached to the solid support, to which primed templates are bound.

Sequencing and imaging. Exemplary sequencing and imaging methods for NGS include, but not limited to, cyclic reversible termination (CRT), sequencing by ligation (SBL), single-molecule addition (pyrosequencing), and real-time sequencing.

CRT uses reversible terminators in a cyclic method that minimally includes the steps of nucleotide incorporation, fluorescence imaging, and cleavage. Typically, a DNA polymerase incorporates a single fluorescently modified nucleotide corresponding to the complementary nucleotide of the template base to the primer. DNA synthesis is terminated after the addition of a single nucleotide and the unincorporated nucleotides are washed away. Imaging is performed to determine the identity of the incorporated labeled nucleotide. Then in the cleavage step, the terminating/inhibiting group and the fluorescent dye are removed. Exemplary NGS platforms using the CRT method include, but not limited to, Illumina/Solexa Genome Analyzer (GA), which uses the clonally amplified template method coupled with the four-color CRT method detected by total internal reflection fluorescence (TIRF); and Helicos BioSciences/HeliScope, which uses the single-molecule template method coupled with the one-color CRT method detected by TIRF.

SBL uses DNA ligase and either one-base-encoded probes or two-base-encoded probes for sequencing. Typically, a fluorescently labeled probe is hybridized to its complementary sequence adjacent to the primed template. DNA ligase is used to ligate the dye-labeled probe to the primer. Fluorescence imaging is performed to determine the identity of the ligated probe after non-ligated probes are washed away. The fluorescent dye can be removed by using cleavable probes to regenerate a 5'-$PO_4$ group for subsequent ligation cycles.

Alternatively, a new primer can be hybridized to the template after the old primer is removed. Exemplary SBL platforms include, but not limited to, Life/APG/SOLiD (support oligonucleotide ligation detection), which uses two-base-encoded probes.

Pyrosequencing method is based on detecting the activity of DNA polymerase with another chemiluminescent enzyme. Typically, the method allows sequencing of a single strand of DNA by synthesizing the complementary strand along it, one base pair at a time, and detecting which base was actually added at each step. The template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. Exemplary pyrosequencing platform include, but not limited to, Roche/454, which uses DNA templates prepared by emPCR with 1-2 million beads deposited into PTP wells.

Real-time sequencing involves imaging the continuous incorporation of dye-labeled nucleotides during DNA synthesis. Exemplary real-time sequencing platforms include, but not limited to, Pacific Biosciences platform, which uses DNA polymerase molecules attached to the surface of individual zero-mode waveguide (ZMW) detectors to obtain sequence information when phospholinked nucleotides are being incorporated into the growing primer strand; Life/VisiGen platform, which uses an engineered DNA polymerase with an attached fluorescent dye to generate an enhanced signal after nucleotide incorporation by fluorescence resonance energy transfer (FRET); and LI-COR Biosciences platform, which uses dye-quencher nucleotides in the sequencing reaction.

Other sequencing methods for NGS include, but not limited to, nanopore sequencing, sequencing by hybridization, nano-transistor array based sequencing, polony sequencing, scanning tunneling microscopy (STM) based sequencing, and nanowire-molecule sensor based sequencing.

Nanopore sequencing involves electrophoresis of nucleic acid molecules in solution through a nano-scale pore which provides a highly confined space within which single-nucleic acid polymers can be analyzed. Exemplary methods of nanopore sequencing are described, e.g., in Branton D. et al., *Nat. Biotechnol.* 2008; 26(10):1146-53.

Sequencing by hybridization is a non-enzymatic method that uses a DNA microarray. Typically, a single pool of DNA is fluorescently labeled and hybridized to an array containing known sequences. Hybridization signals from a given spot on the array can identify the DNA sequence. The binding of one strand of DNA to its complementary strand in the DNA double-helix is sensitive to even single-base mismatches when the hybrid region is short or is specialized mismatch detection proteins are present. Exemplary methods of sequencing by hybridization are described, e.g., in Hanna G. J. et al., *J. Clin. Microbiol.* 2000; 38 (7): 2715-21; and Edwards J. R. et al., *Mut. Res.* 2005; 573 (1-2): 3-12.

Polony sequencing is based on polony amplification and sequencing-by-synthesis via multiple single-base-extensions (FISSEQ). Polony amplification is a method to amplify DNA in situ on a polyacrylamide film. Exemplary polony sequencing methods are described, e.g., in US Patent Application Publication No. 2007/0087362.

Nano-transistor array based devices, such as Carbon NanoTube Field Effect Transistor (CNTFET), can also be used for NGS. For example, DNA molecules are stretched and driven over nanotubes by micro-fabricated electrodes. DNA molecules sequentially come into contact with the carbon nanotube surface, and the difference in current flow from each base is produced due to charge transfer between the DNA molecule and the nanotubes. DNA is sequenced by recording these differences. Exemplary Nano-transistor array based sequencing methods are described, e.g., in U.S. Patent Application Publication No. 2006/0246497.

Scanning tunneling microscopy (STM) can also be used for NGS. STM uses a piezo-electric-controlled probe that performs a raster scan of a specimen to form images of its surface. STM can be used to image the physical properties of single DNA molecules, e.g., generating coherent electron tunneling imaging and spectroscopy by integrating scanning tunneling microscope with an actuator-driven flexible gap. Exemplary sequencing methods using STM are described, e.g., in U.S. Patent Application Publication No. 2007/0194225.

A molecular-analysis device which is comprised of a nanowire-molecule sensor can also be used for NGS. Such device can detect the interactions of the nitrogenous material disposed on the nanowires and nucleic acid molecules such as DNA. A molecule guide is configured for guiding a molecule near the molecule sensor, allowing an interaction and subsequent detection. Exemplary sequencing methods using nanowire-molecule sensor are described, e.g., in U.S. Patent Application Publication No. 2006/0275779.

Double ended sequencing methods can be used for NGS. Double ended sequencing uses blocked and unblocked primers to sequence both the sense and antisense strands of DNA. Typically, these methods include the steps of annealing an unblocked primer to a first strand of nucleic acid; annealing a second blocked primer to a second strand of nucleic acid; elongating the nucleic acid along the first strand with a polymerase; terminating the first sequencing primer; deblocking the second primer; and elongating the nucleic acid along the second strand. Exemplary double ended sequencing methods are described, e.g., in U.S. Pat. No. 7,244,567.

Data analysis. After NGS reads have been generated, they can be aligned to a known reference sequence or assembled de novo.

For example, identifying genetic variations such as single-nucleotide polymorphism and structural variants in a sample (e.g., a tumor sample) can be accomplished by aligning NGS reads to a reference sequence (e.g., a wild-type sequence). Methods of sequence alignment for NGS are described e.g., in Trapnell C. and Salzberg S. L. *Nature Biotech.*, 2009, 27:455-457.

Examples of de novo assemblies are described, e.g., in Warren R. et al., *Bioinformatics*, 2007, 23:500-501; Butler J. et al., *Genome Res.*, 2008, 18:810-820; and Zerbino D. R. and Birney E., *Genome Res.*, 2008, 18:821-829.

Sequence alignment or assembly can be performed using read data from one or more NGS platforms, e.g., mixing Roche/454 and Illumina/Solexa read data.

Alignment

General

Alignment is the process of matching a read with a location, e.g., a genomic location. Misalignment (e.g., the placement of base-pairs from a short read on incorrect locations in the genome)., e.g., misalignment due to sequence context (e.g., presence of repetitive sequence) of reads around an actual cancer mutation can lead to reduction in sensitivity of mutation detection, as reads of the alternate allele may be shifted off the main pile-up of alternate allele reads. If the problematic sequence context occurs where no actual mutation is present, mis-alignment may introduce artifactual reads of "mutated" alleles by placing actual reads of reference genome bases onto the wrong location. Because mutation-calling algorithms for multiplied multigene analysis should be sensitive to even low-abundance mutations, these mis-alignments may increase false positive discovery rates/reduce specificity.

As discussed herein, reduced sensitivity for actual mutations may be addressed by evaluating the quality of alignments (manually or in an automated fashion) around expected mutation sites in the genes being analyzed. The sites to be evaluated can be obtained from databases of cancer mutations (e.g. COSMIC). Regions that are identified as problematic can be remedied with the use of an algorithm selected to give better performance in the relevant sequence context, e.g., by alignment optimization (or re-alignment) using slower, but more accurate alignment algorithms such as Smith-Waterman alignment. In cases where general alignment algorithms cannot remedy the problem, customized alignment approaches may be created by, e.g.: adjustment of maximum difference mismatch penalty parameters for genes with a high likelihood of containing substitutions; adjusting specific mismatch penalty parameters based on specific mutation types that are common in certain tumor types (e.g. C→T in melanoma); or adjusting specific mismatch penalty parameters based on specific mutation types that are common in certain sample types (e.g. substitutions that are common in FFPE). Reduced specificity (increased false positive rate) in the evaluated gene regions due to mis-alignment can be assessed by manual or automated examination of all mutation calls in samples sequenced. Those regions found to be prone to spurious mutation calls due to mis-alignment can be subjected to same alignment remedies as above. In cases where no algorithmic remedy is found possible, "mutations" from the problem regions can be classified or screened out from the test panel.

of 2 bp of a dinucleotide repeat cannot be readily definitively placed.) Both sensitivity and specificity can be reduced by incorrect placement of shorter (<15 bp) apparent indel-containing reads. Larger indels (getting closer in magnitude to the length of individual reads —36 bp in our current process) can cause failure to align the read at all, making detection of the indel impossible in the standard set of aligned reads.

Databases of cancer mutations can be used to address these problems and improve performance. To reduce false positive indel discovery (improve specificity), regions around commonly expected indels can be examined for problematic alignments due to sequence context and addressed similarly to substitutions above. To improve sensitivity of indel detection, several different approaches of using information on the indels expected in cancer can be used. E.g., short-reads contained expected indels can be simulated and alignment attempted. The alignments can be studied and problematic indel regions can have alignment parameters adjusted, for instance by reducing gap open/extend penalties or by aligning partial reads (e.g. the first or second half of a read).

Alternatively, initial alignment can be attempted not just with the normal reference genome, but also with alternate versions of the genome, containing each of the known or likely cancer indel mutations. In this approach, reads of indels that initially failed to align or aligned incorrectly are placed successfully on the alternate (mutated) version of the genome.

In this way, indel alignment (and thus calling) can be optimized for the expected cancer genes/sites. For example, when evaluating a breast cancer sample, alignment in the tumor suppressor PTEN can be optimized for the potential presence of indel mutations as exemplified in Table 5.

TABLE 5

Exemplary Indel Mutations in PTEN for Alignment Optimization

| Gene | Tissue | AA Exchange | Nucleotide Exchange | Chr. | Genome Start GRCh37 | Genome Stop GRCh37 | Nucleotide Exchange Freq. |
|---|---|---|---|---|---|---|---|
| PTEN | breast | K237__Y240>N | 710__718del9 | 10 | 89717685 | 89717693 | 0.128% |
| PTEN | breast | N329fs*12 | 987__996del10 | 10 | 89720836 | 89720845 | 0.128% |
| PTEN | breast | S338fs*1 | 1013__1023del11 | 10 | 89720862 | 89720872 | 0.128% |
| PTEN | breast | L70fs*7 | 208__251del44 | 10 | 89685313 | 89690844 | 0.256% |
| PTEN | breast | 0? | 1__1212del1212 | 10 | 89624227 | 89725229 | 0.128% |
| PTEN | breast | K60fs*9 | 180__181ins? | 10 | 89685285 | 89685286 | 0.128% |
| PTEN | breast | K60fs*39 | 179__179delA | 10 | 89685284 | 89685284 | 0.384% |
| PTEN | breast | K197fs*2 | 590delA | 10 | 89711972 | 89711972 | 0.128% |
| PTEN | breast | N323fs*2 | 968__969insA | 10 | 89720817 | 89720818 | 0.128% |
| PTEN | breast | V317fs*3 | 951__954delACTT | 10 | 89720800 | 89720803 | 0.256% |
| PTEN | breast | T319fs*1 | 955__958delACTT | 10 | 89720804 | 89720807 | 0.128% |
| PTEN | breast | I135del | 403__405delATA | 10 | 89692919 | 89692921 | 0.128% |
| PTEN | breast | S385fs*1 | 1154__1155delCT | 10 | 89725171 | 89725172 | 0.128% |
| PTEN | breast | T277fs*13 | 831__834delCTTC | 10 | 89720680 | 89720683 | 0.128% |
| PTEN | breast | R74fs*25 | 221__221delG | 10 | 89690814 | 89690814 | 0.128% |
| PTEN | breast | V275fs*1 | 823delG | 10 | 89720672 | 89720672 | 0.256% |
| PTEN | breast | F90fs*9 | 270delT | 10 | 89692786 | 89692786 | 0.128% |

Insertions/Deletions (Indels)

Generally, the accurate detection of indel mutations is an exercise in alignment, as the spurious indel rate on the sequencing platforms disabled herein is relatively low (thus, even a handful of observations of correctly aligned indels can be strong evidence of mutation). Accurate alignment in the presence of indels can be difficult however (especially as indel length increases). In addition to the general issues associated with alignment, e.g., of substitutions, the indel itself can cause problems with alignment. (For instance, a deletion Tuning Tuning: Sequence Alignment Algorithms As used herein, a sequence alignment algorithm embodies a computational method or approach used to identify from where in the genome a read sequence (e.g., a short-read sequence, e.g., from next-generation sequencing) most likely originated by assessing the similarity between the read sequence and a reference sequence. A variety of algorithms can be applied to the sequence alignment problem. Some algorithms are relatively slow, but allow relatively high specificity. These include, e.g., dynamic programming-based algorithms. Dynamic programming is a method for solving complex problems by breaking them down into simpler steps. Other approaches are relatively more efficient, but are typically not as thorough. These include, e.g., heuristic algorithms and probabilistic methods designed for large-scale database search.

Typically, there can be two steps in the alignment process: candidate lookup and sequence alignment. Candidate lookup reduces the search space for the sequence alignment from the entire genome to a shorter list of possible alignment locations. Sequence alignment, as the term suggests, includes aligning a sequence with a sequence provided in candidate lookup step. It can be performed using global alignment (e.g., Needleman-Wunsch alignment) or local alignment (e.g., Smith-Waterman alignment).

Most of fast alignment algorithms can be characterized as one of the three types based on the method of indexing: algorithms based on hash tables (e.g., BLAST, ELAND, SOAP), suffix trees (e.g., Bowtie, BWA), and merge sorting (e.g., Slider).

Short read sequences are typically used for alignment. Examples of sequence alignment algorithms/programs for short-read sequences include, but not limited to, BFAST (Horner N. et al., *PLoS One.* 2009; 4(11):e7767), BLASTN (on the worldwide web at blast.ncbi.nlm.nih.gov), BLAT (Kent W. J. *Genome Res.* 2002; 12(4):656-64), Bowtie (Langmead B. et al., *Genome Biol.* 2009; 10(3):R25), BWA (Li H. and Durbin R. *Bioinformatics*, 2009, 25:1754-60), BWA-SW (Li H. and Durbin R. *Bioinformatics*, 2010; 26(5):589-95), CloudBurst (Schatz M. C. *Bioinformatics.* 2009; 25(11):1363-9), Corona Lite (Applied Biosystems, Carlsbad, Calif., USA), CASHX (Fahlgren N. et al., *RNA*, 2009; 15, 992-1002), CUDA-EC (Shi H. et al., *J Comput Biol.* 2010; 17(4):603-15), ELAND (on the worldwide web at bioit.dbi.udel.edu/howto/eland), GNUMAP (Clement N. L. et al., *Bioinformatics.* 2010; 26(1):38-45), GMAP (Wu T. D. and Watanabe C. K. *Bioinformatics.* 2005; 21(9):1859-75), GSNAP (Wu T. D. and Nacu S., *Bioinformatics.* 2010; 26(7): 873-81), Geneious Assembler (Biomatters Ltd., Auckland, New Zealand), LAST, MAQ (Li H. et al., *Genome Res.* 2008; 18(11):1851-8), Mega-BLAST (on the worldwide web at ncbi.nlm.nih.gov/blast/megablast.shtml), MOM (Eaves H. L. and Gao Y. *Bioinformatics.* 2009; 25(7):969-70), MOSAIK (on the worldwide web at bioinformatics.bc.edu/marthlab/Mosaik), Novoalign (on the worldwide web at novocraft.com/main/index.php), PALMapper (on the worldwide web at fml.tuebingen.mpg.de/raetsch/suppl/palmapper), PASS (Campagna D. et al., *Bioinformatics.* 2009; 25(7):967-8), PatMaN (Prufer K. et al., *Bioinformatics.* 2008; 24(13):1530-1), PerM (Chen Y. et al., *Bioinformatics*, 2009, 25 (19): 2514-2521), ProbeMatch (Kim Y. J. et al., *Bioinformatics.* 2009; 25(11):1424-5), QPalma (de Bona F. et al., *Bioinformatics*, 2008, 24(16): i174), RazerS (Weese D. et al., *Genome Research*, 2009, 19:1646-1654), RMAP (Smith A. D. et al., *Bioinformatics.* 2009; 25(21):2841-2), SeqMap (Jiang H. et al. *Bioinformatics.* 2008; 24:2395-2396.), Shrec (Salmela L., *Bioinformatics.* 2010; 26(10):1284-90), SHRiMP (Rumble S. M. et al., *PLoS Comput. Biol.,* 2009, 5(5):e1000386), SLIDER (Malhis N. et al., *Bioinformatics*, 2009, 25 (1): 6-13), SLIM Search (Muller T. et al., *Bioinformatics.* 2001;17 Suppl 1:S182-9), SOAP (Li R. et al., *Bioinformatics.* 2008; 24(5):713-4), SOAP2 (Li R. et al., *Bioinformatics.* 2009; 25(15):1966-7), SOCS (Ondov B. D. et al., *Bioinformatics,* 2008; 24(23):2776-7), SSAHA (Ning Z. et al., *Genome Res.* 2001; 11(10):1725-9), SSAHA2 (Ning Z. et al., *Genome Res.* 2001; 11(10):1725-9), Stampy (Lunter G. and Goodson M. *Genome Res.* 2010, epub ahead of print), Taipan (on the worldwide web at taipan.sourceforge.net), UGENE (on the worldwide web at ugene.unipro.ru), XpressAlign (on the worldwide web at bcgsc.ca/platform/bioinfo/software/XpressAlign), and ZOOM (Bioinformatics Solutions Inc., Waterloo, ON, Canada).

A sequence alignment algorithm can be chosen based on a number of factors including, e.g., the sequencing technology, read length, number of reads, available compute resources, and sensitivity/scoring requirements. Different sequence alignment algorithms can achieve different levels of speed, alignment sensitivity, and alignment specificity. Alignment specificity typically refers to the percentage of aligned target sequence residues, as found in the submission, which are aligned correctly, compared with the predicted alignment. Alignment sensitivity usually refers to the percentage of aligned target sequence residues as found in the predicted alignment, which have also been correctly aligned in the submission.

Alignment algorithms, such as ELAND, or SOAP can be used for the purpose of aligning short reads (e.g., from Illumina/Solexa sequencer) to the reference genome when speed is the first factor to consider. Alignment algorithms, such as BLAST, or Mega-BLAST can be used for the purpose of similarity search using short reads (e.g., from Roche FLX) when specificity is the most important factor, although these methods are relatively slower. Alignment algorithms, such as MAQ, or Novoalign take quality scores into account and therefore can be used for both single- or paired-end data sets when accuracy is of the essence (e.g., in high-throughput SNP surveys).

Alignment algorithms, such as Bowtie, or BWA, use Burrows-Wheeler Transform (BWT) and therefore requires relatively small memory footprint. Alignment algorithms, such as BFAST, PerM, SHRiMP, SOCS, or ZOOM, map color space reads and therefore can be used with ABI's SOLiD platform. In some applications, the results from two or more alignment algorithms can be combined.

Tuning: Alignment Parameters

Alignment parameters are used in alignment algorithms to adjust performance of an algorithm, e.g., to produce an optimal global or local alignment between a read sequence and a reference sequence. Alignment parameters can give weights for match, mismatch, and indels. For example, lower weights allow alignments with more mismatches and indels.

Examples of alignment parameters include, but not limited to, match reward, mismatch penalty, gap penalty (e.g., gap opening penalty, gap extension penalty), expect threshold, word size, filter, or mask.

For example, gap penalties are designed to reduce the alignment score when an alignment has been broken by an insertion in the read sequence or the reference sequence. The gap penalties can be used to help decide whether on not to accept a gap or insertion in an alignment when it is possible to achieve a good alignment residue-to-residue at some other neighboring point in the sequence. In particularly, a penalty can be subtracted from the score for each gap opened (the "gap opening" penalty) and for the total number of gap spaces multiplied by a cost (the "gap extension" penalty). Typically, the cost of extending a gap is set to be at least about 2, 3, 4, 5, 6, 7, 8, 9, or 10 times lower than the cost for opening a gap. The expect threshold is a parameter that describes the number of hits one can "expect" to see by chance when searching a database of a particular size.

Tuning: Sequence Context-Based Selection/Tuning of Algorithms and Parameters

Sequence context, e.g., presence of repetitive sequences (e.g., tandem repeats, interspersed repeats), low-complexity regions, indels, pseudogenes, or paralogs can affect the alignment specificity (e.g., cause misalignment). As used herein, misalignment refers to the placement of base-pairs from the short read on incorrect locations in the genome.

Alignment algorithms, such as slower but more accurate alignment algorithms (e.g., Smith-Waterman alignment, or the multi-sequence (read) aligner CLUSTALW), can be selected to increase the alignment specificity (e.g., to decrease the likelihood of misalignment caused by sequence context, e.g., the presence of repetitive sequences).

Alignment parameters, such as match reward, mismatch penalties, gap penalties (e.g., gap opening penalties, gap extension penalties), expect threshold, word size, filter, or mask), can be adjusted (e.g., increased or decreased), to increase the alignment specificity (e.g., decrease the likelihood of misalignment caused by sequence context).

Tuning: Tumor Type-Based Selection/tuning of Algorithms and Parameters

The sensitivity of alignment can be increased when an alignment algorithm is selected or an alignment parameter is adjusted based on tumor type, e.g., a tumor type that tends to have a particular mutation or mutation type.

Alignment algorithms can be selected to adjust (e.g., increase) the alignment sensitivity, when the nucleic acid is isolated from a sample of certain tumor type.

Alignment parameters, such as match reward, mismatch penalties, gap penalties (e.g., gap opening penalties, gap extension penalties), expect threshold, word size, filter, or mask can be adjusted (e.g., increased or decreased), to adjust (e.g., increase) the alignment sensitivity, when the nucleic acid is isolated from a sample of certain tumor type. For example, C→T substitution is a common mutation type in melanoma. Thus, the sensitivity of alignment can be adjusted (e.g., increased) when the mismatch penalties for nucleic acid sequences from melanoma samples are decreased or increased.

Tuning: Gene Type-Based Selection/Tuning of Algorithms and Parameters

The sensitivity of alignment can be increased when an alignment algorithm is selected or an alignment parameter is adjusted based on a particular gene type (e.g., oncogene, tumor suppressor gene). Mutations in different types of cancer-associated genes can have different impact on cancer phenotype. For example, mutant oncogene alleles are typically dominant. Mutant tumor suppressor alleles are typically recessive, which means that in most cases both alleles of a tumor suppressor genes must be affected before an effect is manifested.

Alignment algorithm can be selected to adjust (e.g., increase) the alignment sensitivity, based on gene type (e.g., oncogene, tumor suppressor gene).

Alignment parameters, such as match reward, mismatch penalties, gap penalties (e.g., gap opening penalties, gap extension penalties), expect threshold, word size, filter, or mask, can be adjusted (e.g., increased or decreased), to adjust (e.g., increase) the alignment sensitivity/specificity, based on gene type (e.g., oncogene, tumor suppressor gene). For example, an inframe indel is commonly associated with a tumor suppressor. Thus, the sensitivity and specificity of alignment can be adjusted (e.g., increased) when the standard gap penalty approach (e.g., gap open+gap extend) is modified to prefer in-frame indels for oncogenes and frame-shift indels for tumor suppressors.

Tuning: Mutation Type-Based Selection/Tuning of Algorithms and Parameters

The sensitivity of alignment can be adjusted (e.g., increased) when an alignment algorithm is selected or an alignment parameter is adjusted based on mutation type (e.g., single-nucleotide polymorphism, indel (insertion or deletion), inversion, translocation, tandem repeat).

Alignment algorithms, such as BWA (fast single short-read), Smith-Waterman (slower, more accurate single short-read) and CLUSTALW (even slower, but considers multiple reads) can be selected to adjust (e.g., increase) the alignment sensitivity, based on mutation type (e.g., single-nucleotide polymorphism, indel (insertion or deletion), inversion, translocation, tandem repeat).

Alignment parameters, such as match reward, mismatch penalties, gap penalties (e.g., gap opening penalties, gap extension penalties), expect threshold, word size, filter, or mask can be adjusted (e.g., increased or decreased), to adjust (e.g., increase) the alignment sensitivity/specificity, based on mutation type (e.g., single-nucleotide polymorphism, indel (insertion or deletion), inversion, translocation, tandem repeat). For example, a point mutations are commonly associated with the KRAS gene. Thus, the sensitivity of alignment can be increased when the mismatch penalties for that position are decreased. Similarly, a deletion is commonly associates with the EGFR gene. Thus, the sensitivity of alignment can be increased when the gap penalties (e.g., gap open penalties, gap extension penalties) for that position(s) or gene are decreased. The sensitivity of alignment can also be increase if partial sequences (e.g., the first or second half of a read) are used for alignment.

Tuning/Mutation Site-Based Selection/Tuning of Algorithms and Parameters

The sensitivity of alignment can be adjusted (e.g., increased) when an alignment algorithm is selected or an alignment parameter is adjusted based on mutation site (e.g., a mutation hotspot). A mutation hotspot refers to a site in the genome where mutations occur up to 100 times more frequently than the normal mutation rate.

Alignment algorithms, can be selected to adjust (e.g., increase) the alignment sensitivity, based on mutation site (e.g., a mutation hotspot).

Alignment parameters, such as match reward, mismatch penalties, gap penalties (e.g., gap opening penalties, gap extension penalties), expect threshold, word size, filter, or mask, can be adjusted (e.g., increased or decreased), to adjust (e.g., increase) the alignment sensitivity, based on mutation site (e.g., a mutation hotspot). For example, mutations at codon 12 are commonly associated with the KRAS gene. Thus, the sensitivity of alignment can be increased when the mismatch penalties for that site are decreased.

Tuning: Sample type-Based Selection/Tuning of Algorithms and Parameters

The sensitivity/specificity of alignment can be adjusted (e.g., increased) when an alignment algorithm is selected or an alignment parameter is adjusted based on sample type (e.g., an FFPE sample).

Alignment algorithms can be selected to adjust (e.g., increase) the alignment sensitivity/specificity, based on sample type (e.g., an FFPE sample).

Alignment parameters, such as match reward, mismatch penalties, gap penalties (e.g., gap opening penalties, gap extension penalties), expect threshold, word size, filter, or mask, can be adjusted (e.g., increased or decreased) to adjust (e.g., increase) the alignment sensitivity/specificity, based on sample type (e.g., an FFPE sample). For example, a transition mutation artifact due to DNA damage is commonly associated with FFPE samples. Thus, the sensitivity/specificity of alignment can be increased when the mismatch penalties for sequences obtained from FFPE samples are increased.

Alignment Module

General Methods for Alignment

Methods disclosed herein allow the use of multiple, individually tuned, alignment methods or algorithms to optimize performance in sequencing methods, particularly in methods that rely on massively parallel sequencing of a large number of diverse genetic events in a large number of diverse genes, e.g., methods of analyzing tumor samples. In embodiments, multiple alignment methods that are individually customized or tuned to each of a number of variants in different genes are used to analyze reads. In embodiments, tuning can be a function of (one or more of) the gene (or other subgenomic interval) being sequenced, the tumor type in the sample, the variant being sequenced, or a characteristic of the sample or the subject. The selection or use of alignment conditions that are individually tuned to a number of subgenomic intervals to be sequenced allows optimization of speed, sensitivity and specificity. The method is particularly effective when the alignment of reads for a relatively large number of diverse subgenomic intervals is optimized.

Accordingly, in one aspect, a method of analyzing a sample, e.g., a tumor sample, is provided. The method comprises:

(a) acquiring a library comprising a plurality members from a sample, e.g., a plurality of tumor members from a tumor sample;

(b) optionally, enriching the library for preselected sequences, e.g., by contacting the library with a bait set (or plurality of bait sets) to provide selected members (sometimes referred to herein as library catch);

(c) acquiring a read for a subgenomic interval from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayeisan method) from said read for the preselected nucleotide position, thereby analyzing said tumor sample, wherein:

a read from each of X unique subgenomic intervals is aligned with a unique alignment method, wherein unique subgenomic interval means different from the other X−1 subgenoimc intervals, and wherein unique alignment method means different from the other X−1 alignment methods, and X is at least 2.

In an embodiment, step (b) is present. In an embodiment step (b) is absent.

In an embodiment X is at least 3, 4, 5, 10, 15, 20, 30, 50, 100, 500, or 1,000.

Thus, in an embodiment, a method described herein, e.g., a method of analyzing a tumor sample comprises an alignment method described herein. By way of example, the method (e.g., step (c)) can comprises selecting an alignment method for analyzing, e.g., aligning, said read, wherein the alignment method is a function of, is selected responsive to, or is optimized for, one or more or all of:

(i) tumor type, e.g., the tumor type in said sample;
(ii) the gene, or type of gene, in which said subgenomic interval being sequenced is located, e.g. wherein the gene or type of gene is associated with a preselected probability for a variant or type of variant, e.g., a mutation;
(iii) the site (e.g., nucleotide position) being analyzed;
(iv) the type of variant, e.g., a substitution, within the subgenomic interval being evaluated;
(v) the type of sample, e.g., an FFPE sample; and
(vi) sequence in or near said subgenomic interval being evaluated, e.g., the expected propensity for misalignment for said subgenomic interval, e.g., the presence of repeated sequences in or near said subgenomic interval.

As referred to elsewhere herein, a method is particularly effective when the alignment of reads for a relatively large number of subgenomic intervals is optimized. Thus, in an embodiment, at least X unique alignment methods are used to analyze reads for at least X unique subgenomic intervals, wherein unique means different from the other X−1, and X is equal to 2, 3, 4, 5, 10, 15, 20, 30, 50, 100, 200, 500 or 1,000.

In an embodiment, subgenomic intervals from at least X genes from Table 1 are analyzed, and X is equal to, 3, 4, 5, 10, 15, 20, or 30.

In an embodiment, subgenomic intervals from at least X genes from Table 1 having the priority 1 annotation are analyzed, and X is equal to, 3, 4, 5, 10, 15, 20, or 30.

In an embodiment, a unique alignment method is applied to a subgenomic intervals in each of at least 3, 5, 10, 20, 40, 50, 60, 70, 80, 90, or 100 different genes.

In an embodiment a nucleotide position in at least 20, 40, 60, 80, 100, 120, 140, 160 or 180 genes, e.g., genes from Table 1 or 1A, is assigned a nucleotide value. In an embodiment, a unique alignment method is applied to subgenomic intervals in each of at least 10, 20, 30, 40, or 50% of said genes analyzed.

In an embodiment, a nucleotide position in at least 5, 10, 20, 30, or 40 genes from Table 1 or 1A having the priority 1 annotation is assigned a nucleotide value. In an embodiment, a unique alignment method is applied to subgenomic intervals in each of at least 10, 20, 30, 40, or 50% of said genes analyzed.

In an embodiment, a nucleotide position for at least 10, 20, 30, 40, 50, 100, 150, 200, 300, 400, or 500 variants or codons, e.g., mutations, from Table 1, 1A, 2, or 3, is assigned a nucleotide value. In an embodiment a unique alignment method is applied to subgenomic intervals in each of at least 10, 20, 30, 40, or 50% of said genes analyzed.

In an embodiment, the method comprises:

applying a unique alignment method to each of X genomic intervals, each of which having a variant which is associated with a tumor phenotype, e.g. wherein the variant is a point mutation, and X is greater than 2, 3, 5, 10, 20, 40, 50, 60, 70, 80, 90, or 100, e.g., wherein each of said subgenomic intervals is located in a different gene.

In an embodiment, the method comprises:

applying a unique alignment method to each of X genomic intervals, each of which having a variant which is associated with a tumor phenotype, e.g. wherein the variant is a rearrangement, e.g., a deletion, insertion, or translocation, and X is greater than 2, 3, 5, 10, 20, 40, 50, 60, 70, 80, 90, or 100, wherein each of said subgenomic intervals is located in a different gene.

In an embodiment:

a first unique alignment, method is applied to a first subgenomic interval comprising a preselected nucleotide position, a variant of which is associated with a tumor phenotype, and a second unique alignment method is applied to a subgenomic interval comprising a preslected nucleotide other than said first preselected nucleotide position, e.g., a position having no variant with a tumor phenotype.

In an embodiment, the method comprises:

a) applying a first unique alignment method to a first genomic interval, a variant of which is associated with a tumor phenotype, e.g. wherein the variant is a point mutation, e.g., a mutation on Table 6;

b) applying a second unique alignment method to a second genomic interval, a variant of which is associated with a tumor phenotype, e.g. wherein the variant is a rearrangement, e.g., a deletion, insertion, or translocation, e.g., a mutation on Table 5; and c) applying a third unique alignment method to a third genomic interval, e.g., a genomic interval in which variants are not associated with a tumor phenotype or with a tumor of the type in said sample.

In an embodiment, the gene or type of gene is:

an oncogene, which can be associated with e.g., activating mutations in tyrosine kinase domains;

a tumor suppressor which can be with de-activating (e.g., non-sense) mutations; or a drug ADME-related gene, which can be with high-activity or low-activity germ-line genetic variation.

In an embodiment, selecting an alignment method comprises, selecting a parameter (or a value therefor) for use in an alignment algorithm, e.g., a match reward, mismatch penalty, gap penalty (e.g., a gap opening penalty, gap extension penalty), expected threshold, word size, filter, or mask. The parameter (or value therefor) can be selected from a panel of preselected parameters, e.g., parameters defined by preselected boundaries or limits.

In an embodiment, when aligning (or, optimizing alignments) for a gene that contains a known cancer substitution and a known germ-line indel, the gap penalties can be reduced so that the germ-line variant is captured correctly and doesn't adversely affect the alignment around the somatic mutation of interest.

In an embodiment, selecting an alignment method comprises selecting a maximum difference mismatch penalty parameter for a gene with a high likelihood of containing a substitution.

In an embodiment, selecting an alignment method comprises, selecting an alignment algorithm, e.g., selecting a slower, but more accurate algorithm, e.g., a Smith-Waterman alignment instead of a faster, e.g., BWA, or selecting alignment optimization using a multiple alignment method such as CLUSTALW.

In an embodiment, said alignment method is a function of, is selected responsive to, or is optimized for, a characteristic of the nucleic acid sample, e.g., sample age, sample tissue source (e.g. pancreatic), presence of carcinogen/mutagen exposure (e.g. smoking, UV), quality of nucleic acid sample (e.g., level of nucleic acid fragmentation) in the sample.

In an embodiment, at least X (wherein X is 1, 2, 3, 4, 5, 10, 15, 20, 30, 40 or 50) alignment method(s) is a function of, is selected responsive to, or is optimized for (i).

In an embodiment, at least X (wherein X is 1, 2, 3, 4, 5, 10, 15, 20, 30, 40 or 50) alignment method(s) is a function of, is selected responsive to, or is optimized for (ii).

In an embodiment, at least X (wherein X is 1, 2, 3, 4, 5, 10, 15, 20, 30, 40 or 50) alignment method(s) is a function of, is selected responsive to, or is optimized for (iii).

In an embodiment, a first alignment method is function of, is selected responsive to, or is optimized for (i), a second alignment method is function of, is selected responsive to, or is optimized for (ii), and a third alignment method is function of, is selected responsive to, or is optimized for (iii).

In an embodiment, at least one alignment method is a function of, is selected responsive to, or is optimized for, (i) and one or more of (ii), (iii), (iv), (v), or (vii).

In an embodiment, at least X (wherein X is 1, 2, 3, 4, 5, 10, 15, 20, 30, 40 or 50) alignment method(s) is a function of, is selected responsive to, or is optimized for, (ii) and one or more of (ii), (iii), (iv), (v), or (vii).

In an embodiment, said alignment method is a function of, is selected responsive to, or is optimized for, the gene, or type of gene, e.g., wherein the gene or type of gene is associated with a preselected probability or type of variant, e.g., mutation.

In an embodiment, said alignment method provides:

adjustment, setting or using, maximum difference mismatch penalty parameters for a gene having a high likelihood of containing substitutions;

adjustment, setting or using, specific mismatch penalty parameters based on specific mutation types that are common in a preselected tumor types (e.g., $C \rightarrow T$ in melanoma); or adjustment, setting or using, specific mismatch penalty parameters based on specific mutation types that are common in certain sample types (e.g., substitutions that are common in FFPE).

In an embodiment the method comprises the use of first alignment methods optimized for a subgenomic interval not associated with a rearrangement and a second alignment method optimized for a subgenomic interval associated with a rearrangement.

In an embodiment the method includes application of 1, 2, 3, 4 or all of the following (in embodiments a group of 2 or more of the following are included and the alignment methods for each of the group are unique):

(i) a first alignment method that is selected responsive to, or is optimized for, a high level target (e.g., a gene, exon, or base) for which the deepest coverage is required to enable a high level of sensitivity for mutations that appears at a relatively low frequency. For example, an alignment method that is selected responsive to or optimized for a variant, e.g., a point mutation, that appear at a frequency of 5% or less in cells in the sample, the nucleic acids of a library, or the nucleic acids of a library catch. Typically these variants require >500× sequencing depth to ensure high detection reliability. An exemplary application is an exon that is frequently mutated in a preselected cancer;

(ii) a second alignment method that is selected responsive to, or is optimized for, a mid-level target (e.g., a gene, exon, or base) for which high coverage (though in embodiments less than that in (i) above) is required to enable a high level of sensitivity for mutations that appear at a relatively high frequency e.g., at a higher frequency than a mutation in (i) above. For example, an alignment method that is selected responsive to or optimized for a variant, e.g., a point mutation, that appear at a frequency of greater than 5% and up to 10, 15 or 20% in cells in the sample, the nucleic acids of a library, or the nucleic acids of a library catch. Typically these variants require >200× sequencing depth to ensure high detection reliability. An exemplary application is in a gene related to cancer;

(iii) a third alignment method that is selected responsive to, or is optimized for, a low-level target (e.g., a gene, exon, or base) for which the low to medium coverage (in embodiments less than that in (i) or (ii) above) is required to enable a high level of sensitivity for heterozygous alleles. For example, an alignment method that is selected responsive to, or optimized for, a variant, e.g., (1) a pharmacogenomic SNP that may be associated with the ability of patient to respond to or metabolize a drug; (2) a genomic SNP that may be used to uniquely identify (fingerprint) a patient; or (3) a genomic SNP/loci that may be used to assess copy number gains/losses of genomic DNA and LOH;

(iv) a fourth alignment method that is selected responsive to, or is optimized for, a mid-level target (e.g., a structural breakpoint, e.g., in a rearrangment, e.g., a translocation or an indel). In embodiments the coverage is less than in one of (i), (ii) or (iii). For example, an alignment method that is selected responsive to, or optimized for, a variant, e.g., an intronic breakpoint, which in embodiments requires 5-50× sequence-pair spanning depth to ensure high detection reliability. An exemplary application is a translocation/indel-prone cancer gene; and (v) a fifth alignment method that is selected responsive to, or is optimized for, a target such as an intron target for which sparse coverage can improve the ability to detect copy number changes. In embodiments the coverage is less than in one of (i), (ii) (iii) or (iv). For example, detection of a 1 copy deletion of several terminal exons requires 0.1-10× coverage to ensure high detection reliability. An exemplary application is to an amplification/deletion-prone cancer gene.

In an embodiment, said alignment method is applied after another alignment method is used in an attempt, e.g., an unacceptable attempt, to align a read.

In an embodiment, the method further comprise selecting and applying a second alignment method in a second or subsequent attempt to align a read for a preselcted subgenomic interval. E.g., in an embodiment a first method comprises the use of a first, relatively fast, algorithm, and a second alignment method comprises the use of a second, slower but more accurate, algorithm.

In an embodiment, said alignment method comprises the Smith-Waterman alignment algorithm or a similar algorithm, or a multiple alignment algorithm such as CLUSTALW.

In an embodiment, in subgenomic intervals resistant to accurate alignment (e.g., by any method), de-novo or reference-guided assembly is undertaken by using methods such ARACHNE or Phusion.

In an embodiment, the a-c, or b-c, are performed in the sequence indicated above.

In an embodiment, the method further comprises:

d) performing a comparison, e.g., an alignment comparison, of a read with said selected alignment method (e.g., a preselected algorithm or parameter); and e) optionally, determining if said read meets a predetermined alignment criterion, e.g., a predetermined criterion can be an alignment to a reference with less than a preselected number of mismatches or gaps.

In an embodiment, (c) comprises selecting the alignment method by:

f) acquiring a value for an alignment selector for a subgenomic interval, e.g., a subgenomic interval comprising a nucleotide position associate with a variant, e.g., a substitution or a rearrangement, e.g., an indel; and g) responsive to said acquired value for alignment selector, selecting an alignment method for analyzing, e.g., aligning, a read.

provided that said alignment selector is a function of, is selected responsive to, or is optimized for, one or more or all of:

i) tumor type, e.g., the tumor type in said sample;
ii) the gene, or type of gene, in which said subgenomic interval being sequenced is located, e.g. wherein the gene or type of gene is associated with a preselected probability or type of variant, e.g., mutation;
iii) the site (e.g., nucleotide position) being analyzed;
iv) the type of variant, e.g., a substitution, associated with the subgenomic interval being evaluated;
v) the type of sample, e.g., an FFPE sample; and
vi) sequence in or near said subgenomic interval being evaluated, e.g., the expected propensity for misalignment for said subgenomic interval, e.g., the presence of repeated sequences in or near said subgenomic interval.

In an embodiment, the method comprises acquiring and applying a threshold value other than an unique threshold value, e.g., a non-unique threshold value, to a subgenomic interval, e.g., one of said subgenomic intervals described herein.

Methods for Aligning Rearrangments

Methods disclosed herein allow the use of multiple, individually tuned, alignment methods or algorithms to optimize performance in the sequencing of subgenomic intervals associated with rearrangments, e.g., indels, particularly in methods that rely on massively parallel sequencing of a large number of diverse genetic events in a large number of diverse genes, e.g., from tumor samples. In embodiments multiple alignment methods that are individually customized or tuned to each of a number of rearrangements in different genes are used to analyze reads. In embodiments tuning can be a function of (one or more of) the gene (or other subgenomic interval) being sequenced, the tumor type in the sample, the variant being sequenced, or a characteristic of the sample or the subject. This selection or use of alignment conditions finely tuned to a number of subgenomic intervals to be sequenced allows optimization of speed, sensitivity and specificity. The method is particularly effective when the alignment of reads for a relatively large number of diverse subgenomic intervals is optimized. In embodiments the method includes the use of alignment methods optimized for rearrangements and others optimized for subgenomic intervals not associated with rearrangements.

Thus, in an embodiment, a method described herein, e.g., a method of analyzing a tumor sample comprises an alignment method for rearrangements described herein.

By way of example, where a read for a subgenomic interval comprises a nucleotide position with a rearrangement, e.g., an indel, the method comprises using an alignment method that includes:

c) selecting a rearrangement reference sequence for alignment with a read, wherein said rearrangement reference sequence is preselected to align with a preselected rearrangement (in embodiments the reference sequence is not identical to the genomic rearrangement) In an embodiment the rearrangement reference sequence fragment (i.e. "alternate reference") is the same as the rearrangement expected to be seen in the read. It is also possible that this alternate reference will also be somewhat different from the expected rearrangement (for example, it may also contain a nearby germ-line variant);

e) comparing, e.g., aligning, a read with said preselected rearrangement reference sequence; and f) optionally, determining if said read meets a predetermined alignment criterion, e.g., a predetermined criterion can be an alignment to said preselected rearrangement reference with less than a preselected level of mismatch or gaps;

thereby analyzing a read, provided that, at least X unique preselected rearrangement alignment sequences are used to analyze reads for at least X unique subgenomic intervals, wherein unique means different from the other X−1, and X is equal to 2, 3, 4, 5, 10, 15, 20, 30, 50, 100, 300, 500, 1000, 2000 or 3000.

In an embodiment, a preselected rearrangement alignment sequence comprises a sequence selected to allow identification of said preselected rearrangement, e.g., a preselected indel.

In an embodiment, a preselected rearrangement alignment sequence comprises a sequence (e.g., either the sequence or its complement) corresponding to said preselected rearrangement, e.g., a preselected indel.

In an embodiment, a preselected rearrangement alignment sequence comprises a simulated sequence (e.g., one that is other than the sequence of the indel or its compliment) selected to align with a read of said preselected sequence.

In an embodiment, a preselected rearrangement alignment sequence comprises sequence, e.g., simulated sequence, flanking one or both sides of the rearrangment.

In an embodiment, a preselected rearrangement alignment sequence comprises sequence, e.g., simulated sequence, from a junction of said rearrangment.

In an embodiment, alignment is performed with a preselected arrangement alignment sequence that is preselected for a tumor type.

In an embodiment, a partial read alignment is performed, e.g., less than all of the read is aligned, e.g., less than 90, 80, 70, 50, 50, 40, 30, 20 or 10% of the read is aligned.

In an embodiment, the method comprises the use of first alignment methods optimized for a subgenomic interval associated with a rearrangement and a second alignment method optimized for a subgenomic interval not associated with a rearrangement.

In an embodiment, the method further includes:
  (g) selecting or applying an alignment method for analyzing, e.g., aligning, said read, thereby analyzing said read, provided that said alignment method is a function of, is selected responsive to, or is optimized for, one or more or all of:
  i) tumor type, e.g., the tumor type in said sample;
  ii) the gene, or type of gene, in which said subgenomic interval being sequenced is located, e.g. wherein the gene or type of gene is associated with a preselected probability for a variant or type of variant, e.g., a mutation;
  iii) the site (e.g., nucleotide position) being analyzed;
  iv) the type of variant, e.g., a substitution, associated with the subgenomic interval being evaluated;
  v) the type of sample, e.g., an FFPE sample; and
  vi) sequence in or near said subgenomic interval being evaluated, e.g., the expected propensity for misalignment for said subgenomic interval, e.g., the presence of repeated sequences in or near said subgenomic interval.

As referred to elsewhere herein, a method is particularly effective when the alignment of reads for a relatively large number of subgenomic intervals is optimized. Thus, in an embodiment, at least X unique alignment methods are used to analyze reads for at least X unique subgenomic intervals, wherein unique means different from the other X−1, and X is equal to 2, 3, 4, 5, 10, 15, 20, or 30.

In an embodiment, subgenomic intervals from at least X genes from Table 1 or 1A are analyzed, and X is equal to 2, 3, 4, 5, 10, 15, 20, or 30.

In an embodiment, subgenomic intervals from at least X genes from Table 1 or 1A having the priority 1 annotation are analyzed, and X is equal to 2, 3, 4, 5, 10, 15, 20, or 30.

In an embodiment a unique alignment method is applied to subgenomic intervals in each of at least 3, 5, 10, 20, 40, 50, 60, 70, 80, 90, or 100 different genes.

In an embodiment, a nucleotide position in at least 20, 40, 60, 80, 100, 120, 140, 160 or 180 genes, e.g., genes from Table 1 or 1A, is assigned a nucleotide value. In an embodiment, a unique alignment method is applied to subgenomic intervals in each of at least 10, 20, 30, 40, or 50% of said genes analyzed.

In an embodiment, a nucleotide position in at least 5, 10, 20, 30, or 40 genes from Table 1 or 1A having the priority 1 annotation is assigned a nucleotide value. In an embodiment, a unique alignment method is applied to subgenomic intervals in each of at least 10, 20, 30, 40, or 50% of said genes analyzed.

In an embodiment, a nucleotide position for at least 10, 20, 30, 40, 50, 100, 150, 200, 300, 400, or 500 variants or codons, e.g., from Table 1, 2, or 3, is assigned a nucleotide value. In an embodiment a unique alignment method is applied to subgenomic intervals in each of at least 10, 20, 30, 40, or 50% of said genes analyzed.

In an embodiment, the method comprises:
  applying a unique alignment method to each of X genomic intervals, each of which having a variant which is associated with a tumor phenotype, e.g. wherein the variant is a point mutation, and X is greater than 2, 3, 5, 10, 20, 40, 50, 60, 70, 80, 90, or 100, e.g., wherein each of said subgenomic intervals is located in a different gene.

In an embodiment, the method comprises:
  applying a unique alignment method to each of X genomic intervals, each of which having a variant which is associated with a tumor phenotype, e.g. wherein the variant is a rearrangement, e.g., a deletion, insertion, or translocation, and X is greater than 2, 3, 5, 10, 20, 40, 50, 60, 70, 80, 90, or 100, wherein each of said subgenomic intervals is located in a different gene.

In an embodiment:
  a first unique alignment method is applied to a first preselected nucleotide position, a variant of which is associated with a tumor phenotype, (e.g., a variant provided in Table 10, e.g., for indel variants in the common epithelial cancers: lung, breast, colon, prostate)
  a second unique alignment method is applied to a preslected nucleotide other than said first preselected nucleotide position, e.g., a position having no variant associated with a tumor phenotype (e.g., a sequence not present as a variable in Table 10).

In an embodiment the method comprises:
  a) applying a first unique alignment method to a first genomic interval, a variant of which is associated with a tumor phenotype, e.g. wherein the variant is a point mutation, e.g., a mutation on Table 6;
  b) applying a second unique alignment method to a second genomic interval, a variant of which is associated with a tumor phenotype, e.g., wherein the variant is a rearrangement, e.g., a deletion, insertion, or translocation, e.g., a mutation on Table 5; and
  c) acquiring and applying a third unique alignment method to a third genomic interval, e.g., a genomic interval in which variants are not associated with a tumor phenotype or with a tumor of the type in said sample.

In an embodiment, the gene or type of gene is:
  an oncogene, which can be associated with, e.g., activating mutations in tyrosine kinase domains;
  a tumor suppressor which can be with de-activating (e.g., non-sense) mutations; or a drug ADME-related gene, which can be with high-activity or low-activity germ-line genetic variation.

In an embodiment, selecting an alignment method comprises, selecting a parameter (or a value therefor) for use in an alignment algorithm, e.g., a match reward, mismatch penalty, gap penalty (e.g., a gap opening penalty, gap extension penalty), expected threshold, word size, filter, or mask. The parameter (or value therefor) can be selected from a panel of preselected parameters, e.g., parameters defined by preselected boundaries or limits.

In an embodiment, when aligning (or optimizing alignments) for a gene that contains a known cancer substitution and a known germ-line indel, the gap penalties can be reduced so that the germ-line variant is captured correctly and doesn't adversely affect the alignment around the somatic mutation of interest.

In an embodiment, selecting an alignment method comprises selecting a maximum difference mismatch penalty parameter for a gene with a high likelihood of containing a substitution.

In an embodiment, selecting an alignment method comprises, selecting an alignment algorithm, e.g., selecting a slower, but more accurate algorithm, e.g., a Smith-Waterman alignment instead of the faster algorithm, e.g., BWA, or selecting alignment optimization using a multiple alignment method such as CLUSTALW.

In an embodiment, said alignment method is a function of, is selected responsive to, or is optimized for, a characteristic of the nucleic acid sample, e.g., sample age, sample tissue source (e.g. pancreatic), presence of carcinogen/mutagen exposure (e.g. smoking, UV), quality of nucleic acid sample (e.g., level of nucleic acid fragmentation) in the sample.

In an embodiment, at least X (wherein X is 1, 2, 3, 4, 5, 10, 15, 20, 30, 40 or 50) alignment method(s) is a function of, is selected responsive to, or is optimized for (i).

In an embodiment, at least X (wherein X is 1, 2, 3, 4, 5, 10, 15, 20, 30, 40 or 50) alignment method(s) is a function of, is selected responsive to, or is optimized for (ii).

In an embodiment, at least X (wherein X is 1, 2, 3, 4, 5, 10, 15, 20, 30, 40 or 50) alignment method(s) is a function of, is selected responsive to, or is optimized for (iii).

In an embodiment, a first alignment method is function of, is selected responsive to, or is optimized for (i), a second alignment method is function of, is selected responsive to, or is optimized for (ii), and a third alignment method is function of, is selected responsive to, or is optimized for (iii).

In an embodiment, at least one alignment method is a function of, is selected responsive to, or is optimized for, (i) and one or more of (ii), (iii), (iv), (v), or (vii).

In an embodiment, at least X (wherein X is 1, 2, 3, 4, 5, 10, 15, 20, 30, 40 or 50) alignment method(s) is a function of, is selected responsive to, or is optimized for, (ii) and one or more of (ii), (iii), (iv), (v), or (vii).

In an embodiment, said alignment method is a function of, is selected responsive to, or is optimized for, the gene, or type of gene, e.g., wherein the gene or type of gene is associated with a preselected probability or type of variant, e.g., mutation.

In an embodiment, said alignment method provides:
adjustment, setting, or using, maximum difference mismatch penalty parameters for a gene having a high likelihood of containing substitutions;
adjustment, setting, or using, gap penalty parameters for a gene having a high likelihood of containing indels (e.g. EGFR in NSCLC);
adjustment, setting, or using, specific mismatch penalty parameters based on specific mutation types that are common in a preselected tumor types (e.g. C→T in melanoma); or
adjustment, setting, or using, specific mismatch penalty parameters based on specific mutation types that are common in certain sample types (e.g. substitutions that are common in FFPE).

In an embodiment the method comprises the use of a first alignment methods optimized for a subgenomic interval not associated with a rearrangement and a second alignment method optimized for a subgenomic interval associated with a rearrangement.

In an embodiment an alignment parameter, e.g., gap open/extend penalty, is adjusted, e.g., reduced.

In an embodiment the method includes application of 1, 2, 3, 4 or all of the following (in embodiments a group of 2 or more of the following are included and the alignment methods for each of the group are unique):

(i) a first alignment method that is selected responsive to, or is optimized for, a high level target (e.g., a gene, exon, or base) for which the deepest coverage is required to enable a high level of sensitivity for mutations that appear at a relatively low frequency. For example, an alignment method that is selected responsive to or optimized for a variant, e.g., a point mutation, that appear at a frequency of 5% or less in cells in the sample, the nucleic acids of a library, or the nucleic acids of a library catch. Typically these variants require >500× sequencing depth to ensure high detection reliability. An exemplary application is an exon that is frequently mutated in a preselected cancer;

(ii) a second alignment method that is selected responsive to, or is optimized for, a mid-level target (e.g., a gene, exon, or base) for which high coverage (though in embodiments less than that in (i) above) is required to enable a high level of sensitivity for mutations that appear at a relatively high frequency e.g., at a higher frequency than a mutation in (i) above. For example, an alignment method that is selected responsive to or optimized for a variant, e.g., a point mutation, that appear at a frequency of greater than 5% and up to 10, 15 or 20% in cells in the sample, the nucleic acids of a library, or the nucleic acids of a library catch. Typically these variants require >200× sequencing depth to ensure high detection reliability. An exemplary application is in a gene related to cancer;

(iii) a third alignment method that is selected responsive to, or is optimized for, a low-level target (e.g., a gene, exon, or base) for which the low to medium coverage (in embodiments less than that in (i) or (ii) above) is required to enable a high level of sensitivity for heterozygous alleles. For example, an alignment method that is selected responsive to, or optimized for, a variant, e.g., (1) a pharmacogenomic SNP that may be associated with the ability of patient to respond to or metabolize a drug; (2) a genomic SNP that may be used to uniquely identify (fingerprint) a patient; or (3) a genomic SNP/loci that may be used to assess copy number gains/losses of genomic DNA and LOH;

(iv) a fourth alignment method that is selected responsive to, or is optimized for, a mid-level target (e.g., a structural breakpoint, e.g., in a rearrangment, e.g., a translocation or an indel). In embodiments the coverage is less than in one of (i), (ii) or (iii). For example, an alignment method that is selected responsive to, or optimized for, a variant, e.g., an intronic breakpoint, which in embodiments requires 5-50× sequence-pair spanning depth to ensure high detection reliability. An exemplary application is a translocation/indel-prone cancer gene; and (v) a fifth alignment method that is selected responsive to, or is optimized for, a target such as an intron target for which sparse coverage can improve the ability to detect copy number changes. In embodiments the coverage is less than in one of (i), (ii) (iii) or (iv). For example, detection of a 1 copy deletion of several terminal exons requires 0.1-10× coverage to ensure high detection reliability. An exemplary application is to an amplification/deletion-prone cancer gene.

In an embodiment, said alignment method is applied after another alignment method is used in an attempt, e.g., an unacceptable attempt, to align a read.

In an embodiment, the method further comprise selecting and applying a second alignment method in a second or subsequent attempt to align a read for a preselected subgenomic interval. E.g., in an embodiment a first method comprises the use of a first, relatively fast, algorithm, and a second alignment method comprises the use of a second, slower but more accurate, algorithm.

In an embodiment, said alignment method comprises the Smith-Waterman or similar alignment algorithm, or a multiple alignment algorithm such as CLUSTALW.

In an embodiment, in subgenomic intervals resistant to accurate alignment (e.g., by any method), de-novo or reference-guided assembly is undertaken by using methods such ARACHNE or Phusion In an embodiment, the a-c, or b-c, are performed in the sequence indicated above.

In an embodiment, the method further comprises:

d) performing a comparison, e.g., an alignment comparison, of a read with said selected alignment method (e.g., a preselected algorithm or parameter); and e) optionally, determining if said read meets a predetermined alignment criterion, e.g., a predetermined criterion can be an alignment to a reference with less than a preselected number of mismatches or gaps.

In an embodiment, the method comprises acquiring a nucleotide sequence read obtained from a tumor and/or control nucleic acid sample (e.g., an FFPE-derived nucleic acid sample).

In an embodiment, the reads are provided by an NGS sequencing method.

In an embodiment, the method includes providing a library of nucleic acid members and sequencing a preselected subgenomic intervals from a plurality of members of said library. IN embodiments the method can include a step of selecting a subset of said library for sequencing, e.g., a solution-based selection.

In an embodiment, (c) comprises selecting the alignment method by:

f) acquiring a value for an alignment selector for a subgenomic interval, e.g., a subgenomic interval comprising a nucleotide position associated with a variant, e.g., a substitution or a rearrangement, e.g., an indel; and g) responsive to said acquired value for alignment selector, selecting an alignment method for analyzing, e.g., aligning, a read.

provided that said alignment selector is a function of, is selected responsive to, or is optimized for, one or more or all of:

i) tumor type, e.g., the tumor type in said sample;
ii) the gene, or type of gene, in which said subgenomic interval being sequenced is located, e.g. wherein the gene or type of gene is associated with a preselected probability or type of variant, e.g., mutation;
iii) the site (e.g., nucleotide position) being analyzed;
iv) the type of variant, e.g., a substitution, associated with the subgenomic interval being evaluated;
v) the type of sample, e.g., an FFPE sample; and
vi) sequence in or near said subgenomic interval being evaluated, e.g., the expected propensity for misalignment for said subgenomic interval, e.g., the presence of repeated sequences in or near said subgenomic interval.

In an embodiment, said acquired value is a function of a characteristics of the nucleic acid sample, e.g., sample age, sample tissue source (e.g. pancreatic), presence of carcinogen/mutagen exposure (e.g. smoking, UV), quality of nucleic acid sample (e.g., level of nucleic acid fragmentation) in the sample.

In an embodiment, e.g., after the failure of a first (or more than one) alignment method, the method comprises assembly (with, e.g., ARACHNE method) of the unaligned reads, e.g., to recover a novel complex rearrangement Alignment of More Difficult Reads Methods disclosed herein allow for the rapid and efficient alignment of troublesome reads. The method is particularly effective when the alignment of reads for a relatively large number of diverse subgenomic intervals is optimized. By way of example, a method of analyzing a tumor sample can comprise:

optionally, sequencing a nucleic acid to acquire a read;

optionally, acquiring a read (e.g., acquiring nucleotide sequence reads obtained from a tumor and/or control nucleic acid sample (e.g., an FFPE-derived nucleic acid sample));

performing a comparison, e.g., an alignment comparison, of a read under a first set of parameters (e.g., a first mapping algorithm or with a first reference sequence), and determining if said read meets a first predetermined alignment criterion (e.g., the read can be aligned with said first reference sequence, e.g., with less than a preselected number of mismatches);

if said read fails to meet the first predetermined alignment criterion, performing a second alignment comparison under a second set of parameters, (e.g., a second mapping algorithm or with a second reference sequence); and, optionally, determining if said read meets said second predetermined criterion (e.g., the read can be aligned with said second reference sequence with less than a preselected number of mismatches), wherein said second set of parameters comprises use of a set of parameters, e.g., said second reference sequence, which, compared with said first set of parameters, is more likely to result in an alignment with a read for a preselected variant, e.g., a rearrangement, e.g., an insertion, deletion, or translocation.

thereby analyzing a read.

In an embodiment, said second reference sequence comprises sequences flanking a preselected variant, e.g., a chromosomal rearrangement, e.g., an insertion, deletion, or translocation.

In an embodiment, said second reference sequence comprises a sequence designed to align with a read from a preselected variant, e.g., a chromosomal rearrangement, e.g., an insertion, deletion, or translocation.

In an embodiment, said second reference sequence comprises a sequence selected to allow identification of said preselected rearrangement, e.g., a preselected indel.

In an embodiment, said second reference sequence comprises a sequence (e.g., either the sequence or its complement) corresponding to said preselected rearrangement, e.g., a preselected indel.

In an embodiment, said second reference sequence comprises a simulated sequence (e.g., one that is other than the sequence of the indel or its compliment) selected to align with a read of said preselected sequence.

In an embodiment, said second reference sequence comprises sequence, e.g., simulated sequence, flanking one or both sides of the rearrangment.

In an embodiment, said second reference sequence comprises sequence, e.g., simulated sequence, from a junction of said rearrangment.

Mutation Calling

Base calling refers to the raw output of a sequencing device. Mutation calling refers to the process of selecting a nucleotide value, e.g., A, G, T, or C, for a nucleotide position being sequenced. Typically, the sequencing reads (or base calling) for a position will provide more than one value, e.g., some reads will give a T and some will give a G. Mutation calling is the process of assigning a nucleotide value, e.g., one of those values to the sequence. Although it is referred to as "mutation" calling it can be applied to assign a nucleotide value to any nucleotide position, e.g., positions corresponding to mutant alleles, wildtype alleles, alleles that have not been characterized as either mutant or wildtype, or to positions not characterized by variability. Methods for mutation calling can include one or more of the following: making independent calls based on the information at each position in the reference sequence (e.g., examining the sequence reads; examining the base calls and quality scores; calculating the probability of observed bases and quality scores given a potential genotype; and assigning genotypes (e.g., using Bayes rule)); removing false positives (e.g., using depth thresholds to reject SNPs with read depth much lower or higher than expected; local realignment to remove false positives due to small indels); and performing linkage disequilibrium (LD)/imputation based analysis to refine the calls.

Equations to calculate the genotype likelihood associated with a specific genotype and position are described, e.g., in Li H. and Durbin R. *Bioinformatics,* 2010; 26(5): 589-95. The prior expectation for a particular mutation in certain cancer type can be used when evaluating samples from that cancer type. Such likelihood can be derived from public databases of cancer mutations, e.g., Catalogue of Somatic Mutation in Cancer (COSMIC), HGMD (Human Gene Mutation Database), The SNP Consortium, Breast Cancer Mutation Data Base (BIC), and Breast Cancer Gene Database (BCGD).

Examples of LD/imputation based analysis are described, e.g., in Browning B. L. and Yu Z. *Am. J. Hum. Genet.* 2009, 85(6):847-61. Examples of low-coverage SNP calling methods are described, e.g., in Li Y. et al., *Annu. Rev. Genomics Hum. Genet.* 2009, 10:387-406.

Mutation Calling: Substitutions

After alignment, detection of substitutions can be performed using a calling method, e.g., Bayesian mutation calling method; which is applied to each base in each of the subgenomic intervals, e.g., exons of the gene to be evaluated, where presence of alternate alleles is observed. This method will compare the probability of observing the read data in the presence of a mutation with the probability of observing the read data in the presence of base-calling error alone. Mutations can be called if this comparison is sufficiently strongly supportive of the presence of a mutation.

Methods have been developed that address limited deviations from frequencies of 50% or 100% for the analysis of cancer DNA. (e.g., SNVMix-Bioinformatics. 2010 March 15; 26(6): 730-736.) Method disclosed herein however allow consideration of the possibility of the presence of a mutant allele at anywhere between 1% and 100% of sample DNA, and especially at levels lower than 50% This approach is particularly important for the detection of mutations in low-purity FFPE samples of natural (multi-clonal) tumor DNA.

An advantage of a Bayesian mutation-detection approach is that the comparison of the probability of the presence of a mutation with the probability of base-calling error alone can be weighted by a prior expectation of the presence of a mutation at the site. If some reads of an alternate allele are observed at a frequently mutated site for the given cancer type, then presence of a mutation may be confidently called even if the amount of evidence of mutation does not meet the usual thresholds. This flexibility can then be used to increase detection sensitivity for even rarer mutations/lower purity samples, or to make the test more robust to decreases in read coverage. The likelihood of a random base-pair in the genome being mutated in cancer is ~1e-6. The likelihood of specific mutations at many sites in a typical multigenic cancer genome panel can be orders of magnitude higher. These likelihoods can be derived from public databases of cancer mutations (e.g., COSMIC). For example, for one of the genes in to be analyzed, KRAS, the following prior expectations of mutations provided in Table 6 may be used when evaluating colon cancer samples:

TABLE 6

Exemplary Prior Expectations for KRAS Gene in Colon Cancer

| Gene | Cancer type | Nucleotide substitution (coding sequence position and nucleotides) | Chr | Genome Position | Probability of the substitution in the cancer type |
|---|---|---|---|---|---|
| KRAS | Colon | 35G > A | 12 | 25398284 | 11.924% |
| KRAS | Colon | 35G > T | 12 | 25398284 | 7.542% |
| KRAS | Colon | 38G > A | 12 | 25398281 | 6.888% |
| KRAS | Colon | 34G > T | 12 | 25398285 | 2.711% |
| KRAS | Colon | 35G > C | 12 | 25398284 | 2.492% |
| KRAS | Colon | 34G > A | 12 | 25398285 | 1.895% |
| KRAS | Colon | 34G > C | 12 | 25398285 | 0.415% |
| KRAS | Colon | 37G > T | 12 | 25398282 | 0.162% |
| KRAS | Colon | 183A > C | 12 | 25380275 | 0.138% |
| KRAS | Colon | 37G > C | 12 | 25398282 | 0.081% |
| KRAS | Colon | 182A > T | 12 | 25380276 | 0.053% |
| KRAS | Colon | 183A > T | 12 | 25380275 | 0.048% |
| KRAS | Colon | 38G > T | 12 | 25398281 | 0.043% |
| KRAS | Colon | 38G > C | 12 | 25398281 | 0.033% |
| KRAS | Colon | 182A > G | 12 | 25380276 | 0.029% |
| KRAS | Colon | 37G > A | 12 | 25398282 | 0.029% |
| KRAS | Colon | 181C > A | 12 | 25380277 | 0.019% |

Such a table can then be created and used in the mutation calling algorithm for any gene in the multigene test where sufficient information in the public databases is available.

Mutation Calling: Indels

Indel calling is a process of finding bases in the sequencing data that differ from the reference sequence by insertion or deletion, typically including an associated confidence score or statistical evidence metric.

Methods of indel calling can include the steps of identifying candidate indel, calculating genotype likelihood through local re-alignment, and performing LD-based genotype inference and calling. Typically, a Bayesian approach is used to obtain potential indel candidates, and then these candidates are tested together with the reference sequence in a Bayesian framework.

Algorithms to generate candidate indels are described, e.g., in McKenna A. et al., *Genome Res.* 2010; 20(9):1297-303; Ye K. et al., *Bioinformatics,* 2009; 25(21):2865-71; Lunter G. and Goodson M. *Genome Res.* 2010, epub ahead of print; Li H. et al., *Bioinformatics* 2009, Bioinformatics 25(16):2078-9.

Methods for generate indel calls and individual-level genotype likelihoods include, e.g., the Dindel algorithm (Albers C. A. et al., *Genome Res.* 2010 Oct. 27. [Epub ahead of print]). For example, the Bayesian EM algorithm can be used to analyze the reads, make initial indel calls, and generate genotype likelihoods for each candidate indel, followed by imputation of genotypes using, e.g., QCALL (Le S. Q. and Durbin R. *Genome Res.* 2010 Oct. 27. [Epub ahead of print]). Parameters, such as prior expectations of observing the indel can be adjusted (e.g., increased or decreased), based on the size or location of the indels.

TABLE 9

Genome Locations Frequently Mutated in Four Common Epithelial Cancers (Ordered by frequency)

| Gene | Tissue | Nucleotide Exchange | chromo | genome position (hg19) | Mutation rate |
|---|---|---|---|---|---|
| KRAS | large_intestine | 35G > A | 12 | 25398284 | 11.924% |
| EGFR | lung | 2155G > T | 7 | 55241707 | 11.194% |
| PIK3CA | breast | 3140A > G | 3 | 178952085 | 11.165% |
| KRAS | large_intestine | 35G > T | 12 | 25398284 | 7.542% |
| KRAS | large_intestine | 38G > A | 12 | 25398281 | 6.888% |
| KRAS | lung | 34G > T | 12 | 25398285 | 6.709% |
| BRAF | large_intestine | 1799T > A | 7 | 140453136 | 5.924% |
| BRAF | large_intestine | 1799T > A | 7 | 140453136 | 4.492% |
| EGFR | lung | 2573T > G | 7 | 55259515 | 4.478% |
| PIK3CA | breast | 1633G > A | 3 | 178936091 | 4.410% |
| PIK3CA | breast | 1624G > A | 3 | 178936082 | 3.508% |
| KRAS | lung | 35G > T | 12 | 25398284 | 3.498% |
| PIK3CA | large_intestine | 1633G > A | 3 | 178936091 | 3.429% |
| KRAS | lung | 35G > A | 12 | 25398284 | 2.899% |
| KRAS | large_intestine | 34G > T | 12 | 25398285 | 2.711% |
| PIK3CA | breast | 1624G > A | 3 | 178936082 | 2.586% |
| PIK3CA | large_intestine | 3140A > G | 3 | 178952085 | 2.540% |
| KRAS | large_intestine | 35G > C | 12 | 25398284 | 2.492% |
| PIK3CA | large_intestine | 1624G > A | 3 | 178936082 | 1.947% |
| KRAS | large_intestine | 34G > A | 12 | 25398285 | 1.895% |
| PIK3CA | large_intestine | 1634A > C | 3 | 178936092 | 1.291% |
| CTNNB1 | large_intestine | 134C > T | 3 | 41266137 | 1.243% |
| PIK3CA | breast | 3140A > T | 3 | 178952085 | 1.183% |
| KRAS | lung | 35G > C | 12 | 25398284 | 1.094% |
| CTNNB1 | large_intestine | 121A > G | 3 | 41266124 | 1.001% |
| CTNNB1 | lung | 110C > G | 3 | 41266113 | 0.817% |
| KRAS | lung | 34G > A | 12 | 25398285 | 0.668% |
| CTNNB1 | large_intestine | 98C > A | 3 | 41266101 | 0.656% |
| BRAF | lung | 1799T > A | 7 | 140453136 | 0.651% |
| KRAS | lung | 37G > T | 12 | 25398282 | 0.529% |
| PIK3CA | lung | 1633G > A | 3 | 178936091 | 0.527% |
| PIK3CA | large_intestine | 1636C > A | 3 | 178936094 | 0.508% |
| CTNNB1 | lung | 110C > T | 3 | 41266113 | 0.490% |
| PIK3CA | large_intestine | 3140A > T | 3 | 178952085 | 0.466% |
| PIK3CA | lung | 1633G > A | 3 | 178936091 | 0.461% |
| KRAS | large_intestine | 34G > C | 12 | 25398285 | 0.415% |
| CTNNB1 | lung | 98C > G | 3 | 41266101 | 0.408% |
| KRAS | lung | 34G > C | 12 | 25398285 | 0.382% |
| PIK3CA | breast | 1634A > C | 3 | 178936092 | 0.381% |
| KRAS | lung | 38G > A | 12 | 25398281 | 0.356% |
| CTNNB1 | large_intestine | 98C > G | 3 | 41266101 | 0.345% |
| PIK3CA | lung | 1624G > A | 3 | 178936082 | 0.329% |
| PIK3CA | lung | 3140A > G | 3 | 178952085 | 0.329% |
| EGFR | lung | 2369C > T | 7 | 55249071 | 0.321% |
| CTNNB1 | lung | 121A > G | 3 | 41266124 | 0.245% |
| CTNNB1 | large_intestine | 133T > C | 3 | 41266136 | 0.242% |
| NRAS | lung | 181C > A | 1 | 115256530 | 0.232% |
| PIK3CA | breast | 1634A > G | 3 | 178936092 | 0.220% |
| PIK3CA | large_intestine | 1634A > G | 3 | 178936092 | 0.212% |
| PIK3CA | lung | 1636C > A | 3 | 178936094 | 0.198% |
| NRAS | lung | 182A > T | 1 | 115256529 | 0.193% |
| PIK3CA | large_intestine | 3139C > T | 3 | 178952084 | 0.190% |
| EGFR | large_intestine | 2155G > A | 7 | 55241707 | 0.170% |
| KRAS | large_intestine | 37G > T | 12 | 25398282 | 0.162% |
| PIK3CA | breast | 3145G > C | 3 | 178952090 | 0.160% |
| NRAS | lung | 182A > G | 1 | 115256529 | 0.155% |
| PIK3CA | large_intestine | 1634A > C | 3 | 178936092 | 0.148% |
| KRAS | lung | 34_35GG > TT | 12 | 25398284 | 0.148% |
| PIK3CA | breast | 1637A > G | 3 | 178936095 | 0.140% |
| KRAS | large_intestine | 183A > C | 12 | 25380275 | 0.138% |
| CTNNB1 | large_intestine | 122C > T | 3 | 41266125 | 0.138% |
| PIK3CA | large_intestine | 263G > A | 3 | 178916876 | 0.127% |
| NRAS | lung | 34G > T | 1 | 115258748 | 0.116% |
| EGFR | lung | 2582T > A | 7 | 55259524 | 0.110% |
| CTNNB1 | large_intestine | 101G > T | 3 | 41266104 | 0.104% |
| PIK3CA | breast | 3139C > T | 3 | 178952084 | 0.100% |
| KRAS | lung | 183A > T | 12 | 25380275 | 0.095% |
| PIK3CA | large_intestine | 1637A > G | 3 | 178936095 | 0.085% |

TABLE 9-continued

Genome Locations Frequently Mutated in Four Common Epithelial Cancers (Ordered by frequency)

| Gene | Tissue | Nucleotide Exchange | chromo | genome position (hg19) | Mutation rate |
|---|---|---|---|---|---|
| CTNNB1 | lung | 94G > T | 3 | 41266097 | 0.082% |
| CTNNB1 | lung | 98C > T | 3 | 41266101 | 0.082% |
| CTNNB1 | lung | 101G > A | 3 | 41266104 | 0.082% |
| CTNNB1 | lung | 101G > T | 3 | 41266104 | 0.082% |
| CTNNB1 | lung | 134C > T | 3 | 41266137 | 0.082% |
| KRAS | large_intestine | 37G > C | 12 | 25398282 | 0.081% |
| PIK3CA | breast | 1636C > A | 3 | 178936094 | 0.080% |
| KRAS | lung | 182A > G | 12 | 25380276 | 0.078% |
| EGFR | lung | 2155G > A | 7 | 55241707 | 0.077% |
| EGFR | lung | 2156G > C | 7 | 55241708 | 0.077% |
| EGFR | lung | 2303G > T | 7 | 55249005 | 0.072% |
| CTNNB1 | large_intestine | 101G > A | 3 | 41266104 | 0.069% |
| CTNNB1 | large_intestine | 110C > G | 3 | 41266113 | 0.069% |
| PIK3CA | lung | 1624G > C | 3 | 178936082 | 0.066% |
| PIK3CA | lung | 1634A > C | 3 | 178936092 | 0.066% |
| PIK3CA | lung | 3140A > T | 3 | 178952085 | 0.066% |
| PIK3CA | large_intestine | 1636C > G | 3 | 178936094 | 0.063% |
| PIK3CA | large_intestine | 1637A > T | 3 | 178936095 | 0.063% |
| KRAS | lung | 182A > T | 12 | 25380276 | 0.061% |
| PIK3CA | breast | 1636C > G | 3 | 178936094 | 0.060% |
| KRAS | large_intestine | 182A > T | 12 | 25380276 | 0.053% |
| KRAS | lung | 183A > C | 12 | 25380275 | 0.052% |
| KRAS | large_intestine | 183A > T | 12 | 25380275 | 0.048% |
| KRAS | lung | 181C > A | 12 | 25380277 | 0.043% |
| KRAS | large_intestine | 38G > T | 12 | 25398281 | 0.043% |
| PIK3CA | large_intestine | 1624G > C | 3 | 178936082 | 0.042% |
| PIK3CA | large_intestine | 1634A > T | 3 | 178936092 | 0.042% |
| PIK3CA | large_intestine | 1637A > C | 3 | 178936095 | 0.042% |
| PIK3CA | breast | 1625A > T | 3 | 178936083 | 0.040% |
| PIK3CA | breast | 1633G > C | 3 | 178936091 | 0.040% |
| PIK3CA | breast | 1637A > C | 3 | 178936095 | 0.040% |
| NRAS | lung | 183A > T | 1 | 115256528 | 0.039% |
| NRAS | lung | 181C > G | 1 | 115256530 | 0.039% |
| NRAS | lung | 35G > C | 1 | 115258747 | 0.039% |
| NRAS | lung | 35G > A | 1 | 115258747 | 0.039% |
| KRAS | lung | 181C > G | 12 | 25380277 | 0.035% |
| CTNNB1 | large_intestine | 94G > A | 3 | 41266097 | 0.035% |
| CTNNB1 | large_intestine | 94G > T | 3 | 41266097 | 0.035% |
| CTNNB1 | large_intestine | 97T > C | 3 | 41266100 | 0.035% |
| CTNNB1 | large_intestine | 100G > A | 3 | 41266103 | 0.035% |
| CTNNB1 | large_intestine | 110C > T | 3 | 41266113 | 0.035% |
| CTNNB1 | large_intestine | 133T > G | 3 | 41266136 | 0.035% |
| CTNNB1 | large_intestine | 134C > G | 3 | 41266137 | 0.035% |
| KRAS | large_intestine | 38G > C | 12 | 25398281 | 0.033% |
| KRAS | large_intestine | 182A > G | 12 | 25380276 | 0.029% |
| KRAS | large_intestine | 37G > A | 12 | 25398282 | 0.029% |
| PIK3CA | large_intestine | 1625A > G | 3 | 178936083 | 0.021% |
| PIK3CA | large_intestine | 1633G > C | 3 | 178936091 | 0.021% |
| PIK3CA | large_intestine | 3145G > C | 3 | 178952090 | 0.021% |
| PIK3CA | large_intestine | 3146G > C | 3 | 178952091 | 0.021% |
| PIK3CA | breast | 263G > A | 3 | 178916876 | 0.020% |
| PIK3CA | breast | 1624G > C | 3 | 178936082 | 0.020% |
| PIK3CA | breast | 3146G > C | 3 | 178952091 | 0.020% |
| EGFR | lung | 2582T > G | 7 | 55259524 | 0.019% |
| KRAS | large_intestine | 181C > A | 12 | 25380277 | 0.019% |
| KRAS | large_intestine | 34_35GG > TT | 12 | 25398284 | 0.019% |
| KRAS | lung | 182A > C | 12 | 25380276 | 0.017% |
| KRAS | lung | 37G > C | 12 | 25398282 | 0.017% |
| KRAS | lung | 37G > A | 12 | 25398282 | 0.017% |
| KRAS | lung | 34_35GG > CT | 12 | 25398284 | 0.017% |
| EGFR | lung | 2154_2155GG > TT | 7 | 55241706 | 0.010% |
| EGFR | lung | 2573_2574TG > GT | 7 | 55259515 | 0.010% |
| KRAS | large_intestine | 34_35GG > AT | 12 | 25398284 | 0.010% |
| KRAS | lung | 38G > C | 12 | 25398281 | 0.009% |
| KRAS | lung | 38G > T | 12 | 25398281 | 0.009% |
| EGFR | lung | 2156G > A | 7 | 55241708 | 0.005% |
| EGFR | lung | 2303G > A | 7 | 55249005 | 0.005% |
| EGFR | lung | 2572C > A | 7 | 55259514 | 0.005% |
| EGFR | lung | 2572_2573CT > AA | 7 | 55259514 | 0.005% |
| EGFR | lung | 2572_2573CT > AG | 7 | 55259514 | 0.005% |
| EGFR | lung | 2581C > G | 7 | 55259523 | 0.005% |
| KRAS | large_intestine | 181C > G | 12 | 25380277 | 0.005% |
| KRAS | large_intestine | 35_36GT > AG | 12 | 25398283 | 0.005% |

TABLE 9-continued

Genome Locations Frequently Mutated in Four Common Epithelial Cancers (Ordered by frequency)

| Gene | Tissue | Nucleotide Exchange | chromo | genome position (hg19) | Mutation rate |
|---|---|---|---|---|---|
| KRAS | large_intestine | 34_36GGT > TGG | 12 | 25398283 | 0.005% |
| KRAS | large_intestine | 34_35GG > CT | 12 | 25398284 | 0.005% |
| KRAS | large_intestine | 34_35GG > TA | 12 | 25398284 | 0.005% |
| BRAF | large_intestine | 1798G > A | 7 | 140453137 | 0.003% |

TABLE 10

Positions of Common Indels in Four Common Epithelial Cancers

| Gene | Cancer tissue of origin | Nucleotide Exchange | Chromosome | Genome Start GRCh37 | Genome Stop GRCh37 |
|---|---|---|---|---|---|
| CBL | lung | 1379_1381delATG | 11 | 119149371 | 119149373 |
| CTNNB1 | prostate | 70_141del72 | 3 | 41266073 | 41266145 |
| CTNNB1 | large_intestine | 14_241del228 | 3 | 41265359 | 41266276 |
| CTNNB1 | large_intestine | 133_135delTCT | 3 | 41266136 | 41266138 |
| CTNNB1 | large_intestine | 14_241del228 | 3 | 41266017 | 41266244 |
| CTNNB1 | prostate | 133_135delTCT | 3 | 41266136 | 41266138 |
| CTNNB1 | large_intestine | 73_96del24 | 3 | 41266076 | 41266099 |
| CTNNB1 | large_intestine | 70_114del45 | 3 | 41266073 | 41266117 |
| CTNNB1 | large_intestine | 14_126del113 | 3 | 41265736 | 41266129 |
| EGFR | lung | 2235_2249del15 | 7 | 55242465 | 55242479 |
| EGFR | lung | 2236_2250del15 | 7 | 55242466 | 55242480 |
| EGFR | breast | 2319_2320ins8 | 7 | 55249021 | 55249022 |
| EGFR | lung | 2236_2250del15 | 7 | 55242466 | 55242480 |
| EGFR | lung | 2240_2257del18 | 7 | 55242470 | 55242487 |
| EGFR | lung | 2240_2254del15 | 7 | 55242470 | 55242484 |
| EGFR | prostate | 2240_2257del18 | 7 | 55242470 | 55242487 |
| EGFR | lung | 2239_2248TTAAGAGAAG > C ("TTAAGAGAAG" disclosed as SEQ ID NO: 50) | 7 | 55242469 | 55242478 |
| EGFR | lung | 2239_2247del9 | 7 | 55242469 | 55242477 |
| EGFR | lung | 2240_2254del15 | 7 | 55242470 | 55242484 |
| EGFR | lung | 2237_2255 > T | 7 | 55242467 | 55242485 |
| ERBB2 | lung | 2322_2323ins12 | 17 | 37880993 | 37880994 |
| ERBB2 | breast | 2263_2278 > G | 17 | 37880219 | 37880234 |
| ERBB2 | lung | 2325_2326ins12 | 17 | 37880996 | 37880997 |
| ERBB2 | lung | 2324_2325ins12 | 17 | 37880995 | 37880996 |
| FBXW7 | prostate | 45_46insCCT | 4 | 153332910 | 153332911 |
| FBXW7 | prostate | 540delT | 4 | 153271238 | 153271238 |
| FBXW7 | breast | 1644_1645ins416 | 4 | 153247156 | 153247156 |
| FBXW7 | large_intestine | 1417_1418insA | 4 | 153249360 | 153249361 |
| FBXW7 | large_intestine | 1205_1206insT | 4 | 153250854 | 153250855 |
| FBXW7 | large_intestine | 388_389insCTGAT | 4 | 153332563 | 153332564 |
| FBXW7 | large_intestine | 2001delG | 4 | 153244156 | 153244156 |
| FBXW7 | large_intestine | 1736_1741delGGCACC | 4 | 153245450 | 153245455 |
| FGFR3 | large_intestine | 850delC | 4 | 1803672 | 1803672 |
| JAK2 | lung | 2749_2750insT | 9 | 5089851 | 5089852 |
| MAP2K4 | lung | 814_891del78 | 17 | 12028611 | 12028688 |
| MAP2K4 | lung | 882delG | 17 | 12028679 | 12028679 |
| MEN1 | lung | 1116delC | 11 | 64573176 | 64573176 |
| MET | lung | 2942_3082del141 | 7 | 116411903 | 116412043 |
| MET | lung | 3083-52insCT | 7 | 116414883 | 116414884 |
| MLH1 | large_intestine | 738_750del13 | 3 | 37055983 | 37055995 |
| MLH1 | large_intestine | 2033_2046del14 | 3 | 37090438 | 37090451 |
| MLH1 | large_intestine | 769delA | 3 | 37056014 | 37056014 |
| MLH1 | large_intestine | 129delA | 3 | 37038122 | 37038122 |
| MLH1 | large_intestine | 1852_1854delAAG | 3 | 37089130 | 37089132 |
| MLH1 | large_intestine | 1988_1989delAG | 3 | 37090099 | 37090100 |
| MLH1 | large_intestine | 1559-9insG | 3 | 37081668 | 37081669 |
| MLH1 | large_intestine | 1497delG | 3 | 37070362 | 37070362 |
| MLH1 | large_intestine | 1897_1904delGAAGGGAA | 3 | 37090005 | 37090015 |
| MLH1 | large_intestine | 872delT | 3 | 37059078 | 37059078 |
| NOTCH1 | large_intestine | 7023delC | 9 | 139391175 | 139391175 |
| NOTCH1 | lung | 7330_7330G > TGT | 9 | 139390864 | 139390865 |
| NOTCH1 | lung | 6824_6825insT | 9 | 139391369 | 139391370 |
| PTEN | large_intestine | 800delA | 10 | 89717775 | 89717775 |
| PTEN | large_intestine | 968delA | 10 | 89720817 | 89720817 |
| PTEN | large_intestine | 955_958delACTT | 10 | 89720804 | 89720807 |

TABLE 10-continued

Positions of Common Indels in Four Common Epithelial Cancers

| Gene | Cancer tissue of origin | Nucleotide Exchange | Chromosome | Genome Start GRCh37 | Genome Stop GRCh37 |
|---|---|---|---|---|---|
| PTEN | breast | 179_179delA | 10 | 89685284 | 89685284 |
| PTEN | prostate | 672_673insA | 10 | 89717647 | 89717648 |
| PTEN | prostate | 16_17delAA | 10 | 89624242 | 89624243 |
| PTEN | prostate | 17_18delAA | 10 | 89624243 | 89624244 |
| PTEN | breast | 208_251del44 | 10 | 89685313 | 89690844 |
| PTEN | breast | 951_954delACTT | 10 | 89720800 | 89720803 |
| PTEN | breast | 823delG | 10 | 89720672 | 89720672 |
| PTEN | lung | 1_1212del1212 | 10 | 89624227 | 89725229 |
| PTEN | large_intestine | 800_801insA | 10 | 89717775 | 89717776 |
| PTEN | large_intestine | 21_22delGA | 10 | 89624247 | 89624248 |
| PTEN | large_intestine | 170delT | 10 | 89685275 | 89685275 |
| PTEN | large_intestine | 170_171insT | 10 | 89685275 | 89685276 |
| PTEN | large_intestine | 270delT | 10 | 89692786 | 89692786 |
| PTEN | large_intestine | 954_957delTACT | 10 | 89720803 | 89720806 |
| PTEN | prostate | 491delA | 10 | 89693007 | 89693007 |
| PTEN | prostate | 730delC | 10 | 89717705 | 89717705 |
| PTEN | prostate | 107delG | 10 | 89653809 | 89653809 |
| PTEN | prostate | 473_474insT | 10 | 89692989 | 89692990 |
| PTEN | prostate | 493-12delT | 10 | 89711863 | 89711863 |
| PTEN | prostate | 226_227delTA | 10 | 89690819 | 89690820 |
| PTEN | prostate | 950_953delTACT | 10 | 89720799 | 89720802 |
| PTEN | prostate | 131_139GCGTATACA > ACAGAAAGACA (SEQ ID NO: 51) | 10 | 89653833 | 89653841 |
| PTEN | breast | 710_718del9 | 10 | 89717685 | 89717693 |
| PTEN | breast | 987_996del10 | 10 | 89720836 | 89720845 |
| PTEN | breast | 1013_1023del11 | 10 | 89720862 | 89720872 |
| PTEN | breast | 1_1212del1212 | 10 | 89624227 | 89725229 |
| PTEN | breast | 590delA | 10 | 89711972 | 89711972 |
| PTEN | breast | 968_969insA | 10 | 89720817 | 89720818 |
| PTEN | breast | 955_958delACTT | 10 | 89720804 | 89720807 |
| PTEN | breast | 403_405delATA | 10 | 89692919 | 89692921 |
| PTEN | breast | 1154_1155delCT | 10 | 89725171 | 89725172 |
| PTEN | breast | 831_834delCTTC | 10 | 89720680 | 89720683 |
| PTEN | breast | 221_221delG | 10 | 89690814 | 89690814 |
| PTEN | breast | 270delT | 10 | 89692786 | 89692786 |
| PTEN | lung | 244_285del42 | 10 | 89690837 | 89692801 |
| PTEN | lung | 968delA | 10 | 89720817 | 89720817 |
| PTEN | lung | 944_945insCT | 10 | 89720793 | 89720794 |
| PTEN | lung | 711delG | 10 | 89717686 | 89717686 |
| PTEN | lung | 246_253delTTGCAGAG | 10 | 89690839 | 89690846 |

TABLE 11

Genes Ordered by Calling Threshold Value (Low to High) in Four Common Epithelial Cancers

| Gene | Tissue |
|---|---|
| APC | large intestine |
| CDKN2A | lung |
| STK11 | prostate |
| CDH1 | breast |
| CDKN2A | breast |
| STK11 | lung |
| CEBPA | prostate |
| MSH2 | prostate |
| SMAD4 | large intestine |
| CDKN2A | large intestine |
| CDKN2A | prostate |
| VHL | large intestine |
| MSH6 | large intestine |
| RB1 | lung |
| APC | breast |
| APC | prostate |
| RB1 | breast |
| APC | lung |
| RB1 | prostate |
| MSH2 | large intestine |
| CEBPA | lung |
| NF1 | prostate |
| STK11 | large intestine |
| NF1 | large intestine |
| SMAD4 | breast |
| SMAD4 | lung |
| NF2 | breast |
| NF2 | large intestine |
| STK11 | breast |
| ATM | large intestine |
| ATM | lung |
| MSH2 | breast |

Mutation Calling Module

Methods disclosed herein provide for the use of customized or tuned mutation calling parameters to optimize performance in sequencing methods, particularly in methods that rely on massively parallel sequencing of a large number of diverse genetic events in a large number of diverse genes, e.g., from tumor samples. In embodiments of the method mutation calling for each of a number of preselected subgenomic intervals is, individually, customized or fine tuned. The customization or tuning can be based on one or more of the factors described herein, e.g., the type of cancer in a sample, the gene in which subgenomic interval to be sequenced is located, or the variant to be sequenced.

This selection or use of alignment conditions finely tuned to a number of subgenomic intervals to be sequenced allows optimization of speed, sensitivity and specificity. The method is particularly effective when the alignment of reads for a relatively large number of diverse subgenomic intervals is optimized.

Accordingly, in one aspect, the invention features, a method of analyzing a sample, e.g., a tumor sample. The method comprises:

(a) acquiring a library comprising a plurality members from a sample, e.g., a plurality of tumor members from a tumor sample;

(b) optionally, enriching the library for preselected sequences, e.g., by contacting the library with a bait set (or plurality of bait sets) to provide selected members (sometimes referred to herein as library catch);

(c) acquiring a read for a subgenomic interval from a member, e.g., a tumor member from said library or library catch, e.g., by a method comprising sequencing, e.g., with a next generation sequencing method;

(d) aligning said read by an alignment method, e.g., an alignment method described herein; and (e) assigning a nucleotide value (e.g., calling a mutation, e.g., with a Bayesian method or a calling method described herein) from said read for the preselected nucleotide position, thereby analyzing said tumor sample.

wherein a nucleotide value is assigned for a nucleotide position in each of X unique subgenomic intervals is assigned by a unique calling method, wherein unique subgenomic interval means different from the other X−1 subgenoimc intervals, and wherein unique calling method means different from the other X−1 calling methods, and X is at least 2. The calling methods can differ, and thereby be unique, e.g., by relying on different Bayesian prior values.

In an embodiment, step (b) is present. In an embodiment, step (b) is absent.

In an embodiment, assigning said nucleotide value is a function of a value which is or represents the prior (e.g., literature) expectation of observing a read showing a preselected variant, e.g., a mutation, at said preselected nucleotide position in a tumor of type.

In an embodiment, the method comprises assigning a nucleotide value (e.g., calling a mutation) for at least 10, 20, 40, 50, 60, 70, 80, 90, or 100 preselected nucleotide positions, wherein each assignment is a function of a unique (as opposed to the value for the other assignments) value which is or represents the prior (e.g., literature) expectation of observing a read showing a preselected variant, e.g., a mutation, at said preselected nucleotide position in a tumor of type.

In an embodiment, assigning said nucleotide value is a function of a set of values which represent the probabilities of observing a read showing said preselected variant at said preselected nucleotide position if the variant is present in the sample at a frequency (e.g., 1%, 5%, 10%, etc.) and/or if the variant is absent (e.g., observed in the reads due to base-calling error alone);

Thus, a method of analyzing a tumor sample can comprise a mutation calling method. The mutation calling methods described herein can include the following:

(b) acquiring, for a preselected nucleotide position in each of said X subgenomic intervals:

(i) a first value which is or represents the prior (e.g., literature) expectation of observing a read showing a preselected variant, e.g., a mutation, at said preselected nucleotide position in a tumor of type X; and (ii) a second set of values which represent the probabilities of observing a read showing said preselected variant at said preselected nucleotide position if the variant is present in the sample at a frequency (e.g., 1%, 5%, 10%, etc.) and/or if the variant is absent (e.g., observed in the reads due to base-calling error alone);

(c) responsive to said values, assigning a nucleotide value (e.g., calling a mutation) from said reads for each of said preselected nucleotide positions by weighing, e.g., by a Bayesian method described herein, the comparison among the values in the second set using the first value (e.g., computing the posterior probability of the presence of a mutation), thereby analyzing said sample, In an embodiment, the method comprises one or more or all of:

(i) assigning a nucleotide value (e.g., calling a mutation) for at least 10, 20, 40, 50, 60, 70, 80, 90, or 100 preselected nucleotide positions, wherein each assignment is based on a unique (as opposed to the other assignments) first and/or second values;

(ii) the assignment of method of (i), wherein at least 10, 20, 30 or 40 of the assignments are made with first values which are a function of a probability of a preselected variant being present of less than 5, 10, or 20%, e.g., of the cells in a preselected tumor type;

(iii) assigning a nucleotide value (e.g., calling a mutation) for at least X preselected nucleotide positions, each of which of which being associated with a preselected variant having a unique (as opposed to the other X−1 assignments) probability of being present in a tumor of preselected type, e.g., the tumor type of said sample, wherein, optionally, each said of X assignments is based on a unique (as opposed to the other X−1 assignments) first and/or second value (wherein X=2 3, 5, 10, 20, 40, 50, 60, 70, 80, 90, or 100);

(iv) assigning a nucleotide value (e.g., calling a mutation) at a first and a second nucleotide position, wherein the likelihood of a first preselected variant at said first nucleotide position being present in a tumor of preselected type (e.g., the tumor type of said sample) is at least 2, 5, 10, 20, 30, or 40 times greater than the likelihood of a second preselected variant at said second nucleotide position being present, wherein, optionally, each assignment is based on a unique (as opposed to the other assignments) first and/or second value;

(v) assigning a nucleotide value to a plurality of preselected nucleotide positions (e.g., calling mutations), wherein said plurality comprises an assignment for variants falling into one or more, e.g., at least 3, 4, 5, 6, 7, or all, of the following probability ranges:

less than 0.01; 0.01-0.02;
greater than 0.02 and less than or equal to 0.03;
greater than 0.03 and less than or equal to 0.04;
greater than 0.04 and less than or equal to 0.05;
greater than 0.05 and less than or equal to 0.1;
greater than 0.1 and less than or equal to 0.2;
greater than 0.2 and less than or equal to 0.5;
greater than 0.5 and less than or equal to 1.0;
greater than 1.0 and less than or equal to 2.0;
greater than 2.0 and less than or equal to 5.0;
greater than 5.0 and less than or equal to 10.0;
greater than 10.0 and less than or equal to 20.0;
greater than 20.0 and less than or equal to 50.0; and
greater than 50 and less than or equal to 100.0%;

wherein, a probability range is the range of probabilities that a preselected variant at a preselected nucleotide position will be present in a tumor of preselected type (e.g., the tumor type of said sample) or the probability that a preselected variant at a preselected nucleotide position will be present in the recited % of the cells in a tumor sample, library from the tumor sample, or library catch from that library, for a preselected type (e.g., the tumor type of said sample), and wherein, optionally, each assignment is based on a unique first and/or second value (e.g., unique as opposed to the other assignments in a recited probability range or unique as opposed to the first and/or second values for one or more or all of the other listed probability ranges).

(vi) assigning a nucleotide value (e.g., calling a mutation) for at least 1, 2 3, 5, 10, 20, 40, 50, 60, 70, 80, 90, or 100 preselected nucleotide positions each, independently, having a preselected variant present in less than 50, 40, 25, 20, 15, 10, 5, 4, 3, 2, 1, 0.5, 0.4, 0.3, 0.2, or 0.1% of the DNA in said sample, wherein, optionally, each assignment is based on a unique (as opposed to the other assignments) first and/or second value;

(vii) assigning a nucleotide value (e.g., calling a mutation) at a first and a second nucleotide position, wherein the likelihood of a preselected variant at the first position in the DNA of said sample is at least 2, 5, 10, 20, 30, or 40 times greater than a the likelihood of a preselected variant at said second nucleotide position in the DNA of said sample, wherein, optionally, each assignment is based on a unique (as opposed to the other assignments) first and/or second value;

(viii) assigning a nucleotide value (e.g., calling a mutation) in one or more or all of the following:

(1) at least 1, 2 3, 4 or 5 preselected nucleotide positions having a preselected variant present in less than 1.0% of the cells in said sample, of the nucleic acid in a library from said sample, or the nucleic acid in a library catch from that library;

(2) at least 1, 2 3, 4 or 5 preselected nucleotide positions having a preselected variant present in 1.0-2.0% of the cells in said sample, of the nucleic acid in a library from said sample, or the nucleic acid in a library catch from that library;

(3) at least 1, 2 3, 4 or 5 preselected nucleotide positions having a preselected variant present in greater than 2.0% and less than or equal to 3% of the cells in said sample, of the nucleic acid in a library from said sample, or the nucleic acid in a library catch from that library (4) at least 1, 2 3, 4 or 5 preselected nucleotide positions having a preselected variant present in greater than 3.0% and less than or equal to 4% of the cells in said sample, of the nucleic acid in a library from said sample, or the nucleic acid in a library catch from that library;

(5) at least 1, 2 3, 4 or 5 preselected nucleotide positions having a preselected variant present in greater than 4.0% and less than or equal to 5% of the cells in said sample, of the nucleic acid in a library from said sample, or the nucleic acid in a library catch from that library;

(6) at least 1, 2 3, 4 or 5 preselected nucleotide positions having a preselected variant present in greater than 5.0% and less than or equal to 10% of the cells in said sample, of the nucleic acid in a library from said sample, or the nucleic acid in a library catch from that library;

(7) at least 1, 2 3, 4 or 5 preselected nucleotide positions having a preselected variant present in greater than 10.0% and less than or equal to 20% of the cells in said sample, of the nucleic acid in a library from said sample, or the nucleic acid in a library catch from that library;

(8) at least 1, 2 3, 4 or 5 preselected nucleotide positions having a preselected variant present in greater than 20.0% and less than or equal to 40% of the cells in said sample, of the nucleic acid in a library from said sample, or the nucleic acid in a library catch from that library;

(9) at least 1, 2 3, 4 or 5 preselected nucleotide positions having a preselected variant present at greater than 40.0% and less than or equal to 50% of the cells in said sample, of the nucleic acid in a library from said sample, or the nucleic acid in a library catch from that library; or

(10) at least 1, 2 3, 4 or 5 preselected nucleotide positions having a preselected variant present in greater than 50.0% and less than or equal to 100% of the cells in said sample, of the nucleic acid in a library from said sample, or the nucleic acid in a library catch from that library;

wherein, optionally, each assignment is based on a unique first and/or second value (e.g., unique as opposed to the other assignments in the recited range (e.g., the range in (i) of less than 1%) or unque as opposed to a first and/or second values for a determination in one or more or all of the other listed ranges); or (ix) assigning a nucleotide value (e.g., calling a mutation) at each of X nucleotide positions, each nucleotide position, independently, having a likelihood (of a preselected variant being present in the DNA of said sample) that is unique as compared with the likelihood for a preselected variant at the other X−1 nucleotide positions, wherein X is equal to or greater than 1, 2 3, 5, 10, 20, 40, 50, 60, 70, 80, 90, or 100, and wherein each assignment is based on a unique (as opposed to the other assignments) first and/or second value.

In an embodiment, the method includes assigning a nucleotide value at least 2, 3, 5, 10, 20, 40, 50, 60, 70, 80, 90, or 100 preselected nucleotide positions, each having, independently, a first value that is a function of a probability that is less than 0.5, 0.4, 0.25, 0.15, 0.10, 0.05, 0.04, 0.03, 0.02, or 0.01.

In an embodiment, the method includes assigning a nucleotide value at each of at least X nucleotide positions, each independently having a first value that is unique as compared with the other X−1 first values, and wherein each of said X first values is a function of a probability that is less than 0.5, 0.4, 0.25, 0.15, 0.10, 0.05, 0.04, 0.03, 0.02, or 0.01,
wherein X is equal to or greater than 1, 2 3, 5, 10, 20, 40, 50, 60, 70, 80, 90, or 100.

In an embodiment, said first and/or second value is weighted by a prior expectation of the presence of a preselected variant at said preselected nucleotide position, e.g., as a function of tumor type.

In an embodiment, the number of reads needed to assign a nucleotide value for a preselected nucleotide position (e.g., calling a mutation) is inversely related to the magnitude of said first value.

In an embodiment, the number of reads needed to assign a nucleotide value for a preselected nucleotide position (e.g., calling a mutation) is positively correlated with the magnitude of the expected probability of a preselected variant.

As referred to elsewhere herein, a method is particularly effective when the calling of mutations for a relatively large number of subgenomic intervals is optimized. Thus, in an embodiment, at least X unique first and/or second values are used to analyze reads for at least X unique subgenomic intervals, wherein unique means different from the other X−1, and X is equal to 2, 3, 4, 5, 10, 15, 20, or 30.

In an embodiment, subgenomic intervals from at least X genes from Table 1 are analyzed, and X is equal to 3, 4, 5, 10, 15, 20, or 30.

In an embodiment, subgenomic intervals from at least X genes from Table 1 having the priority 1 annotation are analyzed, and X is equal to 3, 4, 5, 10, 15, 20, or 30.

In an embodiment, unique first and/or second values are applied to subgenomic intervals in each of at least 3, 5, 10, 20, 40, 50, 60, 70, 80, 90, or 100 different genes.

In an embodiment, a nucleotide position in at least 20, 40, 60, 80, 100, 120, 140, 160 or 180 genes, e.g., genes from Table 1 or 1A, is assigned a nucleotide value. In an embodiment unique first and/or second values are applied to subgenomic intervals in each of at least 10, 20, 30, 40, or 50% of said genes analyzed.

In an embodiment, a nucleotide position in at least 5, 10, 20, 30, or 40 genes from Table 1 or 1A having the priority 1 annotation is assigned a nucleotide value. In an embodiment unique first and/or second values are applied to subgenomic intervals in each of at least 10, 20, 30, 40, or 50% of said genes analyzed.

In an embodiment, a nucleotide position for at least 10, 20, 30, 40, 50, 100, 150, 200, 300, 400, or 500 variants or codons, e.g., mutations, from Table 1, 1A, 2, or 3, is assigned a nucleotide value. In an embodiment unique first and/or second values are applied to subgenomic intervals in each of at least 10, 20, 30, 40, or 50% of said genes analyzed.

In an embodiment, the method comprises:
applying unique first and/or second values to each of X genomic intervals, each of which having a variant which is associated with a tumor phenotype, e.g. wherein the variant is a point mutation, and X is greater than 2, 3, 5, 10, 20, 40, 50, 60, 70, 80, 90, or 100, e.g., wherein each of said subgenomic intervals is located in a different gene.

In an embodiment, the method comprises:
applying unique first and/or second values to each of X genomic intervals, each of which having a variant which is associated with a tumor phenotype, e.g. wherein the variant is a rearrangement, e.g., a deletion, insertion, or translocation, and X is greater than 2, 3, 5, 10, 20, 40, 50, 60, 70, 80, 90, or 100, wherein each of said subgenomic intervals is located in a different gene.

In an embodiment, the method includes 1, 2, 3, 4 or all of the following (in embodiments a group of 2 or more of the following are included and the first and/or second values for each of the group are unique):

(i) responsive to first and/or second values, assigning a nucleotide value (e.g., calling a mutation) from reads for a first preselected nucleotide position for which, e.g., the deepest coverage is required to enable a high level of sensitivity for mutations that appear at a relatively low frequency. Examples include a variant, e.g., a point mutation, that appears at a frequency of 5% or less in cells in the sample, the nucleic acids of a library, or the nucleic acids of a library catch. Typically, these variants require >500× sequencing depth to ensure high detection reliability. An exemplary application is an exon that is frequently mutated in a preselected cancer;

(ii) responsive to first and/or second values, assigning a nucleotide value (e.g., calling a mutation) from reads for a second preselected nucleotide positions for which, e.g., high coverage (though in embodiments less than that in (i) above) is required to enable a high level of sensitivity for mutations that appear at a relatively high frequency, e.g., at a higher frequency than a mutation in (i) above. Examples include a variant, e.g., a point mutation, that appears at a frequency of greater than 5% and up to 10, 15 or 20% in cells in the sample, the nucleic acids of a library, or the nucleic acids of a library catch. Typically, these variants require >200× sequencing depth to ensure high detection reliability. An exemplary application is in a gene related to cancer;

(iii) responsive to first and/or second values, assigning a nucleotide value (e.g., calling a mutation) from reads for a third preselected nucleotide position for which, e.g., low to medium coverage (in embodiments less than that in (i) or (ii) above) is required to enable a high level of sensitivity for heterozygous alleles. Examples include a variant, e.g., (1) a pharmacogenomic SNP that may be associated with the ability of patient to respond to or metabolize a drug; (2) a genomic SNP that may be used to uniquely identify (fingerprint) a patient; or (3) a genomic SNP/loci that may be used to assess copy number gains/losses of genomic DNA and LOH;

(iv) responsive to first and/or second values, assigning a nucleotide value (e.g., calling a mutation) from reads for a fourth preselected nucleotide position, e.g., a structural breakpoint, e.g., in a rearrangment, e.g., a translocation or an indel. In embodiments the coverage is less than in one of (i), (ii) or (iii). Examples include an intronic breakpoint, which in embodiments requires 5-50× sequence-pair spanning depth to ensure high detection reliability. An exemplary application is a translocation/indel-prone cancer gene; and (v) responsive to first and/or second values, assigning a nucleotide value (e.g., calling a mutation) from reads for a fifth preselected nucleotide position for which, e.g., sparse coverage can improve the ability to detect copy number changes. In embodiments the coverage is less than in one of (i), (ii) (iii) or (iv). For example, a 1 copy deletion of several terminal exons, e.g. which requires 0.1-10× coverage to ensure high detection reliability. An exemplary application is to an amplification/deletion-prone cancer gene.

Methods disclosed herein provide for the use of customized or tuned mutation calling parameters to optimize performance in sequencing methods, particularly in methods that rely on massively parallel sequencing of a large number of diverse genetic events in a large number of diverse genes. In embodiments of the method, a "threshold value" is used to evaluate reads, and select from the reads a value for a nucleotide position, e.g., calling a mutation at a specific position in a gene. In embodiments of the method, a threshold value for each of a number of preselected subgenomic intervals is customized or fine tuned. The customization or tuning can be based on one or more of the factors described herein, e.g., the type of cancer in a sample, the gene in which subgenomic interval to be sequenced is located, or the variant to be sequenced. This provides for calling that is finely tuned to each of a number of subgenomic intervals to be sequenced. The method is particularly effective when a relatively large number of diverse subgenomic intervals are analyzed.

Accordingly, in another aspect, a method of analyzing a sample, e.g., a tumor sample, from a subject is featured. The method comprises:

(a) acquiring one or a plurality of reads for each of X subgenomic intervals from nucleic acid from said sample;

(b) acquiring, for each of said X subgenomic intervals, a threshold value, wherein each of said acquired X threshold values is unique as compared with the other X−1 threshold values, thereby providing X unique threshold values;

(c) for each of said X subgenomic intervals, comparing an observed value which is a function of the number of reads having a preselected nucleotide value at a preselected nucleotide position with its unique threshold value, thereby applying to each of said X subgenomic intervals, its unique threshold value: and (d) optionally, responsive to the result of said comparison, assigning a nucleotide value to a preselected nucleotide position,
wherein X is equal to or greater than 2,
thereby analyzing said sample.

Embodiments of the method can be applied where threshold values for a relatively large number of subgenomic intervals are optimized, as is seen, e.g., from the following embodiments.

In an embodiment, X is at least 3, 5, 10, 20, 40, 50, 60, 70, 80, 90, or 100.

In an embodiment, a unique threshold value is applied to subgenomic intervals in each of at least 3, 5, 10, 20, 40, 50, 60, 70, 80, 90, or 100 different genes.

In an embodiment, a nucleotide position in at least 20, 40, 60, 80, 100, 120, 140, 160 or 180 genes, e.g., genes from Table 1 or 1A, is assigned a nucleotide value. In an embodiment a unique threshold value is applied to a subgenomic interval in each of at least 10, 20, 30, 40, or 50% of said genes analyzed.

In an embodiment, a nucleotide position in at least 5, 10, 20, 30, or 40 genes from Table 1 or 1A having the priority 1 annotation is assigned a nucleotide value. In an embodiment a unique threshold value is applied to a subgenomic interval in each of at least 10, 20, 30, 40, or 50% of said genes analyzed.

In an embodiment, a nucleotide position for at least 10, 20, 30, 40, 50, 100, 150, 200, 300, 400, or 500 variants or codons, e.g., mutations, from Table 1, 1A, 2, or 3, is assigned a nucleotide value. In an embodiment, a unique threshold value is applied to a subgenomic interval in each of at least 10, 20, 30, 40, or 50% of said genes analyzed.

In an embodiment, a nucleotide position for at least 10, 20, 30, 40, 50, 100, or 200 variants, e.g., mutations, from the bottom half or bottom third of Table 9 is assigned a nucleotide value. In an embodiment a unique threshold value is applied to a subgenomic interval in each of at least 10, 20, 30, 40, or 50% of said genes analyzed.

In an embodiment, the method comprises:

acquiring and applying unique threshold values to each of X genomic intervals, each of which having a variant which is associated with a tumor phenotype, e.g. wherein the variant is a point mutation, and X is greater than 2, 3, 5, 10, 20, 40, 50, 60, 70, 80, 90, or 100, e.g., wherein each of said subgenomic intervals is located in a different gene.

In an embodiment, the method comprises:

acquiring and applying unique threshold values to each of X genomic intervals, each of which having a variant which is associated with a tumor phenotype, e.g. wherein the variant is a rearrangement, e.g., a deletion, insertion, or translocation, and X is greater than 2, 3, 5, 10, 20, 40, 50, 60, 70, 80, 90, or 100, wherein each of said subgenomic intervals is located in a different gene.

Embodiments of the method can allow the tuning of threshold values relative to other threshold values used in an application, as is seen, e.g., from the following embodiments.

In an embodiment:

unique threshold values are applied to subgenomic intervals to assign a nucleotide value to preselected nucleotide positions corresponding to at least 10, 20, 30, 40, 50, 75, 100, 150, or 200 variants, e.g., mutations, in Table 4, and X of said unique threshold values applied has a threshold value that is higher, e.g., 50% higher, than another threshold value used in the test, e.g., the lowest threshold value used, the average or median threshold value used, or the threshold value for common clinically relevant mutation such as those listed in Table 9 wherein X is equal to or greater than 1, 2, 3, 4, 5, 10, 15, 20, or 30.

In an embodiment, a nucleotide position for at least 10, 20, 30, 40, 50, 100, or 200 variants, e.g., mutations, from the top half or top third of Table 9 is assigned a nucleotide value, and optionally, the assignment transmitted to a third party. In embodiments:

unique threshold values are applied to subgenomic intervals to assign a nucleotide value to preselected nucleotide positions corresponding to at least 10, 20, 30, 40, 50, 75, 100, 150, or 200 variants, and X of said unique threshold values applied has a threshold value that is lower, e.g., 50% lower, than another threshold value used in the test, e.g., the highest threshold value used, the average or median threshold value used, or the threshold value for genome locations not previously observed to be mutated in cancer, wherein X is equal to or greater than 1, 2, 3, 4, 5, 10, 15, 20, or 30.

In an embodiment:

a unique threshold value is applied to a subgenomic interval in each of at least 2, 3, 5, 7, or 8 of the genes listed in genes in Table 11 for cancer of the large intestine, and for X combinations of two (i.e., a pairwise combination) of the unique threshold values applied, the members of the pairwise combination have the same relative rank order to one another as their genes have to one another in Table 11, wherein X is equal to or greater than 1, 2, 3, 4, 5, 10, or 20. By way of example, in an embodiment, in the analysis of a cancer of the large intestine, unique threshold values are applied to subgenomic intervals in APC, SMAD4, and CDNK2a (in order of low to high threshold value). Thus, in each of the three pair-wise combinations of APC/SMAD4, APC/CDNK2a, and SMAD4/CDNK2a, both members of each of the pairwise combinations have the same relative rank to one another as their genes have to one another in Table 11 (e.g., APC is lower than SMAD4 in both the embodiment and in Table 11).

In an embodiment:

a unique threshold value is applied to a subgenomic interval in each of at least 3, 5, 7, or 8 of the genes listed in genes in Table 11 for cancer of the large intestine, and for X combinations of three (i.e., a 3-way combination) of the unique threshold values applied, the members of the 3-way combination have the same relative rank order to one another as their genes have to one another in Table 11, wherein X is equal to or greater than 1, 2, 3, 4, or 5, 10 or 20. By way of example, in an embodiment, in the analysis of a cancer of the large intestine, unique threshold values are applied to subgenomic intervals in APC, SMAD4, CDNK2a and VHL (in order of low to high threshold value). Thus, e.g., in the 3-way combination of APC/SMAD4/CDNK2a, all three members of the 3-way combination have the same relative rank to one another as their genes have to one another in Table 11. Similarly, in the 3-way combination of APC/CDNK2a/VHL, all three members of the 3-way combination have the same relative rank to one another as their genes have to one another in Table 11.

In an embodiment:

a unique threshold value is applied to a subgenomic interval in each of at least 4, 5, 7, or 8 of the genes listed in genes in Table 11 for cancer of the large intestine, and for X combinations of four (i.e., a 4-way combination) of the unique threshold values applied, the members of the 4-way combination have the same relative rank order to one another as their genes have to one another in Table 11, wherein X is equal to or greater than 1, 2, 3, 4, 10 or 20. By way of example, in an embodiment, in the analysis of a cancer of the large intestine, unique threshold values are applied to subgenomic intervals in APC, SMAD4, CDNK2a, VHL, MSH6, and MSH2 (in order of low to high threshold value). Thus, e.g., in the 4-way combination of APC/SMAD4/CDNK2a/MSH2, all four members of the 4-way combination have the same relative rank to one another as their genes have to one another in Table 11.

In an embodiment:
a unique threshold value is applied to a subgenomic interval in each of at least 2, 3, 5, or 7, of the genes listed in genes in Table 11 for lung cancer, and
for X combinations of two (i.e., a pairwise combination) of the unique threshold values applied, the members of the pairwise combination have the same relative rank order to one another as their genes have to one another in Table 11, wherein X is equal to or greater than 1, 2, 3, 4, 5, 10, or 20. By way of example, in an embodiment, in the analysis of a lung cancer, unique threshold values are applied to subgenomic intervals in CDNK2a, STK11, RB1, APC, and SMAD4 (in order of low to high threshold value). Thus, in each of the three pair-wise combinations of CDNK2a/STK11, STK11/APC, and RB1/SMAD4, both members of each of the pairwise combinations have the same relative rank to one another as their genes have to one another in Table 11 (e.g., STK11 is lower than SMAD4 in both the embodiment and in Table 11).

In an embodiment:
a unique threshold value is applied to a subgenomic interval in each of at least 3, 5, or 7, of the genes listed in genes in Table 11 for lung cancer, and
for X combinations of three (i.e., a 3-way combination) of the unique threshold values applied, the members of the 3-way combination have the same relative rank order to one another as their genes have to one another in Table 11, wherein X is equal to or greater than 1, 2, 3, 4, or 5, 10 or 20. By way of example, in an embodiment, in the analysis of lung cancer, unique threshold values are applied to subgenomic intervals in CDNK2a, STK11, RB1, APC, and SMAD4 (in order of low to high threshold value). Thus, e.g., in the 3-way combination of CDNK2/APC/SMAD4, all three members of the 3-way combination have the same relative rank to one another as their genes have to one another in Table 11.

In an embodiment:
a unique threshold value is applied to a subgenomic interval in each of at least 4, 5, or 7 of the genes listed in genes in Table 11 for lung cancer, and
for X combinations of four (i.e., a 4-way combination) of the unique threshold values applied, the members of the 4-way combination have the same relative rank order to one another as their genes have to one another in Table 11, wherein X is equal to or greater than 1, 2, 3, 4, 10 or 20. By way of example, in an embodiment, in the analysis of lung cancer, unique threshold values are applied to subgenomic intervals in CDNK2a, STK11, RB1, APC, and SMAD4 (in order of low to high threshold value). Thus, e.g., in the 4-way combination of CDNK2a/STK11/APC/SMAD4, all four members of the 4-way combination have the same relative rank to one another as their genes have to one another in Table 11.

In an embodiment:
a unique threshold value is applied to a subgenomic interval in each of at least 2, 3, 4, 5, 6 or 7, of the genes listed in genes in Table 11 for prostate cancer, and
for X combinations of two (i.e., a pairwise combination) of the unique threshold values applied, the members of the pairwise combination have the same relative rank order to one another as their genes have to one another in Table 11, wherein X is equal to or greater than 1, 2, 3, 4, 5, 10, or 20. By way of example, in an embodiment, in the analysis of a prostate cancer, unique threshold values are applied to subgenomic intervals in CEBPA, MSH2, CDKN2A, APC, RB1, NF1, (in order of low to high threshold value). Thus, in each of the three pair-wise combinations of STK11/CEBPA, RB1/NF1, and CEBPA/CDKN2A, both members of each of the pairwise combinations have the same relative rank to one another as their genes have to one another in Table 11 (e.g., STK11 is lower than CEBPA in both the embodiment and in Table 11).

In an embodiment:
a unique threshold value is applied to a subgenomic interval in each of at least 3, 4, 5, 6 or 7 of the genes listed in genes in Table 11 for prostate cancer, and
for X combinations of three (i.e., a 3-way combination) of the unique threshold values applied, the members of the 3-way combination have the same relative rank order to one another as their genes have to one another in Table 11, wherein X is equal to or greater than 1, 2, 3, 4, or 5, 10 or 20. By way of example, in an embodiment, in the analysis of prostate cancer, unique threshold values are applied to subgenomic intervals in STK11, CEBPA, MSH2, CDKN2A, APC, and RB1 (in order of low to high threshold value). Thus, e.g., in the 3-way combination of CDNK2/APC/RB1, all three members of the 3-way combination have the same relative rank to one another as their genes have to one another in Table 11.

In an embodiment:
a unique threshold value is applied to a subgenomic interval in each of at least 4, 5, 6 or 7, of the genes listed in genes in Table 11 for prostate cancer, and
for X combinations of four (i.e., a 4-way combination) of the unique threshold values applied, the members of the 4-way combination have the same relative rank order to one another as their genes have to one another in Table 11, wherein X is equal to or greater than 1, 2, 3, 4, 10 or 20. By way of example, in an embodiment, in the analysis of prostate cancer, unique threshold values are applied to subgenomic intervals in STK11, CEBPA, MSH2, CDKN2A, APC, RB1, and NF1, (in order of low to high threshold value). Thus, e.g., in the 4-way combination of STK11/APC/RB1/NF1, all four members of the 4-way combination have the same relative rank to one another as their genes have to one another in Table 11.

In an embodiment:
a unique threshold value is applied to a subgenomic interval in each of at least 2, 3, 5, 7, or 8 of the genes listed in genes in Table 11 for breast cancer, and
for X combinations of two (i.e., a pairwise combination) of the unique threshold values applied, the members of the pairwise combination have the same relative rank order to one another as their genes have to one another in Table 11, wherein X is equal to or greater than 1, 2, 3, 4, 5, 10, or 20. By way of example, in an embodiment, in the analysis of breast cancer, unique threshold values are applied to subgenomic intervals in CDH1, CDKN2A, APC, RB1, SMAD4, NF2, STK11, MSH2 (in order of low to high threshold value). Thus, in each of the three pair-wise combinations of APC/SMAD4, APC/NF2, and SMAD4/MSH2, both members of each of the pairwise combinations have the same relative rank to one another as their genes have to one another in Table 11 (e.g., APC is lower than SMAD4 in both the embodiment and in Table 11).

In an embodiment:
a unique threshold value is applied to a subgenomic interval in each of at least 3, 5, 7, or 8 of the genes listed in genes in Table 11 for breast cancer, and
for X combinations of three (i.e., a 3-way combination) of the unique threshold values applied, the members of the 3-way combination have the same relative rank order to one another as their genes have to one another in Table 11, wherein X is equal to or greater than 1, 2, 3, 4, or 5, 10 or 20. By way of example, in an embodiment, in the analysis of breast cancer, unique threshold values are applied to subgenomic intervals in CDH1, CDKN2A, RB1, SMAD4, NF2, STK11, MSH2 (in order of low to high threshold value). Thus, e.g., in the 3-way combination of CDH1/RB1/STK11, all three members of the 3-way combination have the same relative rank to one another as their genes have to one another in Table 11.

In an embodiment:

a unique threshold value is applied to a subgenomic interval in each of at least 4, 5, 7, or 8 of the genes listed in genes in Table 11 for breast cancer, and for X combinations of four (i.e., a 4-way combination) of the unique threshold values applied, the members of the 4-way combination have the same relative rank order to one another as their genes have to one another in Table 11, wherein X is equal to or greater than 1, 2, 3, 4, 10 or 20. By way of example, in an embodiment, in the analysis of breast cancer, unique threshold values are applied to subgenomic intervals in CDH1, CDKN2A, APC, RB1, SMAD4, NF2, STK11, MSH2 (in order of low to high threshold value). Thus, e.g., in the 4-way combination of CDH1/SMAD4/STK11/MSH2, all four members of the 4-way combination have the same relative rank to one another as their genes have to one another in Table 11.

In an embodiment:

a unique threshold value is applied to a subgenomic interval in each of at least 2, or 3 of the genes APC, SMAD4, and ATM, and for X combinations of two (i.e., a pairwise combination) of the unique threshold values applied, the members of the pairwise combination are in relative rank order of APC, SMAD4, and ATM, wherein X is equal to or greater than 1, 2, or 3. By way of example, in an embodiment, in the analysis of a cancer of the large intestine, unique threshold values are applied to subgenomic intervals in APC, SMAD4, and ATM (in order of low to high threshold value). Thus, in each of the pair-wise combination of APC/SMAD4 and APC/ATM, both members of each of the pairwise combinations have the same relative rank as in APC, SMAD4, and ATM).

In an embodiment:

a unique threshold value is applied to a subgenomic interval in each of the genes APC, SMAD4, and ATM, and the order for the threshold values, from low to high is APC, SMAD4, and ATM.

(Table 11 lists an ordering of genes in order of increasing threshold value for some or all coding base pairs in those genes, e.g., base pairs that are not otherwise specified by another superseding lis of bases specifically known to be mutated at a higher rate such as that in Table 9)

In an embodiment:

wherein a first unique threshold value is applied to a first preselected nucleotide position, a variant of which is associated with a tumor phenotype, and a second unique threshold value is applied to a preslected nucleotide other than said first preselected nucleotide position, e.g., a position having no variant associated with a tumor phenotype, and said first threshold value is higher than the second.

In an embodiment, the method comprises:

a) acquiring and applying a first unique threshold value to a first genomic interval, a variant of which is associated with a tumor phenotype, e.g. wherein the variant is a point mutation, e.g., a mutation on Table 6;

b) acquiring and applying a second unique threshold value to a second genomic interval, a variant of which is associated with a tumor phenotype, e.g. wherein the variant is a rearrangement, e.g., a deletion, insertion, or translocation, e.g., a mutation on Table 5; and c) acquiring and applying a third unique threshold value to a third genomic interval, e.g., a genomic interval in which variants are not associated with a tumor phenotype or with a tumor of the type in said sample.

In an embodiment the method includes 1, 2, 3, 4 or all of the following (in embodiments a group of 2 or more of the following are included and the threshold values for each of the group are unique):

(i) applying a first threshold value toreads for a first preselected nucleotide position for which, e.g., the deepest coverage is required to enable a high level of sensitivity for mutations that appear at a relatively low frequency. Examples include a variant, e.g., a point mutation, that appears at a frequency of 5% or less in cells in the sample, the nucleic acids of a library, or the nucleic acids of a library catch. Typically these variants require >500X sequencing depth to ensure high detection reliability. An exemplary application is an exon that is frequently mutated in a preselected cancer;

(ii) applying a second threshold value to reads for a second preselected nucleotide positions for which, e.g., high coverage (though in embodiments less than that in (i) above) is required to enable a high level of sensitivity for mutations that appear at a relatively high frequency e.g., at a higher frequency than a mutation in (i) above. Examples include a variant, e.g., a point mutation, that appears at a frequency of greater than 5% and up to 10, 15 or 20% in cells in the sample, the nucleic acids of a library, or the nucleic acids of a library catch. Typically these variants require >200X sequencing depth to ensure high detection reliability. An exemplary application is in a gene related to cancer;

(iii) applying a third threshold value to reads for a third preselected nucleotide position for which, e.g., low to medium coverage (in embodiments less than that in (i) or (ii) above) is required to enable a high level of sensitivity for heterozygous alleles. Examples include a variant, e.g., (1) a pharmacogenomic SNP that may be associated with the ability of patient to respond to or metabolize a drug; (2) a genomic SNP that may be used to uniquely identify (fingerprint) a patient; or (3) a genomic SNP/loci that may be used to assess copy number gains/losses of genomic DNA and LOH;

(iv) applying a fourth threshold value to reads for a fourth preselected nucleotide position e.g., a structural breakpoint, e.g., in a rearrangment, e.g., a translocation or an indel. In embodiments the coverage is less than in one of (i), (ii) or (iii). Examples include an intronic breakpoint, which in embodiments requires 5-50X sequence-pair spanning depth to ensure high detection reliability. An exemplary application is a translocation/indel-prone cancer gene; and (v) applying a fifth threshold value to reads for a fifth preselected nucleotide position for which, e.g., sparse coverage can improve the ability to detect copy number changes. In embodiments the coverage is less than in one of (i), (ii) (iii) or (iv). For example, a 1 copy deletion of several terminal exons, e.g. which requires 0.1-10X coverage to ensure high detection reliability. An exempary application is to an amplification/deletion-prone cancer gene.

In an embodiment:

the first threshold value is greater than the second;
the second threshold value is greater than the third;
the third threshold value is greater than the fourth; and
the fourth threshold value is greater than the fifth.

In an embodiment, X threshold values, e.g., unique or non-unique threshold values, are a function of, or are selected on the basis of, 1, 2, 3, 4, or more, or all of the following characteristics:

a) a mutation expectation;
b) a mutation probability value;

c) a Bayesian prior;
d) mutation frequency;
e) the type of variant associated with a preselected nucleotide position, e.g., a variant which is associated with a tumor phenotype, e.g. a point mutation or a rearrangement, e.g., a deletion, insertion, or translocation;
f) copy number;
g) tumor type of a subgenomic interval; or
h) the subgenomic interval;

wherein X is at least 1, 2, 3, 5, 10, 20, 40, 50, 60, 70, 80, 90, or 100.

In an embodiment, X threshold values, e.g., a unique or non-unique threshold values, are a function of, or are selected on the basis of factors that include, or are: a and e; a and g; e and g; wherein X is at least 1, 2, 3, 5, 10, 20, 40, 50, 60, 70, 80, 90, or 100.

In an embodiment, one or more or all of characteristics a-f are a function of one or more of or all of a preselected nucleotide position, a preselected tumor type, or a preselected gene.

In an embodiment, X threshold values, e.g., unique or non-unique threshold values, are a function of, or are selected on the basis of background genomic mutation frequency, wherein X is at least 1, 2, 3, 5, 10, 20, 40, 50, 60, 70, 80, 90, or 100.

In an embodiment, X threshold values, e.g., unique or non-unique threshold values, are a function of, or are selected on the basis of, 1, 2, 3, 4, or more, or all of the following patient characteristics:

Age; gender; prior environmental exposure, e.g., to mutagens or carcinogens; prior exposure to a medication or treatment, e.g., prior treatment with an anti-tumor agent, whether the patent is a current or past smoker; tumor type, or germ-line variation in the subgenomic interval, wherein X is at least 1, 2, 3, 5, 10, 20, 40, 50, 60, 70, 80, 90, or 100.

In an embodiment, X threshold values, e.g., unique or non-unique threshold values, are a function of, or are selected on the basis of, 1, 2, 3, 4, or more, or all of the following sample characteristics:

tumor type; site-specific tumor ploidy (e.g., based on SNP analysis); tumor zygosity; sample purity; tumor sample cellularity (e.g., proportion of tumor cells in the sample); whether tumor and control SNP genotypes for a subject match; or level of expected or observed DNA damage wherein X is at least 1, 2, 3, 5, 10, 20, 40, 50, 60, 70, 80, 90, or 100.

In an embodiment, the method comprises applying an unique threshold value to a plurality of subgenomic intervals.

In an embodiment, the method comprises applying an unique threshold value to a preselected set of positions in a first subgenomic interval, e.g., a gene. E.g., in an embodiment, said preselected set comprises, or is limited to:
  all of the nucleotide positions in a first gene, or preselected portion thereof;
  all of the nucleotide positions in an intron of a first gene, or preselected portion thereof;
  all of the nucleotide positions in an exon of a first gene, or preselected portion thereof;
  all of the nucleotide positions within a preselected range, which includes a nucleotide position in a first gene, e.g., one in which a variant is associated with a tumor phenotype, e.g. wherein the variant is a point mutation or a rearrangement, e.g., a deletion, insertion, or translocation.

In an embodiment, the method comprises applying a unique threshold value to a preselected set of positions in a first subgenomic interval, e.g., a gene, and further applying an unique threshold value to a preselected set of positions in a subsequent, e.g., a second, third, fourth, fifth or sixth subgenomic interval, e.g., a gene. In an embodiment, the preselected set for said subsequent gene comprises, or is limited to:
  all of the nucleotide positions in said subsequent gene, or preselected portion thereof;
  all of the nucleotide positions in an intron of said subsequent gene, or preselected portion thereof;
  all of the nucleotide positions in an exon of said subsequent gene, or preselected portion thereof;
  all of the nucleotide positions within a preselected range which includes a nucleotide position in said subsequent gene, a variant of which is associated with a tumor phenotype, e.g. wherein the variant is a point mutation or a rearrangement, e.g., a deletion, insertion, or translocation.

In embodiments, more than one threshold value is applied to a gene, or other subgenomic interval. Thus, in an embodiment the method comprises:

applying a first unique threshold value, e.g., which is a function of a background mutation rate, to a first preselected position or set of positions in a subgenomic interval, e.g., a gene; and applying a subsequent, e.g., a second, third, forth, fifth, or sixth, unique threshold value, e.g., which is selected responsive to a factor disclosed herein, e.g., the expected frequency of a variant which is associated with a tumor phenotype, to a subsequent, e.g., a second, third, forth, fifth, or sixth, preselected position or set of positions in said subgenomic interval.

In such embodiment, the first preselected set can comprises, or be limited to:
  a nucleotide position, other than a nucleotide position, a variant of which is associated with a tumor phenotype; or
  the majority of the nucleotide positions in a gene.

In an embodiment the second preselected set comprises, or is limited to:
  a nucleotide position, a variant of which is associated with a tumor phenotype;
  a nucleotide position in a first preselected portion of an intron of said gene;
  a nucleotide position in a first preselected portion of an exon of said gene;
  all of the nucleotide positions within a preselected range which includes a nucleotide position, a variant of which is associated with a tumor phenotype, e.g. wherein the variant is a point mutation or a rearrangement, e.g., a deletion, insertion, or translocation;
  a minority of the nucleotide positions in a gene; or
  no more than 1, 2, 3, 3, 5, 10, or 20 nucleotide positions in a gene.

In such embodiment the first preselected set can comprise, or be limited to:
  a nucleotide position, other than said nucleotide position, a variant of which is associated with a tumor phenotype;
  a nucleotide position, other than said nucleotide position in a first preselected portion of an intron of said gene;
  a nucleotide position, other than said nucleotide position in a first preselected portion of an exon of said gene;
  a nucleotide position, other than said nucleotide positions within a preselected range which includes a nucleotide position, a variant of which is associated with a tumor phenotype, e.g. wherein the variant is a point mutation or a rearrangement, e.g., a deletion, insertion, or translocation.

In such embodiment, the first unique threshold value can be lower than said subsequent unique threshold value.

A Bayesian Approach for Sensitive Detection of Somatic Genomic Alterations from Next-generation Sequencing of Clinical Cancer Specimens As discussed elsewhere herein, the invention features a method of analyzing a sample, e.g., a tumor sample. Methods described herein can include the following:

(aaa) acquiring one or a plurality of reads for each of X subgenomic intervals from nucleic acid from said sample;

(bbb) acquiring, for a preselected nucleotide position in each of said X subgenomic intervals:

(i) a first value which is or represents the prior (e.g., literature) expectation of observing a read showing a preselected variant, e.g., a mutation, at said preselected nucleotide position in a tumor of type X; and (ii) a second set of values which represent the probabilities of observing a read showing said preselected variant at said preselected nucleotide position if the variant is present in the sample at a frequency (e.g., 1%, 5%, 10%, etc.) and/or if the variant is absent (e.g., observed in the reads due to base-calling error alone);

(ccc) responsive to said values, assigning a nucleotide value (e.g., calling a mutation) from said reads for each of said preselected nucleotide positions by weighing the comparison among the values in the second set using the first value (e.g., computing the posterior probability of the presence of a mutation), thereby analyzing said sample.

This method, e.g., in the weighing the comparison of among the variables, provides analytical components for an NGS-based approach to tumor genome assessment which incorporates knowledge of somatic mutation frequency and diversity to optimize detection. Although mutations are relatively infrequent in cancer genomes (e.g., base substitutions are expected at a rate of ~1-10 per 1 Mb genome-wide), specific driver mutations are known to occur often in certain tumor types. For instance, the KRAS mutation c.35G>A (p.G12D) can be expected in ~10% of colon cancers. An efficient mutation-detection approach can leverage this prior information to optimize the trade-off between sensitivity and specificity and to maximize detection power in "difficult" samples. E.g., the method can comprise analysis using the following relationship:

$$P(\text{Mutation present}|\text{Read data ``R''}) = P(\text{Frequency of mutation ``}F\text{''}>0|R) = 1 - P(F=0|R)$$

$$P(F=0|R) = \frac{P(R|F=0)P(F=0)}{\sum_{i=0}^{n} P\left(R|F=\frac{i}{n}\right)P\left(F=\frac{i}{n}\right)}$$

$$\sum_{i=0}^{n} P\left(R|F=\frac{i}{n}\right)P\left(F=\frac{i}{n}\right)$$

is an discrete approximation to Equation A, which can alternatively be evaluated in the relationship in place of the discretized approximation:

$$\int_0^1 P(R|F=x)P(F=x)dx \quad \text{Equation A}$$

P(F=0)=1−prior expectation "p" of the mutation in cancer type. The value in (i) above corresponds to p.

$$P\left(F=\frac{i}{n} \mid i>0\right) = p/n \text{ (e.g., } n=100\text{)},$$

which assume a uniform distribution of the prior over frequencies and thus specifies the prior expectation of the mutation frequencies referred to in (ii). This term can be varied from the uniform distribution to adjust for any prior knowledge regarding the expected mutation frequency, such as measured purity or aneuploidy in the specific sample, or expected mutation frequencies given the specific tumor type, extraction method, etc.

$$P\left(R \mid F=\frac{i}{n}\right)$$

is evaluated according to the mutation type, for instance, using the allele count observations, calibrated quality scores and the multinomial distribution for substitution mutations.

The detection approaches provided herein can include the following steps: sequencing and alignment, quality score recalibration, Bayesian mutation calling, and mutation calling filtering. For example, sequencing and alignment can include hybrid selection for exons of 182 cancer-related genes, deep sequencing on the Illumina HiSeq platform, alignment with Burrows-Wheeler Aligner (BWA) (Li H. and Durbin R. (2009) *Bioinformatics*, 25:1754-60), and alignment optimization with The Genome Analysis Toolkit (GATK) (McKenna A. H. et al., *Genome Res.* 2010 20(9): 1297-303). Quality score recalibration maps reported quality scores to empirical error rates. Bayesian mutation calling allows for possibility of mutation being present at any frequency (not limited to diploid). Incorporate tissue-specific prior probability of mutation from COSMIC to boost sensitivity. Mutation calling filtering filters artifacts using indicators like strand bias, low mapping quality, and read location bias; and removes most germ-like variation (dbSNP).

This approach can be extended to additional mutation types (indels/translocations/CNV) by deriving relevant P(Read data R|Frequency of mutation=f).

Duplicate Reads

During the sequencing process, errors can be introduced into the reads at different stages of the process, e.g., by the sequencing chemistry, or by the image analysis software. Duplicate reads are typically sequenced as separate reads. Mutation calling algorithms need to distinguish between sequencing errors and real sequence variations to correctly call the latter. Methods described herein can analyze duplicate reads so as to reduce the sequencing error and thereby improve the sensitivity of the mutation calling algorithm.

This is typically done by comparing independent reads covering the same genomic position. Read duplicates are created during various steps of the library preparation (e.g., PCR amplification) and are sequenced as separate reads. Since these are not independent reads (i.e., they originate from the same original DNA molecule) only one of any number of duplicates is typically used for the mutation detection process, while the rest are discarded.

The use of duplicate reads to reduce sequencing errors and thereby improve the sensitivity of the mutation calling algorithm is described herein. Duplicate reads can be identified by possession of the same starting and ending position. Since duplicate reads are essentially replicate reads of the same original DNA molecule, any difference between duplicates must be a sequencing error and can therefore be ignored. For example, if highly duplicate data is available, the consensus of 3 or more duplicates can be used. Alternatively, the quality score of a base may be redefined to reflect the agreement between 2 or more duplicates of the read, and utilized by any downstream process. For example, a mutation calling algorithm could place less weight on a sequence difference that is not supported by all duplicates.

The suggested method was tested on some sequencing data by generating a consensus sequence for duplicates. The error rate of the consensus read sequences was shown to be significantly lower than for the original reads.

This method can be used, e.g., when 1) some failure modes of the sequencer result in useable sequence data with higher error rates, which negatively impacts the ability to call mutations in this data. Reducing error by using duplicates should be especially effective in the scenario, and make the mutation calling pipeline more robust to machine failure, 2) when sequencing DNA from cancer cells that are especially rare in the sample (e.g., circulating tumor cells may be <1% of cells in the sample) any improvement in the base error rate may significantly increase the ability to correctly identify mutations in these tumor cells.

In one exemplary embodiment, a dataset with a high duplication rate (69%) was scanned for duplicates. When duplicates were removed by a commonly-used software removal tool (Picard MarkDuplicates) which arbitrarily selects one read of the duplicates, the resulting error rate was 0.40%. In parallel, all reads with at least 3 duplicates were processed separately, and a consensus sequence for each set of duplicates was derived by selecting the most common sequence of the duplicates. The error rate of the consensus sequences was 0.20%, demonstrating a lower error rate can be achieved for duplicate reads by comparing their sequences.

Example of Deriving a Consensus Read:

```
Read1:
                                    (SEQ ID NO: 2)
CCAAAACTAAACTGCTCTTTAAATATCTTAGACACT Read2:
                                    (SEQ ID NO: 3)
CCAAAACTAAACTGCTCTTTAAATATCTTAGACACT Read3:
                                    (SEQ ID NO: 4)
CCAACACTAAACTGCTCTTTAAATATCTTAGACACT Consensus:
                                    (SEQ ID NO: 5)
CCAAAACTAAACTGCTCTTTAAATATCTTAGACACT
```

Accordingly, in another aspect, the invention includes a method of analyzing the sequence of a nucleic acid, e.g., from a tumor sample comprising:

(a) optionally, acquiring a plurality of duplicates of a subgenomic interval (formed, e.g., by amplification of an original copy of said subgenomic interval);

(b) acquiring a read for each of said plurality of duplicates to provide a plurality of duplicate reads;

(c) comparing the nucleotide values at a first nucleotide position in each of said plurality of duplicate reads (typically, the nucleotide position in one duplicate read is compared with the corresponding nucleotide position in a second read);

(d) optionally, comparing the nucleotide values at second nucleotide position in each of said plurality of duplicate reads, wherein, for one of the nucleotide positions, each of said plurality of reads does not have the same nucleotide value, and, optionally, for the other of said nucleotide positions, each of said plurality of reads has the same nucleotide value;

(e) assigning a first classifier, e.g., a quality score or a duplicate-adjusted nucleotide value, to the nucleotide value at the position not having the same nucleotide value in all of said plurality of reads, (f) optionally assigning a second classifier, e.g., a quality score or a duplicate-adjusted nucleotide value, to the nucleotide value at the position having the same nucleotide value for each plurality of the reads, wherein said first classifier indicates a first level of quality or confidence that the nucleotide value to which it is assigned is correct and said second classifier indicates a second level of quality or confidence that the nucleotide value to which it is assigned is correct and said first level is equal to or lower than a preselected criterion.

In one embodiment, said first level is lower than what would be assigned if each of said plurality of reads had the same nucleotide value.

In another embodiment, said first level is lower than said second level.

In another embodiment, the classification is a function of the proportion of nucleotide values that differ for that nucleotide position in the plurality.

In another embodiment, the classification is a function of the number of duplicate reads in the plurality.

In yet another embodiment, a method for calling mutations at a nucleotide position is a function of the classification for that nucleotide value at that nucleotide position.

In another embodiment, the duplicate reads are not identified or removed. Not removing duplicate reads can be particularly useful for identifying copy number aberrations in tumor DNA and in evaluation of allele-balance, when the fraction of duplicate reads is significantly different between a control and a test sample. For example, a genomic region with high coverage depth in a sample with a high-duplication rate can lose more reads than the same region with a comparable depth in a sample with low duplication rate, while low-coverage regions are likely to be less prone to this effect. Therefore, when the fraction of duplicate reads differs significantly between a control and a test sample, a comparison between the two can be noisier, thus lowering the sensitivity and/or specificity of callings copy-number alterations.

Sequence analysis of a DNA test sample, e.g., a DNA sample extracted from a tumor, requires comparison of a test sample with a control sample, e.g., a DNA sample from a non-cancerous tissue.

In sequencing a genomic DNA sample, duplicate reads will be generated. Read duplicates are created during various steps of library preparation (e.g., PCR amplification) and are sequenced as separate reads. Since these are not independent reads (i.e., they originate from the same original DNA molecule) only one of any number of duplicates is typically used for the mutation detection process, while the rest are discarded. Typically, duplicate reads from both the control and the test sample are removed prior to performing comparative analysis between the test and the control DNA sequence.

In one embodiment, Applicants have discovered that in situations where the number of duplicate reads is significantly different between the test and the control samples, the removal of duplicate reads (from either or both of the control and test samples) negatively impacts the ability to call alterations, such as copy-number alterations, since it distorts the coverage depth patterns of different samples differently. Thus, in situations where the fraction of duplicate reads is significantly different between the test and control samples (e.g., differing by more than 20%, 30%, 40%, 50%, 60% or more), it is preferred that duplicate reads are not removed prior to comparative analysis, in order to maximize the ability to correctly identify mutations in the test sample. For example, in situations where the number of duplicate reads in the control sample and the test sample are 20% and 80% (or 70% or 60% or 50%), respectively, then duplicate reads are preferably not removed prior to comparative analysis.

Other Embodiments

In embodiments of a method described herein a step or parameter in the method is used to modify a downstream step or parameter in the method.

In an embodiment, a characteristic of the tumor sample is used to modify a downstream step or parameter in one or more or all of: isolation of nucleic acid from said sample; library construction; bait design or selection; hybridization conditions; sequencing; read mapping; selection of a mutation calling method; mutation calling, or mutation annotation.

In an embodiment, a characteristic of an isolated tumor, or control, nucleic acid is used to modify a downstream step or parameter in one or more or all of: isolation of nucleic acid from said sample; library construction; bait design or selection; hybridization conditions; sequencing; read mapping; selection of a mutation calling method; mutation calling, or mutation annotation.

In an embodiment, a characteristic of a library is used to modify a downstream step or parameter in one or more or all of: re-isolation of nucleic acid from said sample; subsequent library construction; bait design or selection; hybridization conditions; sequencing; read mapping; selection of a mutation calling method; mutation calling, or mutation annotation.

In an embodiment, a characteristic of a library-catch is used to modify a downstream step or parameter in one or more or all of: re-isolation of nucleic acid from said sample; subsequent library construction; bait design or selection; hybridization conditions; sequencing; read mapping; selection of a mutation calling method; mutation calling, or mutation annotation.

In an embodiment, a characteristic of the sequencing method is used to modify a downstream step or parameter in one or more or all of: re-isolation of nucleic acid from said sample; subsequent library construction; bait design or selection; subsequent determination of hybridization conditions subsequent sequencing; read mapping; selection of a mutation calling method; mutation calling, or mutation annotation.

In an embodiment, characteristic of the collection of mapped reads is used to modify a downstream step or parameter in one or more or all of: re-isolation of nucleic acid from said sample; subsequent library construction; bait design or selection; subsequent determination of hybridization conditions subsequent sequencing; subsequent read mapping; selection of a mutation calling method; mutation calling, or mutation annotation.

In an embodiment, the method comprises acquiring a value for a tumor sample characteristic, e.g., acquiring a value: for the proportion of tumor cells in said sample, for the cellularity of said tumor sample; or from an image of the tumor sample.

In embodiments, the method includes, responsive to said acquired value for a tumor sample characteristic, selecting a parameter for: isolation of nucleic acid from a tumor sample, library construction; bait design or selection; bait/library member hybridization; sequencing; or mutation calling In an embodiment, a method further comprising acquiring a value for the amount of tumor tissue present in said tumor sample, comparing said acquired value with a reference criterion, and if said reference criterion is met, accepting said tumor sample, e.g., accepting said tumor sample if said tumor sample contains greater than 30, 40 or 50% tumor cells.

In an embodiment, a method further comprises acquiring a sub-sample enriched for tumor cells, e.g., by macrodissecting tumor tissue from said tumor sample, from a tumor sample that fails to meet the reference criterion.

In an embodiment, a method further comprises determining if a primary control, e.g., a blood sample, is available and if so isolating a control nucleic acid (e.g., DNA) from said primary control.

In an embodiment, a method further comprises determining if NAT is present in said tumor sample (e.g., where no primary control sample is available).

In an embodiment, a method further comprises acquiring a sub-sample enriched for non-tumor cells, e.g., by macrodissecting non-tumor tissue from said NAT in a tumor sample not accompanied by a primary control.

In an embodiment, a method further comprises determining that no primary control and no NAT is available and marking said tumor sample for analysis without matched control.

In an embodiment, a method further comprises isolating nucleic acid from said tumor sample to provide an isolated tumor nucleic acid sample In an embodiment, a method further comprises isolating a nucleic acid from a control to provide an isolated control nucleic acid sample.

In an embodiment, a method further comprises rejecting a sample with no detectable nucleic acid.

In an embodiment, a method further comprises acquiring a value for nucleic acid yield in said isolated nucleic acid sample and comparing the acquired value to a reference criterion, e.g., wherein if said acquired value is less than said reference criterion, then amplifying said isolated nucleic acid sample prior to library construction.

In an embodiment, a method further comprises acquiring a value for the size of nucleic acid fragments in said isolated nucleic acid sample and comparing the acquired value to a reference criterion, e.g., a size, e.g., average size, of at least 300, 600, or 900 bp. A parameter described herein can be adjusted or selected in response to this determination.

In an embodiment, a method further comprises acquiring a library wherein the size of said nucleic acid fragments are less than or equal to a reference value said library is made without a fragmentation step between DNA isolation and making the library.

In an embodiment, a method further comprises acquiring nucleic acid fragments and if the size of said nucleic acid fragments are equal to or greater than a reference value and are fragmented and then made into a library.

In an embodiment a method further comprises labeling each of a plurality of library members, e.g., by addition of an identifiable distinct nucleic acid sequence (a barcode), to each of a plurality of members.

In an embodiment, a method further comprises attaching a primer to each of a plurality of library members.

In an embodiment a method further comprises providing a plurality of bait and selecting a plurality of baits, said selection being responsive to: 1) a patient characteristic, e.g., age, stage of tumor, prior treatment, or resistance; 2) tumor type; 3) a characteristic of the tumor sample; 4) a characteristic of a control sample; 5) presence or type of control; 6) a characteristic of the isolated tumor (or control) nucleic acid sample; 7) a library characteristic; 8) a mutation known to be associated with the type of tumor in the tumor sample; 9) a mutation not known to be associated with the type of tumor in the tumor sample; 10) the ability to sequence (or hybridized to or recover) a preselected sequence or identify a preselected mutation, e.g., the difficulty associated with sequence a high gc region or a rearrangement; or 11) the genes being sequenced.

In an embodiment a method further comprises responsive, e.g., to a determination of low number of tumor cells in said tumor sample, selecting a bait, or plurality of baits, giving relatively highly efficient capture of members from a first gene as compared with members of a second gene, e.g., wherein a mutation in the first gene is associated the tumor phenotype for the tumor type of the tumor sample.

In an embodiment a method further comprises acquiring a value for library-catch characteristic, e.g., the nucleic acid concentration or representation, and comparing the acquired value with a reference criterion for nucleic acid concentration, or for representation.

In an embodiment, a method further comprises selecting a library with a value for a library characteristic that does not meet the reference criterion for reworking.

In an embodiment, a method further comprises selecting a library with a value for a library characteristic that meets the reference criterion for library quantitation.

In an embodiment, a method further comprises providing an association of a tumor type, a gene, and a genetic alteration (a TGA) for a subject.

In an embodiment, a method further comprises providing a preselected database having a plurality of elements, wherein each element comprises a TGA.

In an embodiment, a method further comprises characterizing a TGA of a subject comprising:
 determining if said TGA is present in a preselected database, e.g., a database of validated TGAs;
 associating information for the TGA from the predetermined database with said TGA (annotating) from said subject; and
 optionally, determining if a second or subsequent TGA for said subject is present in said preselected database and if so associating information for the second or subsequent TGA from the predetermined database with said second TGA present in said patient.

In an embodiment, a method further comprises memorializing the presence or absence of a TGA, and optionally an associated annotation, of a subject to form a report.

In an embodiment, a method further comprises transmitting said report to a recipient party.

In an embodiment, a method further comprises characterizing a TGA of a subject comprising:
 determining if said TGA is present in a preselected database, e.g., a database of validated TGAs;
 determining if a TGA not in said preselected database has a known clinically relevant G or A and if so providing an entry for said TGA in said preselected database.

In an embodiment, a method further comprises memorializing the presence or absence of a mutation found in the DNA of the tumor sample from a subject to form a report.

In an embodiment, a method further comprises memorializing the presence or absence of a TGA, and optionally an associated annotation, of a subject to form a report.

In an embodiment, a method further comprises transmitting said report to a recipient party.

A flowchart depiction of an embodiment of a method for multigene analysis of a tumor sample is provided in FIG. 1.

EXEMPLIFICATION

This invention is further illustrated by the following examples which should not be construed as limiting. The contents of all references, figures, sequence listing, patents and published patent applications cited throughout this application are hereby incorporated by reference.

Example 1

Nucleic Acid Isolation from a Tumor Sample

3×20 μm sections cut from a paraffin block were mixed with 400 μL Buffer FTL by vortexing and incubated at 90° C. for 15 minutes in a 1.5 mL centrifuge tube. A range of 88-92° C. was acceptable for the incubation. Then, the sample was incubated with 20 μL proteinase K at 55° C. for 6 hours and 10 μL RNase (1 mg/mL) at room temperature for 5 minutes. Next, 460 μL Buffer BL and 500 μL absolute ethanol were added to the sample. The resulting sample solution was kept at room temperature until further use.

To prepare the column for DNA binding, 100 μL Equilibration buffer was added to a MicroElute column and the column was centrifuged at 10,000×g for 30 seconds. 700 μL of the sample solution described above was transferred to the MicroElute column and the column was centrifuged at 10,000×g for 1 minute. The centrifugation step was repeated if fluid did not completely pass through MicroElute column. The remaining sample solution was applied to the MicroElute column in the same way as described above. Then, the MicroElute column was treated with 500 μL Buffer HB and centrifuged at 10,000×g for 1 minute. Next, 700 μL DNA Wash Buffer diluted with ethanol was added into the MicroElute column and the column was centrifuged at 10,000×g for 1 minute. The MicroElute column was washed again using 700 μL DNA Wash Buffer diluted with ethanol, centrifuged at 10,000×g for 1 minute, and centrifuged at >13,000×g for 3 minutes to dry the column. The MicroElute column was placed into a standard 1.5 mL centrifuge tube with the top removed. 50-75 μL Elution Buffer preheated to 70° C. was added into the column and incubated at room temperature for 3 minutes. The column was centrifuged in collection tube at >13,000×g for 1 minute. Another 50-75 μL Elution Buffer preheated to 70° C. was added into the MicroElute column and incubated at room temperature for 3 minutes. The column was centrifuged again in collection tube at >13,000×g for 1 minute. The entire solution was transferred to a fresh 1.5 mL centrifuge tube and stored at −20° C.

FTL buffer, proteinase K, BL Buffer, Equilibration Buffer, MicroElute column, Buffer HB, DNA Wash Buffer, and Elution Buffer were provided in E.Z.N.A.™ FFPE DNA Kit (OMEGA bio-tek, Norcross, Ga.; Cat. Nos. D3399-00, D3399-01, and D3399-02).

Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion Recover-All™ Total Nucleic Acid Isolation Protocol (Ambion, Cat. No. AM1975, September 2008), Maxwell® 16 FFPE Plus LEV DNA Purification Kit Technical Manual (Promega Literature #TM349, February 2011), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. Maxwell® 16 FFPE Plus LEV DNA Purification Kit is used with the Maxwell® 16 Instrument for purification of genomic DNA from 1 to 10 μm sections of FFPE tissue. DNA is purified using silica-clad paramagnetic particles (PMPs), and eluted in low elution volume. QIAamp® DNA FFPE Tissue Kit uses QIAamp® DNA Micro technology for purification of genomic and mitochondrial DNA.

Example 2A

Shearing of DNA

Covaris™ E210 instrument with circulating chiller was set to 4° C. The instrument water tank was filled with distilled/deionized water to level "6" on the fill-line. SonoLab™ software was launched and the system was allowed to execute homing sequence when prompted. The water in instrument tank was degassed for at least 45 minutes before shearing samples.

To prepare the genomic DNA samples for shearing, samples were first quantified using a PicoGreen® assay (Invitrogen) on a microplate reader (Spectramax M2, Molecular Devices) Based on the concentration, 120 µl desired input DNA (2 ng/µl) with low TE (10 mM Tris, 0.2 mM EDTA, pH 8.0) was used for the experiment. The 100 µl individual samples were pipetted slowly into the Covaris MicroTUBEs (Covaris Cat. #520045) through the septa in the lid of the tube. The Covaris MicroTUBEs were then placed in the Covaris E-series tube rack. For 200 bp shearing, the settings were as follows: 10% duty cycle, 5 Intensity, 200 cycles/burst, time 180 sec, and Frequency Sweeping mode. After shearing, the Covaris MicroTUBEs were briefly spun down using an appropriate adapter in a mini-centrifuge, and the sheared samples were transferred to clean 1.5 ml microcentrifuge tubes. Each sheared DNA sample was purified using a QIAGEN MinElute® column Briefly, 5x QIAGEN PBI buffer was added to the sample in a 1.5 ml microcentrifuge tube (e.g., 500 µl of PBI buffer was added to 100 µl of sample). Each sample was vortexed, briefly spun down, and transferred to a MinElute spin column MinElute spin column was centrifuged at 13,000 rpm for 1 minute, and the flow-through was discarded. 750 µl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 minutes. For the first elution, 18 µl of QIAGEN Elution Buffer was added to each column, incubated for 2-3 minutes, and then centrifuged at 13,000 rpm for 1 minute. For the second elution, 15 µl of QIAGEN Elution Buffer was added, incubated for 1 min, and then centrifuged at 13,000 rpm for 1 minute. The eluent was collected and the spin column was discarded.

Typically, 200 ng is used for DNA shearing, but the amount of DNA can range from 20 to 200 ng or higher.

Example 2B

Alternative to DNA Shearing

This example describes an alternative method for DNA shearing from Example 2A.

A double stranded genomic DNA is first denatured to single stranded DNA, and then mixed with primers, DNA polymerase (e.g., Exo–DNA polymerase), dNTPs, and a small amount of ddNTPs. The primer sequence can be a random hexamer, or a random hexamer tagged with an adaptor sequence at the 5' end. Methods to use tagged random hexamer amplification to clone and sequence minute quantities of DNA are described, e.g., in Wong K. K. et al., *Nucleic Acids Res.* 1996; 24(19):3778-83. The reaction is incubated under the conditions that allow primer-template annealing and DNA synthesis. The DNA synthesis will terminate when a ddNTP is incorporated into the newly synthesized first strand. The length of the synthesized first strand DNA can be controlled by the ratio of dNTPs to ddNTPs. For example, the molar ratio of dNTPs to ddNTP is at least about 1000:1, about 5000:1, or about 10000:1. After first strand synthesis, short fragments (such as primers and synthesized first strand DNA with short length and ddNTPs can be removed by size selection (e.g., using a size selection spin column) The resulting first strand DNA is mixed with primers (e.g., random hexamers or random hesamers tagged with an adaptor sequence), DNA polymerase (e.g., Exo+DNA polymerase), and dNTPs. An Exo+DNA polymerase can be used to remove the terminal 3'-ddNTP from the first strand DNA or even to generate blunt ends over the second priming site. The reaction is then incubated under the conditions that allow primer-template annealing and DNA synthesis. After synthesis of the second strand, the resulting double stranded DNA fragments can be purified and used directly in library construction. Alternatively, the double stranded DNA fragments can be PCR amplified using primers containing adaptor sequences if these adaptor sequences have been included in the primers for first- and second-strand synthesis. The primers for PCR amplification can also include the entire sequences and/or bar code sequences.

Example 3

Library Preparation

End Repair reaction

End-repair reagents (NEB #E6050L) were thawed and an end-repair mastermix was prepared on ice. To prepare 70 µl of mastermix per sample, 55 µl nuclease free water was mixed with 10 µl 10x End Repair reaction buffer and 5 µl End Repair enzyme mix. Then 70 µl of mastermix was added to 30 µl of each sheared DNA sample in a 96 well PCR plate on ice. The reaction was incubated in a thermocycler at 20° C. for 30 minutes. Each sample was purified using a QIAGEN MinElute® column Briefly, 5x QIAGEN PBI buffer was added to sample (e.g., 500 µl of PBI buffer was added to 100 µl of sample) in a 1.5 ml microcentrifuge tube. Each sample was vortexed, briefly spun down, and transferred to a MinElute spin column MinElute spin column was centrifuged at 13,000 rpm for 1 minute, and the flow-through was discarded. 750 µl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 minutes. For the first elution, 22 µl of QIAGEN Elution Buffer (10 mM Tris, pH8.5) was added to each column, incubated for 2-3 min, and then centrifuged at 13,000 rpm for 1 minute. For the second elution, 22 µl of QIAGEN Elution Buffer was added, incubated for 1 min, and then centrifuged at 13,000 rpm for 1 minute. The eluent was collected and the spin column was discarded.

3' A-base Addition

A-base addition reagents (NEB #E6053L) were thawed on ice and an A-base addition mastermix was prepared on ice. To prepare 10 µl of mastermix per sample, 2 µl nuclease-free water was mixed with 5 µl 10x dA-Tailing reaction buffer and 3 µl Klenow Fragment (3'–>5'exo–). 10 µl of mastermix was added to 40 µl of each purified end-repaired DNA sample in a 96 well PCR plate on ice. The reaction was incubated in a thermocycler at 37° C. for 30 min Each sample was purified using a QIAGEN MinElute® column Briefly, 5x QIAGEN PBI buffer was added to sample (e.g., 250 µl of PBI buffer was added to 50 µl of sample) in a 1.5 ml microcentrifuge tube. Each sample was vortexed, briefly spun down, and transferred to a MinElute spin column MinElute spin column was centrifuged at 13,000 rpm for 1 minute, and the flow-through was discarded. 750 µl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 min. For the first elution, 13 µl of QIAGEN Elution Buffer (10 mM Tris, pH8.5) was added to each column, incubated for 2-3 min, and then centrifuged at 13,000 rpm for 1 minute. For the second elution, 13 µl of QIAGEN Elution Buffer was added, incubated for 1 min, and then centrifuged at 13,000 rpm for 1 minute. The eluent was collected and the spin column was discarded.

Ligation of Multiplex Adaptors

Ligation reagents (NEB #E6056L) were thawed and a ligation mastermix was prepared on ice. To prepare 36 µl of mastermix per sample, 12 µl 5x Quick Ligation reaction buffer was added to 3.3 µl Illumina Multiplex Adaptor (15 uM, included in Illumina Cat. #PE-400-1001) (3.3 µl adaptor/1 µg starting input DNA was used). For example, for one sample of 500 ng input DNA, the adaptors were first diluted in water (2 µl adaptors plus 2 µl H$_2$O), then 3.3 µl of this diluted adaptor mix, 15.7 µl of nuclease free water, and 5 µl of Quick T4 DNA ligase were added to the ligation reaction. For >1 µg starting material, >3.3 µl of adaptors were used. Thus, less water was added to keep the total volume of diluted adaptor mix and nuclease free water at 19 µl.

36 µl of mastermix and 24 µl of each dA-tailed DNA sample were added to the wells of a 96 well PCR plate on ice. The reaction was incubated in a thermocycler at 25° C. for 30 min. Each sample was purified using a QIAGEN MinElute® column Briefly, 5x QIAGEN PBI buffer was added to sample (e.g., 300 µl of PBI buffer was added to 60 µl of sample) in a 1.5 ml microcentrifuge tube. Each sample was vortexed, briefly spun down, and transferred to a MinElute spin column MinElute spin column was centrifuged at 13,000 rpm for 1 minute, and the flow-through was discarded. 750 µl of QIAGEN PE buffer was added to the column, centrifuged at 13,000 rpm for 1 minute, and the flow-through was discarded. The spin column was centrifuged again at 13,000 rpm for 1 minute and transferred to a clean 1.5 ml microcentrifuge tube. The column was air dried for 2-3 minutes. For the first elution, 20 µl of QIAGEN Elution Buffer (10 mM Tris, pH8.5) was added to each column, incubated for 2-3 minutes, and then centrifuged at 13,000 rpm for 1 minute. For the second elution, 20 µl of QIAGEN Elution Buffer was added, incubated for 1 minute, and then centrifuged at 13,000 rpm for 1 minute. The eluent was collected and the spin column was discarded.

PCR Enrichment

PCR reagents were thawed and a PCR mastermix was prepared on ice. For 62 µl of mastermix per sample, 50 µl of 2X Phusion High Fidelity mastermix with HF Buffer (Finnzyme, NEB Cat. # F-531S), 8 µl nuclease-free water, 2 µl Illumina Primer 1.0 (25 µM), and 2 µl Illumina Primer 2.0 (0.5 µM) were used. Then 62 µl of mastermix was mixed with 2 µl Illumina Index Primer (25 µM, included in Illumina Cat. #PE-400-1001) with appropriate bar code and 36 µl of ligated DNA sample in a 96-well PCR plate. The reaction was incubated in a thermocycler as follows:

| | | |
|---|---|---|
| 1 Cycle | 98° C. | 30 sec |
| 18 Cycles | 98° C. | 10 sec |
| | 65° C. | 30 sec |
| | 72° C. | 30 sec |
| 1 Cycle | 72° C. | 5 min |
| | 4° C. | hold |

Each PCR reaction was size selected with 1.8x volume of AMPureXP beads (Agencourt; Beckman Coulter Genomics Cat. # A6388). Briefly, 1.8x AMPureXP beads were added to sample (e.g., 180 µl of beads were added to 100 µl of sample) in a 1.5 ml microcentrifuge tube, vortexed, and incubated for 5 minutes with end-over-end rotation mixing. Tubes were placed on a magnet stand until the solution cleared (2 minutes). The supernatant was discarded without disturbing the beads captured on the magnet. 600 µl of freshly-made 70% ethanol was added to the beards, incubated for 1 min followed by removal of the ethanol. A second aliquot of 600 µl freshly-made 70% ethanol was added to the beads, incubated for 1 minute, and the ethanol was removed. The tubes were put back on the magnet stand for 1-2 minutes to re-capture the beads. Any remaining ethanol was removed and the beads were air dried at room temperature for 5-10 minutes. 30 µl of QIAGEN Elution Buffer was added to the beads, vortexed, and incubated for 2 minutes. Tubes were placed back on the magnet stand until the solution cleared (2 minutes). The supernatant was transferred to a fresh 1.5 mL tube and the beads were discarded. The eluted DNA samples were quantified using a Q-PCR assay. These quantifications will allow for equimolar pooling to ensure equal representation of each library within a pooled hybrid capture selection.

Example 4

Hybrid Selection

Pool Indexed Sample Libraries

Pools (up to 12-plex) of libraries that had been indexed, purified, and quantified by Q-PCR were made on ice. Equimolar pools were prepared in 1.5 ml microcentrifuge tubes to ensure that each sample was represented in the hybrid selection process equally. The total input of DNA for each of these pools can range from 2000 ng to 500 ng. Typically, the total input DNA is 2000 ng. Thus, if twelve samples are pooled, 166.67 ng of each can be pooled to achieve a total of 2000 ng. The final volume of a 2000 ng library pool should be 4 µl. Due to varying concentrations of the indexed libraries a pool can be made with any larger volume but then the pool should be dried down by speedvac (using low heat) and reconstituted in 4 µl of nuclease-free water.

The greater the yield in a library construction, the greater the complexity of the library.

Hybridize the Pooled DNA Libraries to Biotinylated-RNA Baits

Agilent SureSelect Target Enrichment Paired End kit (#G3360A-J) was used in this experiment. Hybridization Buffer #3, SureSelect Block #1, SureSelect Block #2, Paired End Primer 1.0 block, Index Primer 1-12 block, RNAse block, and biotinylated-RNA bait were thawed on ice. The following mastermixes were prepared.

a. Hybridization Buffer Mix (13 µl per reaction):
   i. Hybridization Buffer #1 (Agilent)—25 µl
   ii. Hybridization Buffer #2 (Agilent)—1 µl
   iii. Hybridization Buffer #3 (Agilent)—10 µl
   iv. Hybridization Buffer #4 (Agilent)—13 µl b. Blocking Mix (8 μl per reaction):
   i. SureSelect Block #1 (Agilent)—2.5 μl
   ii. SureSelect Block #2 (Agilent)—2.5 μl
   iii. Paired End primer 1.0 block (IDT, resuspended to 200 uM with H₂O)—1.5 μl
   iv. Index Primer 1-12 block (IDT, resuspended to 200 uM with H₂O)—1.5 μl
c. Dilution of RNase Block
   i. For custom biotinylated RNA-baits with territory <3 Mb: 1 μl of RNase Block (Agilent) was diluted in 9 μl of water.
   ii. For custom baits with a bait territory >3 Mb: 1 μl of RNase block was diluted in 3 μl of water (still 0.5 μl of RNase block per 7 μL capture reaction)
d. Bait Mix: (7 μl per reaction)
   i. RNA Baits—2 μl (for baits which have a bait territory >3 Mb, 5 μl bait was used)
   ii. Diluted RNase Block—5 μl (for baits which have a bait territory >3 Mb, 2 μl RNase block diluted as indicated above was used)

Once the Hybridization Buffer Mix, Blocking Mix, and Bait Mix(es) were prepared, the hybridization buffer mix was vortexed, spun down, and heated to 65° C. in the heat block. 4 μl of each pooled sample library to be hybrid selected was mixed with 8 μl of the blocking mix in a 96 well PCR plate. The reaction was incubated in a thermocycler at 95° C. for 5 minutes and then held at 65° C. When the pooled sample libraries/blocking mix had been incubating at 95° C. for 5 min and then at 65° C. for 2.5 minutes, the bait mix (=bait/RNAse block mix) were put in the heat block at 65° C. for 2.5 minutes. The hybridization buffer containing tubes were quickly spun down, and then immediately returned to 65° C. heat block. 13 μl of the heated hybridization buffer mix was pipetted into each sample library/block mix while the 96 well plate remained in the thermocycler at 65° C. Once the bait mix had been incubated for 2.5 minutes at 65° C., 7 μl of the bait mix was added to each sample library/block/hybridization buffer mix while the 96 well plate remained in the thermocycler at 65° C. The reaction (total volume was 32 nl) was incubated at 65° C. for 24 hours in a thermocycler.

Preparation of the Magnetic Beads

SureSelect Wash Buffer #2 was prewarmed at 65° C. in the heat block. Dynal MyOne Streptavidin T1 beads (Invitrogen) were vortexed and resuspended. The beads were washed by adding 200 μl of SureSelect Binding Buffer per 50 μl Dynal beads (e.g., 1200 μl of SureSelect Binding Buffer was used to prepare 300 μl of Dynal beads). The beads were vortexed for 5 seconds and spun down briefly. The beads were placed on a magnet stand for about 15 seconds or until all the beads were captured. The supernatant was removed and discarded. Wash was repeated with SureSelect Binding Buffer two more times for a total of three washes. After washing, the beads were resuspended in 200 μl of SureSelect Binding Buffer per 50 μl Dynal beads (e.g., 1200 μl of SureSelect Binding Buffer was used to prepare 300 μl of Dynal beads). The resuspended beads were vortexed and spun down briefly. 200 μl of resuspended beads were aliquoted into individual 1.5 ml microcentrifuge tubes.

Selection of the Hybrid Captured DNA

After 24 hours of incubation, each hybridized sample from the PCR plate in the thermocycler at 65° C. was quickly pipetted into a tube containing 200 μl of prepared beads at room temperature. The mixtures of sample and beads were vortexed for 5 seconds and incubated on a rotator at room temperature for 30 minutes, to ensure proper mixing. Then the tubes were quickly spun down. The beads were captured on a magnet (for 2 minutes) and the supernatant was removed and discarded. The beads were resuspended in 500 μl of SureSelect Wash Buffer #1, for a low stringency wash. The samples were vortexed for 5 seconds and incubated for 15 min at room temperature off the magnet. Samples were vortexed for 5 seconds every 3-5 minutes. The tubes were quickly spun down. The beads were then captured on a magnet stand for 2 minutes and the supernatant was removed and discarded. For a high stringency wash to remove off-target material, the beads were washed with SureSelect Wash Buffer #2 preheated to 65° C. Briefly, the beads were resuspended in 500 μl of prewarmed SureSelect Wash Buffer #2 and mixed on a vortexer for 5 seconds to resuspend the beads. The beads were briefly spun down in a centrifuge and incubated at 65° C. for 10 min in a heat block with occasional vortex mixing for 5 seconds at room temperature. Then the beads were briefly spun down in a centrifuge and captured on a magnet for 2 minutes. Wash was repeated 2 more times with prewarmed SureSelect Wash Buffer #2 at 65° C. for a total of three washes. Then the wash buffer was completely removed and 50 μl of SureSelect Elution Buffer was added to the beads following by vortexing for 5 seconds to mix the beads. The samples were incubated for 10 minutes at room temperature with occasional vortex mixing for 5 seconds. The beads were briefly spun down in a centrifuge and captured on a magnet stand. The supernatant containing the captured DNA was pipetted to a new 1.5 ml microcentrifuge tube. 50 μl of SureSelect Neutralization Buffer was added to the captured DNA. Samples were vortex for 5 seconds, briefly spun down in a centrifuge, and purified using 1.8x volume of AMPureXP beads. DNA was eluted in 40 μl nuclease-free water.

PCR Enrichment of the Captured DNA

PCR reagents were thawed and a PCR mastermix was prepared on ice. For 60 μl of mastermix per sample, 50 μl 2X Phusion High Fidelity mastermix with HF buffer (NEB #F-531S) was mixed with 8 μl nuclease-free water, 1 μl QPCR Primer1.1 (100 μM in H₂O), and 1 μl QPCR Primer2.1 (100 μM in H₂O). The primer sequences for Q-PCR are:

```
QPCR Primer1.1 (HPLC-purified from IDT):
                                    (SEQ ID NO: 48)
5'AATGATACGGCGACCACCGAGAT3'

QPCR Primer2.1 (HPLC-purified from IDT):
                                    (SEQ ID NO: 49)
5'CAAGCAGAAGACGGCATACGA3'
```

60 μl of mastermix was added to 40 μl of each purified captured DNA sample in a 96 well PCR plate. The reaction was incubated in a thermocycler as follows:

| | | |
|---|---|---|
| 1 Cycle | 98° C. | 30 sec |
| 12 Cycles | 98° C. | 10 sec |
| | 65° C. | 30 sec |
| | 72° C. | 30 sec |
| 1 Cycle | 72° C. | 5 min |
| | 4° C. | Hold |

Each 100 μl of PCR reaction was purified with 1.8x volume of AMPureXP beads and eluted in 35 μl of elution buffer (10 mM Tris, pH 8.5). The hybrid selected/captured DNA samples were quantified using a Q-PCR assay. The Q-PCR assay detected the end adaptors and the reads indicated how much of each sample should be loaded on a sequencing flow cell to get the appropriate cluster density.

Example 5

Methods

The following exemplifies certain embodiments of the methods and experimental conditions used to identify the alterations according to the Examples. Additional translocation screening can be done using, e.g., either qRT-PCR analysis of cDNA prepared from a pre-selected tumor sample.

Massively parallel DNA sequencing was done on hybridization captured, adaptor ligation-based libraries using DNA isolated from archived fixed paraffin-embedded tissue. A combination of analysis tools were used to analyze the data and assign DNA alteration calls. Additional translocation screening was done using either qRT-PCR analysis of cDNA prepared from frozen tumors or IHC assessment of archived FFPE specimens. Massively parallel cDNA sequencing was performed to confirm expression of both novel translocations using RNA isolated from FFPE tissue. Matched normal reference genomic DNA from blood was sequenced for the index NSCLC patient to confirm the somatic origin of the rearrangement.

Genomic DNA Sequencing

Sequencing of 2574 exons of 145 cancer genes was done using DNA from archived formalin fixed paraffin embedded (FFPE) tumor specimens; 24 from NSCLC patients. Sequencing libraries were constructed by the adapter ligation method using genomic DNA followed by hybridization selection with optimized RNA hybridization capture probes (Agilent SureSelect custom kit). Sequencing on the HiSeq2000 instrument (Illumina) was done using 36×36 paired reads to an average depth of 253X. Data processing and mutation assignments for base substitutions, indels, copy number alterations and genomic rearrangements were done using a combination of tools optimized for mutation calling from tumor tissue.

cDNA Sequencing cDNA was generated from total RNA extracted from a single 5-10 um FFPE tissue section using the Roche High Pure kit and reverse transcribed to cDNA with random hexamer primers by the SuperScript® III First-Strand Synthesis System (Invitrogen). Double stranded cDNA was made with the NEBNext® mRNA Second Strand Synthesis Module (New England Biolabs) and used as input to library construction, hybrid capture and sequencing as for FFPE DNA samples. Analysis of expression levels was done with a combination of analysis tools.

Example 6

Exemplary Selected Genes and Variants for Multiplex Analysis

This example provides four exemplary tables summarizing a selection of genes, variants and cancer types for multiplex analysis.

TABLE 1

List of exemplary selected genes and variants, associated cancer types, and priority codons for multiplex analysis.

| Hugo Gene | Gene Category | Cancer Types | Priority Codons |
|---|---|---|---|
| ABL1 | Priority 1 | Leukemia (e.g., chronic myeloid leukemia (CML), acute myeloid leukemia (AML), acute lymphoblastic leukemia (ALL)) | 315 |
| AKT1 | Priority 1 | breast cancer, colorectal cancer, ovarian cancer | |
| ALK | Priority 1 | Lymphoma (e.g., non-Hodgkin lymphoma, anaplastic large-cell lymphoma (ALCL)), inflammatory myofibroblastic tumor | |
| APC | Priority 1 | Colorectal cancer, medulloblastoma, mismatch repair cancer syndrome | 1114, 1338, 1450, 1556 |
| AR | Priority 1 | Prostate cancer | |
| BRAF | Priority 1 | Lung cancer, non-Hodgkin lymphoma, colorectal cancer, thyroid cancer, melanoma | 600 |
| CDKN2A | Priority 1 | melanoma, pancreatic cancer, Li-Fraumeni syndrome, lung cancer (e.g., non-small cell lung cancer (NSCLC)), squamous cell carcinoma, retinoblastoma, astrocytoma | |
| CEBPA | Priority 1 | Leukemia (e.g., acute myeloid leukemia (AML), acute myeloid leukemia (AML), monoblastic leukemia), retinoblastoma | |
| CTNNB1 | Priority 1 | Colorectal cancer, ovarian cancer, prostate cancer, liver cancer (e.g., hepatoblastoma (HB), hepatocellular carcinoma (HCC)), pilomatrixoma, medulloblastoma, salivary gland pleiomorphic adenomas | 32, 33, 34, 37, 41, 45 |
| EGFR | Priority 1 | Lung cancer, squamous cell carcinoma, glioblastoma, glioma, colorectal cancer | 719, 746-750, 768, 790, 858, 861 |
| ERBB2 | Priority 1 | Gastric cancer, glioma, ovarian cancer, lung cancer | |
| ESR1 | Priority 1 | Breast cancer, endometrial cancer, endometrial adenocarcinoma, | |

TABLE 1-continued

List of exemplary selected genes and variants, associated cancer types, and priority codons for multiplex analysis.

| Hugo Gene | Gene Category | Cancer Types | Priority Codons |
|---|---|---|---|
| | | leiomyoma, mammary ductal carcinoma | |
| FGFR1 | Priority 1 | Leukemia, lymphoma | |
| FGFR2 | Priority 1 | Breast cancer, prostate cancer | |
| FGFR3 | Priority 1 | Bladder cancer, cervical cancer, multiple myeloma, | |
| FLT3 | Priority 1 | Leukemia (e.g., acute myeloid leukemia (AML), acute promyelocytic leukemia, acute lymphoblastic leukemia) | 835 |
| HRAS | Priority 1 | Hurthle cell thyroid carcinoma, bladder cancer, melanoma, colorectal cancer | 12, 13, 61 |
| JAK2 | Priority 1 | Leukemia (e.g., chronic lymphoblastic leukemia (CLL), acute lymphoblastic leukemia (ALL), chronic myelogenous leukemia (CML), acute myelogenous leukemia (AML)) | 617 |
| KIT | Priority 1 | Gastrointestinal stromal tumor (GIST), testicular tumor, leukemia (e.g., acute myeloid leukemia (AML)), mast cell tumor, mesenchymal tumor, adenoid cystic carcinoma, lung cancer (e.g., small cell lung cancer), lymphoma (e.g., Burkitt lymphoma) | 816 |
| KRAS | Priority 1 | Leukemia (e.g., acute myelogenous leukemia (AML), juvenile myelomonocytic leukemia (JMML)), colorectal cancer, lung cancer | 12, 13, 61 |
| MET | Priority 1 | Gastric cancer, hepatocellular carcinoma (HCC), hereditary papillary renal carcinoma (HPRC), lung cancer (e.g., non-small cell lung cancer), papillary thyroid carcinoma, glioma, esophageal adenocarcinoma, osteosarcoma, endometrial cancer, squamous cell carcinoma, melanoma, breast cancer | |
| MLL | Priority 1 | Leukemia (e.g., acute lymphoblastic leukemia (ALL), acute myeloid leukemia (AML) | |
| MYC | Priority 1 | chronic lymphocytic leukemia (CLL), Burkitt lymphoma, plasmacytoma, | |
| NF1 | Priority 1 | Leukemia (e.g., juvenile myelomonocytic leukemia (JMML)), neurofibroma, | |
| NOTCH1 | Priority 1 | Squamous cell carcinoma, leukemia (e.g., acute lymphoblastic leukemia (ALL)), medullary thyroid carcinoma, lymphoma (e.g., thymic lymphoma, T-cell lymphoma) | 1575, 1601 |
| NPM1 | Priority 1 | Lymphoma (e.g., non-Hodgkin lymphoma, anaplastic large cell lymphoma, anaplastic lymphoma), leukemia (e.g., acute promyelocytic leukemia, acute myelogenous leukemia (AML)) | |
| NRAS | Priority 1 | Leukemia (e.g., juvenile myelomonocytic leukemia (JMML), acute myeloid leukemia (AML), acute lymphoblastic leukemia), melanoma, | 12, 13, 61 |
| PDGFRA | Priority 1 | Gastrointestinal stromal tumor (GIST), leukemia (e.g., chronic eosinophilic leukemia (CEL), acute lymphocytic leukemia (ALL)), mesenchymal tumor | |
| PIK3CA | Priority 1 | Colorectal cancer, breast cancer, ovarian cancer, hepatocellular carcinoma, head and neck squamous cell carcinoma (HNSCC), anaplastic | 88, 542, 545, 546, 1047, 1049 |

TABLE 1-continued

List of exemplary selected genes and variants, associated
cancer types, and priority codons for multiplex analysis.

| Hugo Gene | Gene Category | Cancer Types | Priority Codons |
|---|---|---|---|
| | | thyroid carcinoma, endometrial cancer, gallbladder adenocarcinoma, glioblastoma | |
| PTEN | Priority 1 | Head and neck squamous cell carcinomas (HNSCC), endometrial cancer, glioma, prostate cancer, glioblastoma | 130, 173, 233, 267 |
| RB1 | Priority 1 | Retinoblastoma, bladder cancer, osteosarcoma, lung cancer (e.g., small cell lung cancer, non-small cell lung cancer), leukemia (e.g., acute lymphoblastic leukemia (ALL)) | |
| RET | Priority 1 | Colorectal cancer, medullary thyroid carcinoma, multiple neoplasia type 2B, pheochromocytoma, multiple neoplasia type 2A, thyroid papillary carcinoma, thryoid cancer, retinoblastoma | 918 |
| TP53 | Priority 1 | TP53 is frequently mutated or inactivated in about 60% of cancers, e.g., esophageal squamous cell carcinoma, Li-Fraumeni syndrome, head and neck squamous cell carcinomas (HNSCC), lung cancer, hereditary adrenocortical carcinoma, astrocytoma, squamous cell carcinoma, bladder cancer, colorectal cancer, glioblastoma, retinoblastoma | 175, 245, 248, 273, 306 |
| ABL2 | Cancer Gene | Acute myeloid leukemia (AML) | |
| AKT2 | Cancer Gene | Ovarian cancer, pancreatic cancer | |
| AKT3 | Cancer Gene | Melanoma, glioma, uternine cancer, prostate cancer, oral cancer, ovarian cancer | |
| ARAF | Cancer Gene | Angioimmunoblastic T-cell lymphoma, ehrlich ascites tumor | |
| ARFRP1 | Cancer Gene | Breast cancer | |
| ARID1A | Cancer Gene | Neuroblastoma, acute lymphoblastic leukemia (ALL), neuroendocrine tumor | |
| ATM | Cancer Gene | Leukemia (e.g., T-cell prolymphocytic leukemia (T-PLL)), lymphoma, medulloblastoma, glioma | |
| ATR | Cancer Gene | Pyothorax-associated lymphoma, T-cell lymphoma | |
| AURKA | Cancer Gene | Laryngeal squamous cell carcinoma, ovarian cancer, bladder cancer, head and neck squamous cell carcinoma (HNSCC), laryngeal carcinoma, esophageal squamous cell carcinoma (ESCC), pancreatic cancer | |
| AURKB | Cancer Gene | Colorectal cancer, astrocytoma, ependymal tumor, glioma, esophageal squamous cell carcinoma (ESCC), acute myeloid leukemia (AML) | |
| BCL2 | Cancer Gene | Lymphoma, colorectal adenocarcinoma, esophageal squamous cell carcinoma (ESCC), synovial sarcoma, leukemia | |
| BCL2A1 | Cancer Gene | Pulmonary granuloma, gastric adenoma, burkitt lymphoma, parotid adenoma, kaposi sarcoma, gastric cancer, colon cancer | |
| BCL2L1 | Cancer Gene | Head and neck squamous cell carcinoma, glioblastoma, mesothelioma, pancreatic cancer, adenocarcinoma lung | |
| BCL2L2 | Cancer Gene | Brain cancer, leukemia, lymphoma, colorectal adenocarcinoma, colorectal cancer, adenoma, cervical squamous cell carcinoma | |
| BCL6 | Cancer Gene | Lymphoma, leukemia | |
| BRCA1 | Cancer Gene | Breast cancer, ovarian cancer | |

TABLE 1-continued

List of exemplary selected genes and variants, associated cancer types, and priority codons for multiplex analysis.

| Hugo Gene | Gene Category | Cancer Types | Priority Codons |
|---|---|---|---|
| BRCA2 | Cancer Gene | Breast cancer, ovarian cancer, pancreatic cancer | |
| CARD11 | Cancer Gene | Lymphoma | |
| CBL | Cancer Gene | Lymphoma, leukemia | |
| CCND1 | Cancer Gene | Chronic lymphoblastic leukemia (CLL), B-cell acute lymphoblastic leukemia (B-ALL), breast cancer | |
| CCND2 | Cancer Gene | Retinoblastoma, mantle cell lymphoma, T-cell acute lymphoblastic leukemia (T-ALL), Burkitt lymphoma, testicular germ cell tumor, ovarian granulosa cell tumor, multiple myeloma | |
| CCND3 | Cancer Gene | Retinoblastoma, mantle cell lymphoma, anaplastic large cell lymphoma, lymphoma (non-hodgkins), B-cell lymphoma, laryngeal squamous cell carcinoma, indolent lymphoma, null cell adenoma | |
| CCNE1 | Cancer Gene | Breast cancer, ovarian cancer, bladder cancer, retinoblastoma | |
| CDH1 | Cancer Gene | Gastric cancer, lobular carcinoma, squamous cell carcinoma, invasive ductal carcinoma, invasive lobular carcinoma | |
| CDH2 | Cancer Gene | Melanoma, malignant mesothelioma, pleural mesothelioma, desmoplastic melanoma, lung adenocarcinoma, endometrioid tumor, mesothelioma, bladder cancer, esophageal squamous cell carcinoma (ESCC) | |
| CDH20 | Cancer Gene | Breast cancer | |
| CDH5 | Cancer Gene | Granuloma, epithelioid sarcoma | |
| CDK4 | Cancer Gene | Melanoma | |
| CDK6 | Cancer Gene | Acute lymphoblastic leukemia (ALL) | |
| CDK8 | Cancer Gene | Colon cancer, lung cancer, rectal cancer, acute lymphoblastic leukemia (ALL) | |
| CDKN2B | Cancer Gene | Leukemia, retinoblastoma, laryngeal squamous cell carcinoma | |
| CDKN2C | Cancer Gene | Thyroid carcinoma, pituitary adenoma, oligodendroglioma, pancreatic endocrine tumor, multiple myeloma, hepatoblastoma, lymphoid tumor, multiple endocrine neoplasia type 1, anaplastic oligodendroglioma | |
| CHEK1 | Cancer Gene | Leukemia, colon cancer | |
| CHEK2 | Cancer Gene | Breast cancer | |
| CRKL | Cancer Gene | Leukemia, lymphoma | |
| CRLF2 | Cancer Gene | Leukemia | |
| DNMT3A | Cancer Gene | Testicular germ cell tumor, lymphosarcoma, hepatocellular carcinoma, salivary gland tumor | |
| DOT1L | Cancer Gene | Leukemia | |
| EPHA3 | Cancer Gene | Rhabdomyosarcoma, lymphoma, prostate cancer, hepatocellular carcinoma, leukemia, melanoma | |
| EPHA5 | Cancer Gene | Glioblastoma, breast cancer, astrocytoma, Wilms' tumor, glioma | |
| EPHA6 | Cancer Gene | Breast cancer | |
| EPHA7 | Cancer Gene | Glioblastoma multiforme (GBM), colon cancer, duodenal cancer, parathyroid tumor, prostate cancer | |
| EPHB1 | Cancer Gene | Colorectal cancer, embryonal carcinoma, gastric cancer, teratocarcinoma, mucinous carcinoma | |
| EPHB4 | Cancer Gene | Head and neck squamous cell carcinoma (HNSCC), brain cancer, endometrial cancer, ovarian cancer | |
| EPHB6 | Cancer Gene | Neuroblastoma, melanoma, non-small cell lung cancer (NSCLL) | |

TABLE 1-continued

List of exemplary selected genes and variants, associated
cancer types, and priority codons for multiplex analysis.

| Hugo Gene | Gene Category | Cancer Types | Priority Codons |
|---|---|---|---|
| ERBB3 | Cancer Gene | Breast cancer, non-small cell lung cancer (NSCLC), pancreatic cancer, invasive ductal carcinoma, lung adenocarcinoma, endometrioid carcinoma, pilocytic astrocytoma | |
| ERBB4 | Cancer Gene | Breast cancer, medulloblastoma, cervical squamous cell carcinoma, prostate cancer, leukemia | |
| ERG | Cancer Gene | Prostate cancer, Ewing's sarcoma, leukemia, prostate cancer | |
| ETV1 | Cancer Gene | Prostate cancer, breast cancer, Ewing's sarcoma, desmoplastic small round cell tumor, myxoid liposarcoma, clear cell sarcoma | |
| ETV4 | Cancer Gene | Breast cancer, ovarian cancer, squamous cell carcinoma tongue, Ewing's sarcoma | |
| ETV5 | Cancer Gene | Ganglioglioma, brain tumor | |
| ETV6 | Cancer Gene | Leukemia, congenital fibrosarcoma, secretory carcinoma, myelodysplastic syndrome | |
| EWSR1 | Cancer Gene | Ewing's sarcoma, clear cell sarcoma, desmoplastic small round cell tumor, extraskeletal myxoid chondrosarcoma, myxoid liposarcoma, angiomatoid fibrous histiocytoma | |
| EZH2 | Cancer Gene | Prostate cancer, gallbladder adenocarcinoma, breast cancer, bladder cancer, gastric cancer, Ewing's sarcoma | |
| FANCA | Cancer Gene | Leukemia | |
| FBXW7 | Cancer Gene | Colorectal cancer, endometrial cancer, T-cell acute lymphoblastic leukemia (T-ALL) | |
| FGFR4 | Cancer Gene | Pituitary tumor, prostate cancer, lung cancer, astrocytoma, rhabdomyosarcoma, pituitary adenoma, fibroadenoma | |
| FLT1 | Cancer Gene | Breast cancer, prostate cancer | |
| FLT4 | Cancer Gene | Lung cancer, Kaposi's sarcoma, gastric cancer, lymphangioma, squamous cell carcinoma | |
| FOXP4 | Cancer Gene | Lymphoma, brain tumor | |
| GATA1 | Cancer Gene | Megakaryoblastic leukemia of Downs Syndrome | |
| GNA11 | Cancer Gene | Breast cancer | |
| GNAQ | Cancer Gene | Uveal melanoma | |
| GNAS | Cancer Gene | Pituitary adenoma | |
| GPR124 | Cancer Gene | Colon cancer | |
| GUCY1A2 | Cancer Gene | Breast cancer | |
| HOXA3 | Cancer Gene | Breast cancer | |
| HSP90AA1 | Cancer Gene | Lymphoma, myeloma | |
| IDH1 | Cancer Gene | Glioblastoma multiforme (GBM) | |
| IDH2 | Cancer Gene | Glioblastoma multiforme (GBM) | |
| IGF1R | Cancer Gene | Ewing's sarcoma, breast cancer, uveal melanoma, adrenocortical carcinoma, pancreatic cancer | |
| IGF2R | Cancer Gene | Gastrointestinal tumor, liver cancer | |
| IKBKE | Cancer Gene | Breast cancer | |
| IKZF1 | Cancer Gene | Lymphoma, leukemia | |
| INHBA | Cancer Gene | Erythroleukemia, barrett metaplasia, esophageal adenocarcinoma, granulosa cell tumor, sex cord-stromal tumor, lung adenocarcinoma, pheochromocytoma, krukenberg tumor, ovarian cancer | |
| IRS2 | Cancer Gene | Hyperinsulinemia, uterine leiomyosarcoma | |
| JAK1 | Cancer Gene | Leukemia, ovarian cancer, breast cancer | |
| JAK3 | Cancer Gene | Acute lymphoblastic leukemia (ALL) | |
| JUN | Cancer Gene | Skin cancer, leukemia | |

TABLE 1-continued

List of exemplary selected genes and variants, associated cancer types, and priority codons for multiplex analysis.

| Hugo Gene | Gene Category | Cancer Types | Priority Codons |
|---|---|---|---|
| KDR | Cancer Gene | Non-small cell lung cancer (NSCLC), angiosarcoma | |
| LRP1B | Cancer Gene | Lung cancer, gastric cancer, esophageal cancer | |
| LTK | Cancer Gene | Lymphoma, breast cancer | |
| MAP2K1 | Cancer Gene | Prostate cancer, gastric cancer | |
| MAP2K2 | Cancer Gene | Pancreatic cancer, intestinal tumor | |
| MAP2K4 | Cancer Gene | Pancreatic cancer, breast cancer, colorectal cancer | |
| MCL1 | Cancer Gene | Multiple myeloma, leukemia, lymphoma | |
| MDM2 | Cancer Gene | Sarcoma, glioma, colorectal cancer | |
| MDM4 | Cancer Gene | Glioblastoma multiforme (GBM), bladder cancer, retinoblastoma | |
| MEN1 | Cancer Gene | Parathyroid tumor | |
| MITF | Cancer Gene | Melanoma | |
| MLH1 | Cancer Gene | Colorectal cancer, endometrial cancer, ovarian cancer, CNS cancer | |
| MPL | Cancer Gene | Myeloproliferative disorder (MPD) | |
| MRE11A | Cancer Gene | Breast cancer, lymphoma | |
| MSH2 | Cancer Gene | Colorectal cancer, endometrial cancer, ovarian cancer | |
| MSH6 | Cancer Gene | Colorectal cancer | |
| MTOR | Cancer Gene | Lymphoma lung cancer, renal cancer, clear cell carcinoma, glioma | |
| MUTYH | Cancer Gene | Colorectal cancer | |
| MYCL1 | Cancer Gene | Small cell lung cancer (SCLC) | |
| MYCN | Cancer Gene | Neuroblastoma | |
| NF2 | Cancer Gene | Meningioma, acoustic neuroma, renal cancer | |
| NKX2-1 | Cancer Gene | Lung cancer, thyroid cancer, adenocarcinoma | |
| NTRK1 | Cancer Gene | Papillary thyroid cancer | |
| NTRK3 | Cancer Gene | Congenital fibrosarcoma, secretory breast cancer | |
| PAK3 | Cancer Gene | Lung cancer | |
| PAX5 | Cancer Gene | Non-Hodgkin Lymphoma (NHL), acute lymphoblastic leukemia (ALL, e.g., B-cell ALL) | |
| PDGFRB | Cancer Gene | Myeloproliferative disorder (MPD), acute myeloid leukemia (AML), chronic myeloid leukemia (CML), chronic myelomonocytic leukemia (CMML) | |
| PIK3R1 | Cancer Gene | Glioblastoma, ovarian cancer, colorectal cancer | |
| PKHD1 | Cancer Gene | Pancreatic cancer | |
| PLCG1 | Cancer Gene | Head and neck cancer, leukemia | |
| PRKDC | Cancer Gene | Glioma, glioblastoma, gastric cancer, ovarian cancer | |
| PTCH1 | Cancer Gene | Skin basal cell, medulloblastoma | |
| PTPN11 | Cancer Gene | Juvenile myelomonocytic leukemia (JMML), acute myeloid leukemia (AML), myelodysplastic syndromes (MDS) | |
| PTPRD | Cancer Gene | Lung cancer, cutaneous squamous cell carcinoma, glioblastoma, neuroblastoma | |
| RAF1 | Cancer Gene | Pilocytic astrocytoma | |
| RARA | Cancer Gene | Leukemia | |
| RICTOR | Cancer Gene | Colon cancer, lymphoma, glioma, breast cancer | |
| RPTOR | Cancer Gene | Breast cancer, prostate cancer | |
| RUNX1 | Cancer Gene | Acute myeloid leukemia (AML), pre-B-cell acute lymphoblastic leukemia (preB-ALL), T-cell acute lymphoblastic leukemia (T-ALL) | |
| SMAD2 | Cancer Gene | esophageal squamous cell carcinoma (ESCC) | |
| SMAD3 | Cancer Gene | Skin cancer, choriocarcinoma | |
| SMAD4 | Cancer Gene | Pancreatic cancer, colon cancer | |
| SMARCA4 | Cancer Gene | Non-small cell lung cancer (NSCLC) | |
| SMARCB1 | Cancer Gene | Malignant rhabdoid | |

TABLE 1-continued

List of exemplary selected genes and variants, associated cancer types, and priority codons for multiplex analysis.

| Hugo Gene | Gene Category | Cancer Types | Priority Codons |
|---|---|---|---|
| SMO | Cancer Gene | Skin basal cell cancer | |
| SOX 10 | Cancer Gene | Oligodendroglioma | |
| SOX2 | Cancer Gene | Embryonal carcinoma, germ cell tumor | |
| SRC | Cancer Gene | Sarcoma, colon cancer, breast cancer | |
| STK11 | Cancer Gene | Non-small cell lung cancer (NSCLC), pancreatic cancer | |
| TBX22 | Cancer Gene | Breast cancer | |
| TET2 | Cancer Gene | Myelodysplastic syndromes (MDS) | |
| TGFBR2 | Cancer Gene | Lung cancer, gastric cancer, colon cancer | |
| TMPRSS2 | Cancer Gene | Prostate cancer | |
| TOP1 | Cancer Gene | Acute myeloid leukemia (AML) | |
| TSC1 | Cancer Gene | Hamartoma, renal cell cancer | |
| TSC2 | Cancer Gene | Hamartoma, renal cell cancer | |
| USP9X | Cancer Gene | Leukemia | |
| VHL | Cancer Gene | Renal cancer, hemangioma, pheochromocytoma | |
| WT1 | Cancer Gene | Wilms' tumor, desmoplastic small round cell tumor | |
| ABCB1 | PGx Gene | | |
| ABCC2 | PGx Gene | | |
| ABCC4 | PGx Gene | | |
| ABCG2 | PGx Gene | | |
| C1orf144 | PGx Gene | | |
| CYP1B1 | PGx Gene | | |
| CYP2C19 | PGx Gene | | |
| CYP2C8 | PGx Gene | | |
| CYP2D6 | PGx Gene | | |
| CYP3A4 | PGx Gene | | |
| CYP3A5 | PGx Gene | | |
| DPYD | PGx Gene | | |
| ERCC2 | PGx Gene | | |
| ESR2 | PGx Gene | | |
| FCGR3A | PGx Gene | | |
| GSTP1 | PGx Gene | | |
| ITPA | PGx Gene | | |
| LRP2 | PGx Gene | | |
| MAN1B1 | PGx Gene | | |
| MTHFR | PGx Gene | | |
| NQO1 | PGx Gene | | |
| NRP2 | PGx Gene | | |
| SLC19A1 | PGx Gene | | |
| SLC22A2 | PGx Gene | | |
| SLCO1B3 | PGx Gene | | |
| SOD2 | PGx Gene | | |
| SULT1A1 | PGx Gene | | |
| TPMT | PGx Gene | | |
| TYMS | PGx Gene | | |
| UGT1A1 | PGx Gene | | |
| UMPS | PGx Gene | | |

"Priority 1" refers to the highest priority of selected genes or gene products.
"Cancer Genes" refer to cancer-associated genes or gene products of less priority relative to Priority 1.
"PGx Genes" refers to genes that are important for pharmacogenetics and pharmacogenomics (PGx).

TABLE 1A

Additional exemplary selected genes and variants, associated cancer types, priority codons, actionability category, and potential therapies.

| Hugo Gene | Gene Category | Cancer Types | Priority Codons | Actionability Category | Reason |
|---|---|---|---|---|---|
| ASXL1 | Priority 1 | Mutiple myeloma (MM) | | D | Prognostic (neg MDS) |
| BACH1 | Priority 1 | Breast | | C | PARP Inhibitors |
| BAP1 | Priority 1 | Uveal melanoma, breast, NSCLC | | C | PARP Inhibitors |
| BARD1 | Priority 1 | Breast | | C | PARP Inhibitors |
| BLM | Priority 1 | Leukemia, lymphoma, skin squamous cell, other cancers | | C | |

TABLE 1A-continued

Additional exemplary selected genes and variants, associated cancer types, priority codons, actionability category, and potential therapies.

| Hugo Gene | Gene Category | Cancer Types | Priority Codons | Actionability Category | Reason |
|---|---|---|---|---|---|
| BRIP1 | Priority 1 | Acute myeloid leukemia (AML), leukemia, breast | | C | PARP Inhibitors |
| CDKN1B | Priority 1 | Breast | | D | |
| CREBBP | Priority 1 | Acute lymphoblastic leukemia (ALL), AML, DLBCL, B-cell non-Hodgkin's lymphoma (B-NHL) | | D | |
| DDR2 | Priority 1 | NSCLC | | C | Dasatinib |
| EMSY | Priority 1 | Breast | | C | PARP Inhibitors |
| FANCC | Priority 1 | AML, leukemia | | C | PARP inhibitor |
| FANCD2 | Priority 1 | AML, leukemia | | C | PARP inhibitor |
| FANCE | Priority 1 | AML, leukemia | | C | PARP inhibitor |
| FANCF | Priority 1 | AML, leukemia | | C | PARP inhibitor |
| FANCG | Priority 1 | AML, leukemia | | C | PARP inhibitor |
| FANCL | Priority 1 | AML, leukemia | | C | PARP inhibitor |
| HGF | Priority 1 | MM | | C | Resistance |
| NFKB1 | Priority 1 | Breast | | D | Possible POOR PROGNOSIS |
| NOTCH2 | Priority 1 | Marginal zone lymphoma, DLBCL | | D | — |
| PALB2 | Priority 1 | Wilms tumor, medulloblastoma, AML, breast | | C | PARP Inhibitors |
| PBRM1 | Priority 1 | Clear cell renal carcinoma, breast | | E | HDAC inhibitors? |
| PDK1 | Priority 1 | NSCLC | | C | PDK1 inhibitors |
| PIK3R2 | Priority 1 | NSCLC | | C | P13K-PATHWAY INHIBITORS |
| RAD50 | Priority 1 | Breast | | C | PARP Inhibitors |
| RAD51 | Priority 1 | Breast | | C | PARP Inhibitors |
| ROS1 | Priority 1 | Glioblastoma, NSCLC | | C | |
| SF3B1 | Priority 1 | MDS, CML, ALL, pancreatic, breast | | E | |
| SPOP | Priority 1 | Malignant melanoma | | E | |
| ACVR1B | Cancer Gene | Pancreas, breast | | E | |
| ALOX12B | Cancer Gene | Mutiple myeloma (MM) | | E | |
| ATRX | Cancer Gene | Pancreatic neuroendocrine tumors | | E | |
| AXL | Cancer Gene | Non small cell lung cancer (NSCLC), MM | | E | |
| BCOR | Cancer Gene | Breast | | E | |
| BCORL1 | Cancer Gene | Breast | | E | |
| C17orf39 | Cancer Gene | Breast | | E | |
| CASP8 | Cancer Gene | Breast | | E | |
| CBFB | Cancer Gene | AML | | E | |
| CD22 | Cancer Gene | NSCLC, breast | | E | |
| CD79A | Cancer Gene | Diffuse large B-cell lymphoma (DLBCL) | | E | |
| CD79B | Cancer Gene | DLBCL | | E | |
| CDC73 | Cancer Gene | Parathyroid | | E | |
| CDK12 | Cancer Gene | Ovarian | | E | |
| CHUK | Cancer Gene | Colorectal | | E | |
| CRBN | Cancer Gene | Upper aerodigestive tract | | E | |
| CSF1R | Cancer Gene | NSCLC | | E | |
| CTCF | Cancer Gene | Breast | | E | |
| CTNNA1 | Cancer Gene | Breast | | E | |
| CUL4A | Cancer Gene | Leukemia | | E | |
| CUL4B | Cancer Gene | Leukemia | | E | |
| CYP17A1 | Cancer Gene | Breast | | E | |
| DAXX | Cancer Gene | Pancreatic neuroendocrine tumors | | E | |
| DIS3 | Cancer Gene | MM | | E | |
| EP300 | Cancer Gene | Colorectal, breast, pancreatic, AML, ALL, DLBCL | | E | |
| ERCC2 | Cancer Gene | Skin basal cell, skin squamous cell, melanoma | | E | |
| FAM46C | Cancer Gene | MM | | E | |
| FGF1 | Cancer Gene | Breast | | E | |
| FGF10 | Cancer Gene | Breast | | E | |
| FGF12 | Cancer Gene | Breast | | E | |
| FGF14 | Cancer Gene | Breast | | E | |
| FGF19 | Cancer Gene | Breast | | E | |
| FGF23 | Cancer Gene | Breast | | E | |
| FGF3 | Cancer Gene | Breast | | E | |
| FGF4 | Cancer Gene | Breast | | E | |
| FGF6 | Cancer Gene | Breast | | E | |
| FGF7 | Cancer Gene | Breast | | E | |
| FOXL2 | Cancer Gene | Granulosa-cell tumour of the ovary | 134 | E | |
| GATA2 | Cancer Gene | AML, Chronic Myeloid Leukemia (CML, blast transformation) | | E | |
| GATA3 | Cancer Gene | Breast | | E | |
| GRAF | Cancer Gene | AML, myelodysplastic syndrome (MDS) | | E | |

TABLE 1A-continued

Additional exemplary selected genes and variants, associated cancer types, priority codons, actionability category, and potential therapies.

| Hugo Gene | Gene Category | Cancer Types | Priority Codons | Actionability Category | Reason |
|---|---|---|---|---|---|
| GRIN2A | Cancer Gene | Malignant melanoma | | E | |
| GSK3B | Cancer Gene | NSCLC | | E | |
| HLA-A | Cancer Gene | MM | | E | |
| IGF1 | Cancer Gene | Breast | | E | |
| IGF2 | Cancer Gene | Breast | | E | |
| IL7R | Cancer Gene | T-cell acute lymphoblastic leukemia (T-ALL) | | E | |
| INSR | Cancer Gene | NSCLC, glioblastoma, gastric | | E | |
| IRF4 | Cancer Gene | Multiple myeloma (MM) | | E | |
| KDM4C | Cancer Gene | Ovarian, breast | | E | |
| KDM5A | Cancer Gene | AML | | E | |
| KDM6A | Cancer Gene | Renal, oesophageal squamous cell carcinoma (SCC), MM | | E | |
| KEAP1 | Cancer Gene | NSCLC | | E | |
| KLHL6 | Cancer Gene | Chronic lymphocytic leukaemia (CLL) | | E | |
| LMO1 | Cancer Gene | T-cell acute lymphoblastic leukemia (T-ALL), neuroblastoma | | E | |
| LRP6 | Cancer Gene | NSCLC, malignant melanoma | | E | |
| LRRK2 | Cancer Gene | Ovarian, NSCLC | | E | |
| MAGED1 | Cancer Gene | MM | | E | |
| MAP3K1 | Cancer Gene | Breast | | E | |
| MAP3K13 | Cancer Gene | Breast | | E | |
| MLL2 | Cancer Gene | Medulloblastoma, renal | | E | |
| MLST8 | Cancer Gene | Breast | | E | |
| MYD88 | Cancer Gene | Activated B cell-like-DLBCL (ABC-DLBCL) | | E | |
| MYST3 | Cancer Gene | Breast | | E | |
| NCOR1 | Cancer Gene | Breast | | E | |
| NFE2L2 | Cancer Gene | NSCLC, head and neck squamous cell carcinoma (HNSCC) | | E | |
| NFKBIA | Cancer Gene | Breast | | E | |
| NOTCH3 | Cancer Gene | NSCLC, breast | | E | |
| NOTCH4 | Cancer Gene | NSCLC, breast | | E | |
| NSD1 | Cancer Gene | AML | | E | |
| NTRK2 | Cancer Gene | Renal, NSCLC | | E | |
| NUP93 | Cancer Gene | Breast | | E | |
| PAK7 | Cancer Gene | NSCLC, malignant melanoma | | E | |
| PHLPP2 | Cancer Gene | Ovarian, glioblastoma, NSCLC | | E | |
| PHOX2B | Cancer Gene | Neuroblastoma | | E | |
| PIK3C2G | Cancer Gene | NSCLC | | E | |
| PIK3C3 | Cancer Gene | NSCLC | | E | |
| PIK3CG | Cancer Gene | NSCLC | | E | |
| PNRC1 | Cancer Gene | MM | | E | |
| PRDM1 | Cancer Gene | DLBCL | | E | |
| PRKAR1A | Cancer Gene | Adrenal gland, thyroid | | E | |
| PRSS8 | Cancer Gene | Breast | | E | |
| PTCH2 | Cancer Gene | Malignant melanoma | | E | |
| PTK2 | Cancer Gene | NSCLC, glioblastoma | | E | |
| PTK2B | Cancer Gene | NSCLC, breast | | E | |
| REL | Cancer Gene | Hodgkin Lymphoma | | E | |
| RHEB | Cancer Gene | NSCLC, colorectal | | E | |
| ROCK1 | Cancer Gene | Breast | | E | |
| RUNXT1 | Cancer Gene | NSCLC, colorectal | | E | |
| SETD2 | Cancer Gene | Clear cell renal carcinoma | | E | |
| SH2B3 | Cancer Gene | Myelodysplastic syndrome (MDS) | | E | |
| SOCS1 | Cancer Gene | DLBCL | | E | |
| SPEN | Cancer Gene | Adenoid cystic carcinoma | | E | |
| STAG2 | Cancer Gene | Glioblastoma | | E | |
| STAT3 | Cancer Gene | Breast | | E | |
| STAT4 | Cancer Gene | Breast | | E | |
| STK12 | Cancer Gene | PNET, NSCLC | | E | |
| SUFU | Cancer Gene | Medulloblastoma | | E | |
| TBX23 | Cancer Gene | Breast | | E | |
| TBX3 | Cancer Gene | Breast | | E | |
| TNFAIP3 | Cancer Gene | Marginal zone B-cell lymphomas, Hodgkin's lymphoma, primary mediastinal B cell lymphoma | | E | |
| TNFRSF14 | Cancer Gene | Follicular lymphoma | | E | |
| TNFRSF17 | Cancer Gene | Intestinal T-cell lymphoma | | E | |
| TNKS | Cancer Gene | NSCLC | | E | |
| TNKS2 | Cancer Gene | Melanoma, breast | | E | |
| TRRAP | Cancer Gene | Colorectal, glioblastoma | | E | |
| TYK2 | Cancer Gene | NSCLC, breast | | E | |
| XBP1 | Cancer Gene | MM | | E | |
| XPO1 | Cancer Gene | Chronic lymphocytic leukaemia (CLL) | | E | |

TABLE 1A-continued

Additional exemplary selected genes and variants, associated cancer types, priority codons, actionability category, and potential therapies.

| Hugo Gene | Gene Category | Cancer Types | Priority Codons | Actionability Category | Reason |
|---|---|---|---|---|---|
| ZNF217 | Cancer Gene | Breast | | E | |
| ZNF703 | Cancer Gene | Breast | | E | |

The actionability categories are classified as described below. Table 1B provides a summary of the application of the different categories to exemplary alterations in different cancer types.

Category A: Approved/standard alterations that predict sensitivity or resistance to approved/standard therapies
  KRAS G13D in metastatic colon cancer
  ERBB2 amplification in breast cancer
  EGFR L858R in non small cell lung cancer Category B: Alterations that are inclusion or exclusion criteria for specific experimental therapies
  KRAS G13D in colon cancer, lung cancer, or breast cancer
  BRAF V600E in melanoma, colon cancer, or lung cancer
  NRAS Q61K in melanoma
  PIK3CA H1047R in breast cancer
  FGFR1 amplification in breast cancer
  PTEN biallelic inactivation in breast cancer
  BRCA1 biallelic inactivation in breast cancer or pancreatic cancer Category C: Alterations with limited evidence (early clinical data, conflicting clinical data, pre-clinical data, theoretical) that predict sensitivity or resistance to standard or experimental therapies
  KRAS Q61H in colon cancer (early clinical)
  PIK3CA H1047R in breast cancer (conflicting clinical)
  BRAF V600E in colon cancer (conflicting clinical)
  ERBB2 mutation or amplification in lung cancer (case reports)
  BRAF D594G in lung cancer (pre-clinical)
  FGFR1 amplification in breast cancer (pre-clinical)
  ATM biallelic inactivation in breast cancer (pre-clinical)
  TSC1 biallelic inactivation in colon cancer (pre-clinical)
  ATR biallelic inactivation in breast cancer (theoretical)
  BRAF V600E mutation in sarcoma (theoretical)

Category D: Alterations with prognostic or diagnostic utility in a particular subtype of cancer
  MSH2 biallelic inactivation in colon cancer (strong clinical evidence)
  BRAF V600E in colon cancer (strong clinical evidence)
  KRAS G13D in lung cancer (strong clinical evidence)
  BRCA1 inactivation in breast cancer (strong clinical evidence)

Category E: Alterations with clear biological significance in cancer (i.e. driver mutations) without clear clinical implications
  APC biallelic inactivation in colon cancer
  TP53 biallelic inactivation in breast cancer
  MITF amplification in melanoma
  ARID1A in ovarian cancer Category F: Alterations without known biological significance in cancer
  Novel alterations in known cancer genes
  Targets of therapy
  Orthologues of known cancer genes

TABLE 1B

Exemplary Classification of Alterations in Different Cancer Types

| | | A | B | C | D | E |
|---|---|---|---|---|---|---|
| KRAS G13D | Colon Cancer | x | x | | x | x |
| KRAS G13D | Lung Cancer | | x | | x | x |
| KRAS G13D | Breast Cancer | | x | | | x |
| NRAS Q61K | Melanoma | | x | x | | x |
| KRAS Q61H | Colon Cancer | | x | x | | x |
| BRAF V600E | Melanoma | | x | | | x |
| BRAF V600E | Colon Cancer | | x | x | x | x |
| BRAF V600E | Lung Cancer | | x | | | x |
| BRAF D594G | Lung Cancer | | | x | | x |
| PIK3CA H1047R | Breast Cancer | | x | x | | x |
| PIK3CA H1047R | Colon Cancer | | x | x | | |
| EGFR L858R | Lung Cancer | x | | | | x |
| EGFR T790M | Lung Cancer | x | x | | | x |
| ERBB2 Amplification | Breast Cancer | x | | | | x |
| BRCA1 biallelic inactivation | Breast Cancer | | x | x | x | x |
| BRCA2 biallelic inactivation | Pancreatic Cancer | | x | x | x | x |
| ATM biallelic inactivation | Breast Cancer | | | x | | x |
| TSC1 biallelic inactivation | Colon Cancer | | | x | | x |
| PTEN biallelic inactivation | Colon Cancer | | | x | | x |
| PTEN biallelic inactivation | Breast Cancer | | x | x | | x |
| VHL biallelic inactivation | Kidney Cancer | | | | x | x |
| MSH2 biallelic inactivation | Colon Cancer | | | | x | x |
| ATR biallelic inactiation | Breast Cancer | | | x | | x |
| MYC amplification | Breast Cancer | | | x | | x |

TABLE 2

Exemplary selected genes associated with pharmacogenetics and pharmacogenomics (PGx).

| Gene | Locus | Mutation | Effect |
|---|---|---|---|
| ABCB1 | chr7:86976581 | 3853C>T | Better survival in Asian AML treated with Ida/AraC; Survival in breast cancer patients treated with paclitaxel |
| ABCB1 | chr7:86998554 | 2677G>T/A | Response to taxanes, platinums and GI toxicity; Better survival in Asian AML treated with Ida/AraC |
| ABCC2 | chr10:101610761 | | Doxcetaxel induced leukopenia |
| ABCC4 | chr13:94613416 | | 6MP Toxicity |
| ABCG2 | chr4:89252551 | | MTX |
| ABCG2 | chr4:89271347 | q141K | Diarrhea after gefitinib |
| ABCG2 | chr4:89274403 | | MTX |

TABLE 2-continued

Exemplary selected genes associated with pharmacogenetics and pharmacogenomics (PGx).

| Gene | Locus | Mutation | Effect |
|---|---|---|---|
| C1orf144 | chr1:16578662 | | Toxicity from daunorubicin |
| CYP1B1 | chr2:38151707 | CYP1B1*3 | Toxicity from daunorubicin; Survival in breast cancer patients treated with paclitaxel |
| CYP2C19 | chr10:96509051 | CYP2C19*17 | Improved benefit from tamoxifen |
| CYP2C19 | chr10:96511647 | CYP2C19*17 | Improved benefit from tamoxifen |
| CYP2C8 | chr10:96786964 | 461delV | Paclitexel metabolism |
| CYP2C8 | chr10:96788739 | K399R | Paclitexel metabolism |
| CYP2C8 | chr10:96808096 | | Paclitexel metabolism |
| CYP2C8 | chr10:96808109 | | Paclitexel metabolism |
| CYP2C8 | chr10:96817020 | | Paclitexel metabolism |
| CYP2D6 | chr22:40853554 | CYP2D6: 3183 G>A | CYP2D6*29, present in Tanzanians |
| CYP2D6 | chr22:40853749 | CYP2D6: 2988 G>A | CYP2D6*41 (IM) |
| CYP2D6 | chr22:40853887 | CYP2D6: 2850 C>T | CYP2D6*2 (EM) |
| CYP2D6 | chr22:40854122 | CYP2D6: 2613-2615 del AGA | CYP2D6*9 (unclear function?) |
| CYP2D6 | chr22:40854188 | CYP2D6: 2549 del A | CYP2D6*3 |
| CYP2D6 | chr22:40854891 | CYP2D6: 1846 G>A | CYP2D6*4 |
| CYP2D6 | chr22:40855030 | CYP2D6: 1707 del T | CYP2D6*6 |
| CYP2D6 | chr22:40855078 | CYP2D6: 1659G>A | CYP2D6*29, present in Tanzanians |
| CYP2D6 | chr22:40855716 | CYP2D6: 1023 C>T | Present in CYP2D6*17 |
| CYP2D6 | chr22:40856638 | CYP2D6: 100C>T | Present in CYP2D6*10 (casuative) and *4 (associated) |
| CYP3A4 | chr7:99196395 | | |
| CYP3A4 | chr7:99196460 | | |
| CYP3A4 | chr7:99197606 | | |
| CYP3A4 | chr7:99204017 | | |
| CYP3A4 | chr7:99204029 | CYP3A4*16B | Paclitaxel metabolism in Japanse |
| CYP3A4 | chr7:99205328 | | |
| CYP3A4 | chr7:99205363 | | |
| CYP3A4 | chr7:99219597 | | |
| CYP3A4 | chr7:99220032 | CYP3A4*1B | Greater clearance of docetaxel |
| CYP3A5 | chr7:99088330 | | |
| CYP3A5 | chr7:99100771 | | |
| CYP3A5 | chr7:99108475 | | |
| DPYD | chr1:97688202 | DPYD*2A | Toxicity to 5FU |
| DPYD | chr1:97753983 | DPYD*5 | Toxicity to 5FU |
| DPYD | chr1:97937679 | 496A>G | 5FU, Xeloda toxicity |
| DPYD | chr1:98121473 | DPYD*9A | Toxicity to 5FU |
| ERCC2 | chr19:50546759 | 2251A>C | Relapse after 5FU in Asians |
| ESR1 | chr6:152205074 | | Tamoxifen induced hypercholesterolemia |
| ESR2 | chr14:63769569 | | Tamoxifen induced hypercholesterolemia |
| FCGR3A | chr1:159781166 | V158F | Response to cetuximab |
| FGFR4 | chr5:176452849 | GLY388ARG | |
| GSTP1 | chr11:67109265 | I105V | Resistance to multiple chemotherapies |
| GSTP1 | chr11:67110155 | A114V | Unclear, linkage disequlibrium with I105V |
| ITPA | chr20:3141842 | | 6MP Toxicity |
| LRP2 | chr2:169719231 | | Associated with ototoxicity from cisplatin |
| MAN1B1 | chr9:139102689 | | Toxicity from daunorubicin |
| MTHFR | chr1:11777044 | | MTX |
| MTHFR | chr1:11777063 | | MTX |
| MTHFR | chr1:11778965 | 677C>T | MTX |
| NQO1 | chr16:68302646 | NQO1*2 | Rapid degradation (cisplatin, doxorubicin); poor survival in breast cancer treated with anthracyclines |
| NRP2 | chr2:206360545 | | Toxicity from daunorubicin |
| SLC19A1 | chr21:45782222 | | MTX |
| SLC22A2 | chr6:160590272 | Ala270Ser | Reduced cisplatin nephrotoxicity |
| SLCO1B3 | chr12:20936961 | | Doxcetaxel induced leukopenia |
| SOD2 | chr6:160033862 | V16A | Inferior survival in breast cancer treated with cyclophosphamide |
| SULT1A1 | chr16:28524986 | | |
| SULT1A1 | chr16:28525015 | | |
| SULT1A1 | chr16:28528073 | | |
| SULT1A1 | chr16:28528301 | | |
| TMPT | chr6:18247207 | TPMT*3B | Purine toxicity |
| TPMT | chr6:18238897 | | 6MP Toxicity |
| TPMT | chr6:18238991 | | 6MP Toxicity |
| TPMT | chr6:18251934 | | 6MP Toxicity |

TABLE 2-continued

Exemplary selected genes associated with pharmacogenetics and pharmacogenomics (PGx).

| Gene | Locus | Mutation | Effect |
| --- | --- | --- | --- |
| TYMS | chr18:647646 | 28bp tandem repeat | Toxicity to 5FU |
| TYMS | chr18:663451 | 6bp deletion | Toxicity to 5FU |
| UGT1A1 | chr2:234255266 | | Anemia from irinotecan |
| UGT1A1 | chr2:234255709 | | thrombocytopenia from irinotecan |
| UGT1A1 | chr2:234330398 | | UGT1A1*60 |
| UGT1A1 | chr2:234330521 | | UGT1A1*93 |
| UGT1A1 | chr2:234333620 | | UGT1A1*28 |
| UGT1A1 | chr2:234333883 | | UGT1A1*6 |
| UGT1A1 | chr2:234334358 | | UGT1A1*27 |
| UMPS | chr3:125939432 | Gly213Ala | Toxicity to 5FU |

TABLE 3

Exemplary selected genes associated with translocation mutations in solid tumors

| Hugo Gene | Gene Category | Translocation Partner | Cancer Types |
| --- | --- | --- | --- |
| ACSL3 | Priority 1 | ETV1 | prostate |
| ALK | Priority 1 | NPM1, TPM3, TFG, TPM4, ATIC, CLTC, MSN, ALO17, CARS, EML4 | ALCL, NSCLC, Neuroblastoma |
| BRAF | Priority 1 | AKAP9, KIAA1549 | melanoma, colorectal, papillary thyroid, borderline ov, Non small-cell lung cancer (NSCLC), cholangiocarcinoma, pilocytic astrocytoma |
| C15orf21 | Priority 1 | ETV1 | prostate |
| CANT1 | Priority 1 | ETV4 | prostate |
| CCND1 | Priority 1 | IGH, FSTL3 | CLL, B-ALL, breast |
| DDX5 | Priority 1 | ETV4 | prostate |
| ELK4 | Priority 1 | SLC45A3 | prostate |
| EML4 | Priority 1 | ALK | NSCLC |
| EP300 | Priority 1 | MLL, RUNXBP2 | colorectal, breast, pancreatic, AML |
| ERG | Priority 1 | EWSR1, TMPRSS2, ELF4, FUS, HERPUD1 | Ewing sarcoma, prostate, AML |
| ETV1 | Priority 1 | EWSR1, TMPRSS2, SLC45A3, C15orf21, HNRNPA2B1. ACSL3 | Ewing sarcoma, prostate |
| ETV4 | Priority 1 | EWSR1, TMPRSS2, DDX5, KLK2, CANT1 | Ewing sarcoma, Prostate carcinoma |
| ETV5 | Priority 1 | TMPRSS2, SCL45A3 | Prostate |
| FGFR3 | Priority 1 | IGH@, ETV6 | bladder, MM, T-cell lymphoma |
| HERPUD1 | Priority 1 | ERG | prostate |
| HNRNPA2B1 | Priority 1 | ETV1 | prostate |
| KLK2 | Priority 1 | ETV4 | prostate |
| RET | Priority 1 | H4, PRKAR1A, NCOA4, PCM1, GOLGA5, TRIM33, KTN1, TRIM27, HOOK3 | medullary thyroid, papillary thyroid, pheochromocytoma |
| ROS1 | Priority 1 | GOPC, ROS1 | glioblastoma, NSCLC |
| SLC45A3 | Priority 1 | ETV1, ETV5, ELK4, ERG | prostate |
| TMPRSS2 | Priority 1 | ERG, ETV1, ETV4, ETV5 | prostate |
| AKAP9 | | BRAF | papillary thyroid |
| ASPSCR1 | | TFE3 | alveolar soft part sarcoma |
| ATF1 | | EWSR1, FUS | malignant melanoma of soft parts, angiomatoid fibrous histiocytoma |
| BRD3 | | NUT | lethal midline carcinoma of young people |
| BRD4 | | NUT | lethal midline carcinoma of young people |
| C12orf9 | | LPP | lipoma |
| CD74 | | ROS1 | NSCLC |
| CDH11 | | USP6 | aneurysmal bone cysts |
| CHCHD7 | | PLAG1 | salivary adenoma |
| CHN1 | | TAF15 | extraskeletal myxoid chondrosarcoma |
| CIC | | DUX4 | soft tissue sarcoma |
| CMKOR1 | | HMGA2 | lipoma |
| COL1A1 | | PDGFB, USP6 | dermatofibrosarcoma protuberans, aneurysmal bone cyst |
| COX6C | | HMGA2 | uterine leiomyoma |
| CREB1 | | EWSR1 | clear cell sarcoma, angiomatoid fibrous histiocytoma |
| CREB3L2 | | FUS | fibromyxoid sarcoma |

TABLE 3-continued

Exemplary selected genes associated with translocation mutations in solid tumors

| Hugo Gene | Gene Category | Translocation Partner | Cancer Types |
|---|---|---|---|
| CRTC3 | | MAML2 | salivary gland mucoepidermoid |
| CTNNB1 | | PLAG1 | colorectal, ovarian, hepatoblastoma, others, pleomorphic salivary adenoma |
| D10S170 | | RET, PDGFRB | papillary thyroid, CML |
| DDIT3 | | FUS | liposarcoma |
| DUX4 | | CIC | soft tissue sarcoma |
| ELKS | | RET | papillary thyroid |
| ETV6 | | NTRK3, RUNX1, PDGFRB, ABL1, MN1, ABL2, FACL6, CHIC2, ARNT, JAK2, EVI1, CDX2, STL, HLXB9, MDS2, PER1, SYK, TTL, FGFR3, PAX5 | congenital fibrosarcoma, multiple leukemia and lymphoma, secretory breast, MDS, ALL |
| EWSR1 | | FLI1, ERG, ZNF278, NR4A3, FEV, ATF1, ETV1, ETV4, WT1, ZNF384, CREB1, POU5F1, PBX1 | Ewing sarcoma, desmoplastic small round cell tumor, ALL, clear cell sarcoma, sarcoma, myoepithelioma |
| FEV | | EWSR1, FUS | Ewing sarcoma |
| FLI1 | | EWSR1 | Ewing sarcoma |
| FOXO1A | | PAX3 | alveolar rhabdomyosarcomas |
| FUS | | DDIT3, ERG, FEV, ATF1, CREB3L2 | liposarcoma, AML, Ewing sarcoma, angiomatoid fibrous histiocytoma, fibromyxoid sarcoma |
| GOLGA5 | | RET | papillary thyroid |
| HEI10 | | HMGA2 | uterine leiomyoma |
| HMGA1 | | ? | microfollicular thyroid adenoma, various benign mesenchymal tumors |
| HMGA2 | | LHFP, RAD51L1, LPP, HEI10, COX6C, CMKOR1, NFIB | lipoma |
| HOOK3 | | RET | papillary thyroid |
| JAZF1 | | SUZ12 | endometrial stromal tumours |
| KTN1 | | RET | papillary thyroid |
| LHFP | | HMGA2 | lipoma |
| LIFR | | PLAG1 | salivary adenoma |
| LPP | | HMGA2, MLL, C12orf9 | lipoma, leukemia |
| MAML2 | | MECT1, CRTC3 | salivary gland mucoepidermoid |
| MECT1 | | MAML2 | salivary gland mucoepidermoid |
| MN1 | | ETV6 | AML, meningioma |
| MYB | | NFIB | adenoid cystic carcinoma |
| MYC | | IGK, BCL5, BCL7A, BTG1, TRA, IGH | Burkitt lymphoma, amplified in other cancers, B-CLL |
| NCOA1 | | PAX3 | alveolar rhadomyosarcoma |
| NCOA4 | | RET | papillary thyroid |
| NFIB | | MYB, HGMA2 | adenoid cystic carcinoma, lipoma |
| NONO | | TFE3 | papillary renal cancer |
| NR4A3 | | EWSR1 | extraskeletal myxoid chondrosarcoma |
| NTRK1 | | TPM3, TPR, TFG | papillary thyroid |
| NTRK3 | | ETV6 | congenital fibrosarcoma, Secretory breast |
| NUT | | BRD4, BRD3 | lethal midline carcinoma of young people |
| OMD | | USP6 | aneurysmal bone cysts |
| PAX3 | | FOXO1A, NCOA1 | alveolar rhabdomyosarcoma |
| PAX7 | | FOXO1A | alveolar rhabdomyosarcoma |
| PAX8 | | PPARG | follicular thyroid |
| PBX1 | | TCF3, EWSR1 | pre B-ALL, myoepithelioma |
| PCM1 | | RET, JAK2 | papillary thyroid, CML, MPD |
| PDGFB | | COL1A1 | DFSP |
| PDGFRA | | FIP1L1 | GIST, idiopathic hypereosinophilic syndrome |
| PLAG1 | | TCEA1, LIFR, CTNNB1, CHCHD7 | salivary adenoma |
| POU5F1 | | EWSR1 | sarcoma |
| PPARG | | PAX8 | follicular thyroid |
| PRCC | | TFE3 | papillary renal |
| PRKAR1A | | RET | papillary thyroid |
| PRO1073 | | TFEB | renal cell carcinoma (childhood epithelioid) |
| RAD51L1 | | HMGA2 | lipoma, uterine leiomyoma |
| RAF1 | | SRGAP3 | pilocytic astrocytoma |
| SFPQ | | TFE3 | papillary renal cell |
| SRGAP3 | | RAF1 | pilocytic astrocytoma |
| SS18 | | SSX1, SSX2 | synovial sarcoma |
| SS18L1 | | SSX1 | synovial sarcoma |
| SSX1 | | SS18 | synovial sarcoma |
| SSX2 | | SS18 | synovial sarcoma |

TABLE 3-continued

Exemplary selected genes associated with translocation mutations in solid tumors

| Hugo Gene | Gene Category | Translocation Partner | Cancer Types |
|---|---|---|---|
| SSX4 | | SS18 | synovial sarcoma |
| SUZ12 | | JAZF1 | endometrial stromal tumours |
| TAF15 | | TEC, CHN1, ZNF384 | extraskeletal myxoid chondrosarcomas, ALL |
| TCEA1 | | PLAG1 | salivary adenoma |
| TCF12 | | TEC | extraskeletal myxoid chondrosarcoma |
| TFE3 | | SFPQ, ASPSCR1, PRCC, NONO, CLTC | papillary renal, alveolar soft part sarcoma, renal |
| TFEB | | ALPHA | renal (childhood epithelioid) |
| TFG | | NTRK1, ALK | papillary thyroid, ALCL, NSCLC |
| THRAP3 | | USP6 | aneurysmal bone cysts |
| TPM3 | | NTRK1, ALK | papillary thyroid, ALCL |
| TPR | | NTRK1 | papillary thyroid |
| TRIM27 | | RET | papillary thyroid |
| TRIM33 | | RET | papillary thyroid |
| USP6 | | COL1A1, CDH11, ZNF9, OMD | aneurysmal bone cysts |
| ZNF278 | | EWSR1 | Ewing sarcoma |
| ZNF331 | | ? | follicular thyroid adenoma |
| ZNF9 | | USP6 | aneurysmal bone cysts |

TABLE 4

Exemplary selected genes associated with translocation mutations in hematologic malignancies.

| Hugo Gene | Gene Category | Translocation Partner | Cancer Types |
|---|---|---|---|
| ABL1 | Priority 1 | BCR, ETV6, NUP214 | CML, ALL, T-ALL |
| ALK | Priority 1 | NPM1, TPM3, TFG, TPM4, ATIC, CLTC, MSN, ALO17, CARS, EML4 | ALCL, NSCLC, Neuroblastoma |
| BCL2 | Priority 1 | IGH | NHL, CLL |
| BCL6 | Priority 1 | IG loci, ZNFN1A1, LCP1, PIM1, TFRC, MHC2TA, NACA, HSPCB, HSPCA, HIST1H4I, IL21R, POU2AF1, ARHH, EIF4A2, SFRS3 | NHL, CLL |
| CCND1 | Priority 1 | IGH, FSTL3 | CLL, B-ALL, breast |
| CREBBP | Priority 1 | MLL, MORF, RUNXBP2 | AL, AML |
| FGFR1 | Priority 1 | BCR, FOP, ZNF198, CEP1 | MPD, NHL |
| FGFR3 | Priority 1 | IGH, ETV6 | bladder, MM, T-cell lymphoma |
| JAK2 | Priority 1 | ETV6, PCM1, BCR | ALL, AML, MPD, CML |
| MLL | Priority 1 | MLL, MLLT1, MLLT2, MLLT3, MLLT4, MLLT7, MLLT10, MLLT6, ELL, EPS15, AF1Q, CREBBP, SH3GL1, FNBP1, PNUTL1, MSF, GPHN, GMPS, SSH3BP1, ARHGEF12, GAS7, FOXO3A, LAF4, LCX, SEPT6, LPP, CBFA2T1, GRAF, EP300, PICALM, HEAB | AML, ALL |
| PDGFRA | Priority 1 | FIP1L1 | GIST, idiopathic hypereosinophilic syndrome |
| RARA | Priority 1 | PML, ZNF145, TIF1, NUMA1, NPM1 | APL |
| SEPT6 | | MLL | AML |
| ABL2 | | ETV6 | AML |
| AF15Q14 | | MLL | AML |
| AF1Q | | MLL | ALL |
| AF3p21 | | MLL | ALL |
| AF5q31 | | MLL | ALL |
| ALO17 | | ALK | ALCL |
| ARHGEF12 | | MLL | AML |
| ARHH | | BCL6 | NHL |
| ARNT | | ETV6 | AML |
| ATIC | | ALK | ALCL |
| BCL10 | | IGH | MALT |
| BCL11A | | IGH | B-CLL |
| BCL11B | | TLX3 | T-ALL |
| BCL3 | | IGH | CLL |
| BCL5 | | MYC | CLL |
| BCL7A | | MYC | BNHL |
| BCL9 | | IGH, IGL | B-ALL |

TABLE 4-continued

Exemplary selected genes associated with translocation mutations in hematologic malignancies.

| Hugo Gene | Gene Category | Translocation Partner | Cancer Types |
|---|---|---|---|
| BCR | | ABL1, FGFR1, JAK2 | CML, ALL, AML |
| BIRC3 | | MALT1 | MALT |
| BTG1 | | MYC | BCLL |
| CARS | | ALK | ALCL |
| CBFA2T1 | | MLL, RUNX1 | AML |
| CBFA2T3 | | RUNX1 | AML |
| CBFB | | MYH11 | AML |
| CBL | | MLL | AML, JMML, MDS |
| CCND2 | | IGL | NHL, CLL |
| CCND3 | | IGH | MM |
| CDK6 | | MLLT10 | ALL |
| CDX2 | | ETV6 | AML |
| CEP1 | | FGFR1 | MPD, NHL |
| CHIC2 | | ETV6 | AML |
| CLTC | | ALK, TFE3 | ALCL, renal |
| CLTCL1 | | ? | ALCL |
| DDX10 | | NUP98 | AML* |
| DDX6 | | IGH | B-NHL |
| DEK | | NUP214 | AML |
| EIF4A2 | | BCL6 | NHL |
| ELF4 | | ERG | AML |
| ELL | | MLL | AL |
| ELN | | PAX5 | B-ALL |
| EP300 | | MLL, RUNXBP2 | colorectal, breast, pancreatic, AML |
| EPS15 | | MLL | ALL |
| ERG | | EWSR1, TMPRSS2, ELF4, FUS, HERPUD1 | Ewing sarcoma, prostate, AML |
| ETV6 | | NTRK3, RUNX1, PDGFRB, ABL1, MN1, ABL2, FACL6, CHIC2, ARNT, JAK2, EVI1, CDX2, STL, HLXB9, MDS2, PER1, SYK, TTL, FGFR3, PAX5 | congenital fibrosarcoma, multiple leukemia and lymphoma, secretory breast, MDS, ALL |
| EVI1 | | RUNX1, ETV6, PRDM16, RPN1 | AML, CML |
| EWSR1 | | FLI1, ERG, ZNF278, NR4A3, FEV, ATF1, ETV1, ETV4, WT1, ZNF384, CREB1, POU5F1, PBX1 | Ewing sarcoma, desmoplastic small round cell tumor, ALL, clear cell sarcoma, sarcoma, myoepithelioma |
| FACL6 | | ETV6 | AML, AEL |
| FCGR2B | | ? | ALL |
| FGFR1OP | | FGFR1 | MPD, NHL |
| FIP1L1 | | PDGFRA | idiopathic hypereosinophilic syndrome |
| FNBP1 | | MLL | AML |
| FOXO3A | | MLL | AL |
| FOXP1 | | PAX5 | ALL |
| FSTL3 | | CCND1 | B-CLL |
| FUS | | DDIT3, ERG, FEV, ATF1, CREB3L2 | liposarcoma, AML, Ewing sarcoma, angiomatoid fibrous histiocytoma, fibromyxoid sarcoma |
| FVT1 | | IGK | B-NHL |
| GAS7 | | MLL | AML* |
| GMPS | | MLL | AML |
| GPHN | | MLL | AL |
| GRAF | | MLL | AML, MDS |
| HCMOGT-1 | | PDGFRB | JMML |
| HEAB | | MLL | AML |
| HIP1 | | PDGFRB | CMML |
| HIST1H4I | | BCL6 | NHL |
| HLF | | TCF3 | ALL |
| HLXB9 | | ETV6 | AML |
| HOXA11 | | NUP98 | CML |
| HOXA13 | | NUP98 | AML |
| HOXA9 | | NUP98, MSI2 | AML* |
| HOXC11 | | NUP98 | AML |
| HOXC13 | | NUP98 | AML |
| HOXD11 | | NUP98 | AML |
| HOXD13 | | NUP98 | AML* |
| HSPCA | | BCL6 | NHL |
| HSPCB | | BCL6 | NHL |
| IGH | | MYC, FGFR3, PAX5, IRTA1, IRF4, CCND1, BCL9, BCL8, BCL6, BCL2, BCL3, BCL10, BCL11A. LHX4, DDX6, NFKB2, PAFAH1B2, PCSK7 | MM, Burkitt lymphoma, NHL, CLL, B-ALL, MALT, MLCLS |
| IGK | | MYC, FVT1 | Burkitt lymphoma, B-NHL |
| IGL | | BCL9, MYC, CCND2 | Burkitt lymphoma |

TABLE 4-continued

Exemplary selected genes associated with translocation mutations in hematologic malignancies.

| Hugo Gene | Gene Category | Translocation Partner | Cancer Types |
|---|---|---|---|
| IL2 | | TNFRSF17 | intestinal T-cell lymphoma |
| IL21R | | BCL6 | NHL |
| IRF4 | | IGH | MM |
| IRTA1 | | IGH | B-NHL |
| ITK | | SYK | peripheral T-cell lymphoma |
| KDM5A | | NUP98 | AML |
| LAF4 | | MLL, RUNX1 | ALL, T-ALL |
| LASP1 | | MLL | AML |
| LCK | | TRB | T-ALL |
| LCP1 | | BCL6 | NHL |
| LCX | | MLL | AML |
| LMO1 | | TRD | T-ALL |
| LMO2 | | TRD | T-ALL |
| LPP | | HMGA2, MLL, C12orf9 | lipoma, leukemia |
| LYL1 | | TRB | T-ALL |
| MAF | | IGH | MM |
| MAFB | | IGH | MM |
| MALT1 | | BIRC3 | MALT |
| MDS1 | | RUNX1 | MDS, AML |
| MDS2 | | ETV6 | MDS |
| MHC2TA | | BCL6 | NHL |
| MKL1 | | RBM15 | acute megakaryocytic leukemia |
| MLF1 | | NPM1 | AML |
| MLLT1 | | MLL | AL |
| MLLT10 | | MLL, PICALM, CDK6 | AL |
| MLLT2 | | MLL | AL |
| MLLT3 | | MLL | ALL |
| MLLT4 | | MLL | AL |
| MLLT6 | | MLL | AL |
| MLLT7 | | MLL | AL |
| MN1 | | ETV6 | AML, meningioma |
| MSF | | MLL | AML* |
| MSI2 | | HOXA9 | CML |
| MSN | | ALK | ALCL |
| MTCP1 | | TRA | T cell prolymphocytic leukemia |
| MUC1 | | IGH | B-NHL |
| MYC | | IGK, BCL5, BCL7A, BTG1, TRA, IGH | Burkitt lymphoma, amplified in other cancers, B-CLL |
| MYH11 | | CBFB | AML |
| MYH9 | | ALK | ALCL |
| MYST4 | | CREBBP | AML |
| NACA | | BCL6 | NHL |
| NCOA2 | | RUNXBP2 | AML |
| NFKB2 | | IGH | B-NHL |
| NIN | | PDGFRB | MPD |
| NOTCH1 | | TRB | T-ALL |
| NPM1 | | ALK, RARA, MLF1 | NHL, APL, AML |
| NSD1 | | NUP98 | AML |
| NUMA1 | | RARA | APL |
| NUP214 | | DEK, SET, ABL1 | AML, T-ALL |
| NUP98 | | HOXA9, NSD1, WHSC1L1, DDX10, TOP1, HOXD13, PMX1, HOXA13, HOXD11, HOXA11, RAP1GDS1, HOXC11 | AML |
| OLIG2 | | TRA | T-ALL |
| PAFAH1B2 | | IGH | MLCLS |
| PAX5 | | IGH, ETV6, PML, FOXP1, ZNF521, ELN | NHL, ALL, B-ALL |
| PBX1 | | TCF3, EWSR1 | pre B-ALL, myoepithelioma |
| PCM1 | | RET, JAK2 | papillary thyroid, CML, MPD |
| PCSK7 | | IGH | MLCLS |
| PDE4DIP | | PDGFRB | MPD |
| PDGFRB | | ETV6, TRIP11, HIP1, RAB5EP, H4, NIN, HCMOGT-1, PDE4DIP | MPD, AML, CMML, CML |
| PERI | | ETV6 | AML, CMML |
| PICALM | | MLLT10, MLL | TALL, AML, |
| PIM1 | | BCL6 | NHL |
| PML | | RARA, PAX5 | APL, ALL |
| PMX1 | | NUP98 | AML |
| PNUTL1 | | MLL | AML |
| POU2AF1 | | BCL6 | NHL |
| PRDM16 | | EVI1 | MDS, AML |
| PSIP2 | | NUP98 | AML |
| RAB5EP | | PDGFRB | CMML |
| RANBP17 | | TRD | ALL |

TABLE 4-continued

Exemplary selected genes associated with translocation mutations in hematologic malignancies.

| Hugo Gene | Gene Category | Translocation Partner | Cancer Types |
|---|---|---|---|
| RAP1GDS1 | | NUP98 | T-ALL |
| RBM15 | | MKL1 | acute megakaryocytic leukemia |
| RPL22 | | RUNX1 | AML, CML |
| RPN1 | | EVI1 | AML |
| RUNX1 | | RPL22, MDS1, EVI1, CBFA2T3, CBFA2T1, ETV6, LAF4 | AML, preB- ALL, T-ALL |
| RUNXBP2 | | CREBBP, NCOA2, EP300 | AML |
| SET | | NUP214 | AML |
| SFRS3 | | BCL6 | follicular lymphoma |
| SH3GL1 | | MLL | AL |
| SIL | | TAL1 | T-ALL |
| SSH3BP1 | | MLL | AML |
| STL | | ETV6 | B-ALL |
| SYK | | ETV6, ITK | MDS, peripheral T-cell lymphoma |
| TAF15 | | TEC, CHN1, ZNF384 | extraskeletal myxoid chondrosarcomas, ALL |
| TAL1 | | TRD, SIL | lymphoblastic leukemia/biphasic |
| TAL2 | | TRB | T-ALL |
| TCF3 | | PBX1, HLF, TFPT | pre B-ALL |
| TCL1A | | TRA | T-CLL |
| TCL6 | | TRA | T-ALL |
| TFG | | NTRK1, ALK | papillary thyroid, ALCL, NSCLC |
| TFPT | | TCF3 | pre-B ALL |
| TFRC | | BCL6 | NHL |
| TIF1 | | RARA | APL |
| TLX1 | | TRB, TRD | T-ALL |
| TLX3 | | BCL11B | T-ALL |
| TNFRSF17 | | IL2 | intestinal T-cell lymphoma |
| TOP1 | | NUP98 | AML* |
| TPM3 | | NTRK1, ALK | papillary thyroid, ALCL |
| TPM4 | | ALK | ALCL |
| TRA | | ATL, OLIG2, MYC, TCL1A, TCL6, MTCP1, TCL6 | T-ALL |
| TRB | | HOX11, LCK, NOTCH1, TAL2, LYL1 | T-ALL |
| TRD | | TAL1, HOX11, TLX1, LMO1, LMO2, RANBP17 | T-cell leukemia |
| TRIP11 | | PDGFRB | AML |
| TTL | | ETV6 | ALL |
| WHSC1 | | IGH | MM |
| WHSC1L1 | | NUP98 | AML |
| ZNF145 | | RARA | APL |
| ZNF198 | | FGFR1 | MPD, NHL |
| ZNF384 | | EWSR1, TAF15 | ALL |
| ZNF521 | | PAX5 | ALL |
| ZNFN1A1 | | BCL6 | ALL, DLBL |

Example 7

Exemplary Bait Sequences for Hybrid Capture

Table 7 provides exemplary baits for three targets: SMAD3_target_10, SMAD3_target_11, SMAD3_target_12.

TABLE 7

Exemplary Baits

```
1. Gene    Target           Bait genomic location
SMAD3      SMAD3_target_10  chr15: 67477013-67477132

CCATTGTGTGTGAGCAAAGGCACCCTGTCCAGTCTAACCTGAATCTCTGTAGGAAGA
GGCGTGCGGCTCTACTACATCGGAGGGGAGGTCTTCGCAGAGTGCCTCAGTGACAG
CGCTATT (SEQ ID NO: 6)
(Bait ID: SMAD3_target_10.2)
```

TABLE 7-continued

Exemplary Baits

| 2. Gene | Target | Bait genomic location |
|---|---|---|
| SMAD3 | SMAD3_target_ 10 | chr15: 67477037-67477156 |

CTGTCCAGTCTAACCTGAATCTCTGTAGGAAGAGGCGTGCGGCTCTACTACATCGGA
GGGGAGGTCTTCGCAGAGTGCCTCAGTGACAGCGCTATTTTTGTCCAGTCTCCCAAC
TGTAAC (SEQ ID NO: 7)
(Bait ID: SMAD3_target_10.4)

| 3. Gene | Target | Bait genomic location |
|---|---|---|
| SMAD3 | SMAD3_target_ 10 | chr15: 67477061-67477180 |

GTAGGAAGAGGCGTGCGGCTCTACTACATCGGAGGGGAGGTCTTCGCAGAGTGCCT
CAGTGACAGCGCTATTTTTGTCCAGTCTCCCAACTGTAACCAGCGCTATGGCTGGCA
CCCGGCC (SEQ ID NO: 8)
(Bait ID: SMAD3_target_10.6)

| 4. Gene | Target | Bait genomic location |
|---|---|---|
| SMAD3 | SMAD3_target_ 10 | chr15: 67477085-67477204 |

TACATCGGAGGGGAGGTCTTCGCAGAGTGCCTCAGTGACAGCGCTATTTTTGTCCAG
TCTCCCAACTGTAACCAGCGCTATGGCTGGCACCCGGCCACCGTCTGCAAGATCCCA
CCAGGT (SEQ ID NO: 9)
(Bait ID: SMAD3_target_10.1)

| 5. Gene | Target | Bait genomic location |
|---|---|---|
| SMAD3 | SMAD3_target_ 10 | chr15: 67477109-67477228 |

GAGTGCCTCAGTGACAGCGCTATTTTTGTCCAGTCTCCCAACTGTAACCAGCGCTAT
GGCTGGCACCCGGCCACCGTCTGCAAGATCCCACCAGGTAAACGAGCCGCACAGGC
ACCCCTG (SEQ ID NO: 10)
(Bait ID: SMAD3_target_10.5)

| 6. Gene | Target | Bait genomic location |
|---|---|---|
| SMAD3 | SMAD3_target_10 | chr15: 67477133-67477252 |

TTTGTCCAGTCTCCCAACTGTAACCAGCGCTATGGCTGGCACCCGGCCACCGTCTGC
AAGATCCCACCAGGTAAACGAGCCGCACAGGCACCCCTGCCTTGAGGTCCCTCTCC
GAGTGCA (SEQ ID NO: 11)
(Bait ID: SMAD3_target_10.3)

| 7. Gene | Target | Bait genomic location |
|---|---|---|
| SMAD3 | SMAD3_target_11 | chr15: 67479655-67479774 |

GACCTGGCCACTTCCATCCCCACAGCCCTGTTTCTGTGTTTTTGGCAGGATGCAACCT
GAAGATCTTCAACAACCAGGAGTTCGCTGCCCTCCTGGCCCAGTCGGTCAACCAGG
GCTTTG (SEQ ID NO: 12)
(Bait ID: SMAD3_target_11.1)

| 8. Gene | Target | Bait genomic location |
|---|---|---|
| SMAD3 | SMAD3_target_11 | chr15: 67479679-67479798 |

GCCCTGTTTCTGTGTTTTTGGCAGGATGCAACCTGAAGATCTTCAACAACCAGGAGT
TCGCTGCCCTCCTGGCCCAGTCGGTCAACCAGGGCTTTGAGGCTGTCTACCAGTTGA
CCCGAA (SEQ ID NO: 13)
(Bait ID: SMAD3_target_11.5)

| 9. Gene | Target | Bait genomic location |
|---|---|---|
| SMAD3 | SMAD3_target_11 | chr15: 67479703-67479822 |

GATGCAACCTGAAGATCTTCAACAACCAGGAGTTCGCTGCCCTCCTGGCCCAGTCGG
TCAACCAGGGCTTTGAGGCTGTCTACCAGTTGACCCGAATGTGCACCATCCGCATGA
GCTTCG (SEQ ID NO: 14)
(Bait ID: SMAD3_target_11.3)

| 10. Gene | Target | Bait genomic location |
|---|---|---|
| SMAD3 | SMAD3_target_11 | chr15: 67479727-67479846 |

ACCAGGAGTTCGCTGCCCTCCTGGCCCAGTCGGTCAACCAGGGCTTTGAGGCTGTCT
ACCAGTTGACCCGAATGTGCACCATCCGCATGAGCTTCGTCAAAGGCTGGGGAGCG
GAGTACA (SEQ ID NO: 15)
(Bait ID: SMAD3_target_11.4)

TABLE 7-continued

Exemplary Baits

| 11. Gene | Target | Bait genomic location |
|---|---|---|
| SMAD3 | SMAD3_target_11 | chr15: 67479751-67479870 |

CCCAGTCGGTCAACCAGGGCTTTGAGGCTGTCTACCAGTTGACCCGAATGTGCACCA
TCCGCATGAGCTTCGTCAAAGGCTGGGGAGCGGAGTACAGGTCAGTTATGGGTGCT
GCCTACA (SEQ ID NO: 16)
(Bait ID: SMAD_target_11.2)

| 12. Gene | Target | Bait genomic location |
|---|---|---|
| SMAD3 | SMAD3_target_11 | chr15: 67479775-67479894 |

AGGCTGTCTACCAGTTGACCCGAATGTGCACCATCCGCATGAGCTTCGTCAAAGGCT
GGGGAGCGGAGTACAGGTCAGTTATGGGTGCTGCCTACATCAGGGGACCCAACTCC
AGGTGAC (SEQ ID NO: 17)
(Bait ID: SMAD3_target_11.6)

| 13. Gene | Target | Bait genomic location |
|---|---|---|
| SMAD3 | SMAD3_target_12 | chr15: 67482692-67482811 |

TGTAACCCCTGGAGATTTTTAAGTCCCCCACCCCACCCCTTTCCCTATTTCTTACA
GGAGACAGACTGTGACCAGTACCCCCTGCTGGATTGAGCTGCACCTGAATGGGCCTT
TGCAG (SEQ ID NO: 18)
(Bait ID: SMAD3_target_12.5)

| 14. Gene | Target | Bait genomic location |
|---|---|---|
| SMAD3 | SMAD3_target_12 | chr15: 67482716-67482835 |

GTCCCCCACCCCACCCCTTTCCCTATTTCTTACAGGAGACAGACTGTGACCAGTACC
CCCTGCTGGATTGAGCTGCACCTGAATGGGCCTTTGCAGTGGCTTGACAAGGTCCTC
ACCCAG (SEQ ID NO: 19)
(Bait ID: SMAD3_target_12.3)

| 15. Gene | Target | Bait genomic location |
|---|---|---|
| SMAD3 | SMAD3_target_12 | chr15: 67482740-67482859 |

ATTTCTTACAGGAGACAGACTGTGACCAGTACCCCCTGCTGGATTGAGCTGCACCTG
AATGGGCCTTTGCAGTGGCTTGACAAGGTCCTCACCCAGATGGGCTCCCCAAGCATC
CGCTGT (SEQ ID NO: 20)
(Bait ID: SMAD3_target_12.2)

| 16. Gene | Target | Bait genomic location |
|---|---|---|
| SMAD3 | SMAD3_target_12 | chr15: 67482764-67482883 |

ACCAGTACCCCCTGCTGGATTGAGCTGCACCTGAATGGGCCTTTGCAGTGGCTTGAC
AAGGTCCTCACCCAGATGGGCTCCCCAAGCATCCGCTGTTCCAGTGTGTCTTAGAGA
CATCAA (SEQ ID NO: 21)
(Bait ID: SMAD3_target_12.4)

| 17. Gene | Target | Bait genomic location |
|---|---|---|
| SMAD3 | SMAD3_target_12 | chr15: 67482788-67482907 |

CTGCACCTGAATGGGCCTTTGCAGTGGCTTGACAAGGTCCTCACCCAGATGGGCTCC
CCAAGCATCCGCTGTTCCAGTGTGTCTTAGAGACATCAAGTATGGTAGGGGAGGGC
AGGCTTG (SEQ ID NO: 22)
(Bait ID: SMAD3_target_12.6)

| 18. Gene | Target | Bait genomic location |
|---|---|---|
| SMAD3 | SMAD3_target_12 | chr15: 67482812-67482931 |

TGGCTTGACAAGGTCCTCACCCAGATGGGCTCCCCAAGCATCCGCTGTTCCAGTGTG
TCTTAGAGACATCAAGTATGGTAGGGGAGGGCAGGCTTGGGGAAAATGGCCATGCA
GGAGGTG (SEQ ID NO: 23)
(Bait ID: SMAD3_target_12.1)

Table 8 provides baits with sequences for two targets: FLT3_target_24 modified to reduce the secondary structure. FLT4_target_31 has some arbitrary sequence on both ends of the baits which is effectively similar to a shorter bait. Both improve coverage by about 4X (~4x improvement in coverage).

TABLE 8

Exemplary Baits

| 1. Gene | Target | Bait genomic location |
|---|---|---|
| FLT3 | FLT3_target_24 | chr13: 28674626-28674745 |

TABLE 8-continued

Exemplary Baits

Original sequence
CGTCGCGCGCCAACGCCGGCATGGCCTCCGGAGCCCGGGGTCCCCAGGCCGCGCCG
GCCCAGCCCTGCGATGCCGCCTGGAGCGGCGCGCCTCGCGCTGCAGGTGGCTCTCTT
AAGGATG (SEQ ID NO: 24)

Modified sequence
CGTCTCACGCCAACGCAAGCATGTCCTCCGGAGCCCGGGGTCCCCAGGCCGCGCCG
GCCCAGCCCTGCGATGCCGCCTGGAGCGGCGCGCCTCGCACTGCAGATGGCTCTCTT
AAGGATG(SEQ ID NO: 25)
(Bait ID: FLT3_target_24.1)

| 2. Gene | Target | Bait genomic location |
|---|---|---|
| FLT3 | FLT3_target_24 | chr13: 28674602-28674721 |

Original sequence
TACCGAGCAGCGGCAGCTGGCCGCCGTCGCGCGCCAACGCCGGCATGGCCTCCGGA
GCCCGGGGTCCCCAGGCCGCGCCGGCCCAGCCCTGCGATGCCGCCTGGAGCGGCGC
GCCTCGCG(SEQ ID NO: 26)

Modified sequence
TACCGAGCAGCGGCAGCTGGCCGCCGTCGCGCGCCAACGCCGGCATGGCCTCCGGA
GCCCGGGGTCCCCAGGCCGCGCATGCCCAGCCCTGCGATGCCGCCTTGAGCAACGC
GCCTCACG (SEQ ID NO: 27)
(Bait ID: FLT3_target_24.2)

| 3. Gene | Target | Bait genomic location |
|---|---|---|
| FLT3 | FLT3_target_24 | chr13: 28674578-28674697 |

Original sequence
GCTGCGAGCGAGCGAGCGGGGCCTTACCGAGCAGCGGCAGCTGGCCGCCGTCGCGC
GCCAACGCCGGCATGGCCTCCGGAGCCCGGGGTCCCCAGGCCGCGCCGGCCCAGCC
CTGCGATG(SEQ ID NO: 28)

Modified sequence
GCTTCGAGAGAGCGAGCGGGGCCTTACCGAGCAGCAGCAGCTGGCCGCCGTCGCGC
GCCAACGCCGGCATGGCCTCCGGAGCCCGGGGTCCCCAGGCCGCGCCAGCCCAGCC
CTGCGAGATG (SEQ ID NO: 29)
(Bait ID: FLT3_target_24.3)

| 4. Gene | Target | Bait genomic location |
|---|---|---|
| FLT3 | FLT3_target_24 | chr13: 28674554-28674673 |

Original sequence
GTGGGGGCTGAGGGACCGCGAGGGGCTGCGAGCGAGCGAGCGGGGCCTTACCGAG
CAGCGGCAGCTGGCCGCCGTCGCGCGCCAACGCCGGCATGGCCTCCGGAGCCCGGG
GTCCCCAGG(SEQ ID NO: 30)

Modified sequence
GAGGTGGCTGAGAGACCGCGAGGAGCTGCGAGCGAGCGAGCGGGGCCTTACCGAG
CAGCGGCAGCTGGCCGCCGTCGCGCGCCAACGCAGGCATGGCCTCCGGAGCCCAGG
GTCCCCAGG (SEQ ID NO: 31)
(Bait ID: FLT3_target_24.4)

| 5. Gene | Target | Bait genomic location |
|---|---|---|
| FLT3 | FLT3_target_24 | chr13: 28674506-28674625 |

Original sequence
CGAGGCGGCTGGGCCGGAGGAGGCGCGCGCCCGGGTCCACACTGCGGGGTGGGGG
CTGAGGGACCGCGAGGGGCTGCGAGCGAGCGAGCGGGGCCTTACCGAGCAGCGGC
AGCTGGCCGC (SEQ ID NO: 32)

Modified sequence
CGAGGCGGCTGGGCCGGAGGAGGCGCGCGCCCGGATCCACACTGCGGGTGGGGG
CTGAGGGACCGCGAGGGGCTGCGAGCGAGCGAGCGGGGACTTACCGAGCAGCGGC
AACTGGACGC (SEQ ID NO: 33)
(Bait ID: FLT3_target_24.5)

| 6. Gene | Target | Bait genomic location |
|---|---|---|
| FLT3 | FLT3_target_24 | chr13: 28674530-28674649 |

Original sequence
GCGCGCCCGGGTCCACACTGCGGGGTGGGGGCTGAGGGACCGCGAGGGGCTGCGA
GCGAGCGAGCGGGGCCTTACCGAGCAGCGGCAGCTGGCCGCCGTCGCGCGCCAACG
CCGGCATGG(SEQ ID NO: 34)

Modified sequence
GCACGCACGGATCCACACTGCGGGGTGGGGGCTGAGGGACCGCGAGGAGCTGCGA
GCGAGCGAGCGGGGCCTTACCGAGCAGCGGCAGCTGGCAGCCGTCGCGCGCCAACG TABLE 8-continued Exemplary Baits CCGGCATGG (SEQ ID NO: 35)
(Bait ID: FLT3_target_24.6)

| 7. Gene | Target | Bait genomic location |
|---|---|---|
| FLT4 | FLT4_target_31 | chr5: 180076516-180076635 |

Original sequence
TCGCAGGCACAGCGCGGCGCCCCGCTGCATCTCCGGCCGCTGCGCGTGGGTCCGAC
CCGAGCGGCCGCGGCTCGGGGCTGAAAGTGTCCGCGCGGGCGCCGGCTGGCCTGGG
GCGGGGCG (SEQ ID NO: 36)

Modified sequence
CACACACACAAGCGCGGCGCCCCGCTGCATCTCCGGCCGCTGCGCGTGGGTCCGAC
CCGAGCGGCCGCGGCTCGGGGCTGAAAGTGTCCGCGCGGGCGCCGGCTGGCCTGCA
CACACACA (SEQ ID NO: 37)
(Bait ID: FLT4_target_31.1)

| 8. Gene | Target | Bait genomic location |
|---|---|---|
| FLT4 | FLT4_target_31 | chr5: 180076396-180076515 |

Original sequence
GGCGGAGCGGTCTCAGCGCCCGCCCCAGGTGCGCGGTACCCCCTCCCCGGCCAGCC
CCACGCTCGGGCGGGTGGCCCGTTCGCCGCGCTCACCGTCCAGGAGTCCCAGGCAG
AGCCACAG(SEQ ID NO: 38)

Modified sequence
CACACACACATCTCAGCGCCCGCCCCAGGTGCGCGGTACCCCCTCCCCGGCCAGCCC
CACGCTCGGGCGGGTGGCCCGTTCGCCGCGCTCACCGTCCAGGAGTCCCAGGCCAC
ACACACA (SEQ ID NO: 39)
(Bait ID: FLT4_target_31.2)

| 9. Gene | Target | Bait genomic location |
|---|---|---|
| FLT4 | FLT4_target_31 | chr5: 180076420-180076539 |

Original sequence
CCAGGTGCGCGGTACCCCCTCCCCGGCCAGCCCCACGCTCGGGCGGGTGGCCCGTTC
GCCGCGCTCACCGTCCAGGAGTCCCAGGCAGAGCCACAGTCGCAGGCACAGCGCGG
CGCCCCG (SEQ ID NO: 40)

Modified sequence
CACACACACAGGTACCCCCTCCCCGGCCAGCCCCACGCTCGGGCGGGTGGCCCGTTC
GCCGCGCTCACCGTCCAGGAGTCCCAGGCAGAGCCACAGTCGCAGGCACAGCGCAC
ACACACA (SEQ ID NO: 41)
(Bait ID: FLT4_target_31.3)

| 10. Gene | Target | Bait genomic location |
|---|---|---|
| FLT4 | FLT4_target_31 | chr5: 180076468-180076587 |

Original sequence
GGCCCGTTCGCCGCGCTCACCGTCCAGGAGTCCCAGGCAGAGCCACAGTCGCAGGC
ACAGCGCGGCGCCCCGCTGCATCTCCGGCCGCTGCGCGTGGGTCCGACCCGAGCGG
CCGCGGCT(SEQ ID NO: 42)

Modified sequence
CACACACACACCGCGCTCACCGTCCAGGAGTCCCAGGCAGAGCCACAGTCGCAGGC
ACAGCGCGGCGCCCCGCTGCATCTCCGGCCGCTGCGCGTGGGTCCGACCCGAGCCA
CACACACA (SEQ ID NO: 43)
(Bait ID: FLT4_target_31.4)

| 11. Gene | Target | Bait genomic location |
|---|---|---|
| FLT4 | FLT4_target_31 | chr5: 180076444-180076563 |

Original sequence
GGCCAGCCCCACGCTCGGGCGGGTGGCCCGTTCGCCGCGCTCACCGTCCAGGAGTC
CCAGGCAGAGCCACAGTCGCAGGCACAGCGCGGCGCCCCGCTGCATCTCCGGCCGC
TGCGCGTG(SEQ ID NO: 44)

Modified sequence
CACACACACAACGCTCGGGCGGGTGGCCCGTTCGCCGCGCTCACCGTCCAGGAGTC
CCAGGCAGAGCCACAGTCGCAGGCACAGCGCGGCGCCCCGCTGCATCTCCGGCCCA
CACACACA (SEQ ID NO: 45)
(Bait ID: FLT4_target_31.5)

| 12. Gene | Target | Bait genomic location |
|---|---|---|
| FLT4 | FLT4_target_31 | chr5: 180076492-180076611 |

Original sequence
CAGGAGTCCCAGGCAGAGCCACAGTCGCAGGCACAGCGCGGCGCCCCGCTGCATCT

TABLE 8-continued

Exemplary Baits

```
CCGGCCGCTGCGCGTGGGTCCGACCCGAGCGGCCGCGGCTCGGGGCTGAAAGTGTC
CGCGCGGG(SEQ ID NO: 46)

Modified sequence
CACACACACAAGGCAGAGCCACAGTCGCAGGCACAGCGCGGCGCCCCGCTGCATCT
CCGGCCGCTGCGCGTGGGTCCGACCCGAGCGGCCGCGGCTCGGGGCTGAAAGTGCA
CACACACA (SEQ ID NO: 47)
(Bait ID: FLT4_target_31.6)
```

Example 8

A Bayesian Approach for Sensitive Detection of Somatic Genomic Alterations from Next-Generation Sequencing of Clinical Cancer Specimens The Bayesian approach described herein was implemented in the following examples.

Figure 2:
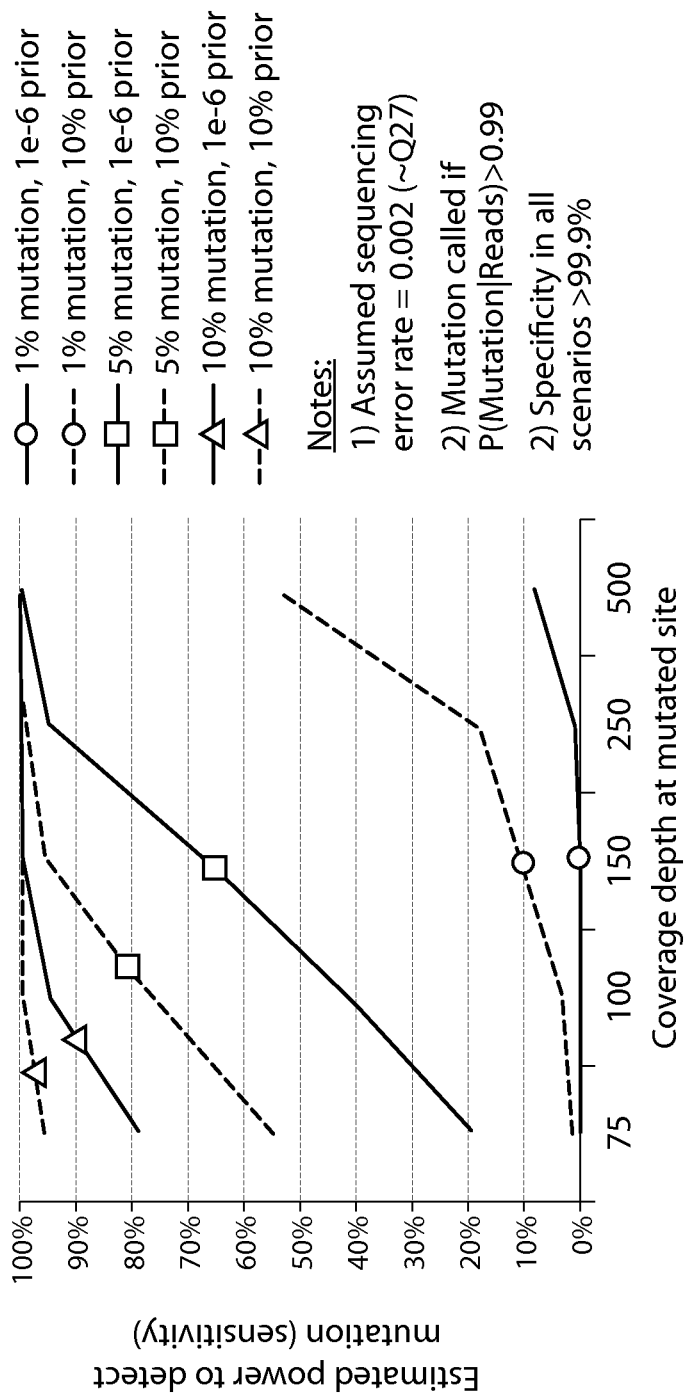
FIG. 2 depicts the impact of prior expectation and read depth on mutation detection.

The utility of this approach is illustrated by power calculations describing the impact of data-driven priors on substitution detection in the lower range of mutation frequencies relevant in the clinical setting. As shown in FIG. 2, the values of prior expectation (e.g., 1e-6 or 10% prior) and mutation frequency (e.g., 1%, 5%, or 15% mutation) correspond to the values described in (i) and (ii) of "A Bayesian Approach for Sensitive Detection of Somatic Genomic Alterations from Next-generation Sequencing of Clinical Cancer Specimens," respectively. FIG. 2 shows that incorporating prior expectations can improve detection power for rarer mutations, e.g., by reducing the required coverage depth at mutated sites, or increasing the estimated power (sensitivity) to detect mutations.

Example 9

A Bayesian Approach: Application to a Constructed Low Purity Multi-Clonal Sample To further demonstrate these benefits of the Bayesian approach disclosed herein, an artificial low-purity, multi-clonal "tumor" sample was constructed by equal admixture of DNA from 10 participants in the 1000 Genomes project, thereby creating a DNA pool containing a large number of sequence variants present at ~5% or 10% of the total DNA (arising from private heterozygous SNPs.) The mix was subjected to hybrid selection for exons of 182 cancer-related genes and sequenced on the Illumina HiSeq2000 platform, yielding an average coverage of approximately 350X across the gene panel. Each constituent sample was likewise processed individually to determine genotype at all SNP sites. Of the approximately 260~5% "mutations" present in the pool, 89% were detected with high-confidence using a prior of 1e-6, whereas 94% and 95% were detectable using a prior of 1% and 10% (average coverage of missed sites ~125x), respectively, supporting the theoretical conclusions above. Of the 102 10% "mutations" present in the pool, 98% were detected with high-confidence using a prior of 1e-6, whereas 99% and 99% were detectable using a prior of 1% and 10% (coverage of missed site 13x).

Example 10

A Bayesian Approach: Application to Lung and Colon Tumor Samples

Prior expectations of the frequency of relevant mutations in several cancer types from the COSMIC database (on the worldwide web at sanger.ac.uk/genetics/CGP/cosmic) were derived and analyzed more than 80 lung and colon cancer samples extracted from routine clinical specimens. Known mutations in more than 20 different genes were observed, including a 1% PIK3CA mutation p.H1047R in a colon cancer that could only be detected by incorporation of the 3% prior for this mutation in this cancer type. These results show that judicious incorporation of prior expectations around tumor type specific mutation spectra can be beneficial in translation of NGS-based tumor genome analysis to the clinical setting.

Example 11

A Bayesian Approach: Application to Breast Cancer Samples

Substitution mutation calling in exons of 182 cancer-related genes sequenced to ~260x for an FFPE breast cancer samples was performed. The number of sites with >2 copies of an alternate allele is 1,793. The number of sites with >99% posterior belief in presence of mutation is 402. The number of sites remaining after filters is 188, which is approximately the expected number of variant sites. The number of sites that are not in dbSNP is 14, which is approximately the expected number of sites not in dbSNP as dbSNP captures >90% of variation. The number of non-synonymous sites is 5. The number of sites in COSMIC is 2 (PIK3CA p.H1047R and P53 p.F113S).

Example 12

A Bayesian Approach: Detection of Infrequent Mutations

Figure 3:
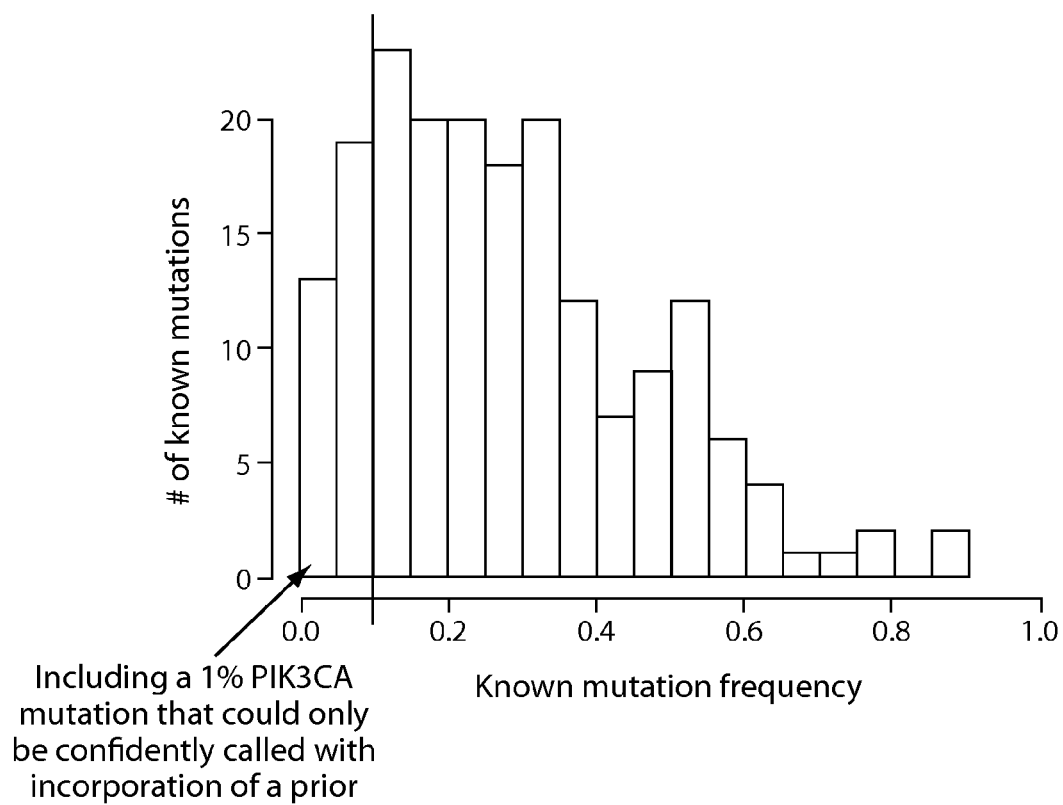
FIG. 3 depicts the mutation frequencies in more than 100 clinical cancer samples.

Many routine clinical specimens contain relevant rare mutations. FIG. 3 shows mutation frequencies in more than 100 clinical cancer samples. Samples were FFPE biopsies, surgical resections, or fine-needle aspirates of predominantly colon and lung cancers. The frequency spectrum of known mutations found in a series of clinical sample is show in Table 12.

TABLE 12

Frequency spectrum of known mutations found in a series of clinical samples
Frequency spectrum of known mutations found in a series of clinical samples

| Fraction of mutation < 5% | Fraction of mutation < 10% | Fraction of mutation < 25% | Fraction of mutation < 50% | Fraction of mutation < 100% |
|---|---|---|---|---|
| 7%* | 17% | 50% | 85% | 100% |

*likely underestimated

Example 13A

High Performance Solution-Based Target Selection Using Individually Synthesized Oligonucleotide Capture Probes The availability of solution-based genomic target selection techniques has enabled rapid development of targeted sequencing applications, some of which have led to the introduction of clinical sequencing tests. Commercialized hybridization capture reagents are based on array-synthesized oligonucleotides, which are converted to biotinylated DNA or RNA probes ("baits"). However, methods of generating these complex pools of probes face performance challenges, for example capturing high-GC content targets.

An alternative approach using individually synthesized, 5'-biotinylated oligonucleotides ("oligo-baits") for capturing a target region of ~130 kb representing 57 clinically relevant and actionable cancer-related genes is described herein. Indexed sequencing libraries selected using these oligo-baits with a 24-hour hybridization procedure yielded 5,000-fold target enrichment. 50M 49x49 paired-end reads generated an average target coverage of 2100x with a standard deviation of 568x (27%). All targets were covered successfully, with 99.95% of the targeted bases covered at >500x. Furthermore, the target coverage had virtually no GC-bias. Targets with GC content >70% averaged 1,975x coverage, and targets with GC content <35% averaged 1,996x coverage.

High performance was retained using even shorter hybridization times: 99.3% of targeted bases were covered at >500x after a 2.5 hour hybridization.

Use of SSPE (Salmon Sperm, PE)/Denhardt's outperformed hyb/wash buffers containing TEAC1, TMAC1, and/or dextran sulfate.

Oligo-baits can be spiked into array-derived bait pools to increase the coverage of otherwise difficult to capture (e.g., high % GC) regions, or to rapidly add new gene content. This approach offers a highly effective and scalable method for developing high performance targeted clinical sequencing tests.

Example 13B

Method of Optimizing Capture Baits

Three bait sets were tested. The results are summarized in FIG. 5. The bait sets were as follows:

Bait set #1 consists of 5'-biotinylated, individually synthesized DNA oligonucleotide baits only.

Bait set #2 includes biotinylated, array-derived RNA baits spiked with 5'-biotinylated, individually synthesized DNA oligonucleotide baits.

Bait set #3 consists of biotinylated, array-derived RNA baits only.

All 5'-biotinylated, individually synthesized DNA oligonucleotide were 120 bases with a 5' biotin.

Figure 5:
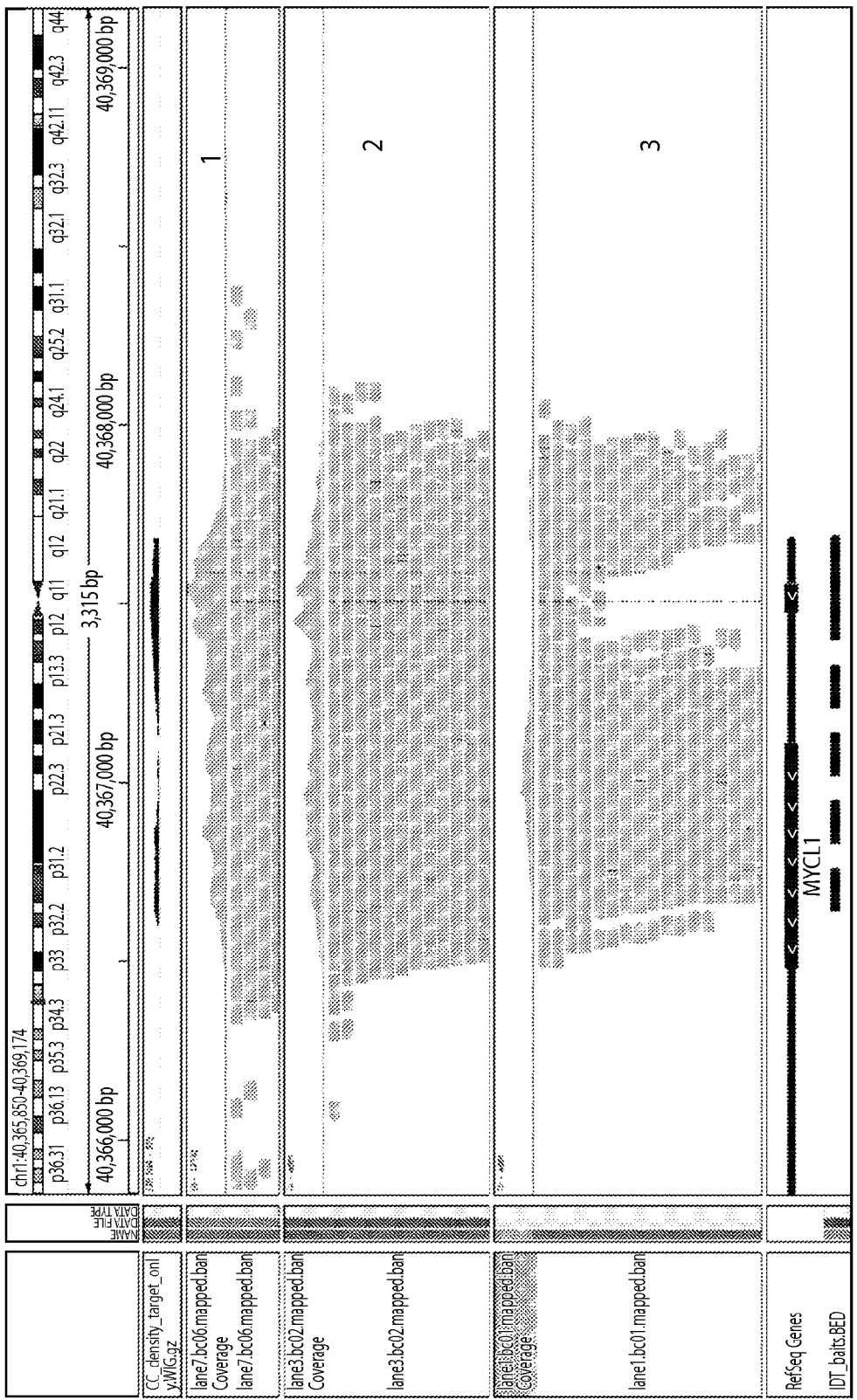
FIG. 5 is a coverage histogram comparing the uniformity in coverage detected with a bait set consisting of biotinylated, individually synthesized DNA oligonucleotide baits only (Bait set #1) and a bait set that includes biotinylated, array-derived RNA oligonucleotide baits spiked with biotinylated, individually synthesized DNA oligonucleotide baits ("Bait set #2"), compared to a bait set that includes biotinylated, array-derived RNA oligonucleotide baits only ("Bait set #3"). The bait sets are shown as #1, 2, and 3 in FIG. 5. Several gaps in coverage were detected using Bait set #3, but were not detected using Bait sets #1-2, as depicted in FIG. 5.

FIG. 5 is a coverage histogram comparing the uniformity in coverage detected with Bait set #1 and Bait set #2, compared to Bait set #3. The bait sets are shown as #1, 2, and 3 in FIG. 5. Several gaps in coverage were present using Bait set #3 corresponding to high % GC, whereas the corresponding regions were deeply covered using Bait sets #1 and #2, as depicted in FIG. 5. In FIG. 5, the left-hand panel labeled "GC_density_target . . . " indicates the local GC content within the target, The line represents 65% GC content, where any values above the line represent a higher GC content. As shown in the histogram, the coverage is the lowest for Bait set #3 in areas of high GC content. The bottom panel in FIG. 5 labeled "IDT_baits . . . " indicates the placement of the oligos covering the target shown.

Figure 4:
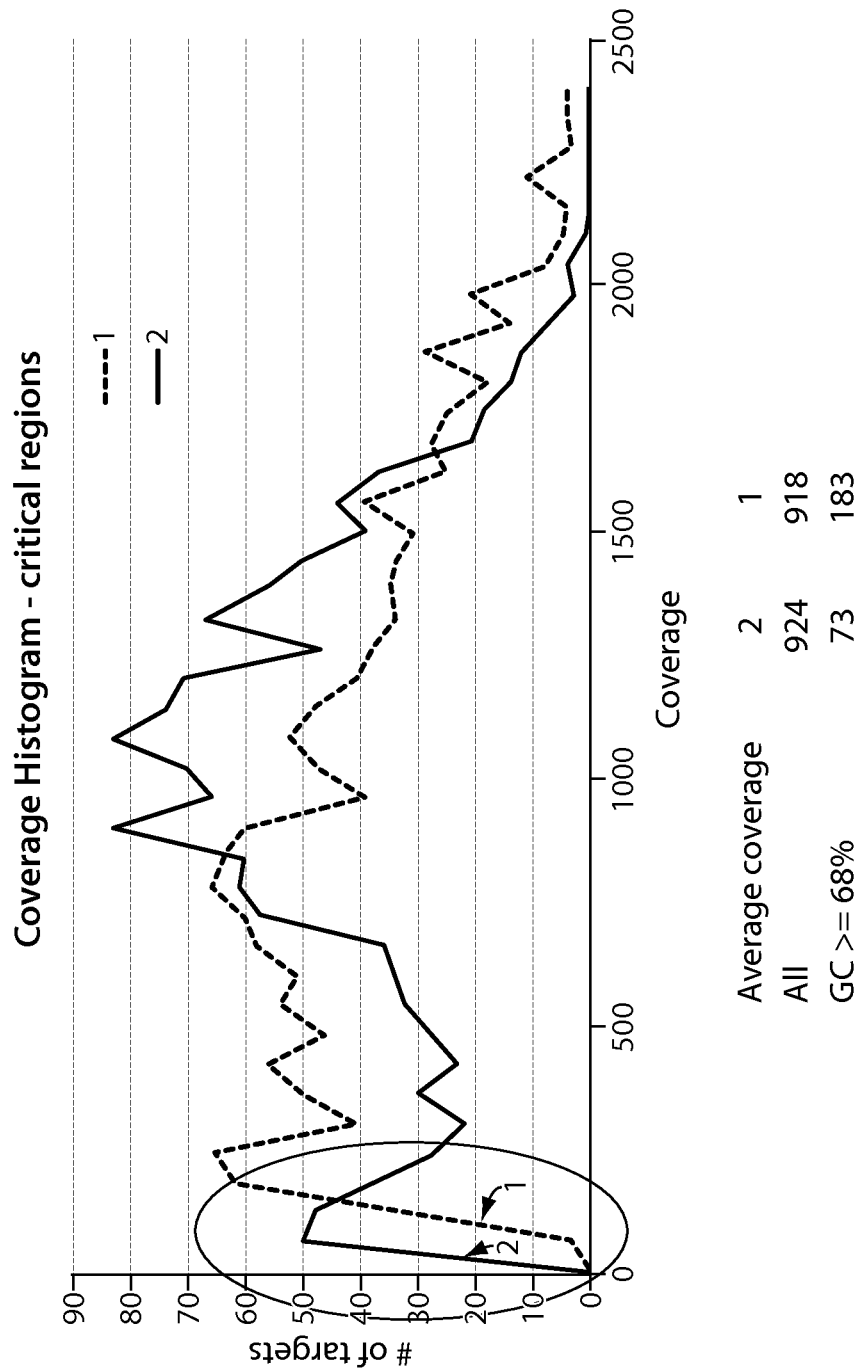
FIG. 4 is a linear representation of a coverage histogram. The number of targets (y-axis) are depicted as a function of coverage (x-axis). Line #1 represents the coverage using a bait set that includes biotinylated, array-derived RNA oligonucleotide baits spiked with biotinylated, individually synthesized DNA oligonucleotide baits (referred to herein as "Bait set #1"). Line #2 represents the coverage obtained using a bait set that includes biotinylated, array-derived RNA oligonucleotide baits only (referred to herein as "Bait set #2"). The overall average coverage using Bait set #2 was 924, whereas the coverage in areas of high GC content (about 68%) using Bait set #2 was 73. In contrast, when Bait set #1 was used, the overall coverage was about 918, but the coverage was improved to 183 in areas of high GC content.

A graphic representation of the changes in the number of targets and coverage using array-derived bait sets alone or spiked with individually-synthesised baits is depicted in FIG. 4. More specifically, FIG. 4 is a linear representation of a coverage histogram. The number of targets (y-axis) are depicted as a function of coverage (x-axis) Line #1 represents the coverage using a bait set that includes 5'-biotinylated, array-derived RNA oligonucleotide baits spiked with 5'-biotinylated, individually synthesized DNA oligonucleotide baits (referred to in FIG. 4 as "Bait set #1"). Line #2 represents the coverage obtained using a bait set that includes biotinylated, array-derived RNA oligonucleotide baits only (referred to in FIG. 4 as "Bait set #2"). The overall average coverage using Bait set #2 was 924, whereas the coverage in areas of high GC content (about 68%) using Bait set #2 was 73. In contrast, when Bait set #1 was used, the overall coverage was similar to Bait Set #1, about 918, but the coverage was improved to 183 in areas of high GC content.

Example 13C

Exemplary Experimental Conditions for Evaluating Bait Sets

Bait set A consists of 5'-biotinylated, individually synthesized DNA oligonucleotide baits only. The original set was 1000 oligos, covering 133 kb of target territory (referred to herein as "the large set," "Bait set A" or "DNA oligo baits").

For the "spike-in" experiments, the original 1000 DNA oligo set ("the large set") was added to a bait set consisting of biotinylated, array-derived RNA oligonucleotide baits (referred to in this example as "Bait set B" or "RNA baits"). Different ratios of DNA oligo baits from Bait set A were mixed with RNA baits from Bait set B. In particular, a DNA oligo bait:RNA bait ratio of 1:10 was used (10 ng total DNA oligo baits to 100 ng total RNA baits). Hybridization and washing conditions were matched to those that are most ideal for the RNA baits (the main difference being that the optimal wash temperature for RNA baits is ~70 C, whereas it is ~50 C for DNA oligo baits).

With low tiling densities, strong periodicities in coverage were detected when using DNA oligo baits that corresponded to bait placement. In addition, low tiling densities may make capturing of alleles with in/dels more difficult. Therefore, bait sets were designed for MAP3K1 with the different tiling densities depicted in Table 13. In the below mixes, Mix 1 containing 5'-biotinylated, individually synthesized DNA oligo baits designed to capture the exons of six cancer-relevant genes (DAXX, TRRAP, CREBBP, GRIN2A, SPOP, GNA11) were spiked into the array-derived RNA oligonucleotide baits only (Bait set B). DAXX, TRRAP, CREBBP, GRIN2A, and SPOP were not present in the RNA bait set. Mixes 2-4 were spiked into Bait Set A (the large set of DNA oligo baits) to test different tiling densities (with Mix 2 being the densest) of capture baits for the exons of MAP3K1. The RNA bait set alone covered about 1 MB of sequence.

TABLE 13

Mixes for methods using capture probes

| Category | Number |
|---|---|
| Mix 1 | 369 oligos to melanoma genes |
| Mix 2 | 91 oligos tiling density of 60 to MAP3K1 |
| Mix 3 | 57 oligos tiling density of 100 to MAP3K1 |
| Mix 4 | 40 oligos tiling density of 150 to MAP3K1 |
| Mix 5 | 3 oligos to STK11 exon 3 |

Input into capture was 2 μg of pooled cell-line DNA libraries. 2 μg library was mixed with blocking mix (Table 14), dried down, and resuspended in 9 μl water. This mixture was then put in a plate, transferred to a cycler, and run at 98° C. for 5 minutes, followed by 68° C. for 2 minutes. The plate was then unsealed, and 11 μL DNA bait/hyb buffer mixture @ 68° C. was added. The DNA bait/hyb mixture at 68° C.=10 μL hyb buffer+1 μL bait (containing 10 ng, 50 ng, or 100 ng bait).

For captures with DNA baits alone (e.g. Bait set A), hybridization was performed at 68° C., and washes were performed at 50° C. Baits were tested at 5 ng, 10 ng, 100 ng, 1000 ng, and 2000 ng (per 2 ug input library). For 24 hr. hybs, the 5-10 ng conditions were ideal, and the 100 ng conditions were also acceptable. For 2.5 hour hybridizations, 100 ng worked best.

For captures with the large DNA bait set (100 kb) spiked into the RNA-array bait set (B) to rescue poor performing/high GC regions, hybridization was performed at 68° C., and washes were performed at 70° C. Bait sets were tested at 1:10 DNA oligo: RNA baits (i.e., 10 ng total mass of oligo baits, and 100 ng total mass of RNA baits).

For captures with the small, gene focused DNA bait set spiked into the RNA bait set, hybridization was performed at 68° C., and a range of wash temperatures were tested (62° C., 64° C., 66° C., 68° C., 70° C., and 72° C.).

Mix 1 (adding 6 new genes) was tested at the following ratios: 1:5, 1:10 and 1:20 total oligo DNA bait mass: RNA bait mass (i.e., 20 ng:100 ng, 10 ng:100 ng, and 5 ng:100 ng).

Mix 5 (3 oligos representing exon 3 of STK11 to path low coverage) was tested at 1:500, 1:1000, and 1:2000 DNA oligo:RNA oligo. 100 ng of total RNA baits were used. STK11 was tested as it represents an important cancer target with poor detection performance when captured with the RNA baits alone. DNA oligo spiking of exon 3 of STK11 boosts coverage from an average of 70X to 300X.

TABLE 14

Buffers for methods using capture probes

| Baits (pooled IDT oligos) | 39600 (g/mol) | 100 nmol = | 0.0039600 grams = 396000 nanograms |
|---|---|---|---|
| Resuspended in low TE | 25 mL | 250 uL Tris 5 uL EDTA | |

| Blocking Mix | [Stock] | [Working] | 14.5 ul/rxn |
|---|---|---|---|
| Cot1 | 1 ug/ul | 1 ug/ul | 10 |
| SalmonSperm | 10 ug/ul | 10.0 ug/ul | 1 |
| PE 1.0 | 800 uM | 800 uM | 1.75 |
| Universal Index | 800 uM | 800 uM | 1.75 |

| 2X Hyb Buffer | [Stock] | [Final] | in 10 ml (10 ul/rxn) |
|---|---|---|---|
| SSPE | 20X | 10X | 5 ml |
| Denhardt's | 50X | 10X | 2 ml |
| EDTA | 0.5M | 0.01M | 200 ul |
| SDS | 10% | 0.20% | 200 ul |
| Water | | | 2.6 ml |

TABLE 14-continued

Buffers for methods using capture probes

| Bead Wash | [Stock] | [Final] | in 50 ml (200 ul/wash) |
|---|---|---|---|
| NaCl | 5M | 1M | 10 ml |
| Tris | 1M | 10 mM | 500 ul |
| EDTA | 0.5M | 1 mM | 100 ul |
| Water | | | 39.4 ml |

| Wash Buffer1 | [Stock] | [Final] | in 50 ml (150 ul/wash) |
|---|---|---|---|
| SSC | 20X | 1X | 2.5 ml |
| SDS | 10% | 0.10% | 500 ul |
| Water | | | 47 ml |

| Wash Buffer2 | [Stock] | [Final] | in 50 ml (150 ul/wash) |
|---|---|---|---|
| SSC | 20X | 0.1X | 250 ul |
| SDS | 10% | 0.10% | 500 ul |
| Water | | | 49.25 ml |

Example 14

Routine, Ultra-Deep Sequencing For Sensitive Tumor Profiling Using Low Inputs of DNA Derived from Formalin Fixed Tissue The wide adoption of high-throughput DNA sequencing technologies has facilitated rapid advances in cancer genomics. However, the standard of care in genomic cancer diagnostics still involves testing focused on individual genes and specific mutations. As the number of clinically actionable mutations grows, this single mutation per test paradigm becomes unfeasible, particularly when tissue specimens are limiting as is generally the case with biopsies. To address the clinical need for comprehensive genomic profiling of tumor samples, we have developed a clinical test that delivers massively parallel sequence data for 200+ cancer-related genes. Furthermore, this test was shown to be clinically relevant, producing ultra-deep sequencing data from formalin-fixed paraffin-embedded (FFPE) tissue samples with DNA inputs as low as 50 ng, and from samples as old as eleven years.

To evaluate this test's performance on a wide variety of samples, DNA was isolated from 96 FFPE specimens from an aged-block set, which included 12 tumor/normal pairs from each of breast, colon, lung, and renal tissues evenly distributed for each tissue over the following ages: 1, 3, 5, 7, 9 and 11-years old. 200 ng and/or 50 ng of input DNA was used to construct indexed sequencing libraries, which were then enriched for 200+ cancer-related genes using a solution-based hybrid capture method and sequenced on an Illumina HiSeq™ 2000 platform.

For the 76 samples yielding at least 200 ng of DNA for library construction, sequencing coverage averaged 1,000x after removal of PCR duplicates, with >95% of the samples yielding a median coverage of >350x. For samples where 50 ng was used for library construction, the coverage averaged 450x. Sequencing performance was consistent across all sample tissue types and ages. Such ultra-deep sequencing enables high confidence detection of mutations present at frequencies as low as 5-10%.

Example 15

Profiling the Tumor Genome Using Circulating Tumor Cells

Circulating tumor cells (CTC) provide a unique opportunity to sample human malignancies in a minimally invasive, serial fashion. Use of CTC for molecular characterization of cancer genomes presents two key challenges. First, CTC must be efficiently isolated from blood, where they may be outnumbered $10^7$-fold by non-tumor cells. Second, the limited number of tumor genomes present in a CTC sample must be captured in accessible form while minimizing loss of material and introduction of bias.

Previous CTC genetic analyses have used allele-specific PCR; these methods permit detection of very low copy numbers of specific mutations in >$10^4$-fold background of wild-type sequences. While addressing the dual challenges of CTC abundance and capture efficiency, this approach is intrinsically limited to narrow characterizations of select, prespecified variants. To bring molecular CTC analysis into the genomic era, we have coupled a microfluidic rare-cell capture system that allows recovery of CTC with a background of only hundreds, rather than tens of thousands, of white blood cells, with a next-generation platform enabling deep resequencing of more than 200 cancer-associated genes from a single CTC sample.

Using complex mixtures of up to ten cancer cell lines, sensitive mutation detection (~94% for alleles ≥10% abundance) from as few as 100 total cells, while largely preserving allele frequencies ($R^2$~0.90). By recapturing cultured cells spiked into whole blood, multi-gene mutation profiles from specimens containing as few as ten cancer cells were obtained. This level of sensitivity places the majority of clinical CTC samples within reach of NGS analysis. In a series of blood samples from breast cancer patients, potential CTC heterogeneity was investigated by comparing frequency of Her2Neu positive cells with the relative abundance of somatic mutation positive DNA.

Example 16

Detection of Cancer-Associated Mutations, Translocations and Changes in Gene Expression through Integration of Targeted DNA and RNA Deep Sequencing of FFPE Tumor Samples Broad application of personalized therapy to cancer requires comprehensive, sensitive and timely characterization of the diverse aberrations present in the genome and transcriptome of a tumor. The RNA and DNA from most clinical cancer samples, commonly stored as formalin fixed paraffin embedded (FFPE) blocks, are of poor quality and have been difficult to use for molecular profiling. Emerging next-generation DNA sequencing assays work well with damaged DNA and are sufficiently sensitive to detect many types of genomic aberrations. Currently, there is no comparableRNA sequencing protocol for comprehensive analysis of the transcriptome from FFPE tumor samples.

Results:

An FFPE-compatible targeted RNA sequencing and analysis method for sensitive detection of mutations, rearrangements and expression changes in over 200 cancer-associated genes was developed. Protocols were validated on cell line RNA and used to study over 50 FFPE non-small cell lung cancer (NSCLC) tumors. Known mutations and gene fusions (e.g. BCR-ABL1) were detected in cell lines. Technical reproducibility in digital expression profiling exceeded $R^2$=0.99 and >0.9 for cell lines and FFPE RNA, respectively. As expected in cancer genomes, RNA-seq provided evidence of aberrations in the genome including point mutations and novel rearrangements involving known oncogenes. Highly significant differential expression of oncogenes including EGFR, FGFR3, CDH5, KIT and RET was revealed, ranging from 2.5- to 70-fold across different tumors. Combination of RNA and DNA sequencing data on identical FFPE samples corroborated functional consequences of genomic alterations; examples included expression of mutated TP53 alleles and reduced STK11 expression in a tumor which exhibited loss-of-heterozygosity at the DNA level. Application of next generation sequencing technologies to FFPE RNA and integration with extant DNA sequencing methods is anticipated to expand understanding of clinically relevant cancer biology and improve patient care.

Methods:

RNA is extracted from FFPE tissue sections, typically 1 or 2 10 µm curls, using the Roche High Pure Paraffin Kit according to the manufacturer's instructions. Extracted RNA is stored @-80° C. RNA yield and quality is assessed by RiboGreen (Invitrogen) and a Bioanalyzer RNA Pico Chip (Agilent), respectively, according to the manufacturer's instructions. Typical yields are between 500 ng and 2 µg with a RIN score of less than 4.

The first strand of complimentary DNA (cDNA) is produced from between 100 and 600 ng of FFPE RNA in a 20 µL reaction using SuperScript 111 (Invitrogen) according to the manufactuter's protocol, with 550 pmols of random hexamer as primer. Second strand synthesis, to generate a fully double-stranded cDNA, is performed immediately after first strand synthesis by addition of 60 µL of a NEBNext Second Strand Synthesis Module (New England Biolabs) master-mix and incubation for 150 minutes at 16° C. according to the manufacturer's protocol. The quality and yield of double-stranded cDNA can be assessed using PicoGreen (Invitrogen) and a Bioanalyzer High Sensitivity Chip (Agilent), respectively. Generally, the entire cDNA synthesis yield is used as input to the standard FMI library construction protocol.

Construction of a paired-end compatible sequencing library and subsequent hybrid selection and sequencing of cDNA generated from FFPE RNA is performed using similar protocols as for FFPE DNA described herein, but starting directly at the End Repair step since the highly fragmented nature of FFPE RNA obviates the need for shearing.

Analysis of sequencing data from FFPE RNA can be performed using methods known in the art. For example, analysis of sequencing data from FFPE RNA can be performed by mapping all of the read pairs to a reference genome sequence (hg19) and/or a reference transcriptome (all of the sequences of known transcripts, e.g. RefSeq). Mapped reads are then used to identify gene fusion, mutations in gene sequences, alternative splicing, and to quantify gene expression as described in the literature, e.g., by Berger et al. (2010) Genome Res. 20(4):413-27 (PMID 20179022) and Garber et al. (2011) Nat. Methods. 8(6):469-77 (PMID 21623353). As demonstrated by Levin et al. (2009) Genome Biol. 10(10): R115 (PMID 19835606), targeted RNA-seq can be employed to improve mutation detection and fusion discovery in a selected set of genes, and preserves quantitative information for expression profiling.

Example 17

Sensitive and Accurate Mutation Calling by Ultra-Deep Sequencing of Clinical Tumor Samples Rapid advancement in the understanding of cancer genomics and the growing number of available targeted therapies provide expanding opportunities for effective cancer treatment based on comprehensive tumor profiling. Although significant progress has been made in experimental and computational approaches for analyzing tumor genomes by next-generation sequencing in the research setting, extending these techniques to the clinic poses significant additional challenges. Key among these is the limited purity and heterogeneity of clinical specimens, coupled with the requirement to provide high sensitivity and accuracy for a wide range of potentially clinically-actionable mutations.

To address this challenge we have developed a clinical test that is capable of generating ultra-deep sequence data (>700x) for 200+cancer-related genes from routine FFPE tumor samples, and computational tools that are capable of exploiting this depth to provide high levels of sensitivity and accuracy for different types of mutations present at low fractions. Our analytical pipeline detects short variants in mapped sequence data accounting for known mutation frequencies, and combines breakpoint detection and local assembly to identify larger insertions and deletions, which are often missed by alternative methods. In addition, copy-number alterations and rearrangements involving key cancer genes are identified.

To validate the analytical performance of our newly-developed methods we designed and implemented an extensive study of sample mixtures as a model for rare events in heterogeneous DNA, including 20 normal HapMap cell-lines and 28 individually characterized cancer cell-lines. We report 100% sensitivity for substitutions and >90% sensitivity for indels of length 1-50 bp present in >10% of a mixture, both with PPV>99%. Application of our test to a cohort of 227 melanoma, prostate, breast, colon, and lung tumor samples revealed 427 known and likely somatic driver mutations, 40% of which were present at sample fractions below 20% and 18% below 10%, underlining the importance of sensitive mutation calling Example 18

Detection of Cancer Mutations at Surgical Margins

It has been discovered that even when the tissue at the margins of a tumor is histologically normal, cancer-associated mutations can be detected. Tissue samples associated with a hyperplastic colonic polyp were purchased as triads from BioServe (Beltsville, Md.). The Triads included genomic DNA from peripheral blood leukocytes, normal tissue FFPE (Formalin-Fixed Paraffin-Embedded), and tumor tissue FFPE.

For example, in 6 sections tested incrementally from a normal colon sample isolated from the margins of a hyperplastic colonic polyp, no has mutation was observed in the most distal section from the polyp (section 1). A KRAS p.G13D mutation was observed in 1% of cells from the second most distal section (section 2), in 2% of the cells in the third most distal section (section 3), in 3% of the cells in the fourth most distal section (section 4), in 4% of the cells in the fifth most distal section (section 5), and in 5% of the cells in the section closest to the polyp (section 6). The mutation was observed in 6% of cells isolated from a section from the edge of the polyp.

H&E staining of tissue samples from sections 1, 3 and 5 confirmed no histological evidence of cancer tissue. H&E staining of tissue from section 6 confirmed the presence of the polyp.

Tumor heterogeneity was detected in sections from invasive moderately-differentiated adenocarcinoma from distal rectum. In particular, the sections 1-6 tested incrementally included the following mutations: BRAF p.V600E, TP53 p.R213X, BRCA1c.2105delG, APC c.5541insG and APC c.6463delA, respectively.

The results of these experiments indicated that genetic testing of tissue at the surgical margins is more sensitive to detection of cancerous or pre-cancerous tissues. Thus, by performing genetic testing of tissues at the surgical margins, such as by the sequencing methods described herein, medical personnel can make more informed recommendations regarding the course of further therapy. For example, depending on the results of the genetic testing, a recommendation for further therapy or no further therapy can be made. Further therapy can include, for example, chemotherapy or radiation, or both, or in the case of chemotherapy, a particular drug or combination of drugs, or a particular dosing regimen, based on mutations identified by the genetic testing.

Incorporation By Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm nih.gov.

Equivalents

Those skilled in the art will recognize, or be able to ascertain using no more than routine experimentation, many equivalents to the specific embodiments of the invention described herein. Such equivalents are intended to be encompassed by the following claims

What is claimed is:

1. A method of analyzing a tumor sample for a somatic mutation, comprising:
   (a) acquiring a library comprising a plurality of tumor members from the tumor sample;
   (b) contacting the library with at least two bait sets to provide selected tumor members, wherein said bait sets hydridize with the tumor members, thereby providing a library catch;
   (c) sequencing by a next generation sequencing method a subgenomic interval comprising the somatic mutation from a tumor member from said library or library catch, thereby acquiring a read for the subgenomic interval;
   (d) aligning said read by an alignment method; and
   (e) assigning a nucleotide value from said read for a preselected nucleotide position, thereby analyzing said tumor sample,
wherein the at least two bait sets of step (b) are chosen from two of the following bait sets:
   (i) a first bait set that selects a high-level target chosen from one or more tumor nucleic acid molecules that comprise a subgenomic interval comprising a somatic mutation that appears at a frequency of about 5% or less of the cells from the tumor sample;
   (ii) a second bait set that selects a mid-level target chosen from one or more tumor nucleic acid molecules that comprise a subgenomic interval comprising a somatic mutation that appears at a frequency of about 10% or higher of the cells from the tumor sample;
   (iii) a third bait set that selects a low-level target chosen from one or more nucleic acid molecules that comprise a subgenomic interval chosen from one or more of:
      a) a pharmacogenomic (PGx) single nucleotide polymorphism (SNP) that distinguishes the ability of a patient to metabolize different drugs,
      b) a plurality of genomic SNPs that uniquely identify (fingerprint) a patient, or
      c) a genomic SNP or locus that is used to assess copy number gains or losses of genomic DNA and loss-of-heterozygosity (LOH);
   (iv) a fourth bait set that selects a nucleic acid molecule that comprises an intron sequence that detects a structural breakpoint; or
   (v) a fifth bait set that selects a one-copy deletion of several terminal exons, wherein each bait set of said plurality has a unique preselected efficiency for selection for its target as compared with the other bait sets in the plurality.

2. The method of claim 1, wherein the efficiency for selection in step (b) is modified by one or more of:
   (i) differential representation of different bait sets;
   (ii) differential overlap of bait subsets;
   (iii) differential bait parameters;
   (iv) mixing of different bait sets at different molar ratios to enhance or reduce relative target coverage depths;
   (v) using different types of oligonucleotide baits.

3. The method of claim 2, wherein different types of oligonucleotide baits are chosen from one or more of:
   (a) one or more chemically (non-enzymatically) individually synthesized baits,
   (b) one or more baits synthesized in an array,
   (c) one or more in vitro transcribed baits,
   (d) any combination of (a), (b) or (c),
   (e) one or more naturally or non-naturally occurring DNA oligonucleotides,
   (f) one or more naturally or non-naturally occurring RNA oligonucleotides,
   (g) a combination of (e) and (f), or
   (h) a combination of any of the above.

4. The method of claim 3, wherein the different types of oligonucleotide baits are mixed at a ratio chosen from 1:1, 1:2, 1:3, 1:4, 1:5, 1:10, 1:20, 1:50; 1:100, or 1:1000.

5. The method of claim 4, wherein the ratio of chemically individually synthesized baits to the baits synthesized in an array is chosen from 1:5, 1:10, or 1:20.

6. The method of claim 3, wherein the non-naturally occurring DNA or RNA oligonucleotides are chosen from one or more of: a locked nucleic acid (LNA); a peptide nucleic acid (PNA); a DNA or RNA oligonucleotide modified to capture low GC regions; a bicyclic nucleic acid (BNA); a crosslinked oligonucleotide; a modified 5-methyl deoxycytidine; or 2,6-diaminopurine.

7. The method of claim 2, wherein one or more of the following bait parameters are modified:
   (i) increasing or decreasing bait representation or overlap to enhance or reduce coverage of tumor members, which are under or over-covered relative to other targets in the same category;
   (ii) for low coverage, hard to capture target sequences comprising high GC content sequences, targeting with the bait sets covering adjacent sequences;
   (iii) modifying a bait sequence to reduce secondary structure of the bait and enhance its efficiency of selection;
   (iv) modifying a bait length to equalize melting hybridization kinetics of different baits within the same category;

(v) modifying baits of different orientation for the same target region forward and reverse strand, to have different binding efficiencies;

(vi) modifying the amount of a binding entity present on each that affects its binding efficiency;

(vii) modifying the type of nucleotide used for different baits to affect binding affinity to the target, and enhance or reduce the relative target coverage; or (viii) using modified oligonucleotide baits having more stable base pairing, to equalize melting hybridization kinetics between areas of low or normal GC content relative to high GC content.

8. The method of claim 1, wherein the bait sets are chosen from two or more of:

A. a bait set that selects an exon sequence that comprises a single nucleotide alteration associated with a cancerous phenotype;

B. a bait set that selects an in-frame deletion of 1 or more codons from a reference nucleotide sequence;

C. a bait set that selects an intragenic deletion;

D. a bait set that selects an intragenic insertion;

E. a bait set that selects a deletion of a full gene;

F. a bait set that selects an inversion;

G. a bait set that selects an interchromosal translocation;

H. a bait set that selects a tandem duplication;

I. a bait set that selects a nucleotide sequence of interest flanked by adjacent non-repetitive sequences;

J. a bait set that selects one or more subgenomic intervals corresponding to a fusion sequence;

K. a bait set that selects a subgenomic interval adjacent to a nucleotide sequence that includes an undesirable feature chosen from a nucleotide sequence of high GC content, or a nucleotide sequence comprising repeated elements, inverted repeats, or both;

L. a bait set that selects a genomic rearrangement that comprises an intron sequence; or M. a bait set that selects a subgenomic interval that comprises an exon adjacent to a cancer associated gene fusion.

9. The method of claim 1, wherein the subgenomic interval comprises or consists of one or more of: a single nucleotide position; an intragenic region or an intergenic region; an exon or an intron, or a fragment thereof; a coding region or a non-coding region; a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; a point or a single mutation; a deletion mutation; an in-frame deletion, an intragenic deletion, a full gene deletion; an insertion mutation; an intragenic insertion; an inversion mutation; an intrachromosomal inversion; a linking mutation; a linked insertion mutation; an inverted duplication mutation; a tandem duplication; an intrachromosomal tandem duplication; a translocation; a chromosomal translocation, a non-reciprocal translocation; a rearrangement; a genomic rearrangement; a rearrangement of one or more introns, or a fragment thereof; a rearranged intron; a 5'- or a 3'-UTR, or a combination thereof.

10. The method of claim 1, wherein the subgenomic interval comprises an altered nucleotide sequence, encodes an altered amino acid sequence, a chromosomal translocation, an intra-chromosomal inversion, a change in copy number, a change in expression level, a change in protein level, a change in protein activity, or a change in methylation status, in a cancer tissue or cancer cell, as compared to a normal, healthy tissue or cell.

11. The method of claim 1, wherein the tumor sample comprises: one or more premalignant or malignant cells; cells from a solid tumor, a soft tissue tumor or a metastatic lesion; tissue or cells from a surgical margin; a histologically normal tissue; one or more circulating tumor cells (CTC); a normal adjacent tissue (NAT); a blood sample from the same subject having or at risk of having the tumor; or an FFPE-sample.

12. The method of claim 1, wherein the methods comprises sequencing of a cDNA derived from an RNA acquired from the tumor sample.

13. The method of claim 12, further comprising a step chosen from one or more of: detecting a change in the level of a gene or gene product comprising the somatic mutation, enriching a sample for a target RNA, or depleting the sample of certain high abundance RNAs.

14. The method of claim 1, further comprising one or more of:

(i) fingerprinting the tumor sample;

(ii) quantifying the abundance of a gene or gene product;

(iii) quantifying the relative abundance of a transcript in the tumor sample;

(iv) identifying the tumor sample as belonging to a particular subject;

(v) identifying a genetic trait in the tumor sample comprising one or more of a subject's genetic make-up, ethnicity, race, or familial traits;

(vi) determining the ploidy in the tumor sample;

(vii) determining a loss of heterozygosity in the tumor sample;

(viii) determining the presence or absence of a gene duplication event in the tumor sample;

(ix) determining the presence or absence of a gene amplification event in the tumor sample; or (x) determining the level of tumor/normal cellular admixture in the tumor sample.

15. The method of claim 1, wherein the method comprises sequencing a subgenomic interval chosen from at least 1, 2, 3, 4, 5, 6, 7, 8, 9, 10, 11, 12, 13 or all of the following:

A) at least five, six, seven, eight, nine, ten, fifteen, twenty, twenty-five, thirty or more subgenomic intervals from a mutated or wild-type gene or gene product chosen from at least five or more of: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53;

B) at least five, six, seven, eight, nine, ten, fifteen, twenty, twenty-five, thirty, thirty-five, forty, forty-five, fifty, fifty-five, sixty, sixty-five, seventy, seventy-five, eighty, eighty-five, ninety, ninety-five, one hundred, one hundred and five, one hundred and ten, one hundred and fifteen, one hundred and twenty or more of subgenomic intervals from a mutated or wild type gene or gene product chosen from at least five or more of: ABL2, ARAF, ARFRP1, ARID1A, ATM, ATR, AURKA, AURKB, BAP1, BCL2, BCL2A1, BCL2L1, BCL2L2, BCL6, BRCA1, BRCA2, CBL, CARD11, CBL, CCND2, CCND3, CCNE1, CD79A, CD79B, CDH1, CDH2, CDH20, CDH5, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, INHBA, IRS2, JAK1, JAK3, JUN, KDM6A, KDR, LRP1B, LRP6, LTK, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK2, PAK3, PAX5, PDGFRB, PKHD1, PLCG1, PRKDC, PTPN11, PTPRD, RAF1, RARA, RICTOR, RPTOR, RUNX1, SMAD2, SMAD3, SMAD4, SMARCA4, SMARCB1, SOX10, SOX2, SRC, TBX22, TET2, TGFBR2, TMPRSS2, TNFAIP3, TNK, TNKS2, TOP1, TSC1, TSC2, USP9X, VHL, or WT1;

C) at least five, six, seven, eight, nine, ten, fifteen, twenty, or more subgenomic intervals from a gene or gene product according to Table 1, 1A, 2, 3, or 4;

D) at least five, six, seven, eight, nine, ten, fifteen, twenty, or more subgenomic intervals from a gene or gene product chosen from one or more of: ABL1, AKT1, ALK, AR, BRAF, BRCA1, BRCA2, CEBPA, EGFR, ERBB2, FLT3, JAK2, KIT, KRAS, MET, NPM1, PDGFRA, PIK3CA, RARA, AKT2, AKT3, MAP2K4, NOTCH1, or TP53;

E) at least five, six, seven, eight, nine, ten, or more subgenomic intervals including a mutated or a wild type codon chosen from one or more of: codon 315 of the ABL1 gene; codon 1114, 1338, 1450 or 1556 of APC; codon 600 of BRAF; codon 32, 33, 34, 37, 41 or 45 of CTNNB1; codon 719, 746-750, 768, 790, 858 or 861 of EGFR; codon 835 of FLT3; codon 12, 13, or 61 of HRAS; codon 617 of JAK2; codon 816 of KIT; codon 12, 13, or 61 of KRAS; codon 88, 542, 545, 546, 1047, or 1049 of PIK3CA; codon 130, 173, 233, or 267 of PTEN; codon 918 of RET; or codon 175, 245, 248, 273, or 306 of TP53;

F) at least five, six, seven, eight, nine, ten, fifteen, twenty, twenty-five, thirty, or more subgenomic intervals from a mutated or wild type gene or gene product chosen from: ABCB1,BCC2, ABCC4, ABCG2, C1orf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, or UMPS;

G) at least five, six, seven, eight, nine, ten, fifteen, twenty, twenty-five, thirty, or more subgenomic intervals from a mutated or wild type PGx gene or gene product associated with one or more of: (i) better survival of a cancer patient treated with a drug; (ii) paclitaxel metabolism; (iii) toxicity to a drug; or (iv) a side effect to a drug;

H) a translocation alteration of at least 5, 10, 15, 20, 25, 30, 35, 40, 45, 50, 75, 110 or more genes or gene products according to Table 3;

I) a translocation alteration of at least 5, 10, 15, 20, 25, 30, 35, 40, 45, 50, 75, 110 or more genes or gene products according to Table 3 in a solid tumor sample from the cancer types specified therein;

J) a translocation alteration of at least 5, 10, 15, 20, 25, 30, 35, 40, 45, 50, 75, 100, 150, 200 or more genes or gene products according to Table 4;

K) a translocation alteration of at least 5, 10, 15, 20, 25, 30, 35, 40, 45, 50, 75, 100, 150, 200 or more genes or gene products according to Table 4 in a heme tumor sample from the cancer types specified therein;

L) at least five genes or gene products selected from the genes in any of Table 1, 1A, 2, 3, or 4, wherein an allelic variation is associated with a preselected type of tumor and wherein said allelic variation is present in less than 5% of the cells in said tumor type;

M) at least five genes or gene products selected from the genes in any of Table 1, 1A, 2, 3, or 4, which are embedded in a GC-rich region; or N) at least five genes or gene products indicative of a genetic factor for developing cancer chosen from one or more of BRCA1, BRCA2, EGFR, HRAS, KIT, MPL, ALK, PTEN, RET, APC, CDKN2A, MLH1, MSH2, MSH6, NF1, NF2, RB1, TP53, VHL, or WT1.

16. A method of claim 1, wherein the method comprises sequencing a subgenomic interval from at least twenty, twenty-five, thirty or more genes or gene products from the sample, wherein the genes or gene products are chosen from: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11,SUFU, or TP53.

17. The method of claim 15, wherein the method further comprises providing a report in electronic, web-based, or paper form, to a patient or to another person or entity, a caregiver, a physician, an oncologist, a hospital, clinic, third-party payor, insurance company or government office.

18. The method of claim 17, wherein said report comprises one or more of:
(a) output from the method, comprising the identification of nucleotide values, the indication of the presence or absence of an alteration, mutation, or wild-type sequence for sugenomic intervals associated with a tumor of the type of the sample;
(b) information on the role of a sequence, an alteration, mutation, or wild-type sequence, in a disease, wherein said information comprises information on prognosis, resistance, or potential or suggested therapeutic options;
(c) information on the likely effectiveness of a therapeutic option, the acceptability of a therapeutic option, or the advisability of applying the therapeutic option to a patient having a sequence, alteration or mutation identified in the report;
(d) information, or a recommendation on, the administration of a drug, the administration at a preselected dosage or in a preselected treatment regimen, in combination with other drugs, to the patient;
(e) wherein not all mutations identified in the method are identified in the report, the report can be limited to mutations in genes having a preselected level of correlation with the occurrence, prognosis, stage, or suseptability of the cancer to treatment, with a preselected therapeutic option; or
(f) is provided to the patient or to another person or entity within 7, 14, or 21 from receipt of the sample by the entity practicing the method.

19. The method of claim 1, wherein a nucleotide value assigned for a nucleotide position in each of X unique subgenomic intervals is assigned by a unique calling method and X is at least 2, and wherein unique subgenomic interval means different from the other X−1 subgenomic intervals, and wherein unique calling method means different from the other X−1 calling methods.

20. The method of claim 19, wherein:
(i) assigning said nucleotide value is a function of a value which is or represents a prior expectation of observing said read showing a preselected variant at said preselected nucleotide position in a tumor of type; or (ii) assigning said nucleotide value is a function of a set of values which represent the probabilities of observing a read showing a preselected variant at said preselected nucleotide position if the variant is present in the sample at a frequency of at least 1%, at least 5%, at least 10%, or more, or if the variant is absent.

21. The method of claim 19, wherein the calling method comprises:
acquiring, for a preselected nucleotide position in each of said X unique subgenomic intervals:
(i) a first value which is or represents a prior expectation of observing a read showing a preselected variant at said preselected nucleotide position in a type of tumor; and
(ii) a second set of values which represent the probabilities of observing a read showing said preselected variant at said preselected nucleotide position if the variant is present in the sample at a frequency of at least 1%, at least 5%, at least 10%, or more, or if the variant is absent;
responsive to said values, assigning a nucleotide value from said reads for each of said preselected nucleotide positions by weighing the comparison among the values in the second set using the first value, thereby analyzing said sample.

22. The method of claim 21, wherein the method comprises assigning a nucleotide value for at least X, where X is 10 preselected nucleotide positions, wherein each assignment is a function of a unique value which is or represents the prior expectation of observing a read showing a preselected variant at said preselected nucleotide position in a tumor of type, wherein unique value means different from the values for the other X−1 assignments.

23. The method of claim 22, wherein the preselected nucleotide position and the type of tumor are according to Tables 6, 9 and 10.

24. The method of claim 19, wherein the unique calling methods differ by relying on different Bayesian prior values.

25. The method of claim 19, comprising one or more or all of:
(i) assigning a nucleotide value for at least 10 preselected nucleotide positions, wherein each assignment is based on a unique first or second value, as compared with the values for the other assignments;
(ii) the assignment of method of (i), wherein at least 10 of the assignments are made with first values which are a function of a probability of a preselected variant being present in less than 5, 10, or 20% of the cells in a preselected type of tumor;
(iii) assigning a nucleotide value for at least X preselected nucleotide positions, each of which is associated with a preselected variant having a unique probability of being present in the tumor of preselected type as compared with the probability for the other X−1assignments, wherein each of said X assignments is based on a unique first or second value as compared with the values for the other X−1assignments, wherein X=10; or
(iv) assigning a nucleotide value at a first and a second nucleotide position, wherein the likelihood of a first preselected variant at said first nucleotide position being present in a tumor of preselected type is at least 2 times greater than the likelihood of a second preselected variant at said second nucleotide position being present, wherein each assignment is based on a unique first and/or second value as compared with the values for the other assignments.

26. The method of claim 19, comprising assigning a nucleotide value to a plurality of preselected nucleotide positions, wherein said plurality comprises an assignment for variants falling into at least 3, or all, of the following probability ranges:
less than 0.01%;
greater than 0.01 and less than or equal to 0.02%;
greater than 0.02 and less than or equal to 0.03%;
greater than 0.03 and less than or equal to 0.04%;
greater than 0.04 and less than or equal to 0.05%;
greater than 0.05 and less than or equal to 0.1%;
greater than 0.1 and less than or equal to 0.2%;
greater than 0.2 and less than or equal to 0.5%;
greater than 0.5 and less than or equal to 1.0%;
greater than 1.0 and less than or equal to 2.0%;
greater than 2.0 and less than or equal to 5.0%;
greater than 5.0 and less than or equal to 10.0%;
greater than 10.0 and less than or equal to 20.0%;
greater than 20.0 and less than or equal to 50.0%; and
greater than 50 and less than or equal to 100.0%;
wherein, a probability range is the range of probabilities that a preselected variant at a preselected nucleotide position is present in a tumor of preselected type or the probability that a preselected variant at a preselected nucleotide position is present in the cells in a tumor sample, a library from the tumor sample, or library catch from that library, for a preselected type, and wherein each assignment is based on a unique first or second value, wherein unique first or second value means different from the values for the other assignments in a probability range or different from the first or second value for one or more or all of the other probability ranges.

27. The method of claim 19, comprising one or both of:
(i) assigning a nucleotide value for at least 3 preselected nucleotide positions each, independently, having a preselected variant present in less than 5, 4, 3, 2, 1, 0.5, 0.4, 0.3, 0.2, or 0.1% of the DNA in said sample, wherein each assignment is based on a unique first and/or second value as compared with the values for the other assignments; or
(ii) assigning a nucleotide value at a first and a second nucleotide position, wherein the likelihood of a preselected variant at the first position in the DNA of said sample is at least 2 times greater than the likelihood of a preselected variant at said second nucleotide position in the DNA of said sample, wherein each assignment is based on a unique first or second value as compared with the values for the other assignments.

28. The method of claim 19, comprising assigning a nucleotide value to at least 3 preselected nucleotide positions having a preselected variant present in X % of the cells in said sample, of the nucleic acid in a library from said sample, or the nucleic acid in a library catch from that library,
wherein X is independently chosen from less than 1.0%; between and equal to 1.0-2.0%; greater than 2.0% and less than or equal to 3%; greater than 3.0% and less than or equal to 4%; greater than 4.0% and less than or equal to 5%; greater than 5.0% and less than or equal to 10%; greater than 10.0% and less than or equal to 20%; greater than 20.0% and less than or equal to 40%; greater than 40.0% and less than or equal to 50%; or greater than 50.0% and less than or equal to 100%, of the cells in said sample, of the nucleic acid in a library from said sample, or the nucleic acid in a library catch from that library;
wherein each assignment is based on a unique first or second value, wherein unique means different from the values for the other assignments in the range in (i) of less than 1% or different from a first or second values for a determination in one or more or all of the other ranges.

29. The method of claim 19, comprising assigning a nucleotide value at each of X nucleotide positions, each nucleotide position, independently, having a likelihood of a preselected variant being present in the DNA of said sample that is unique as compared with the likelihood for a preselected variant at the other X−1 nucleotide positions, wherein X is equal to or greater than 1, 2, 3, 5, 10, 20, 40, 50, 60, 70, 80, 90, or 100, and wherein each assignment is based on a unique first or second value as compared with the values for the other assignments.

30. The method of claim 19, said method comprising assigning a nucleotide value at each of at least 3 preselected nucleotide positions, each having, independently, a first value that is a function of a probability that is less than 0.5.

31. The method of claim 19, said method comprising assigning a nucleotide value at each of at least X nucleotide positions, each independently having a first value that is unique as compared with the other X−1 first values, and wherein each of said X first values is a function of a probability that is less than 0.5%, wherein X is equal to or greater than 3.

32. The method of claim 19, wherein a nucleotide position in at least 20 genes from Table 1 or 1A is assigned a nucleotide value.

33. The method of claim 32, wherein a unique first value, second value, or both values are applied to subgenomic intervals in each of at least 10% of said genes analyzed.

34. The method of claim 32, wherein a nucleotide position in at least 10 genes from Table 1 or 1A having the priority 1 annotation is assigned a nucleotide value.

35. The method of claim 33, further comprising 2, 3, 4 or all of the following:
(i) responsive to said first value, second value or both values, assigning a nucleotide value from reads for a first preselected nucleotide position for which a coverage greater than 500× sequencing depth is required to enable a high level of sensitivity for a mutation that appears at a frequency of 5% or less in cells in the sample;
(ii) responsive to said first value, second value or both values, assigning a nucleotide value from reads for a second preselected nucleotide position for which greater than 200× sequencing depth is required to enable a high level of sensitivity for a mutation that appears at a frequency of greater than 5% and up to 10, 15 or 20% in cells in the sample;
(iii) responsive to said first value, second value or both values, assigning a nucleotide value from reads for a third preselected nucleotide position for which coverage less than that in (i) or (ii) above is required to enable a high level of sensitivity for heterozygous alleles, wherein said third preselected nucleotide position is chosen from (1) a pharmacogenomic SNP associated with the ability of a patient to respond to or metabolize a drug; (2) a plurality of genomic SNPs that are used to uniquely identify (fingerprint) a patient; or (3) a genomic SNP or locus that is used to assess copy number gains or losses of genomic DNA and LOH;
(iv) responsive to said first value, second value or both values, assigning a nucleotide value from reads for a fourth preselected nucleotide position chosen from a structural breakpoint, a rearrangement, a translocation or an indel; and
(v) responsive to said first value, second value or both values, assigning a nucleotide value from reads for a fifth preselected nucleotide position for which the coverage is less than in one of (i), (ii) (iii) or (iv) to ensure high detection reliability.

36. The method of claim 19, further comprising acquiring a threshold value for each of a number of preselected subgenomic intervals, wherein said threshold value is customized based on one or more of: the type of cancer in a sample, the gene in which the subgenomic interval to be sequenced is located, or the variant to be sequenced.

37. The method of claim 19, wherein the calling method comprises:
acquiring, for each of said X subgenomic intervals, a threshold value, wherein each of said acquired X threshold values is unique as compared with the other X−1 threshold values, thereby providing X unique threshold values;
for each of said X subgenomic intervals, comparing an observed value which is a function of the number of reads having a preselected nucleotide value at a preselected nucleotide position with its unique threshold value, thereby applying to each of said X subgenomic intervals, its unique threshold value; and
responsive to the result of said comparison, assigning a nucleotide value to a preselected nucleotide position, wherein X is equal to or greater than 2.

38. The method of claim 37, wherein a unique threshold value is applied to subgenomic intervals in each of at least 10 different genes.

39. The method of claim 38, wherein a unique threshold value is applied to a subgenomic interval in each of at least 10% of said genes analyzed.

40. The method of claim 37, wherein a nucleotide position in at least 20 genes from Table 1 or 1A is assigned a nucleotide value; and a unique threshold value is applied to a subgenomic interval in each of at least 10% of said genes analyzed.

41. The method of claim 37, wherein a nucleotide position in at least 10 genes from Table 1 or 1A having the priority 1 annotation is assigned a nucleotide value; and a unique threshold value is applied to a subgenomic interval in each of at least 10% of said genes analyzed.

42. The method of claim 37, wherein a nucleotide position for at least 20 variants or codons from Table 1, 1A, 2, or 3, is assigned a nucleotide value; and a unique threshold value is applied to a subgenomic interval in each of at least 10% of said genes analyzed.

43. The method of claim 37, wherein a nucleotide position for at least 10 variants from the bottom half or bottom third of Table 9 is assigned a nucleotide value; and a unique threshold value is applied to a subgenomic interval in each of at least 10% of said genes analyzed.

44. The method of claim 1, wherein:
a read from each of X unique subgenomic intervals is aligned with a unique alignment method and X is at least 2,
wherein unique subgenomic interval means different from the other X−1 subgenomic intervals, and wherein unique alignment method means different from the other X−1 alignment methods.

45. The method of claim 44, wherein subgenomic intervals from at least X genes from Table 1 or 1A having the priority 1 annotation, are aligned with unique alignment methods, and X is equal to 10.

46. The method of claim 44, comprising:
a) applying a first unique alignment method to a first genomic interval, a variant of which is associated with a tumor phenotype, wherein the variant is a point mutation from Table 6;
b) applying a second unique alignment method to a second genomic interval, a variant of which is associated with a tumor phenotype, wherein the variant is a rearrangement chosen from a deletion, insertion, or translocation on Table 5; and c) applying a third unique alignment method to a third genomic interval comprising a genomic interval in which variants are not associated with a tumor phenotype or with a tumor of the type in said sample.

47. The method of claim 44, wherein a subgenomic interval being analyzed comprises a nucleotide position with a genomic rearrangement, and the method comprises using an alignment method that includes:

selecting a rearrangement reference sequence for alignment with a read, wherein said rearrangement reference sequence is preselected to align with a preselected rearrangement, wherein the preselected rearrangement reference sequence is not identical to the preselected rearrangement;

comparing a read with said preselected rearrangement reference sequence; and determining if said read meets a predetermined alignment criterion, wherein the predetermined alignment criterion is an alignment to said preselected rearrangement reference sequence with less than a preselected level of mismatch or gaps; thereby analyzing a read.

48. The method of claim 1, wherein the method comprises 2, 3, 4 or 5 of:

a) sequencing a first subgenomic interval to provide for about 500× or higher sequencing depth, thereby detecting a mutation present in no more than 5% of the cells from the tumor sample;

b) sequencing a second subgenomic interval to provide for about 200×-500× sequencing depth, thereby detecting a mutation present in no more than 10% of the cells from the tumor sample;

c) sequencing a third subgenomic interval to provide for about 200×-500× sequencing depth, thereby detecting a subgenomic interval chosen from one or more of: 1) a pharmacogenomic (PGx) single nucleotide polymorphism (SNP) that distinguishes the ability of a patient to metabolize different drugs, or 2) a plurality of genomic SNPs that uniquely identifies a patient;

d) sequencing a fourth subgenomic interval to provide for about 5×-50× sequencing depth, thereby detecting a structural breakpoint; or e) sequencing a fifth subgenomic interval to provide for about 100×-300× sequencing depth, thereby detecting a copy number change.

49. The method of claim 48, wherein the detection of the copy number change comprises detection of a genomic SNP or locus that is used to assess copy number gains or losses of genomic DNA or loss-of-heterozygosity (LOH).

50. The method of claim 1, wherein said contacting step (b) is performed in solution.

51. The method of claim 1, wherein the method comprises contacting the library with at least three, four, or five bait sets.

52. The method of claim 8, wherein the bait set is chosen from five, six, seven, eight, nine, ten, eleven, twelve or all of A-M.

53. The method of claim 8, wherein the bait set is chosen from ten, eleven, twelve or all of A-M.

54. The method of claim 24, wherein the unique calling methods differ by relying on different Bayesian prior values chosen from a first calling method applied to a first nucleotide position that is a function of a first Bayesian prior and a second calling method applied to a second nucleotide position that is a function of a second Bayesian prior.

55. The method of claim 44, wherein the aligning step comprises two or more of the following:

(i) a first alignment method that is selected responsive to, or is optimized for, a high level target comprising a gene, an exon, or a base that appears at a frequency of 5% or less, in cells in the tumor sample, the nucleic acid molecules of the library, or the nucleic acid molecules of the library catch;

(ii) a second alignment method that is selected responsive to, or is optimized for, a mid-level target comprising a gene, an exon, or a base that appears at a frequency of greater than 5% and up to 10, 15 or 20%, in cells in the tumor sample, the nucleic acid molecules of the library, or the nucleic acid molecules of the library catch;

(iii) a third alignment method that is selected responsive to, or is optimized for, a low-level target comprising a gene, exon, or base, chosen from one or more of:

(1) a pharmacogenomic SNP that is associated with the ability of patient to respond to or metabolize a drug;

(2) a plurality of genomic SNPs that uniquely identify (fingerprint) a patient; or (3) a genomic SNP or locus that is used to assess copy number gains or losses of genomic DNA and LOH;

(iv) a fourth alignment method that is selected responsive to, or is optimized for, a structural breakpoint; and (v) a fifth alignment method that is selected responsive to, or is optimized for, a target comprising an intron for which sparse coverage can improve the ability to detect copy number changes.

56. The method of claim 55, wherein the structural breakpoint is in a rearrangement, a translocation or an indel.

57. The method of claim 47, wherein the preselected rearrangement is a preselected indel.

58. The method of claim 47, wherein:

(i) the preselected rearrangement reference sequence comprises a sequence or its complement corresponding to said preselected rearrangement;

(ii) the preselected rearrangement reference sequence comprises a simulated sequence that is other than the sequence of the preselected rearrangement or its complement selected to align with a read of said preselected rearrangement; or (iii) the preselected rearrangement reference sequence is not identical to the preselected rearrangement.

59. The method of claim 1, wherein the sequenced somatic mutation in step (c) is from said library catch.

60. The method of claim 2, wherein the different types of oligonucleotide baits are chosen from one or more of: non-naturally occurring DNA oligonucleotides, or one or more non-naturally occurring RNA oligonucleotides, or a combination thereof.

61. The method of claim 60, wherein the non-naturally occurring DNA or RNA oligonucleotides are chosen from one or more of: a locked nucleic acid (LNA); a peptide nucleic acid (PNA); a DNA or RNA oligonucleotide modified to capture low GC regions; a bicyclic nucleic acid (BNA); a crosslinked oligonucleotide; a modified 5-methyl deoxycytidine; or 2,6-diaminopurine.

62. The method of claim 1, wherein the tumor member comprises a sequence from a subject and a sequence not derived from the subject.

63. The method of claim 62, wherein the tumor member comprises an adapter sequence, a primer sequence, or other sequences that allow for identification.

64. The method of claim 63, wherein the tumor member comprises a barcode sequence.

65. A method of analyzing a tumor sample for a somatic mutation, comprising:
(a) acquiring a library comprising a plurality of tumor members from the tumor sample;
(b) contacting the library with at least two bait sets to provide selected tumor members, wherein said bait sets hybridize with the tumor members, thereby providing a library catch;
(c) sequencing by a next generation sequencing method a subgenomic interval comprising the somatic mutation from a tumor member from said library catch, thereby acquiring a read for the subgenomic interval;
thereby analyzing said tumor sample for the somatic mutation,
wherein the at least two bait sets of step (b) are chosen from two of the following bait sets:
(i) a first bait set that selects a high-level target chosen from one or more tumor nucleic acid molecules that comprise a subgenomic interval comprising a somatic mutation that appears at a frequency of about 5% or less of the cells from the tumor sample;
(ii) a second bait set that selects a mid-level target chosen from one or more tumor nucleic acid molecules that comprise a subgenomic interval comprising a somatic mutation that appears at a frequency of about 10% or higher of the cells from the tumor sample;
(iii) a third bait set that selects a low-level target chosen from one or more nucleic acid molecules that comprise a subgenomic interval chosen from one or more of:
a) a pharmacogenomic (PGx) single nucleotide polymorphism (SNP) that distinguishes the ability of a patient to metabolize different drugs,
b) a plurality of genomic SNPs that uniquely identify (fingerprint) a patient, or
c) a genomic SNP or locus that is used to assess copy number gains or losses of genomic DNA and loss-of-heterozygosity (LOH);
(iv) a fourth bait set that selects a nucleic acid molecule that comprises an intron sequence that detects a structural breakpoint; or
(v) a fifth bait set that selects a one-copy deletion of several terminal exons,
wherein each bait set of said plurality has a unique preselected efficiency for selection for its target as compared with the other bait sets in the plurality.

66. The method of claim 65, wherein the efficiency for selection in step (b) is modified by one or more of:
(i) differential representation of different bait sets;
(ii) differential overlap of bait subsets;
(iii) differential bait parameters;
(iv) mixing of different bait sets at different molar ratios to enhance or reduce relative target coverage depths; or
(v) using different types of oligonucleotide baits.

67. The method of claim 66, wherein the different types of oligonucleotide baits are chosen from one or more of:
(a) one or more chemically (non-enzymatically) individually synthesized baits,
(b) one or more baits synthesized in an array,
(c) one or more in vitro transcribed baits;
(d) any combination of (a), (b) or (c),
(e) one or more naturally or non-naturally occurring DNA oligonucleotides,
(f) one or more naturally or non-naturally occurring RNA oligonucleotides,
(g) a combination of (e) and (f), or
(h) a combination of any of the above.

68. The method of claim 67, wherein the different types of oligonucleotide baits are mixed at a ratio chosen from 1:1, 1:2, 1:3, 1:4, 1:5, 1:10, 1:20, 1:50; 1:100, or 1:1000.

69. The method of claim 68, wherein the ratio of the chemically individually synthesized baits to the baits synthesized in an array is chosen from 1:5, 1:10, or 1:20.

70. The method of claim 67, wherein the non-naturally occurring DNA or RNA oligonucleotides are chosen from one or more of: a locked nucleic acid (LNA); a peptide nucleic acid (PNA); a DNA or RNA oligonucleotide modified to capture low GC regions; a bicyclic nucleic acid (BNA); a crosslinked oligonucleotide; a modified 5-methyl deoxycytidine; or 2,6-diaminopurine.

71. The method of claim 65, wherein one or more of the following bait parameters are modified:
(i) increasing or decreasing bait representation or overlap to enhance or reduce coverage of tumor members, which are under- or over-covered relative to other targets in the same category;
(ii) for low coverage, hard to capture target sequences comprising high GC content sequences, targeting with the bait sets covering adjacent sequences;
(iii) modifying a bait sequence to reduce secondary structure of the bait and enhance its efficiency for selection;
(iv) modifying a bait length to equalize melting hybridization kinetics of different baits within the same category;
(v) modifying baits of different orientation for the same target region, forward and reverse strand, to have different binding efficiencies;
(vi) modifying the amount of a binding entity present on each bait that affects the bait's binding efficiency;
(vii) modifying the type of nucleotide used for different baits to affect binding affinity to the target, and enhance or reduce the relative target coverage; or
(viii) using modified oligonucleotide baits having more stable base pairing to equalize melting hybridization kinetics between areas of low or normal GC content relative to high GC content.

72. The method of claim 65, wherein the bait sets are chosen from two or more of:
A. a bait set that selects an exon sequence that comprises a single nucleotide alteration associated with a cancerous phenotype;
B. a bait set that selects an in-frame deletion of 1 or more codons from a reference nucleotide sequence;
C. a bait set that selects an intragenic deletion;
D. a bait set that selects an intragenic insertion;
E. a bait set that selects a deletion of a full gene;
F. a bait set that selects an inversion;
G. a bait set that selects an interchromosal translocation;
H. a bait set that selects a tandem duplication;
I. a bait set that selects a nucleotide sequence of interest flanked by adjacent non-repetitive sequences;
J. a bait set that selects one or more subgenomic intervals corresponding to a fusion sequence;
K. a bait set that selects a subgenomic interval adjacent to a nucleotide sequence that includes an undesirable feature chosen from a nucleotide sequence of high GC content, or a nucleotide sequence comprising repeated elements, inverted repeats, or both;
L. a bait set that selects a genomic rearrangement that comprises an intron sequence; or
M. a bait set that selects a subgenomic interval that comprises an exon adjacent to a cancer associated gene fusion.

73. The method of claim 65, wherein the subgenomic interval comprises or consists of one or more of: a single nucleotide position; an intragenic region or an intergenic region; an exon or an intron, or a fragment thereof; a coding region or a non-coding region; a promoter, an enhancer, a 5' untranslated region (5' UTR), or a 3' untranslated region (3' UTR), or a fragment thereof; a cDNA or a fragment thereof; an SNP; a somatic mutation, a germ line mutation or both; a point or a single mutation; a deletion mutation; an in-frame deletion, an intragenic deletion; a full gene deletion; an insertion mutation; an intragenic insertion; an inversion mutation; an intra-chromosomal inversion; a linking mutation; a linked insertion mutation; an inverted duplication mutation; a tandem duplication; an intrachromosomal tandem duplication; a translocation; a chromosomal translocation, a non-reciprocal translocation; a rearrangement; a genomic rearrangement; a rearrangement of one or more introns, or a fragment thereof; a rearranged intron; a 5'- or a 3'- UTR, or a combination thereof.

74. The method of claim 65, wherein the subgenomic interval comprises an altered nucleotide sequence, encodes an altered amino acid sequence, a chromosomal translocation, an intra-chromosomal inversion, a change in copy number, a change in expression level, a change in protein level, a change in protein activity, or a change in methylation status, in a cancer tissue or cancer cell, as compared to a normal, healthy tissue or cell.

75. The method of claim 65, wherein the tumor sample comprises: one or more premalignant or malignant cells; cells from a solid tumor, a soft tissue tumor or a metastatic lesion; tissue or cells from a surgical margin; a histologically normal tissue; one or more circulating tumor cells (CTCs); a normal adjacent tissue (NAT); a blood sample from a subject having or at risk of having the tumor; or an FFPE-sample.

76. The method of claim 75, wherein the tumor sample comprises the FFPE-sample.

77. The method of claim 75, wherein the tumor sample comprises one or more CTCs.

78. The method of claim 65, wherein the different types of oligonucleotide baits are chosen from one or more non-naturally occurring DNA oligonucleotides, or one or more non-naturally occurring RNA oligonucleotides, or a combination thereof.

79. The method of claim 65, wherein the non-naturally occurring DNA or RNA oligonucleotides are chosen from one or more of: a locked nucleic acid (LNA); a peptide nucleic acid (PNA); a DNA or RNA oligonucleotide modified to capture low GC regions; a bicyclic nucleic acid (BNA); a crosslinked oligonucleotide; a modified 5-methyl deoxycytidine; or 2,6-diaminopurine.

80. The method of claim 65, wherein the tumor member comprises a sequence from a subject and a sequence not derived from the subject.

81. The method of claim 80, wherein the tumor member comprises an adapter sequence, a primer sequence, or other sequences that allow for identification.

82. The method of claim 81, wherein the tumor member comprises a barcode sequence.

83. The method of claim 65, wherein the method comprises sequencing a subgenomic interval chosen from at least 1, 2, 3, 4, 5, 6, 7, 8, 9, 10, 11, 12, 13 or all of the following:
  A) at least five, six, seven, eight, nine, ten, fifteen, twenty, twenty-five, thirty or more subgenomic intervals from a mutated or wild-type gene or gene product chosen from at least five or more of: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53;
  B) at least five, six, seven, eight, nine, ten, fifteen, twenty, twenty-five, thirty, thirty-five, forty, forty-five, fifty, fifty-five, sixty, sixty-five, seventy, seventy-five, eighty, eighty-five, ninety, ninety-five, one hundred, one hundred and five, one hundred and ten, one hundred and fifteen, one hundred and twenty or more of subgenomic intervals from a mutated or wild type gene or gene product chosen from at least five or more of: ABL2, ARAF, ARFRP1, ARID1A, ATM, ATR, AURKA, AURKB, BAP1, BCL2, BCL2A1, BCL2L1, BCL2L2, BCL6, BRCA1, BRCA2, CBL, CARD11, CBL, CCND2, CCND3, CCNE1, CD79A, CD79B, CDH1, CDH2, CDH20, CDH5, CDK6, CDK8, CDKN2B, CDKN2C, CHEK1, CHEK2, CRKL, CRLF2, DNMT3A, DOT1L, EPHA3, EPHA5, EPHA6, EPHA7, EPHB1, EPHB4, EPHB6, ERBB3, ERBB4, ERG, ETV1, ETV4, ETV5, ETV6, EWSR1, EZH2, FANCA, FBXW7, FGFR4, FLT1, FLT4, FOXP4, GATA1, GNA11, GNAQ, GNAS, GPR124, GUCY1A2, HOXA3, HSP90AA1, IDH1, IDH2, IGF1R, IGF2R, IKBKE, IKZF1, INHBA, IRS2, JAK1, JAK3, JUN, KDM6A, KDR, LRP1B, LRP6, LTK, MAP2K4, MCL1, MDM2, MDM4, MEN1, MITF, MLH1, MPL, MRE11A, MSH2, MSH6, MTOR, MUTYH, MYCL1, MYCN, NF2, NKX2-1, NTRK1, NTRK2, PAK3, PAX5, PDGFRB, PKHD1, PLCG1, PRKDC, PTPN11, PTPRD, RAF1, RARA, RICTOR, RPTOR, RUNX1, SMAD2, SMAD3, SMAD4, SMARCA4, SMARCB1, SOX10, SOX2, SRC, TBX22, TET2, TGFBR2, TMPRSS2, TNFAIP3, TNK, TNKS2, TOP1, TSC1, TSC2, USP9X, VHL, or WT1;
  C) at least five, six, seven, eight, nine, ten, fifteen, twenty, or more subgenomic intervals from a gene or gene product according to Table 1, 1A, 2, 3, or 4;
  D) at least five, six, seven, eight, nine, ten, fifteen, twenty, or more subgenomic intervals from a gene or gene product chosen from one or more of: ABL1, AKT1, ALK, AR, BRAF, BRCA1, BRCA2, CEBPA, EGFR, ERBB2, FLT3, JAK2, KIT, KRAS, MET, NPM1, PDGFRA, PIK3CA, RARA, AKT2, AKT3, MAP2K4, NOTCH1, and TP53;
  E) at least five, six, seven, eight, nine, ten, or more subgenomic intervals including a mutated or a wild type codon chosen from one or more of: codon 315 of the ABL1 gene; codon 1114, 1338, 1450 or 1556 of APC; codon 600 of BRAF; codon 32, 33, 34, 37, 41 or 45 of CTNNB1; codon 719, 746-750, 768, 790, 858 or 861 of EGFR; codon 835 of FLT3; codon 12, 13, or 61 of HRAS; codon 617 of JAK2; codon 816 of KIT; codon 12, 13, or 61 of KRAS; codon 88, 542, 545, 546, 1047, or 1049 of PIK3CA; codon 130, 173, 233, or 267 of PTEN; codon 918 of RET; or codon 175, 245, 248, 273, or 306 of TP53;
  F) at least five, six, seven, eight, nine, ten, fifteen, twenty, twenty-five, thirty, or more of subgenomic intervals from a mutated or wild type gene or gene product chosen from: ABCB1, BCC2, ABCC4, ABCG2, C1orf144, CYP1B1, CYP2C19, CYP2C8, CYP2D6, CYP3A4, CYP3A5, DPYD, ERCC2, ESR2, FCGR3A, GSTP1, ITPA, LRP2, MAN1B1, MTHFR, NQO1, NRP2, SLC19A1, SLC22A2, SLCO1B3, SOD2, SULT1A1, TPMT, TYMS, UGT1A1, or UMPS;
  G) at least five, six, seven, eight, nine, ten, fifteen, twenty, twenty-five, thirty, or more of subgenomic intervals from a mutated or wild type PGx gene or gene product associated with one or more of: (i) better survival of a cancer patient treated with a drug; (ii) paclitaxel metabolism; (iii) toxicity to a drug; or (iv) a side effect to a drug;

H) a translocation alteration of at least 5, 10, 15, 20, 25, 30, 35, 40, 45, 50, 75, 110 or more genes or gene products according to Table 3;

I) a translocation alteration of at least 5, 10, 15, 20, 25, 30, 35, 40, 45, 50, 75, 110 or more genes or gene products according to Table 3 in a solid tumor sample from the cancer types specified therein;

J) a translocation alteration of at least 5, 10, 15, 20, 25, 30, 35, 40, 45, 50, 75, 100, 150, 200 or more genes or gene products according to Table 4;

K) a translocation alteration of at least 5, 10, 15, 20, 25, 30, 35, 40, 45, 50, 75, 100, 150, 200 or more genes or gene products according to Table 4 in a heme tumor sample from the cancer types specified therein;

L) at least five genes or gene products selected from the genes in any of Table 1, 1A, 2, 3, or 4, wherein an allelic variation is associated with a preselected type of tumor and wherein said allelic variation is present in less than 5% of the cells in said tumor type;

M) at least five genes or gene products selected from the genes in any of Table 1, 1A, 2, 3, or 4, which are embedded in a GC-rich region; or N) at least five genes or gene products indicative of a genetic factor for developing cancer chosen from one or more of BRCA1, BRCA2, EGFR, HRAS, KIT, MPL, ALK, PTEN, RET, APC, CDKN2A, MLH1, MSH2, MSH6, NF1, NF2, RB1, TP53, VHL, or WT1.

84. The method of claim 65, wherein the method comprises sequencing a subgenomic interval from at least twenty, twenty-five, thirty or more genes or gene products from the sample, wherein the genes or gene products are chosen from: ABL1, AKT1, AKT2, AKT3, ALK, APC, AR, BRAF, CCND1, CDK4, CDKN2A, CEBPA, CTNNB1, EGFR, ERBB2, ESR1, FGFR1, FGFR2, FGFR3, FLT3, HRAS, JAK2, KIT, KRAS, MAP2K1, MAP2K2, MET, MLL, MYC, NF1, NOTCH1, NPM1, NRAS, NTRK3, PDGFRA, PIK3CA, PIK3CG, PIK3R1, PTCH1, PTCH2, PTEN, RB1, RET, SMO, STK11, SUFU, or TP53.

85. The method of claim 65, wherein the method comprises sequencing a subgenomic interval comprising one or more codons chosen from: codon 315 of the ABL1 gene; codon 1114, 1338, 1450 or 1556 of APC; codon 600 of BRAF; codon 32, 33, 34, 37, 41 or 45 of CTNNB1; codon 719, 746-750, 768, 790, 858 or 861 of EGFR; codon 835 of FLT3; codon 12, 13, or 61 of HRAS; codon 617 of JAK2; codon 816 of KIT; codon 12, 13, or 61 of KRAS; codon 88, 542, 545, 546, 1047, or 1049 of PIK3CA; codon 130, 173, 233, or 267 of PTEN; codon 918 of RET; or codon 175, 245, 248, 273, or 306 of TP53.

* * * * *